United States Patent
Hayashizaki et al.

(10) Patent No.: US 8,067,162 B2
(45) Date of Patent: Nov. 29, 2011

(54) PRIMER, PRIMER SET, AND NUCLEIC ACID AMPLIFICATION METHOD AND MUTATION DETECTION METHOD USING THE SAME

(75) Inventors: Yoshihide Hayashizaki, Yokohama (JP); Akimitsu Okamoto, Wako (JP); Alexander Lezhava, Yokohama (JP); Yasushi Kogo, Yokohama (JP)

(73) Assignees: Riken, Saitama (JP); Kabushiki Kaisha Dnaform, Kanagawa (JP)

( * ) Notice: Subject to any disclaimer, the term of this patent is extended or adjusted under 35 U.S.C. 154(b) by 417 days.

(21) Appl. No.: 12/075,198

(22) Filed: Mar. 10, 2008

(65) Prior Publication Data

US 2008/0227104 A1    Sep. 18, 2008

(30) Foreign Application Priority Data

| Mar. 9, 2007 | (JP) | 2007-059921 |
| Sep. 21, 2007 | (JP) | 2007-246253 |
| Sep. 25, 2007 | (JP) | 2007-248257 |
| Dec. 26, 2007 | (JP) | 2007-335352 |
| Feb. 15, 2008 | (JP) | 2008-035325 |

(51) Int. Cl.
C12Q 1/68    (2006.01)
C12P 19/38    (2006.01)
C07H 21/02    (2006.01)

(52) U.S. Cl. ....... 435/6; 435/91.1; 435/91.2; 536/24.33; 422/68.1

(58) Field of Classification Search ............ 435/6, 91.1, 435/91.2; 536/24.33; 422/68.1
See application file for complete search history.

(56) References Cited

U.S. PATENT DOCUMENTS 5,547,860 A    8/1996    Köcher
(Continued)

FOREIGN PATENT DOCUMENTS

EP    0 527 433 A1    2/1993
(Continued)

OTHER PUBLICATIONS

Stratagene, Catalog, 1988, p. 39.*
(Continued)

*Primary Examiner* — Jezia Riley
(74) *Attorney, Agent, or Firm* — Hamre, Schumann, Mueller & Larson, P.C.

(57) ABSTRACT

The present invention provides a primer that effectively can detect, for example, the double helix structure of a nucleic acid. The primer is a labeled nucleic acid containing at least one structure represented by the following formula (16),

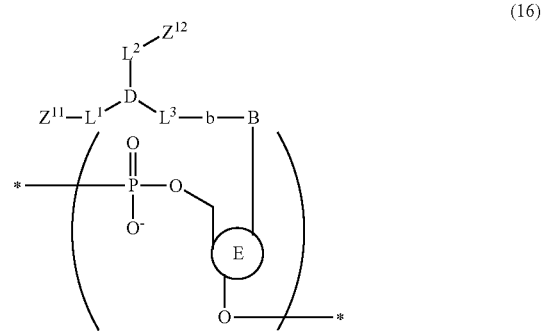

where B is an atomic group having a nucleobase skeleton, E is an atomic group having a deoxyribose skeleton, a ribose skeleton, or a structure derived from either one of them, or an atomic group having a peptide structure or a peptoid structure, and $Z^{11}$ and $Z^{12}$ are each an atomic group that exhibits fluorescence and are identical to or different from each other.

58 Claims, 47 Drawing Sheets

U.S. PATENT DOCUMENTS

| | | | |
|---|---|---|---|
| 2002/0192670 | A1 | 12/2002 | Tokunaga et al. |
| 2007/0048773 | A1 | 3/2007 | Lee et al. |
| 2010/0092971 | A1 | 4/2010 | Okamoto et al. |

FOREIGN PATENT DOCUMENTS

| | | |
|---|---|---|
| EP | 0 608 737 A1 | 8/1994 |
| EP | 1 712 618 A1 | 10/2006 |
| JP | 6-271599 | 9/1994 |
| JP | 11-127862 A | 5/1999 |
| JP | 2002-327130 | 11/2002 |
| JP | 2003-344290 A | 12/2003 |
| JP | 2004-081057 | 3/2004 |
| JP | 2004-529618 | 9/2004 |
| JP | 2005-518819 | 6/2005 |
| JP | 2006-320267 | 11/2006 |
| WO | WO 98/58942 A1 | 12/1998 |
| WO | 02/061121 | 8/2002 |
| WO | 03/076566 | 9/2003 |
| WO | WO 2004/074503 A2 | 9/2004 |
| WO | WO 2006/097320 A2 | 9/2006 |

OTHER PUBLICATIONS

Office Action of the corresponding JP Application No. JP2008-035325, dated Oct. 14, 2008.
Hwang et al., "Fluorescent oligonucleotide incorporating 5-(1-ethynylpyrenyl)-2'-deoxyuridine: sequence-specific fluorescence changes upon duplex formation", Tetrahedron Letters, Apr. 26, 2004, vol. 45, No. 18, pp. 3543-3546.
Okamoto et al., "Synthesis and ESR studies of nitronyl nitroxide-tethered oligodeoxynucleotides", Tetrahedron Letters, Jan. 31, 2005, vol. 46, No. 5, pp. 791-795.
Jarikote et al., "Divergent and Linear Solid-Phase Synthesis of PNA Containing Thiazole Orange as Artificial Base", Eur. J. Org. Chem., 2005, No. 15, pp. 3187-3195.
Bordelon et al., "Viscometry and Atomic Force Microscopy Studies of the Interactions of a Dimeric Cyanine Dye with DNA", J. Phys. Chem. B., Apr. 17, 2002, vol. 106, No. 18, pp. 4838-4843.
Lartia et al., "New Cyanine-Oligonucleotide Conjugates: Relationships between Chemical Structures and Properties", Chemistry, Mar. 1, 2006, Vol. 12, No. 8, pp. 2270-2281.
Inoue et al., "Fluorescence Property of Oxazole Yellow-linked Oligonucleotide. Triple Helix Formation and Photocleavage of Double-stranded DNA in the Presence of Spermine", Bioorganic & Medicinal Chemistry, Jun. 1999, vol. 7, No. 6, pp. 1207-1211.
Office Action for corresponding Japanese Patent Application No. JP 2008-035325 mailed Jan. 26, 2009 with its partial English translation (6 pages).
Tyaig et al. "Molecular Beacons: Probes that Fluoresce upon Hybridization." Nature Biotechnology 14, 1996, p. 303-308.
Nazarenko et al. "A closed tube format for amplification and detection of DNA based on energy transfer." Nucleic Acids Research, 25, 1997, p. 2516-2521.
Gelmini et al. "Quantitative polymerase chain reaction-based homogeneous assay with fluorogenic probes to measure c-erbB-2 oncogene amplification." Clinical Chemistry, 43, 1997, p. 752-758.
Whitcombe et al. "Detection of PCR products using self-probing ampl icons and fluorescence." Nature Biotechnology, 17, 1999, p. 804-807.
Nygren et al. "The Interactions between the Fluorescent Dye Thiazole Orange and DNA." Biopolymers, 46, 1998, p. 39-51.
Wang et al. "Tethered thiazole orange intercalating dye for development of fibre-optic nucleic acid biosensors." Analytica Chimica Acta, 470, 2002, p. 57-70.
Mitani et al. "Rapid SNP diagnostics using asymmetric isothermal amplification and a new mismatch-suppression technology." Nature Methods 4(3), 2007, p. 257-262.
Written Opinion of the International Searching Authority of PCT/JP2008/054054 dated May 20, 2008.
International Search Report of PCT/JP2008/054054 dated May 20, 2008.
Partial European Search Report of EP 08 00 4171, dated Jun. 18, 2008.
Ikeda et al. "Novel Fluorescent probes for detection of nucleic acids." Book of Abstracts for the Annual Meetings on Photochemistry, Sep. 21, 2007, p. 182.
Mitsui et al. "Characterization of fluorescent, unnatural base pairs". Tetrahedron, vol. 63, 2007, p. 3528-3537.
European Office Action issued in corresponding European Application No. 08 004 171.8-2402 and mailed Jun. 2, 2009, 4 pages.
Office Action of the corresponding European Patent Application No. 08004171.8 dated May 12, 2010—5 pages.
Telser, et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", J. Am. Chem. Soc., vol. 111, 1989, pp. 6966-6976.
Supplementary European Search Report of the related European Patent Application No. 08721474.8 dated May 18, 2010—14 pages.
Kasha, "Energy Transfer Mechanisms and Molecular Exciton Model for Molecular Aggregates", Radiation Research, vol. 20, pp. 55-70, 1963.
Kasha, et al., "The Exciton Model in Molecular Spectroscopy", Pure Appl. Chem., vol. 11 pp. 371-392, 1965.
Okamoto, et al., "Pyrene-Labeled Oligodeoxynucleotide Probe for Detecting Base Insertion by Excimer Fluorescene Emission", Journal of the American Chemical Society, vol. 126, No. 27, pp. 8364-8365, 2004.
Furstenberg, et al., "Ultrafast Excited-State Dynamics of DNA Fluorescent Intercalators: New Insight into the Fluorescence Enhancement Mechanism", Journal of the American Chemical Society, vol. 128, No. 23, pp. 7661-7669, 2006.
Office Action issued for Japanese Application No. 2009-504009, which corresponds to co-pending U.S. Appl. No. 12/530,574, dated Nov. 4, 2010 with its partial English translation (4 pages).
Tainaka et al, "Development of novel base-discriminating fluorescent probes containing polarity-sensitive chromophore", Lecture Summary of Photochemistry Forum, vol. 2006, p. 560, 2006 with English translation (4 pages).
Kodate et al, "New Interpretation for Dual Fluorescence Mechanism of Pyrene Type DNA Fluorescence Probe", Lecture Summary of Photochemistry Forum, vol. 2006, p. 385, 2006 with English translation (3 pages).
Imae, T. et al, "Interaction between acridine orange and polyriboadenylic acid", International Journal of Biological Macromolecules, vol. 3, No. 4, p. 259-266, 1981 (8 pages).

* cited by examiner

¹H NMR spectrum
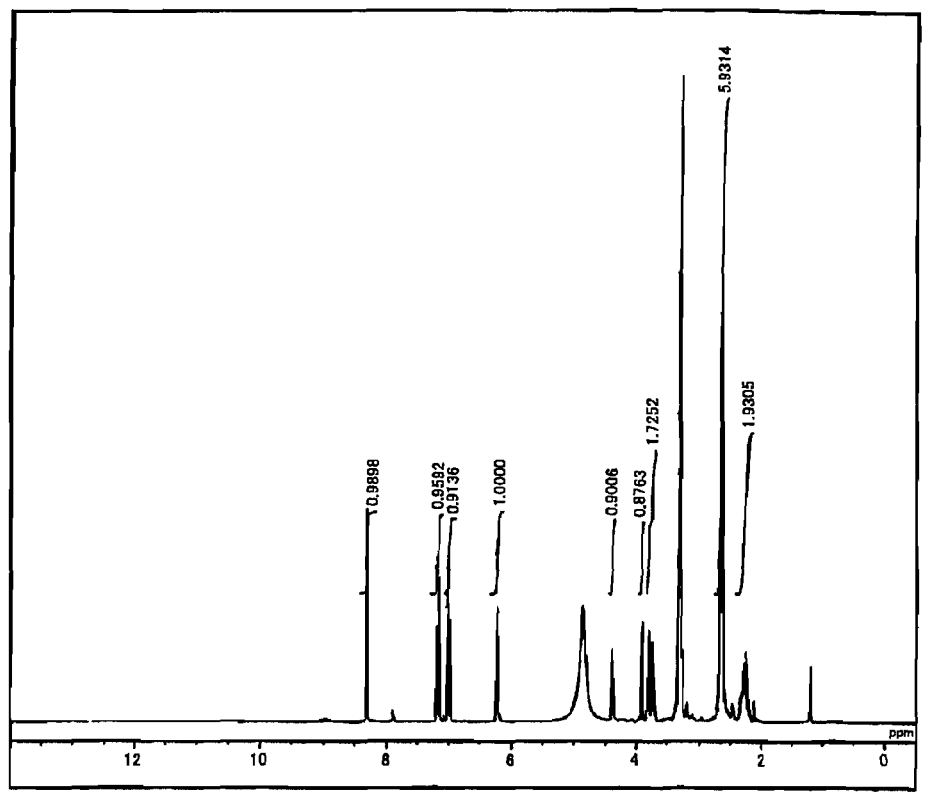
¹³C NMR spectrum
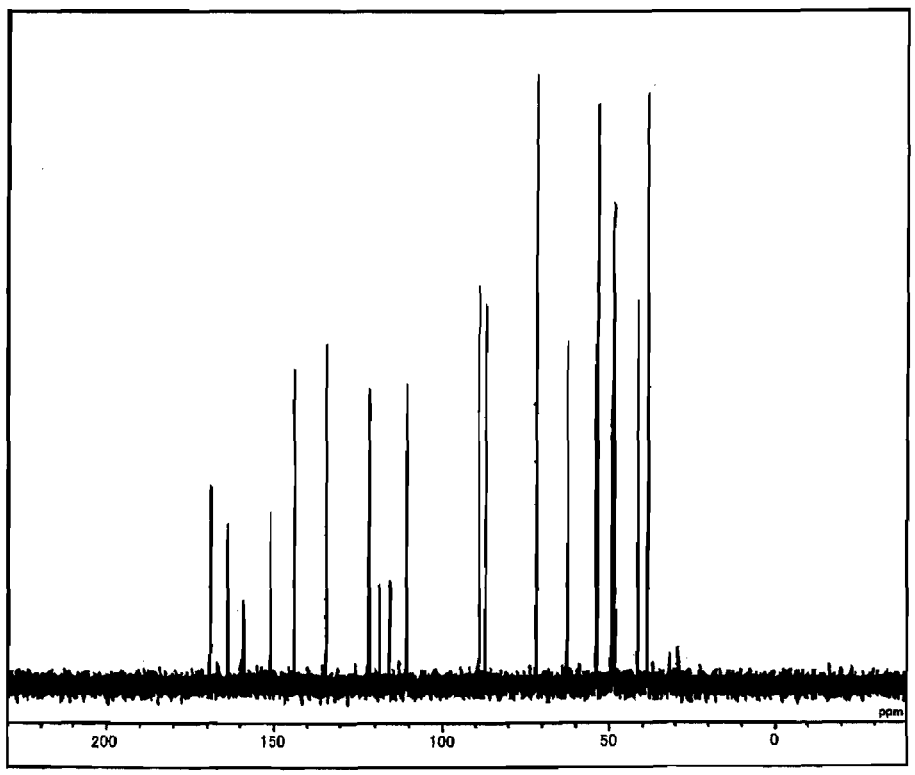
Fig. 2

¹H NMR spectrum
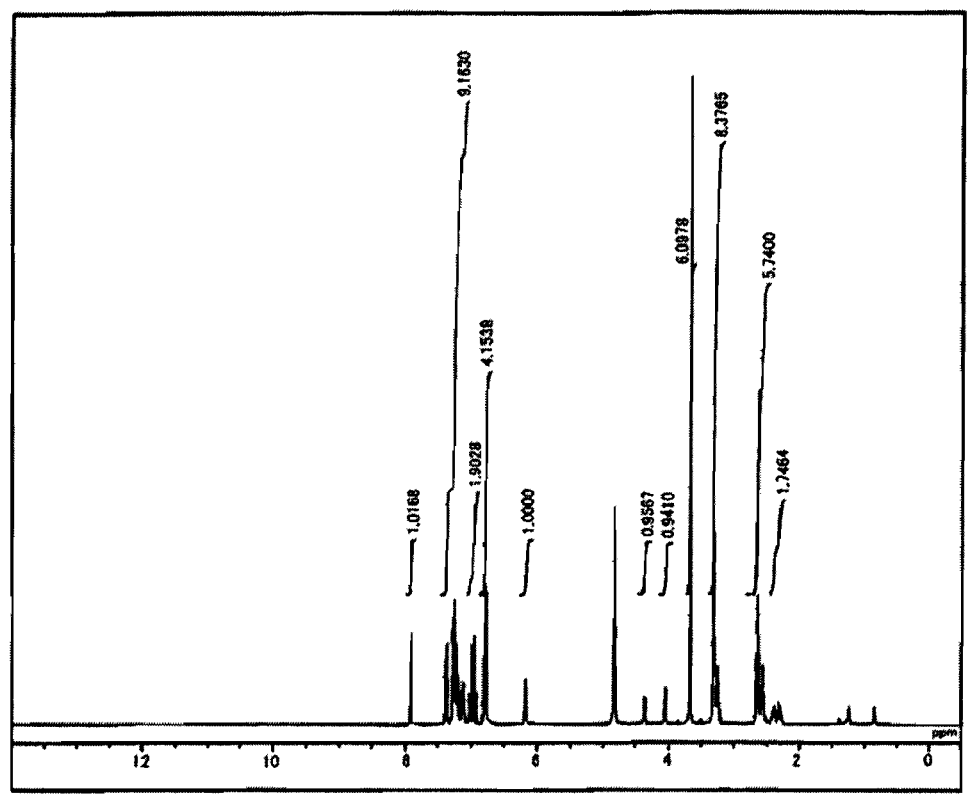
¹³C NMR spectrum
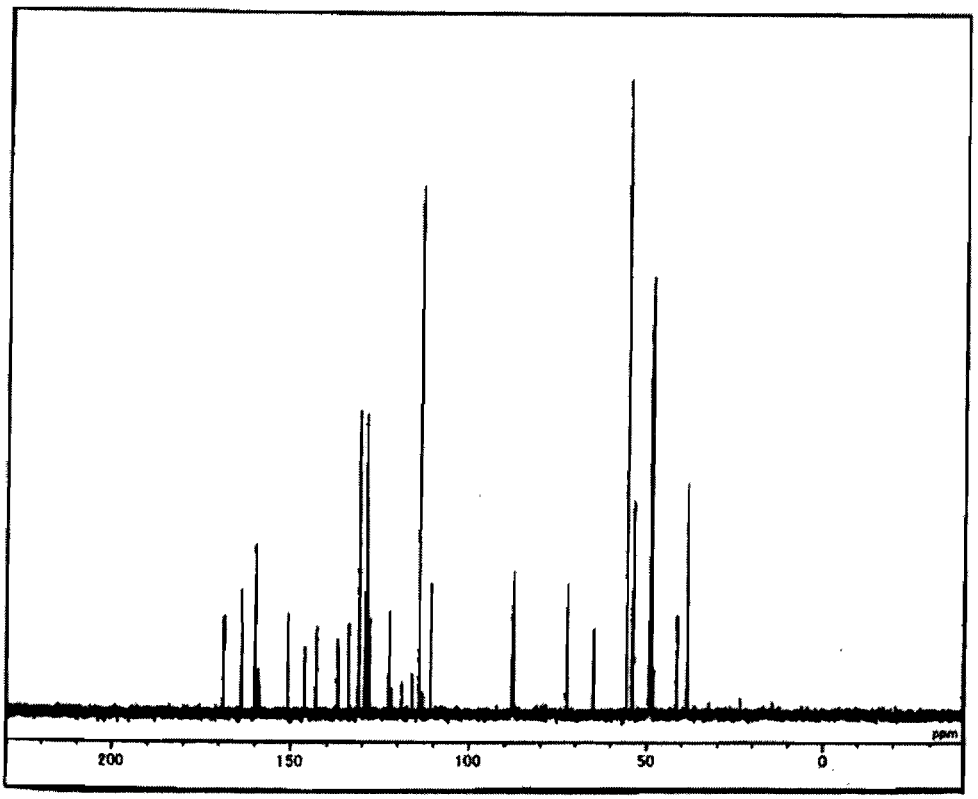
Fig. 3

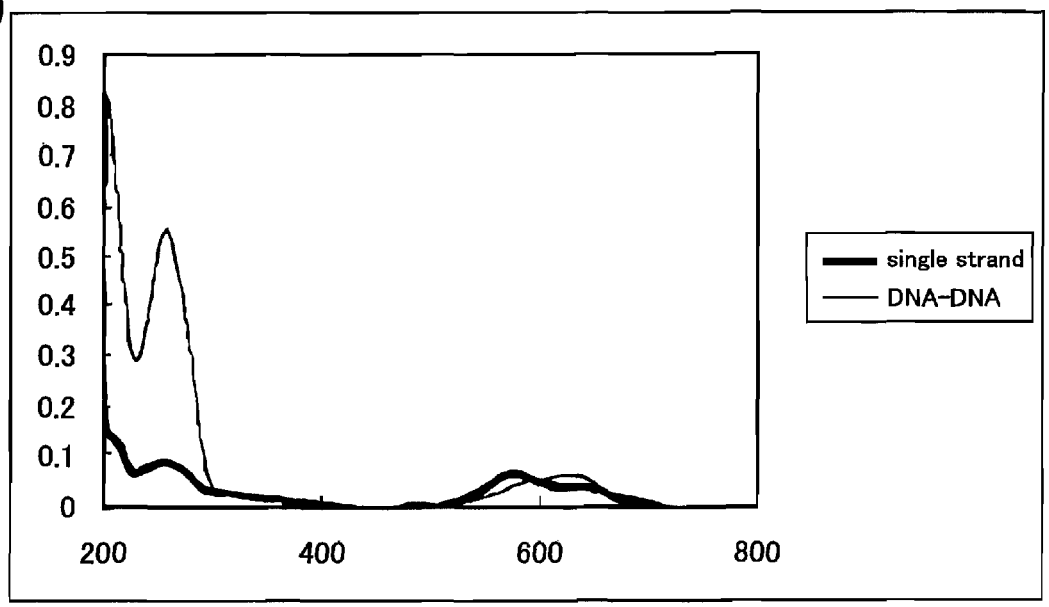
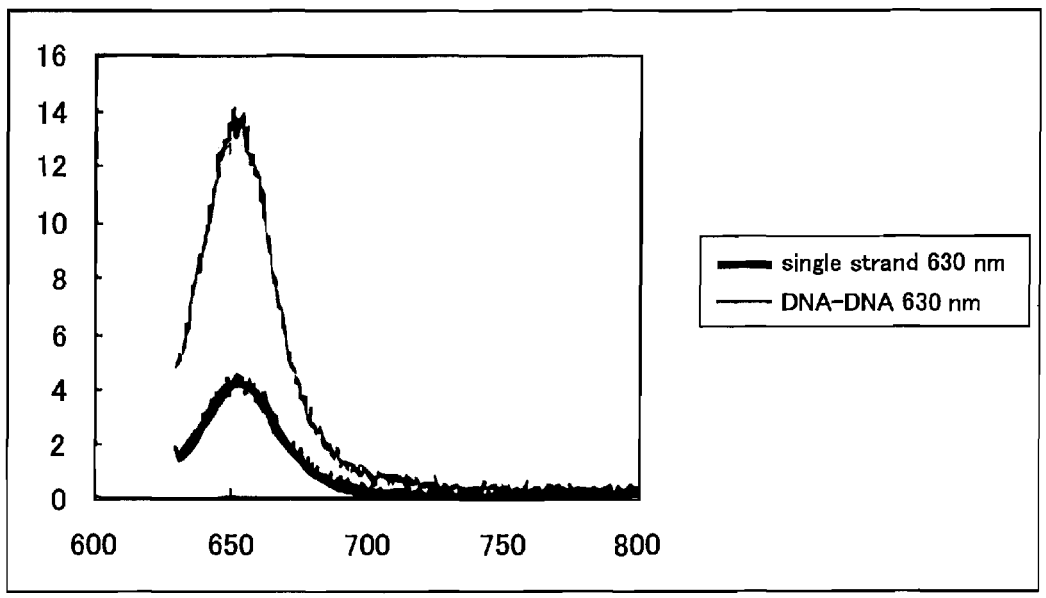
Fig. 24

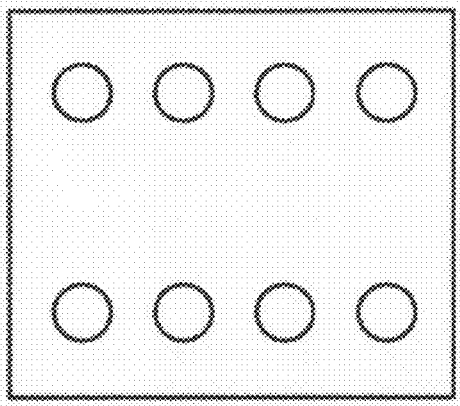
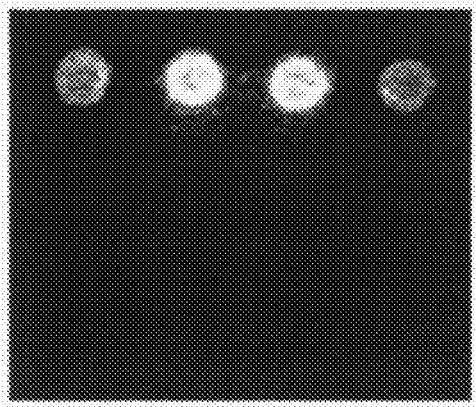
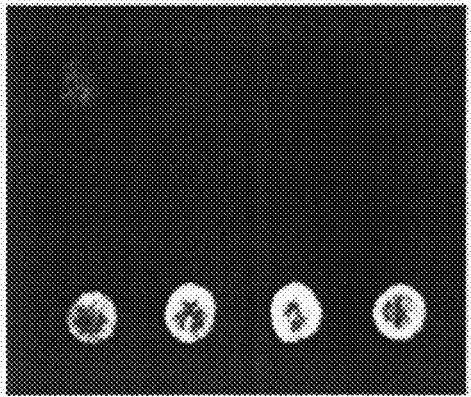
FIG. 27

EGFR Exon21 Mutant

A. Target DNA

B. Primer set

Mutant-type specific Folding Primer
ex21(M) FP Tail I          5' AGGACGCTGAGATGCGTCCTGATCACAGATTTTGGGCGAG 3'

Mutant-type specific Turn-back Primer
EGFR exon21 TP(M1)-121     5' CGAGCCAAACGCCTCCTTCTGCATGGTATT 3'

Boost Primer    EGFR exon21 BP3    5' TGGGTGCGGAAGAGAAAG 3'

Outer Primer2   EGFR exon21 OP3    5' TAAAGCCACCTCCTTAC 3'

Influenza H3N2 119

A. Target DNA 119E (wild)

5' AACATTAC<u>AGGATTTGCACCCTTTTC</u>TAAGGACAATTCGATTAGGCTTTCC GCTGGTGGGGACA
             OP1                                                    TP2

TCTGGGTGA CAAGAG<u>a</u>ACCTTATGTGTCAT GCGATCCTGAC AAGTGTTA<u>TCAATTTGCCCTTGG</u>
   BPw                                TP1                          FP

ACAGGG<u>AA</u>CAACACTAAA <u>CAACGTGCATTCAAATGA</u> CACAGTACGTGATAGGACC 3'
                         OP2

119V (mutant)

5' AACATTAC<u>AGGATTTGCACCCTTTTC</u>TAAGGACAATTCGATTAGGCTTTCC GCTGGTGGGGACA
             OP1                                                    TP2

TCTGGGTGA CAAGAG<u>t</u>ACCTTATGTGTCAT GCGATCCTGAC AAGTGTTA<u>TCAATTTGCCCTTGG</u>
   BPm                                TP1                          FP

ACAGGG<u>AA</u>CAACACTAAA <u>CAACGTGCATTCAAATGA</u> CACAGTACGTGATAGGACC 3'
                         OP2

B. Primer set

| | | |
|---|---|---|
| TP | 119E TP-F9 | 5' GTCAGGATCGC GCTGGTGGGGACATCTGGGTGA 3' |
| FP | 119E FP-R12 | 5' ACCTTCTGTACCCTCAGAAGGTTCCCTGTCCAAGGGCAAATTGA 3' |
| BPw | 119E BP-R10 | 5' CATGACACA<u>T</u>AAGGTTC 3' |
| BPm | 119v BP-R10m | 5' CATGACACA<u>T</u>AAGGTAC 3' |
| OP1 | 119E OP-F11 | 5' AGGATTTGCACCCTTTTC 3' |
| OP2 | 119E OP-R9 | 5' TCATTTGAATGCACGTTG 3' |

FIG. 37

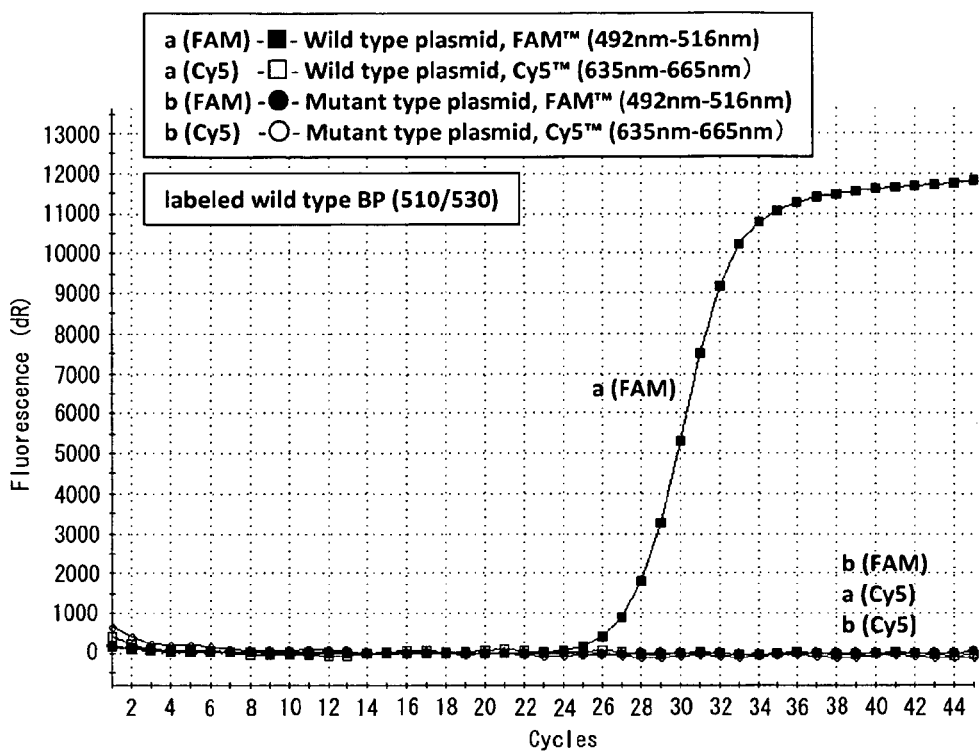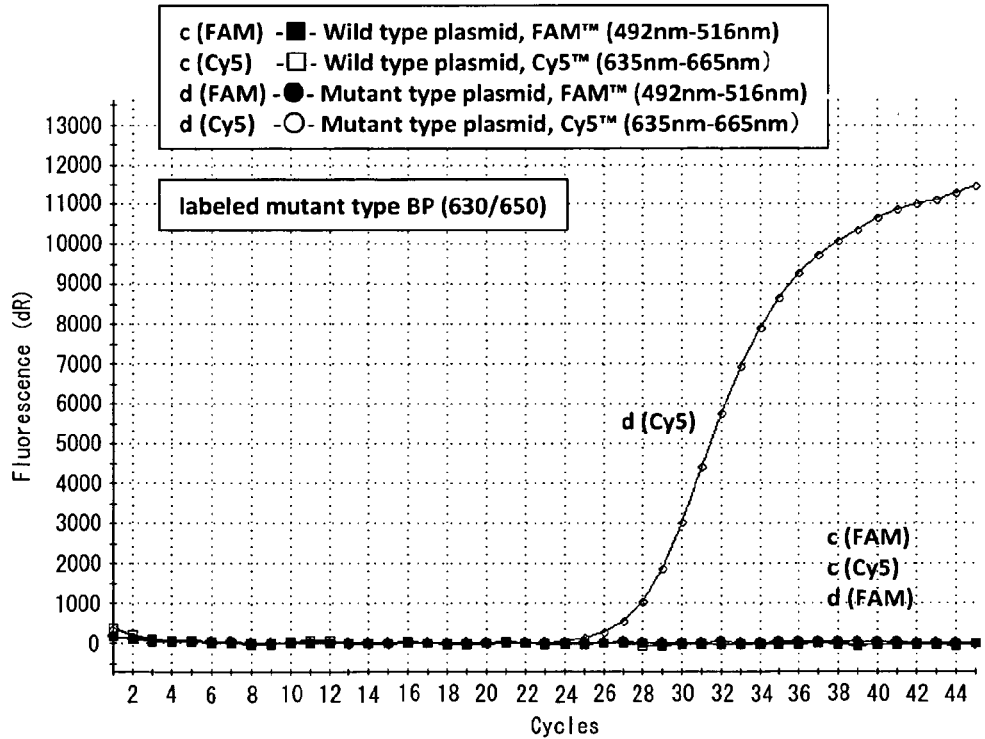
FIG. 38

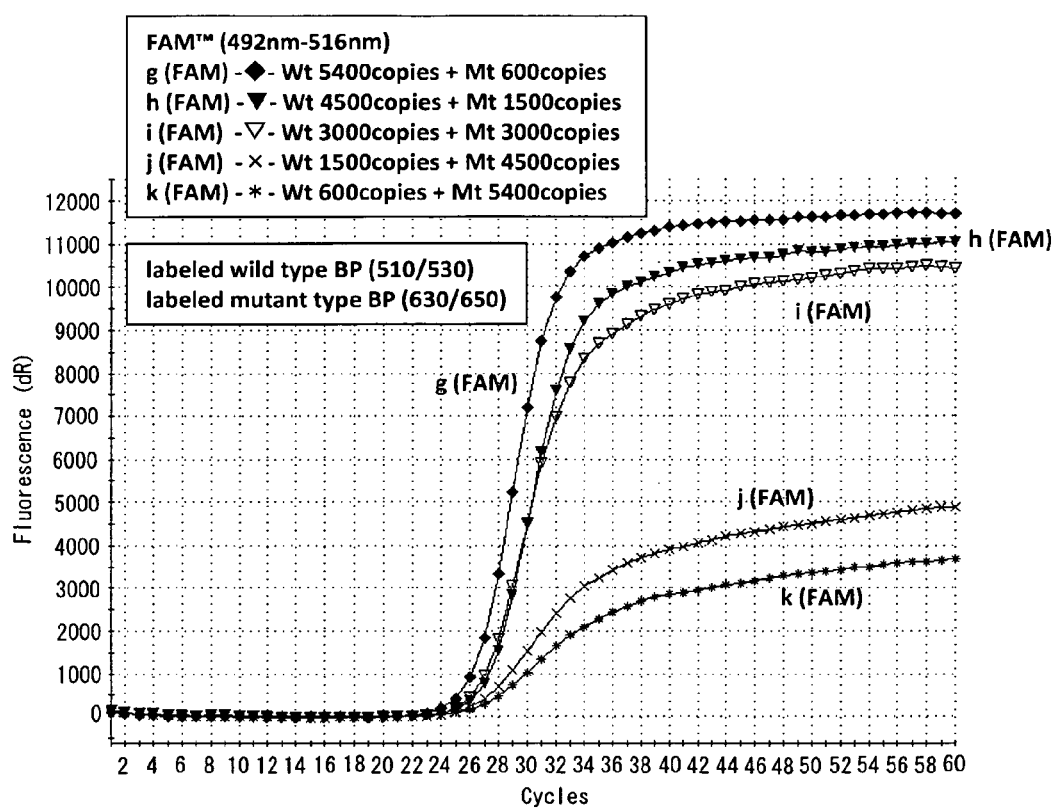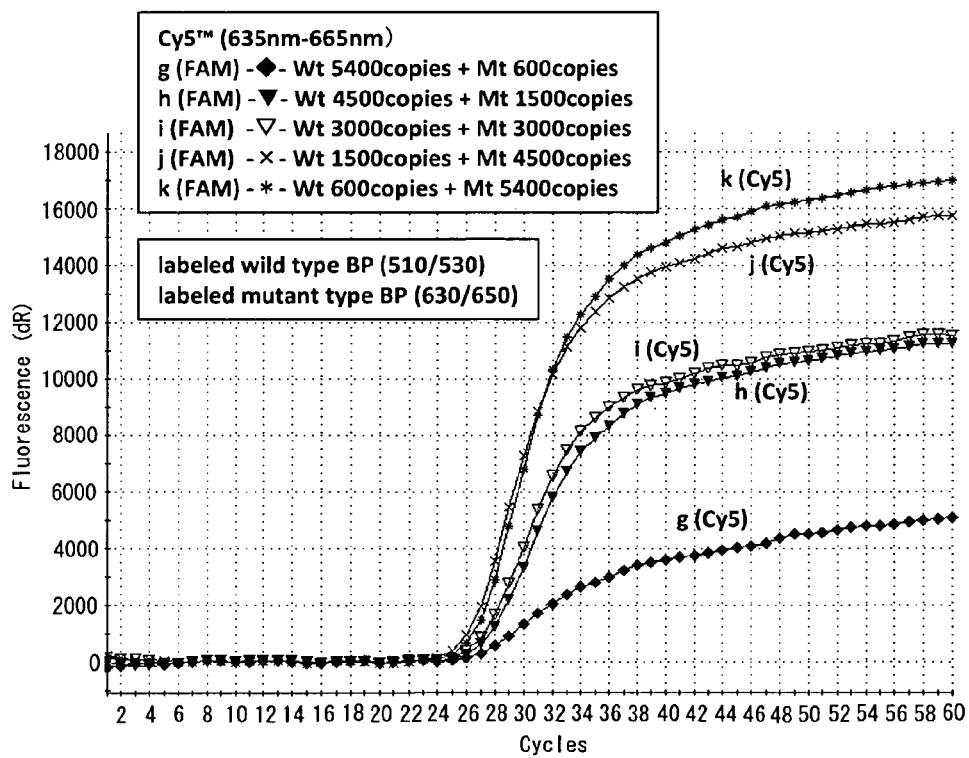
FIG. 41B

SEQUENCE LISTING

```
<160> NUMBER OF SEQ ID NOS: 34

<210> SEQ ID NO 1
<211> LENGTH: 13
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (7)..(7)
<223> OTHER INFORMATION: n represents for modified pyrimidine

<400> SEQUENCE: 1
cgcaatntaa cgc                                                        13

<210> SEQ ID NO 2
<211> LENGTH: 13
<212> TYPE: DNA
<213> ORGANISM: Artificial
<220> FEATURE:
<223> OTHER INFORMATION: DNA oligomer

<400> SEQUENCE: 2
gcgttaaatt gcg                                                        13

<210> SEQ ID NO 3
<211> LENGTH: 13
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (7)..(8)
<223> OTHER INFORMATION: n represents for modified pyrimidine

<400> SEQUENCE: 3
tttttnnntt ttt                                                        13

<210> SEQ ID NO 4
<211> LENGTH: 13
<212> TYPE: DNA
<213> ORGANISM: Artificial
<220> FEATURE:
<223> OTHER INFORMATION: DNA oligomer
```

```
<220> FEATURE:
<221> NAME/KEY: misc_feature
<222> LOCATION: (7)..(7)
<223> OTHER INFORMATION: n represents for modified pyrimidine

<400> SEQUENCE: 4
tttttntttt ttt                                                            13

<210> SEQ ID NO 5
<211> LENGTH: 13
<212> TYPE: DNA
<213> ORGANISM: Artificial
<220> FEATURE:
<223> OTHER INFORMATION: DNA oligomer

<400> SEQUENCE: 5
aaaaaaaaaa aaa                                                            13

<210> SEQ ID NO 6
<211> LENGTH: 20
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (11)..(11)
<223> OTHER INFORMATION: n represents for modified pyrimidine

<400> SEQUENCE: 6
tgaagggctt ntgaactctg                                                     20

<210> SEQ ID NO 7
<211> LENGTH: 20
<212> TYPE: DNA
<213> ORGANISM: Artificial
<220> FEATURE:
<223> OTHER INFORMATION: DNA oligomer

<400> SEQUENCE: 7
cagagttcaa aagcccttca                                                     20

<210> SEQ ID NO 8
<211> LENGTH: 13
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (7)..(8)
<223> OTHER INFORMATION: n represents for modified pyrimidine

<400> SEQUENCE: 8
cgcaatnnaa cgc                                                            13

<210> SEQ ID NO 9
<211> LENGTH: 28
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (8)..(8)
<223> OTHER INFORMATION: n represents for modified pyrimidine
<220> FEATURE:
<221> NAME/KEY: misc_feature
<222> LOCATION: (19)..(19)
<223> OTHER INFORMATION: n represents for modified pyrimidine
```

```
<400> SEQUENCE: 9
gcctcctnca gcaaatccna ccggcgtg                                              28

<210> SEQ ID NO 10
<211> LENGTH: 28
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (10)..(10)
<223> OTHER INFORMATION: n represents for modified pyrimidine
<220> FEATURE:
<221> NAME/KEY: misc_feature
<222> LOCATION: (19)..(19)
<223> OTHER INFORMATION: n represents for modified pyrimidine

<400> SEQUENCE: 10
cctcccaagn gctgggatna aaggcgtg                                              28

<210> SEQ ID NO 11
<211> LENGTH: 95
<212> TYPE: DNA
<213> ORGANISM: Artificial
<220> FEATURE:
<223> OTHER INFORMATION: DNA fragment of mouse

<400> SEQUENCE: 11
gccggtagtg gtggcgcacg ccggtaggat ttgctgaagg aggcagaggc aggaggatca          60
cgagttcgag gccagcctgg gctacacatt ttttt                                     95

<210> SEQ ID NO 12
<211> LENGTH: 95
<212> TYPE: DNA
<213> ORGANISM: Artificial
<220> FEATURE:
<223> OTHER INFORMATION: DNA fragment of mouse

<400> SEQUENCE: 12
gccgggcatg gtggcgcacg cctttaatcc cagcacttgg gaggcagagg caggcggatt          60
tctgagttcg aggccagcct ggtctacaga gtgag                                     95

<210> SEQ ID NO 13
<211> LENGTH: 49
<212> TYPE: DNA
<213> ORGANISM: Artificial
<220> FEATURE:
<223> OTHER INFORMATION: DNA oligomer
<220> FEATURE:
<221> NAME/KEY: misc_feature
<222> LOCATION: (25)..(25)
<223> OTHER INFORMATION: n represents for modified pyrimidine

<400> SEQUENCE: 13
tttttttttt tttttttttt ttttnttttt tttttttttt ttttttttt                      49

<210> SEQ ID NO 14
<211> LENGTH: 120
<212> TYPE: DNA
<213> ORGANISM: Homo sapiens

<400> SEQUENCE: 14
tgaaaacacc gcagcatgtc aagatcacag attttgggcg ggccaaactg ctgggtgcgg          60
aagagaaaga ataccatgca gaaggaggca aagtaaggag gtggctttag gtcagccagc         120
```

<210> SEQ ID NO 15
<211> LENGTH: 40
<212> TYPE: DNA
<213> ORGANISM: Artificial
<220> FEATURE:
<223> OTHER INFORMATION: primer

<400> SEQUENCE: 15
aggacgctga gatgcgtcct gatcacagat tttgggcgag            40

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
cgagccaaac gcctccttct gcatggtatt                        30

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
tgggtgcgga agagaaag                                     18

<210> SEQ ID NO 18
<211> LENGTH: 17
<212> TYPE: DNA
<213> ORGANISM: Artificial
<220> FEATURE:
<223> OTHER INFORMATION: primer

<400> SEQUENCE: 18
taaagccacc tccttac                                      17

<210> SEQ ID NO 19
<211> LENGTH: 183
<212> TYPE: DNA
<213> ORGANISM: Homo sapiens

<400> SEQUENCE: 19
aacattacag gatttgcacc cttttctaag gacaattcga ttaggctttc cgctggtggg      60
gacatctggg tgacaagaga accttatgtg tcatgcgatc ctgacaagtg ttatcaattt    120
gcccttggac agggaacaac actaaacaac gtgcattcaa atgacacagt acgtgatagg    180
acc                                                                   183

<210> SEQ ID NO 20
<211> LENGTH: 183
<212> TYPE: DNA
<213> ORGANISM: Homo sapiens

<400> SEQUENCE: 20
aacattacag gatttgcacc cttttctaag gacaattcga ttaggctttc cgctggtggg      60
gacatctggg tgacaagagt accttatgtg tcatgcgatc ctgacaagtg ttatcaattt    120
gcccttggac agggaacaac actaaacaac gtgcattcaa atgacacagt acgtgatagg    180
acc                                                                   183

<210> SEQ ID NO 21
<211> LENGTH: 33
<212> TYPE: DNA
<213> ORGANISM: Artificial
<220> FEATURE:
<223> OTHER INFORMATION: primer

<400> SEQUENCE: 21
gtcaggatcg cgctggtggg gacatctggg tga                           33

<210> SEQ ID NO 22
<211> LENGTH: 44
<212> TYPE: DNA
<213> ORGANISM: Artificial
<220> FEATURE:
<223> OTHER INFORMATION: primer

<400> SEQUENCE: 22
accttctgta ccctcagaag gttccctgtc caagggcaaa ttga               44

<210> SEQ ID NO 23
<211> LENGTH: 17
<212> TYPE: DNA
<213> ORGANISM: Artificial
<220> FEATURE:
<223> OTHER INFORMATION: primer

<400> SEQUENCE: 23
catgacacat aaggttc                                             17

<210> SEQ ID NO 24
<211> LENGTH: 17
<212> TYPE: DNA
<213> ORGANISM: Artificial
<220> FEATURE:
<223> OTHER INFORMATION: primer

<400> SEQUENCE: 24
catgacacat aaggtac                                             17

<210> SEQ ID NO 25
<211> LENGTH: 18
<212> TYPE: DNA
<213> ORGANISM: Artificial
<220> FEATURE:
<223> OTHER INFORMATION: primer

<400> SEQUENCE: 25
aggatttgca ccctttttc                                           18

<210> SEQ ID NO 26
<211> LENGTH: 18
<212> TYPE: DNA
<213> ORGANISM: Artificial
<220> FEATURE:
<223> OTHER INFORMATION: primer

<400> SEQUENCE: 26
tcatttgaat gcacgttg                                            18

<210> SEQ ID NO 27
<211> LENGTH: 17
<212> TYPE: DNA
<213> ORGANISM: Artificial
<220> FEATURE:
<223> OTHER INFORMATION: primer

```
<400> SEQUENCE: 27
aaacaccgca gcatgtc                                                      17

<210> SEQ ID NO 28
<211> LENGTH: 17
<212> TYPE: DNA
<213> ORGANISM: Artificial
<220> FEATURE:
<223> OTHER INFORMATION: primer

<400> SEQUENCE: 28
taaagccacc tccttac                                                      17

<210> SEQ ID NO 29
<211> LENGTH: 17
<212> TYPE: DNA
<213> ORGANISM: Artificial
<220> FEATURE:
<223> OTHER INFORMATION: primer

<400> SEQUENCE: 29
taaagccacc tccttac                                                      17

<210> SEQ ID NO 30
<211> LENGTH: 106
<212> TYPE: DNA
<213> ORGANISM: Homo sapiens

<400> SEQUENCE: 30
aaacaccgca gcatgtcaag atcacagatt ttgggcgggc caaactgctg ggtgcggaag       60
agaaagaata ccatgcagaa ggaggcaaag taaggaggtg ctttta                    106

<210> SEQ ID NO 31
<211> LENGTH: 29
<212> TYPE: DNA
<213> ORGANISM: Artificial
<220> FEATURE:
<223> OTHER INFORMATION: primer

<400> SEQUENCE: 31
ccaaaatctg ggaacgtact ggtgaaaca                                         29

<210> SEQ ID NO 32
<211> LENGTH: 30
<212> TYPE: DNA
<213> ORGANISM: Artificial
<220> FEATURE:
<223> OTHER INFORMATION: primer

<400> SEQUENCE: 32
cgagccaaac gcctccttct gcatggtatt                                        30

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
tgggtgcgga agagaaag                                                     18

<210> SEQ ID NO 34
<211> LENGTH: 17
```

```
<212> TYPE: DNA
<213> ORGANISM: Artificial
<220> FEATURE:
<223> OTHER INFORMATION: primer

<400> SEQUENCE: 34
taaagccacc tccttac                                              17
```

PRIMER, PRIMER SET, AND NUCLEIC ACID AMPLIFICATION METHOD AND MUTATION DETECTION METHOD USING THE SAME

BACKGROUND OF THE INVENTION

1. Field of the Invention

The present invention relates generally to a primer set for amplifying a target nucleic acid sequence, and a nucleic acid amplification method and mutation detection method that use the same.

2. Description of the Related Art

In, for example, genetic diagnoses of diseases and gene expression analysis, it is necessary to detect a target nucleic acid having a specific sequence. For the detection, fluorescence is used widely. Specifically, a known method uses a fluorescent substance whose fluorescence intensity increases with an increase in target nucleic acid sequence. A typical example of the fluorescent substance is a substance that intercalates into a double helix structure and emits fluorescence by irradiation with excitation light. When a target nucleic acid sequence is amplified using a primer labeled with such a fluorescent substance, for instance, the primer hybridizes to a target nucleic acid sequence of a template DNA to form a double strand, and thereby the fluorescent substance emits fluorescence. Therefore measurement of the fluorescence intensity of the fluorescent substance of the primer makes it possible to detect, for example, the occurrence or amount of amplification, or the presence or absence of a mutation to be detected in the target nucleic acid sequence.

However, there is a possibility that a conventional fluorescent substance may emit fluorescence, even when, for example, no double helix structure has been formed. Furthermore, for the purpose of quenching fluorescence of only a primer or probe labeled with a fluorescent substance, the method using fluorescence resonance energy transfer (FRET) is effective (for example, Tyagi, S., Kramer, F. R. (1996) Nat. Biotechnol. 14, 303-308; Nazarenko, I. A., Bhatnagar, S. K., Hohman, R. J. (1997) Nucleic Acids Res. 25, 2516-2521; Gelmini, S., Orlando, C., Sestini, R., Vona, G., Pinzani, P., Ruocco, L., Pazzagli, M. (1997) Clin. Chem. 43, 752-758; and Whitcombe, D., Theaker, J., Guy, S. P., Brown, T., Little, S. (1999) Nat. Biotechnol. 17, 804-807). However, it has problems in, for example, cost due to the introduction of two types of fluorescent dyes.

Thiazole orange, which is one type of cyanine dye, is known as a fluorescent dye whose fluorescence intensity increases through an interaction with DNA or RNA. There are examples in which a fluorescent probe was intended to be produced with thiazole orange being bonded to DNA by a covalent bond. However, it also emits strong fluorescence through an interaction with a single-stranded DNA containing a purine base (Biopolymers 1998, 46, 39-51). Accordingly, the increase in fluorescence intensity obtained when a double helix is formed is small, and therefore it cannot be considered as being successful (Analytica Chimica Acta 2002, 470, 57-70, and Chemistry—A European Journal 2006, 12, 2270-2281).

Furthermore, recently, the present inventors have reported an innovative method that allows a gene mutation to be detected easily and quickly by merely amplifying nucleic acid of a target nucleic acid sequence under an isothermal condition (Mitani Y., Lezhava A., Kawai Y., Kikuchi T., Oguchi-Katayama A., Kogo Y., Itoh M., Miyagi T. et al. 2007. "Rapid SNP diagnostics using asymmetric isothermal amplification and a new mismatch-suppression technology." Nat. Methods 4(3): 257-262; JP 3897926 B; and JP 3942627 B). Similarly in this method, a fluorescent substance as described above is used, and there are demands for a fluorescent substance that allows more effective detection.

SUMMARY OF THE INVENTION

Hence, the present invention is intended to provide a labeled primer and primer set that are used for amplifying, for example, a target nucleic acid and that allow the double helix structure of nucleic acid to be detected effectively, as well as a nucleic acid amplification method and mutation detection method that use the same.

In order to solve the aforementioned object, a primer of the present invention is a primer for amplifying a target nucleic acid sequence, wherein the primer is a labeled nucleic acid including at least one of structures represented by the following formulae (16), (16b), (17), (17b), (18), and (18b):

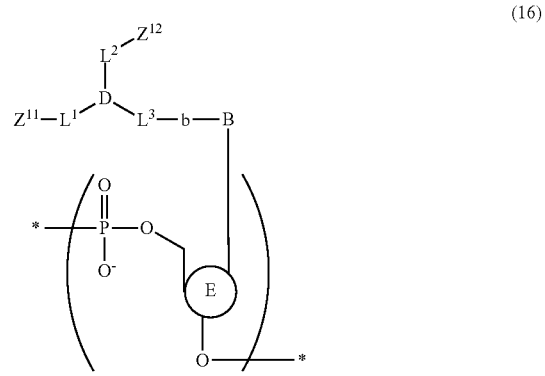

(16)

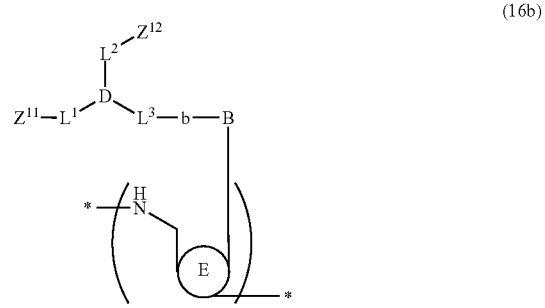

(16b)

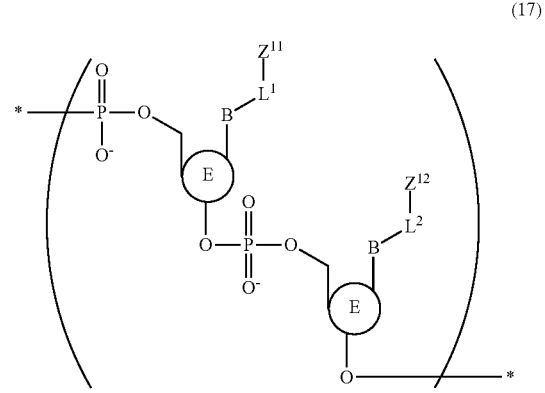

(17)

-continued

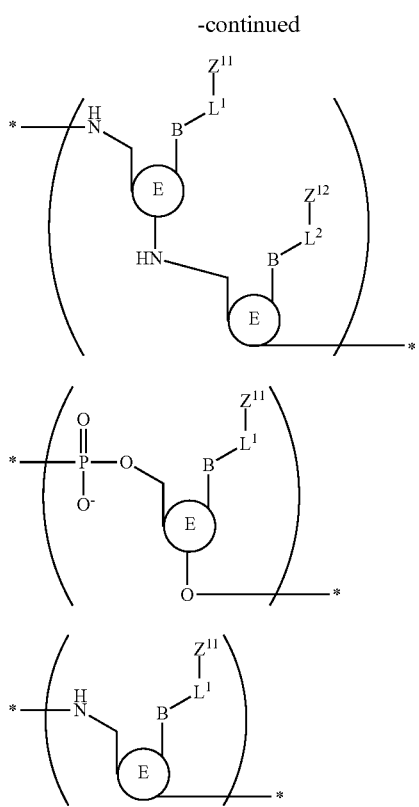

where in the formulae (16), (16b), (17), (17b), (18), and (18b),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each an atomic group that exhibits fluorescence, and may be identical to or different from each other, $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formulae (16) and (16b), $L^1$ and $L^2$ are each the linker, $L^3$, D, and b may not be present, and $L^1$ and $L^2$ may be bonded directly to B, where in the formulae (16), (17), and (18), E is the atomic group described in item (i), and at least one O atom in a phosphoric acid linkage may be substituted with an S atom, in the formulae (16b), (17b), and (18b), E is the atomic group described in item (ii), and in the formulae (17) and (17b), the respective Bs may be identical to or different from each other, and the respective Es may be identical to or different from each other.

A primer set of the present invention is a primer set for amplifying a target nucleic acid sequence, wherein the primer set includes a pair of primers, and at least one of the pair of primers is a primer according to the present invention.

A kit for nucleic acid amplification of the present invention is used for a nucleic acid amplification method for amplifying a target nucleic acid sequence, wherein the kit includes a primer or primer set according to the present invention and instructions for use.

A mutation detection kit of the present invention is used for a mutation detection method for detecting the presence or absence of a mutation in a target nucleic acid sequence, wherein the mutation detection kit includes a kit for nucleic acid amplification according to the present invention and instructions for use.

A nucleic acid amplification method of the present invention is a method of amplifying a target nucleic acid sequence contained in a nucleic acid sample, wherein the method includes:

(A) a process of preparing the nucleic acid sample, and (B) a process of amplifying the target nucleic acid sequence contained in the nucleic acid sample using a primer or a primer set of the present invention, or (B') a process of including:

(B1') a process of amplifying the target nucleic acid sequence contained in the nucleic acid sample using a primer or a primer set including a pair of primers, and (B2') a process of hybridizing a single-stranded nucleic acid sequence that has been amplified in the process (B1') with a probe formed of a labeled nucleic acid containing at least one of structures represented by the formulae (16), (16b), (17), (17b), (18), and (18b).

A mutation detection method of the present invention is a method of detecting the presence or absence of a mutation in a target nucleic acid sequence contained in a nucleic acid sample, wherein the method includes:

(a) a process of amplifying the target nucleic acid sequence contained in the nucleic acid sample by a nucleic acid amplification method according to the present invention, (b) a process of measuring fluorescence intensity before and after the process (a), and (c) a process of detecting the presence or absence of a mutation by comparing the fluorescence intensities to each other that are obtained before and after the process (a) that have been measured in the process (b).

When the primer of the present invention and the primer set of the present invention are each a labeled nucleic acid containing one of the structures represented by the aforementioned formulae, it becomes possible effectively to detect amplification of a target nucleic acid sequence, for example, when they are used for a method of amplifying the target nucleic acid sequence. Furthermore, since amplification can be detected effectively as described above, for example, the presence or absence of a target mutation in a target nucleic acid sequence also can be detected with excellent sensitivity. The present invention is excellent in nucleic acid detection sensitivity as described above and therefore can be used for wide range of applications, for example, study, clinical use, diagnosis, in vitro gene detection, and in vivo gene detection.

BRIEF DESCRIPTION OF THE DRAWINGS

FIG. 2 shows $^1$H and $^{13}$C NMR spectra obtained from a compound of an example.

FIG. 3 shows $^1$H and $^{13}$C NMR spectra obtained from another compound of an example.

FIG. 24 shows graphs illustrating absorption spectra and emission spectra of another fluorescent DNA oligomer according to an example.

FIG. 27 shows diagrams illustrating the states of fluorescence emission in a blotting assay according to a reference example.

FIG. 37 shows regions containing a target nucleic acid sequence of H3N2 and sequences of various primers in an example.

FIG. 38 shows graphs illustrating amplification profiles obtained when isothermal amplification reactions were carried out by the SMAP method in an example; FIG. 38A, with respect to the reaction solutions a and b, and FIG. 38B, with respect to the reaction solutions c and d, show the results of fluorescence intensity detection carried out at the FAM wavelength (492 nm/516 nm) and the Cy5 wavelength (635 nm/665 nm), respectively.

FIG. 41B is a graph showing amplification profiles obtained when isothermal amplification reactions were carried out by the SMAP method in an example, and shows the results of fluorescence intensity detection carried out at the FAM wavelength (492 nm/516 nm) and the Cy5 wavelength (635 nm/665 nm), respectively, with respect to the reaction solutions g, h, i, j and k.

BEST MODE FOR CARRYING OUT THE INVENTION

Figure 1:
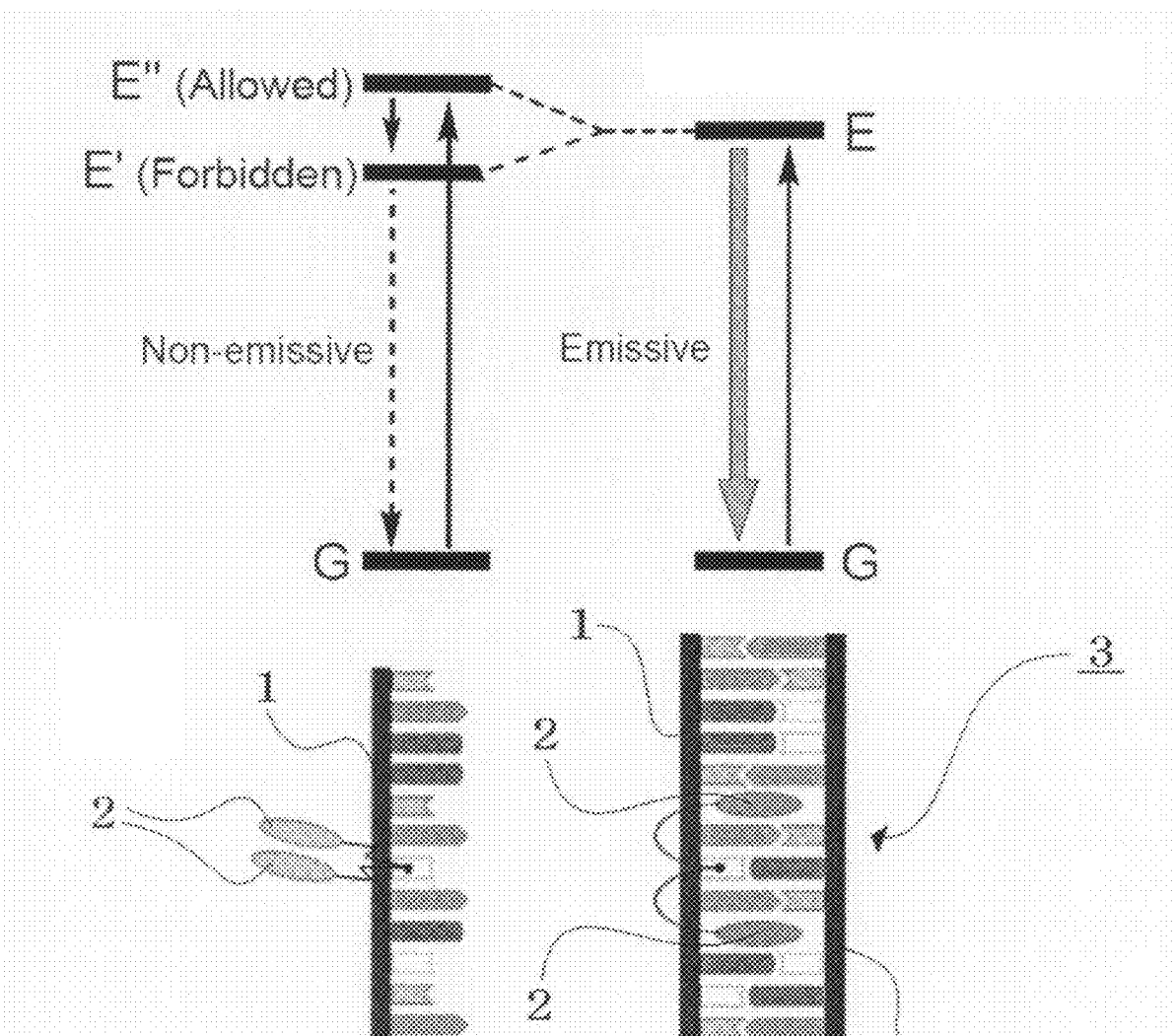
FIG. 1 is a diagram that schematically shows the principle of the present invention.

Next, embodiments of the present invention are described in further detail.

[Primer and Primer Set]

As described above, the primer of the present invention is a primer for amplifying a target nucleic acid sequence, wherein the primer is a labeled nucleic acid containing at least one of the structures represented by the following formulae (16), (16b), (17), (17b), (18), and (18b). Furthermore, tautomers or stereoisomers thereof or salts thereof also are included in the labeled nucleic acid of the present invention. The primer set of the present invention is a primer set for amplifying a target nucleic acid sequence, wherein the primer set includes a pair of primers, and at least one of the pair of primers is a primer of the present invention. Hereinafter, the structures that are represented by the following respective formulae and have atomic groups $Z^{11}$ and $Z^{12}$, which exhibit fluorescence, each are referred to as a "labeled structure". The labeled nucleic acid containing the labeled structure, i.e. a primer of the present invention, also is referred to as a "labeled primer".

In the present invention, the "target nucleic acid sequence" embraces not only a nucleic acid sequence to be amplified but also a sequence complementary thereto.

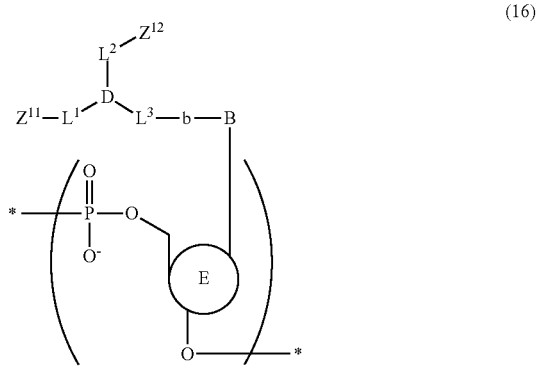

(16)

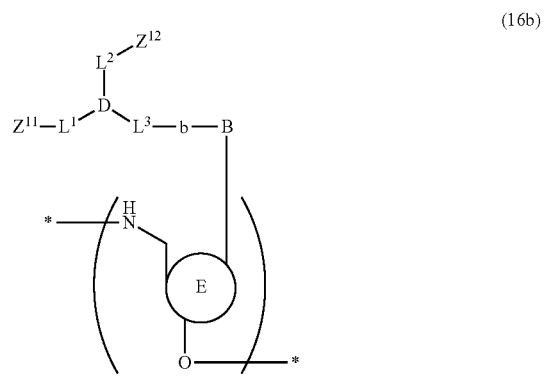

(16b)

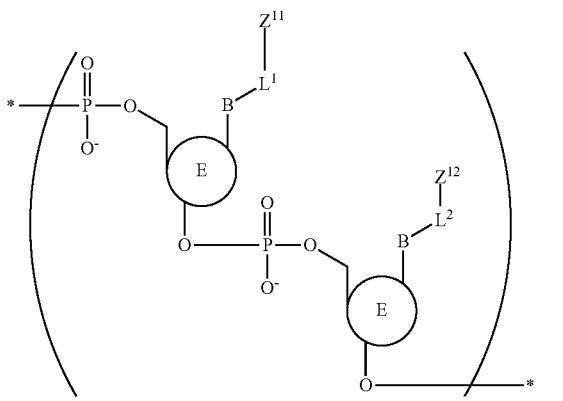

(17)

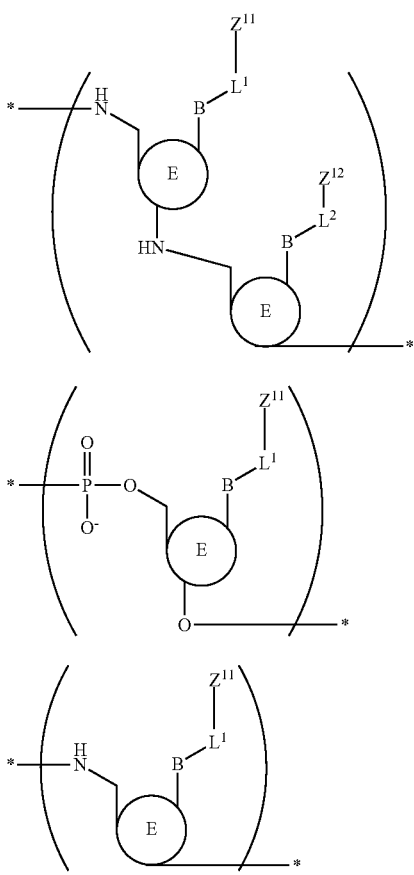

In the formulae (16), (16b), (17), (17b), (18), and (18b),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each an atomic group that exhibits fluorescence, and may be identical to or different from each other, $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formulae (16) and (16b), $L^1$ and $L^2$ are each the linker, $L^3$, D, and b may not be present, and $L^1$ and $L^2$ may be bonded directly to B, where in the formulae (16), (17), and (18), E is the atomic group described in item (i), and at least one O atom in a phosphoric acid linkage may be substituted with an S atom, in the formulae (16b), (17b), and (18b), E is the atomic group described in item (ii), and in the formulae (17) and (17b), the respective Bs may be identical to or different from each other, and the respective Es may be identical to or different from each other.

In the formulae (16), (17), (16b), (17b), (18), and (18b), it is preferable that the main chain length (the number of main chain atoms) of each of $L^1$, $L^2$ and $L^3$ be an integer of 2 or more. With respect to the main chain length (the number of main chain atoms) of each of $L^1$, $L^2$ and $L^3$, the upper limit thereof is not particularly limited and is, for example, 100 or less, more preferably 30 or less, and particularly preferably 10 or less.

Preferably, $Z^{11}$ and $Z^{12}$ are each an atomic group that exhibits an exciton effect. This results in, for example, a greater increase in fluorescence obtained when a double helix structure is formed and thereby allows the double helix structure to be detected further effectively. In the present invention, however, even when $Z^{11}$ and $Z^{12}$ each are not an atomic group that exhibits the exciton effect or even when only one atomic group (dye) that exhibits fluorescence has been introduced into one molecule, it is possible to detect the double helix structure effectively.

$Z^{11}$ and $Z^{12}$ are not limited as long as they each are an atomic group having fluorescence, and the atomic group having fluorescence is not particularly limited. More preferably, $Z^{11}$ and $Z^{12}$ are each independently, for example, a group derived from thiazole orange, oxazole yellow, cyanine, hemicyanine, another cyanine dye, methyl red, azo dye, or a derivative thereof. Furthermore, groups that are derived from other known dyes also can be used suitably. A large number of fluorescent dyes that change the fluorescence intensity by being bonded to nucleic acid such as DNA have been reported. In a typical example, it has been known that ethidium bromide intercalates into a double helix structure of DNA and thereby exhibits strong fluorescence. Ethidium bromide is used frequently for DNA detection. Moreover, a fluorescent dye that can control the fluorescence intensity according to the microscopic polarity, such as pyrenecarboxyamide or prodan, also has been known. The thiazole orange is a fluorescent dye with a benzothiazole ring and quinoline ring that are linked together with a methine group. It usually exhibits weak fluorescence but gives strong fluorescence emission when intercalating into DNA having a double helix structure. Other examples thereof include dyes such as fluorescein and Cy3.

More preferably, $Z^{11}$ and $Z^{12}$ are each independently an atomic group represented by any one of the following formulae (7) to (9).

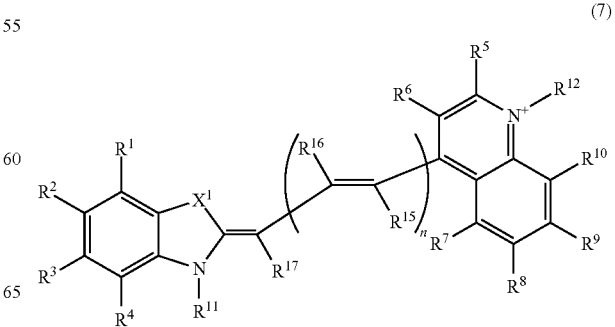

-continued (8)

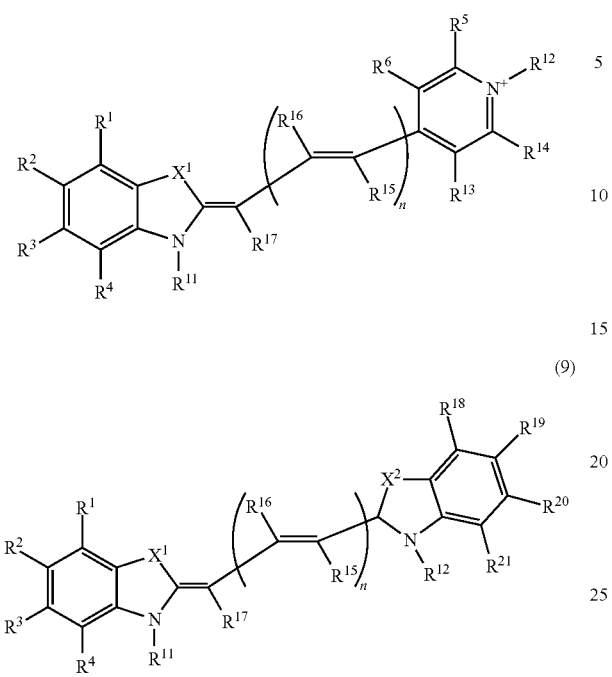

(9)

In the formulae (7) to (9), $X^1$ and $X^2$ are S or O, n is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that is bonded to $L^1$ or $L^2$ in the formulae (16), (17), (16b), (17b), (18), and (18b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$ and $R^1$ to $R^{21}$ in $Z^{11}$ and $X^1$, $X^2$ and $R^1$ to $R^{21}$ in $Z^{12}$ may be identical to or different from each other, respectively.

In the formulae (7) to (9), it is further preferable that in $R^{11}$ to $R^{12}$, the lower alkyl group be a linear or branched alkyl group with a carbon number of 1 to 6, and the lower alkoxy group be a linear or branched alkoxy group with a carbon number of 1 to 6.

In the formulae (7) to (9), it is further preferable that in $R^{11}$ and $R^{12}$, the linking group be a polymethylene carbonyl group with a carbon number of at least 2 and be bonded to $L^1$ or $L^2$ in the formulae (16), (16b), (17), (17b), (18), and (18b) in a carbonyl group moiety. The upper limit of the carbon number of the polymethylene carbonyl group is not particularly limited and is, for example, 100 or lower, preferably 50 or lower, more preferably 30 or lower, and particularly preferably 10 or lower.

When $Z^{11}$ and $Z^{12}$ are represented by the formulae (7) to (9), it is more preferable that, for example, they be each independently a group represented by the following formula (19) or (20).

(19)

(20)

In the formulae (19) and (20), $X^1$ indicates —S— or —O—. $R^1$ to $R^{10}$ as well as $R^{13}$ and $R^{14}$ indicate each independently a hydrogen atom, a halogen atom, a lower alkyl group, a lower alkoxy group, a nitro group, or an amino group. One of $R^{11}$ and $R^{12}$ indicates a linking group that is bonded to $L^1$ and $L^2$ in the formula (16), (17), (16b), (17b), (18), and (18b), and the other denotes a hydrogen atom or a lower alkyl group.

In the formulae (16), (17), (16b), (17b), (18), and (18b), B may have a natural nucleobase skeleton but may have an artificial nucleobase skeleton as described above. For instance, B is preferably a structure represented by Py (pyrimidine ring), Py der., Pu (purine ring), or Pu der., where the Py is an atomic group having a covalent bond to E in the 1-position and a covalent bond to a linker moiety in the 5-position in the six-membered ring represented by the following formula (11), the "Py der." is an atomic group in which at least one of all the atoms of the six-membered ring of the Py has been substituted with an N, C, S, or O atom, and the N, C, S, or O atom may have an electric charge, a hydrogen atom, or a substituent suitably, the Pu is an atomic group having a covalent bond to E in the 9-position and a covalent bond to a linker moiety in the 8-position in the condensed ring represented by the following formula (12), and the Pu der. is an atomic group in which at least one of all the atoms of the five-membered ring of the Pu has been substituted with an N, C, S, or O atom, and the N, C, S, or O atom may have an electric charge, a hydrogen atom, or a substituent suitably.

(11)

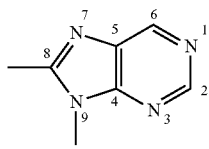

(12)

The number of the labeled structures contained in the labeled primer is not particularly limited and is, for example, approximately 1 to 100 and preferably approximately 1 to 20. In the labeled primer, the site where the labeled structure is contained also is not particularly limited.

In a labeled primer (labeled nucleic acid) of the present invention and a primer set of the present invention including the same, as well as a nucleic acid sample and a target nucleic acid sequence to be described later, the basic skeleton of each nucleic acid is not particularly limited. It may be, for example, any of oligonucleotide, modified oligonucleotide, oligonucleoside, modified oligonucleoside, polynucleotide, modified polynucleotide, polynucleoside, modified polynucleoside, DNA, modified DNA, RNA, modified RNA, LNA, PNA (peptide nucleic acid), or chimeric molecules thereof, or another structure. Furthermore, the basic skeleton of nucleic acid may be a natural one or artificially synthesized one. In the case of the primer and primer set of the present invention, the nucleic acid is not particularly limited as long as, for example, it can form base pairing. In the case of the nucleic acid sample and target nucleic acid sequence, the nucleic acid is not particularly limited as long as, for example, it serves as a template for synthesizing a complementary strand. Therefore the nucleic acid may be, for example, a nucleotide derivative, a part or the whole of which is formed of a completely artificial structure. Examples of artificial bases that compose the nucleic acid include 2-amino-6-(N,N-dimethylamino)purine pyridin-2-one, 5-methylpyridin-2-one, 2-amino-6-(2-thienyl)purine, pyrrole-2-carbaldehyde, 9-Methylimidazo[(4,5)-b]pyridine, 5-iodo-2-oxo(1H)pyridine 2-oxo-(1H)pyridine, 2-amino-6-(2-thiazolyl)purine, and 7-(2-thienyl)-imidazo[4,5-b]pyridine. However, the artificial bases are not limited thereto. In the primer of the present invention, the basic skeleton thereof is preferably oligonucleotide, polynucleotide, DNA, or a modified product thereof. In the present invention, the "nucleotide" may be either deoxynucleotide or ribonucleotide, and the "oligonucleotide" and "polynucleotide" each may be composed of either one of deoxynucleotide or ribonucleotide or may contain both of them. In the present invention, the number of bases that compose nucleic acid is not particularly limited. Generally, the term "nucleic acid" is synonymous with the term "polynucleotide". Generally, the term "oligonucleotide" is used as a term indicating a particular polynucleotide having a lower number of bases that compose nucleic acid, among others. Polynucleotide generally with a base length of, for example, 2 to 100 and more generally with a base length of approximately 2 to 50 is referred to as "oligonucleotide", but it is not limited by the numerical values. In the present invention, the term "polynucleotide" also should embrace, for example, polynucleotide and oligonucleotide, as well as artificially synthesized nucleic acids such as peptide nucleic acid, morpholine nucleic acid, methylphosphonate nucleic acid, and S-oligonucleic acid.

Generally, the peptide nucleic acid (PNA) has a structure in which a deoxyribose main chain of oligonucleotide has been substituted with a peptide main chain. Examples of the peptide main chain include a repeating unit of N-(2-aminoethyl) glycine bonded by an amide bond. Examples of the base to be bonded to the peptide main chain of PNA include, but not limited to, naturally-occurring bases such as thymine, cytosine, adenine, guanine, inosine, uracil, 5-methylcytosine, thiouracil, and 2,6-diaminopurine as well as artificial bases such as bromothymine, azaadenine, and azaguanine.

Generally, LNA is nucleic acid having two ring structures in which in a sugar-phosphoric acid skeleton, an oxygen atom in the 2-position and a carbon atom in the 4-position of ribose are bonded to each other by methylene crosslinking. When oligonucleotide containing LNA anneals to DNA, the double-stranded conformation is changed and thereby the thermal stability is improved. Since LNA has high avidity to nucleic acid as compared to common oligonucleotide, more reliable and stronger hybridization can be achieved depending on, for example, the conditions for designing nucleotide.

The labeled primer of the present invention contains at least one labeled structure having the fluorescent atomic group and thereby has higher specificity to a target and hybridizes more strongly as compared to, for example, unlabeled nucleic acid that does not contain the fluorescent atomic group. That is, the labeled primer of the present invention has an increased melting temperature (Tm value) as compared to unlabeled nucleic acid having a basic skeleton with the same base sequence and the same nucleic acid fragment length. This allows it to hybridize to a target more strongly as compared to the unlabeled nucleic acid. Accordingly, the labeled primer of the present invention allows detection to be carried out, for example, efficiently with high specificity.

The labeled nucleic acid of the present invention also has the characteristics as described above. Accordingly, as in the case of, for example, conventional PNA or LNA, applied technology is provided in which an increase in Tm value improves the specificity of amplification. Furthermore, when PNA or LNA is employed for the basic skeleton of the labeled primer of the present invention, the Tm value further can be increased as compared to unlabeled PNA or LAN, and therefore the hybridization efficiency further can be improved. Particularly, as described later, when mutations of one to several bases are to be discriminated or when insertion or deletion is to be detected, the use of the labeled nucleic acid (including, for example, labeled PNA and labeled LNA) of the present invention allows detection to be carried out efficiently with high specificity. When the labeled nucleic acid of the present invention is used as, for example, a primer or a probe, a large difference in Tm value and a difference in hybridization efficiency are obtained between the cases where it fully matches or mismatches with a target sequence. Accordingly, mutation detection such as one base discrimination further is facilitated. Moreover, since the labeled primer of the present invention has a higher Tm value than that of unlabeled nucleic acid, it also can be used for, for example, a PCR clamp method, a PNA PCR clamp method, an LNA PCR clamp method, and a PNA-LNA PCR clamp method, where it binds to a specific region strongly, masks the region, and does not serve as a template for amplification.

The number of bases contained in the primer of the present invention and in each primer included in the primer set of the present invention is not particularly limited. The respective primers may have the same number of bases or different numbers of bases from each other. With consideration given to the fact that the number of bases is that of a primer, specific examples of the number of bases are preferably approximately 10 to 100 bp, such as that of oligonucleotide, further preferably approximately 10 to 50 bp, and particularly preferably 10 to 30 bp.

The sequence of the primer according to the present invention is not particularly limited, as long as it has the labeled structure. The sequence of each primer of the pair of primers according to the present invention is not particularly limited, as long as at least one of the primers has the labeled structure. The sequence of each primer can be set suitably according to, for example, the sequence of the target nucleic acid sequence to be amplified, information about the sequences around the target nucleic acid sequence in, for example, DNA or RNA, and the type of the nucleic acid amplification reaction (the nucleic acid amplification method) for which the primer or primer set of the present invention is used. The sequence of each primer can be set by a conventionally known method. Usually, it is designed in such a manner that the target nucleic acid sequence in a nucleic acid such as DNA or RNA hybridizes with the nucleic acid under a stringent condition so that the target nucleic acid sequence is contained in the amplification product. The "stringent condition" can be determined depending on, for example, the melting temperature Tm (° C.) of the double strand that is formed of a primer of the present invention or each primer of the primer set of the present invention and a complementary strand thereto, and the salt concentration of the hybridization solution. Specific examples can be found in references such as J. Sambrook, E. F. Frisch, T. Maniatis; Molecular Cloning $2^{nd}$ edition, Cold Spring Harbor Laboratory (1989). For example, when hybridization is carried out at a temperature that is slightly lower than the melting temperature of the primer to be used, the primer can be hybridized specifically with a nucleic acid having a target nucleic acid sequence. The primer as described above can be designed using a commercial primer construction software, for example, Primer 3 (manufactured by Whitehead Institute for Biomedical Research). The primer (labeled nucleic acid) of the present invention may be used, for example, with unlabeled primer (unlabeled nucleic acid) having the same nucleic sequence with the labeled nucleic acid. Thereby, for example, an increase in cost due to labeling can sufficiently be prevented. Further, the primer of the present invention can obtain excellent detection sensitivity even when the primer is used with the unlabeled nucleic acid. The ratios of the labeled nucleic acid of the present invention and the unlabeled nucleic acid are not particularly limited. However, for example, in the total amount of the labeled nucleic acid and the unlabeled nucleic acid, the ratio of the labeled nucleic acid is preferably in the range of 0.01-100%, more preferably in the range of 1-100%, further preferably in the range of 5-50%, and particularly preferably in the range of 10-50%. As described above, in a case of conducting a visual observation, the ratio of the labeled nucleic acid is preferably higher.

The labeled primer of the present invention may have only one atomic group (dye) having fluorescence per molecule but has preferably at least two atomic groups (dye) having fluorescence per molecule. This allows, for example, the atomic groups (dye) having fluorescence to have an exciton effect. The exciton effect, for example, suppresses the fluorescence intensity in a single-stranded state and thereby allows a double helix structure to be detected further effectively. The "exciton effect" (exciton coupling) is an effect in which, for example, a plurality of dyes aggregate in parallel to form an H-aggregate and thereby hardly exhibit fluorescence emission. Conceivably, this effect is obtained as follows. That is, the excitation state of the dye is split into two energy levels by Davydov splitting, excitation to the higher energy level and then internal conversion into the lower energy level occur, and thereby the emission is thermally forbidden. However, these descriptions do not limit the present invention by any means.

The possible occurrence of the exciton effect can be confirmed by the appearance of the absorption band of the dyes that have formed the H-aggregate, in a shorter wavelength as compared to the absorption band of a single dye. Examples of the dyes that exhibit such an effect include thiazole orange and a derivative thereof, oxazole yellow and a derivative thereof, cyanine and a derivative thereof, hemicyanine and a derivative thereof, and methyl red and a derivative thereof as described above, as well as dye groups generally referred to as cyanine dyes and azo dyes.

These dyes tend to bind to a DNA-DNA double strand or DNA-RNA double strand that forms a double helix or a double strand formed of DNA or RNA and an artificial nucleic acid such as phosphothioate nucleic acid, PNA (peptide nucleic acid), or LNA (BNA), by intercalation. When a plurality of such dyes have been introduced into a primer, strong quenching occurs due to the exciton effect in a normal single-stranded state (i.e. in the state where the primer has not been hybridized yet), but an aggregate is broken down through hybridization with a target DNA or RNA and then the respective dyes intercalate into the double strand separately. In this case, no electronic interaction occurs between the dyes and therefore the exciton effect does not occur, which results in exhibition of strong fluorescence emission. The absorption band of the dyes in this stage is identical to that of a single dye, which indicates that no exciton effect occurs between the dyes. Furthermore, when dyes intercalate into a double strand, the structural torsion inherent to the dyes is cancelled, which results in further stronger fluorescence emission.

Accordingly, for example, a primer is designed in such a manner that a plurality of dyes allow the exciton effect to be obtained, so that it is possible to turn fluorescence on or off very clearly through hybridization thereof to a target sequence. The exciton effect does not occur through bonding of only one molecule of dye to a primer sequence. However, for the reasons that, for example, the intercalation of the dye caused by the double strand formation planarizes the structure of the dye, it also is possible that stronger fluorescence than that exhibited in the single-stranded state is exhibited. On the other hand, even in the case where at least two molecules of dyes are bonded, when the respective dyes are apart from each other by a distance that does not allow them to exhibit electronic correlation, the exciton effect does not occur. That is, in order to allow the exciton effect to be exhibited, at least two molecules of the dye have to be bonded to a molecule of a nucleic acid or compound of the present invention in such a manner that they are located at a distance that allows them to be close enough. In other words, it is preferable that in the labeled primer of the present invention, at least two molecules of a dye be bonded to one nucleotide in the primer or one molecule of a dye be bonded to each of at least two contiguous nucleotides.

Since the primer and primer set of the present invention can improve, for example, the efficiency of nucleic acid amplification, the primer set further may include an outer primer. An example of the outer primer is a primer that can provide an origin of complementary strand synthesis for the portion located on the outer side of the target nucleic acid sequence on a template nucleic acid. When the primer set of the present invention includes an outer primer, the outer primer may be a labeled nucleic acid in addition to or instead of a labeled primer of the primer set described above.

Since the primer and primer set of the present invention are used for the nucleic acid amplification method as described later, they further may include a reagent that can be used for nucleic acid amplification. Examples of the reagent include polymerase such as DNA polymerase; substrates such as dNTP mix (dATP, dTTP, dCTP, and dGTP); buffer solutions such as a tris-hydrochloride buffer, a trysine buffer, a sodium phosphate buffer, and a potassium phosphate buffer; catalysts such as magnesium chloride, magnesium acetate, and magnesium sulfate; additives such as dimethyl sulfoxide and betaine (N,N,N-trimethylglycine); acidic substances and cation complexes described in WO 99/54455; and an enzyme stabilizer. The enzyme stabilizer is not limited. Examples thereof include glycerol, bovine serum albumin, and saccharide. Particularly, the enzyme stabilizer is preferably saccharide, more preferably monosaccharide or oligosaccharide, and further preferably trehalose, sorbitol, mannitol, or a mixture of two or more of them. Furthermore, since the primer and primer set of the present invention can improve, for example, nucleic acid amplification efficiency, they further may include a melting temperature regulator. Examples of the melting temperature regulator include dimethylsulfoxide (DMSO), betaine, formamide, glycerol, and arbitrary combinations thereof. It is preferably DMSO. Furthermore, when the nucleic acid sample used for the nucleic acid amplification method contains RNA and is used as a template as described later, it is preferable that further a reverse transcriptase be contained. In the primer and primer set of the present invention, for example, the ratios of these reagents are not limited and can be determined suitably by persons skilled in the art.

The primer and primer set of the present invention can be used for conventionally known various nucleic acid amplification methods, and the types of reactions therein are not limited. Examples of the nucleic acid amplification method include an isothermal amplification method and a polymerase chain reaction (PCR) method. Hereinafter, the primer and primer set of the present invention that are used for the isothermal amplification method are referred to as an "isothermal amplification primer" and an "isothermal amplification primer set", respectively, and the primer and primer set of the present invention that are used for the PCR method are referred to as a "PCR primer" and a "PCR primer set", respectively.

Isothermal Amplification Primer and Primer Set

Generally, the isothermal amplification method is a method of carrying out a nucleic acid amplification reaction isothermally. Examples of such a method include the strand displacement amplification (SDA) method disclosed in, for example, JP 7-114718 A; improved SDA methods disclosed in, for example, U.S. Pat. No. 5,824,517, WO 99/09211, and WO 95/25180; the nucleic acid sequence based amplification (NASBA) method disclosed in, for example, JP 2650159 B; the loop-mediated isothermal amplification (LAMP) method disclosed in, for example, WO 00/28082; the isothermal and chimeric primer-initiated amplification of nucleic acids (ICAN) method disclosed in, for example, WO 02/16639; a self-sustained sequence replication (3SR) method; the transcription-mediated amplification (TMA) method; the Q beta replicase method disclosed in JP 2710159 B; methods disclosed in, for example, JP 389726 B, JP 3942627 B, and NATURE METHODS (Vol. 4, No. 3, March 2007, pp. 257-262), Mitani Y., Lezhava A., Kawai Y., Kikuchi T., Oguchi-Katayama A., Kogo Y., Itoh M., Miyagi T. et al. 2007. "Rapid SNP diagnostics using asymmetric isothermal amplification and a new mismatch-suppression technology." Nat. Methods 4(3): 257-262. (hereinafter referred to as a "SMAP (Smart Amplification Process) method"), an Invader method, and a rolling cycle amplification (RCA) method.

In the case of the isothermal amplification method, it is preferable that polymerase having strand displacement ability (strand displacement activity) be used. Therefore, it is preferable that the isothermal amplification primer and primer set of the present invention contain polymerase having strand displacement ability. The polymerase having strand displacement ability may be, for example, any one of normal-temperature, mesophilic, and thermostable polymerases. The polymerase having strand displacement ability may be, for example, a naturally occurring enzyme, an enzyme prepared by, for instance, genetic engineering, or a mutant enzyme mutated artificially. The polymerase as described above is, for example, preferably a DNA polymerase and more preferably a DNA polymerase that substantially has no 5'→3' exonuclease activity. Specific examples of DNA polymerase having strand displacement ability include: a DNA polymerase derived from thermophilic Bacillus bacteria, such as Bacillus stearothermophilus (hereinafter referred to as "B. st") and Bacillus caldotenax (hereinafter referred to as "B. ca"), and mutants obtained by deleting the 5'→3' exonuclease activity therefrom, as well as a E. coli DNA polymerase I and a Klenow fragment thereof. Furthermore, other examples include Vent DNA polymerase, Vent (Exo⁻) DNA polymerase, DeepVent DNA polymerase, DeepVent (Exo⁻) DNA polymerase, phage phi 29 DNA polymerase, MS-2 phage DNA polymerase, Z-Taq DNA polymerase, Pfu DNA polymerase, Pfu turbo DNA polymerase, KOD DNA polymerase, 9° Nm DNA polymerase, Therminater DNA polymerase, Aac DNA polymerase, Gca DNA polymerase, and Bsm DNA polymerase.

Preferably, the polymerase having strand displacement ability is a DNA polymerase additionally having reverse transcription activity. For example, BcaBEST DNA polymerase or Bca(exo⁻) DNA polymerase can be used as the above-mentioned DNA polymerase. When using the DNA polymerase as described above, the reverse transcription reaction from whole RNA or mRNA and the DNA polymerase reaction that is performed using cDNA as a template can be conducted with one type of polymerase. Moreover, a DNA polymerase and the above-mentioned reverse transcriptase such as an MMLV reverse transcriptase can be used in combination.

Since the isothermal amplification primer and primer set of the present invention can improve, for example, specificity, it is preferable that they further include a mismatch binding protein. The mismatch binding protein (also called a "mismatch recognition protein") is not limited, as long as it is a protein capable of recognizing a mismatch in, for example, double-stranded nucleic acid and binding to a mismatch site. For example, proteins known by persons skilled in the art can be used. Furthermore, the mismatch binding protein may be, for example, a protein (a mutant) formed of an amino acid sequence obtained by substitution, deletion, addition, and/or insertion of one or more amino acids in an amino acid sequence of a wildtype protein, as long as it can recognize the mismatch in, for example, a double-stranded nucleic acid. Many mismatch binding proteins are known including, for example, a MutS protein (for example, JP 9-504699 A), a MutM protein (for example, JP 2000-300265 A), a MutS protein bonded to a green fluorescent protein (GFP) (WO 99/06591), Taq MutS, and analogs thereof (for example, Radman, M. et al., Annu. Rev. Genet. 20:523-538 (1986); Radaman, M. et al., Sci. Amer., August 1988, pp 40-46; Modrich, P., J. Biol. Chem. 264:6597-6600 (1989); Lahue, R. S. et al., Science 245:160-164 (1988); Jiricny, J. et al., Nucl. Acids Res. 16:7843-7853 (1988); Su, S. S. et al., J. Biol. Chem. 263; 6829-6835 (1988); Lahue, R. S. et al., Mutat. Res. 198:37-43 (1988); Dohet, C. et al., Mol. Gen. Gent. 206:181-184 (1987); Jones, M. et al., Gentics 115:605-610 (1987); MutS of Salmonella typhimurium (Lu, A. L., Genetics 118:593-600

(1988); Haber L. T. et al., J. Bacteriol. 170:197-202 (1988); Pang, P. P. et al., J. Bacteriol. 163:1007-1015 (1985)); and Priebe S. D. et al., J. Bacterilo. 170:190-196 (1988)). In the present invention, preferable mismatch binding proteins include MutS, MSH2, MSH6, MutH, MutL, and one derived from yeast.

Preferably, the aforementioned mismatch binding protein is being activated by an activator, for example, in order to prevent it from binding to a double-stranded nucleic acid containing no mismatch. The activator is not particularly limited. Examples thereof include ATP (adenosine 5'-triphosphate), ADP (adenosine 5'-diphosphate), ATP-gamma-S (adenosine 5'-O-(3-thiotriphosphate)), and AMP-PNP (adenosine 5'-[beta, gamma-imide]triphosphate). Furthermore, the activator may be one of the nucleotides that can bind to a mismatch binding protein. A mismatch binding protein can be activated by incubating the mismatch binding protein and the activator at room temperature for several seconds to several minutes.

Preferably, the isothermal amplification primer and primer set of the present invention further includes a single-stranded binding protein (SSB), for example, in order to prevent the mismatch binding protein from binding to a single-stranded nucleic acid. The SSB is not particularly limited and conventionally known proteins can be used. Specific examples of the SSB include single-stranded binding proteins derived from *Escherichia coli*, *Drosophila*, and *Xenopus laevis*, T4 Bacteriophage gene 32 proteins, and in addition, those proteins derived from other species. In this case, examples of the mismatch binding protein include MutS, MutH, MutL, HexA, MSH1 to 6, Rep3, RNaseA, uracil-DNA glycosidase, T4 endonuclease VII, and resolvase. The mismatch binding protein is preferably MutS, MSH2, MSH6, or a mixture of two or more of them, and is more preferably MutS.

Examples of the isothermal amplification primer set of the present invention include a primer set of an asymmetric type in which one of the primers is different from the other in morphology (hereinafter, referred to as an "asymmetric primer set") and a primer set of a symmetrical type in which one of the primers is identical to the other in morphology (hereinafter, referred to as a "symmetrical primer set"). The asymmetric primer set is suitable for, for example, the SMAP method, and the symmetrical primer set is suitable for, for example, the LAMP method. The asymmetric primer set and symmetrical primer set are described later.

PCR Primer and Primer Set

The PCR method is a conventionally, widely known nucleic acid amplification method. It is a method in which the reaction temperature is changed contrary to the isothermal amplification method, so that, for example, double-stranded nucleic acid is dissociated, a primer is annealed to a single strand thus dissociated, and nucleic acid is synthesized from the primer. The polymerase to be used for the PCR method can be, for example, a conventionally known polymerase such as Taq DNA polymerase.

Specific examples of the primer and primer set according to the present invention for various nucleic acid amplification methods are described later together with the nucleic acid amplification method of the present invention.

The effects of the labeled primer of the present invention include the following advantages as compared to the conventional single-stranded quenching fluorescence primers (for example, a molecular beacon). However, they are mere examples and do not limit the present invention.

(1) It is easy to synthesize when only one type of dye is used.
(2) It is easy to use as a primer when the DNA primer according to the present invention has a free end.
(3) It is not necessary to form any special conformation such as a hairpin structure and therefore sequences that are not associated with the sequence recognition, such as a stem sequence, are not required (neither useless sequences nor restrained sequences are present).
(4) Fluorescent dyes can be introduced into a plurality of sites (desired sites) in a primer.
(5) When at least two dye structures are contained in one molecule, the positional relationship between the dyes is restrained and thereby the S/N ratio (the fluorescence intensity ratio before and after hybridization) is high.

[Materials for Labeled Primer]

The labeled primer (the labeled nucleic acid) of the present invention can be prepared from, for example, the compound, nucleic acid, and labeling substance described below. The compound and nucleic acid can be used as, for example, the labeled primer of the present invention, or a raw material for synthesizing it or a synthetic intermediate thereof. The compound, nucleic acid, and labeling substance of the present invention are described in further detail as follows.

The aforementioned compound is a compound having a structure derived from mononucleoside or mononucleotide, with the structure being represented by the following formula (1), (1b), or (1c), a tautomer or stereoisomer thereof, or a salt thereof

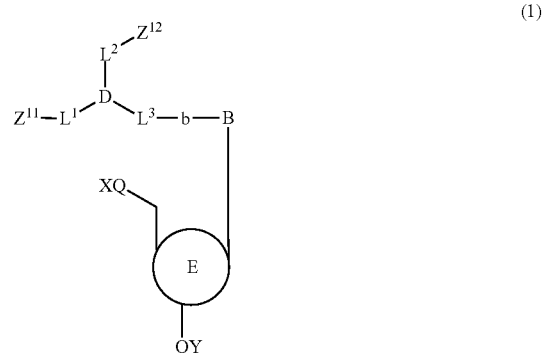

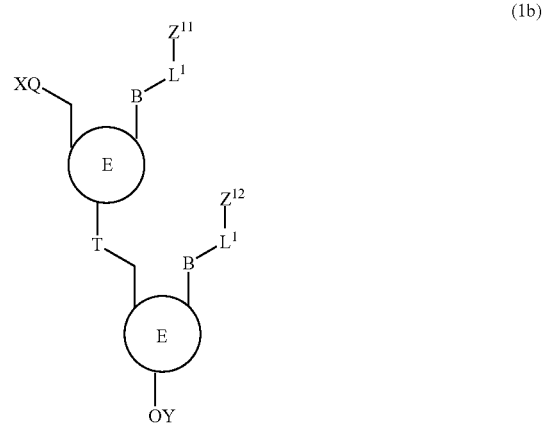

-continued (1c)

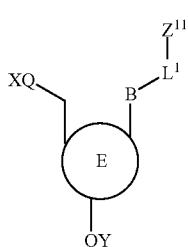

In the formulae (1), (1b), and (1c),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each a hydrogen atom, a protecting group, or an atomic group that exhibits fluorescence, and may be identical to or different from each other, Q is:

O, when E is an atomic group described in item (i), or

NH, when E is an atomic group described in item (ii),

X is:

a hydrogen atom, a protecting group of a hydroxy group that can be deprotected with acid, a phosphate group (a monophosphate group), a diphosphate group, or a triphosphate group, when E is an atomic group described in item (i) or a hydrogen atom or a protecting group of an amino group, when E is an atomic group described in item (ii), Y is:

a hydrogen atom, a protecting group of a hydroxy group, or a phosphoramidite group, when E is an atomic group described in item (i), or a hydrogen atom or a protecting group, when E is an atomic group described in item (ii), $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formula (1), $L^1$ and $L^2$ are each the aforementioned linker, $L^3$, D, and b may not be present, and $L^1$ and $L^2$ may be bonded directly to B, in the formula (1b), T is:

a phosphoric acid linkage ($PO_4^-$) in which at least one oxygen atom (O) may be substituted with a sulfur atom (S), when E is an atomic group described in item (i), or NH, when E is an atomic group described in item (ii).

In the formulae (1), (1b), and (1c), it is preferable that E be an atomic group having a main chain structure of, for example, DNA, modified DNA, RNA, modified RNA, LNA, or PNA (peptide nucleic acid).

Furthermore, in the formulae (1) and (1c), preferably, the atomic group represented by:

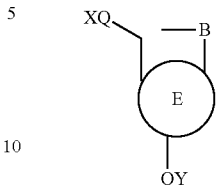

is an atomic group represented by any one of the following formulae (2) to (4), (2)

XO—[structure]—B
OY A (3)

XO—[structure]—B
OY
J—M (4)

NX—[structure]—B
N—O
O—OY and in the formula (1b), an atomic group represented by:

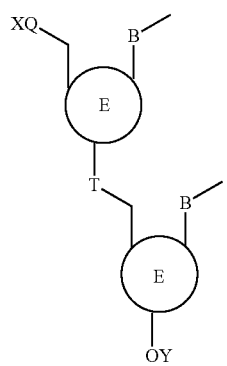

is an atomic group represented by any one of the following formulae (2b) to (4b).

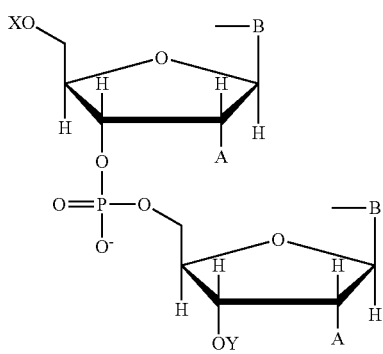

(2b)

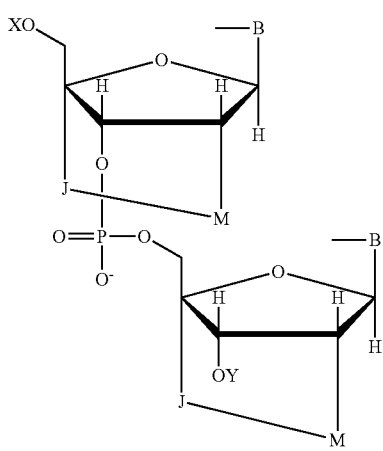

(3b)

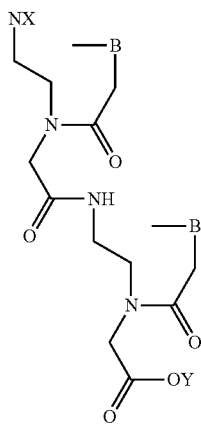

(4b)

In the formulae (2) to (4) and (2b) to (4b),

A is a hydrogen atom, a hydroxy group, an alkyl group, or an electron-withdrawing group, M and J are each $CH_2$, NH, O, or S and may be identical to or different from each other, B, X, and Y are identical to those, respectively, in the formula (1), (1b), or (1c), and in the formulae (2), (3), (2b), and (3b), at least one O atom contained in a phosphoric acid linkage may be substituted with an S atom.

E is preferably an atomic group having a main chain structure of, for example, DNA, modified DNA, RNA, or modified RNA from the viewpoint of, for example, easy synthesis. However, E may be an atomic group having a main chain structure of LNA or PNA (peptide nucleic acid).

In the formulae (2) and (2b), it is preferable that, for example, the alkyl group be a methoxy group and the electron-withdrawing group be halogen.

In the formula (1), (1b), or (1c), it is preferable that each main chain length (the number of main chain atoms) of $L^1$, $L^2$, and $L^3$ be an integer of 2 or more. The upper limit of each main chain length (the number of main chain atoms) of $L^1$, $L^2$, and $L^3$ is not particularly limited as described above and is, for example, 100 or less.

Preferably, the aforementioned compound is a compound represented by the following formula (5), (6), (6b), or (6c), a tautomer or stereoisomer thereof, or a salt thereof.

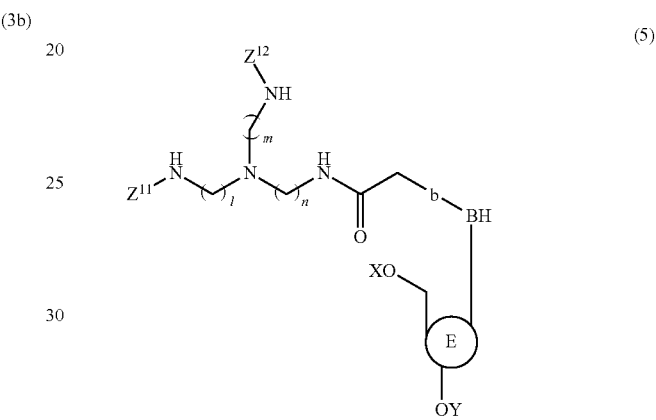

(5)

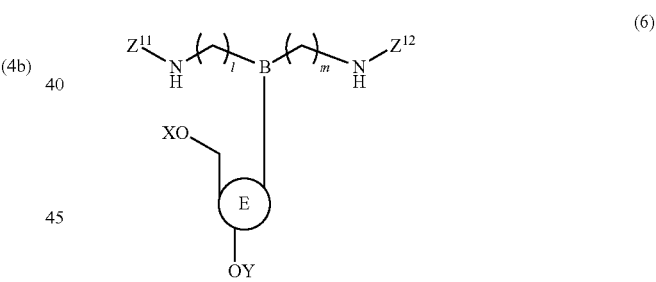

(6)

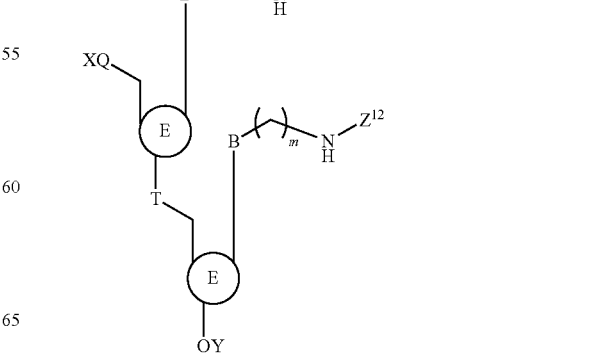

(6c)

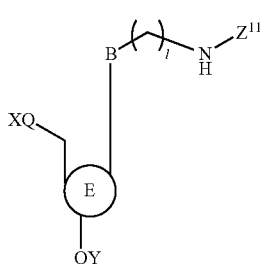

In the formulae (5), (6), (6b) and (6c), l, m, and n are arbitrary and may be identical to or different from one another, and B, E, $Z^{11}$, $Z^{12}$, X, Y, and T are identical to those of the formulae (1) and (1b), respectively. In the formulae (5), (6), (6b), and (6c), l, m, and n each are preferably an integer of 2 or more. The upper limits of l, m, and n are not particularly limited and are, for example 100 or less, more preferably 30 or less, and particularly preferably 10 or less.

In the compound, it is preferable that $Z^{11}$ and $Z^{12}$ each be an atomic group that exhibits an exciton effect. This allows fluorescence to be increased greatly when, for example, a double helix structure is formed, and thereby the double helix structure can be detected further effectively. However, in the aforementioned compound, it is possible to detect the double helix structure effectively even when $Z^{11}$ and $Z^{12}$ each is not an atomic group that exhibits an exciton effect or even when only one atomic group (dye) that exhibits fluorescence is introduced into one molecule.

Preferably, $Z^{11}$ and $Z^{12}$ each are, for example, an atomic group having fluorescence as described above. The atomic group having fluorescence is not particularly limited. More preferably, $Z^{11}$ and $Z^{12}$ are, for example, each independently a group derived from thiazole orange, oxazole yellow, cyanine, hemicyanine, another cyanine dye, methyl red, azo dye, or a derivative thereof. Furthermore, a group derived from another known dye also can be used suitably. Many fluorescent dyes that change the fluorescence intensity by binding to nucleic acid such as DNA have been reported. In a typical example, it has been known that ethidium bromide exhibits strong fluorescence by intercalating into a double helix structure of DNA, and it is used frequently for DNA detection. Furthermore, fluorescent dyes whose fluorescence intensity can be controlled according to the microscopic polarity, such as pyrenecarboxyamide and prodan, also are known. The thiazole orange is a fluorescent dye with a benzothiazole ring and quinoline ring being linked to each other with a methine group. It usually exhibits weak fluorescence but gives strong fluorescence emission by intercalating into DNA having a double helix structure. Other examples include dyes such as fluorescein and Cy3.

Further preferably, $Z^{11}$ and $Z^{12}$ are, for example, each independently an atomic group represented by any one of the following formulae (7) to (9).

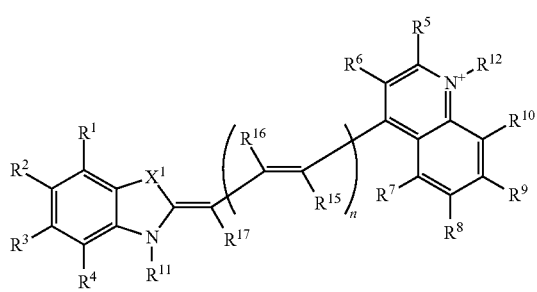

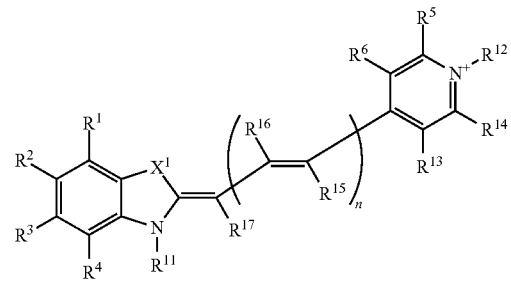

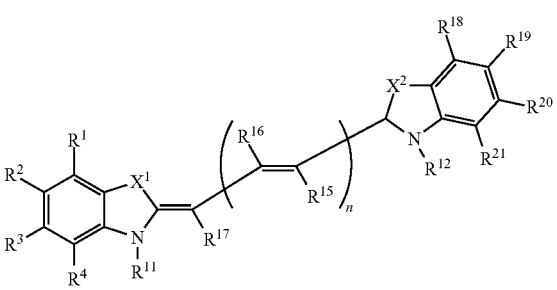

In the formulae (7) to (9), $X^1$ is S or O, n is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group that binds to $L^1$ or $L^2$ in the formula (1), (1b), or (1c) or NH in the formula (5), (6), (6b), or (6c), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$ and $R^1$ to $R^{21}$ in $Z^{11}$ and $X^1$ and $R^1$ to $R^{21}$ in $Z^{12}$ may be identical to or different from each other, respectively.

In the formulae (7) to (9), it is further preferable that in $R^1$ to $R^{21}$, the lower alkyl group be a linear or branched alkyl group with a carbon number of 1 to 6, and the lower alkoxy group be a linear or branched alkoxy group with a carbon number of 1 to 6.

In the formulae (7) to (9), it is further preferable that in $R^{11}$ and $R^{12}$, the linking group be a polymethylene carbonyl group with a carbon number of at least 2 and bind to $L^1$ or $L^2$ in the formula (1), (1b), or (1c) or NH in the formula (5), (6), (6b), or (6c), by the carbonyl group moiety thereof. The upper limit of the carbon number of the polymethylene carbonyl group is not particularly limited and is, for example, 100 or lower.

When $Z^{11}$ and $Z^{12}$ each are represented by any one of the formulae (7) to (9), it is more preferable that they be, for example, each independently a group represented by formula (19) or (20).

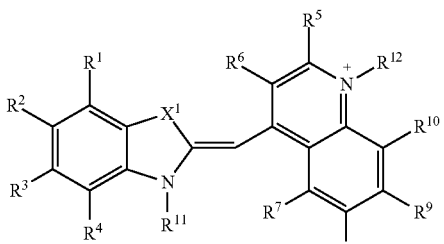

(19)

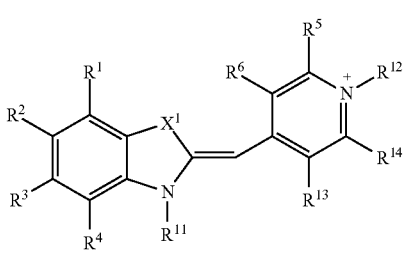

(20)

In the formulae (19) and (20), $X^1$ denotes —S— or —O—. $R^1$ to $R^{10}$, $R^{13}$ and $R^{14}$ indicates each independently a hydrogen atom, a halogen atom, a lower alkyl group, a lower alkoxy group, a nitro group, or an amino group. One of $R^{11}$ and $R^{12}$ is a linking group that binds to $L^1$ or $L^2$ in the formula (1), (1b), or (1c) or NH in the formula (5), (6), (6b), or (6c), and the other is a hydrogen atom or a lower alkyl group.

The aforementioned compound may be, for example, a compound having a structure represented by the following formula (10), a tautomer or stereoisomer thereof, or a salt thereof.

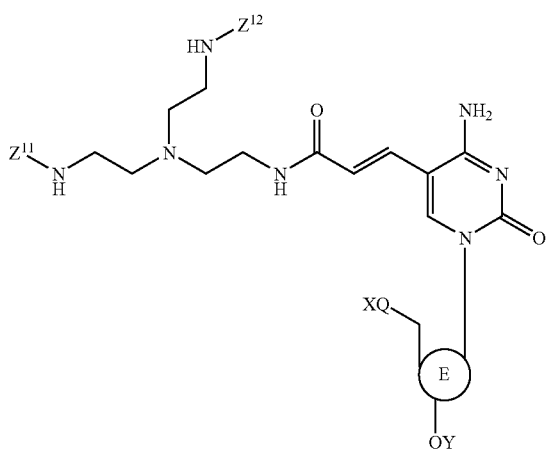

(10)

In the formula (10),

E, $Z^{11}$, $Z^{12}$, Q, X, and Y are identical to those used in the formula (1), respectively.

In the formulae (1), (1b), and (1c), B may have a natural nucleobase skeleton but may have an artificial nucleobase skeleton as described above.

For example, B is preferably a structure represented by Py, Py der., Pu, or Pu der., where the Py is an atomic group having a covalent bond to E in the 1-position and a covalent bond to a linker moiety in the 5-position in the six-membered ring represented by the following formula (11), the "Py der." is an atomic group in which at least one of all the atoms of the six-membered ring of the Py has been substituted with an N, C, S, or atom, and the N, C, S, or O atom may have an electric charge, a hydrogen atom, or a substituent suitably, the Pu is an atomic group having a covalent bond to E in the 9-position and a covalent bond to a linker moiety in the 8-position in the condensed ring represented by the following formula (12), and the Pu der. is an atomic group in which at least one of all the atoms of the five-membered ring of the Pu has been substituted with an N, C, S, or O atom, and the N, C, S, or O atom may have an electric charge, a hydrogen atom, or a substituent suitably.

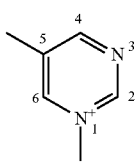

(11)

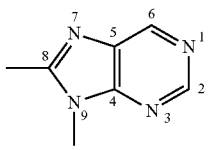

(12)

The aforementioned compound may be, for example, a compound represented by the following formula (13) or (14), a tautomer or stereoisomer thereof, or a salt thereof

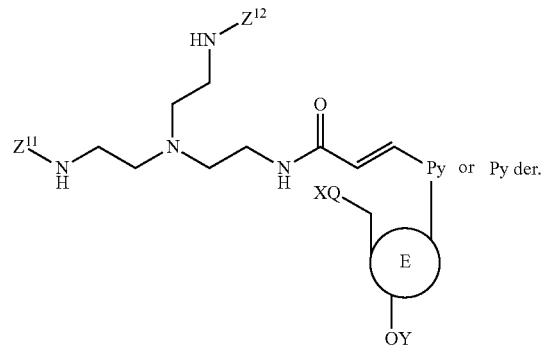

(13)

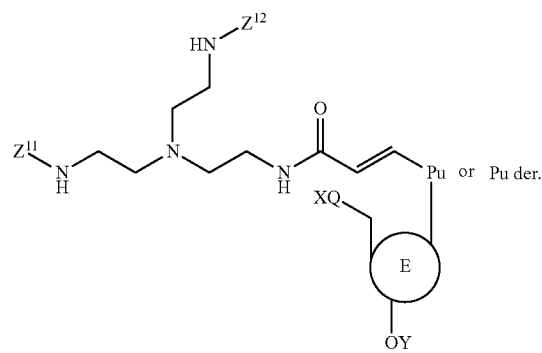

(14)

In the formulae (13) and (14),

E, $Z^{11}$, $Z^{12}$, Q, X, and Y are identical to those used in the formula (1), respectively, and Py, Py der., Pu, and Pu der. are as defined above.

When the compound has a phosphoramidite group, it is preferable that the phosphoramidite group be expressed by, for example, the following formula (15):

where $R^{22}$ is a protecting group of a phosphate group, and $R^{23}$ and $R^{24}$ are each an alkyl group or an aryl group.

Further preferably, in the formula (15), $R^{15}$ is a cyanoethyl group, and in $R^{16}$ and $R^{17}$, the alkyl group is an isopropyl group and the aryl group is a phenyl group.

In the aforementioned compound, for example, the compound represented by the formula (1) may be a compound represented by the following formula (21).

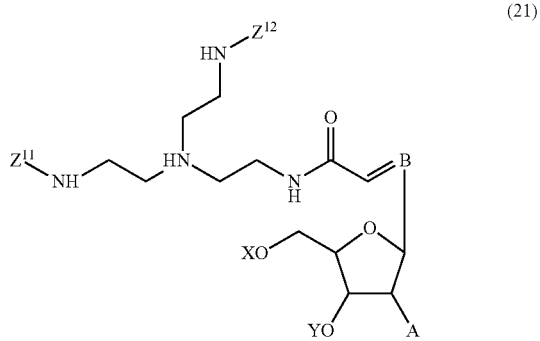

In the formula (21), A denotes a hydrogen atom or a hydroxy group. Preferably, A is a hydrogen atom. B denotes a residue of adenine, guanine, cytosine, thymine, or uracil. For example, adenine and guanine have been bonded to a double bond in the 8-position, and cytosine, thymine, or uracil have been bonded to a double bond in the 5-position. $Z^{11}$ and $Z^{12}$ each indicates independently an atomic group that exhibits fluorescence, a hydrogen atom, or a protecting group of an amino group, and are particularly preferably a residue of an oxazole yellow derivative or a thiazole orange derivative. X denotes a hydrogen atom, a protecting group of a hydroxy group that can be deprotected with acid, a monophosphate group, a diphosphate group, or a triphosphate group. Y is a hydrogen atom, a protecting group of a hydroxy group, or a phosphoramidite group.

It is further preferable that the compound represented by the formula (21) be represented by the following formula (22).

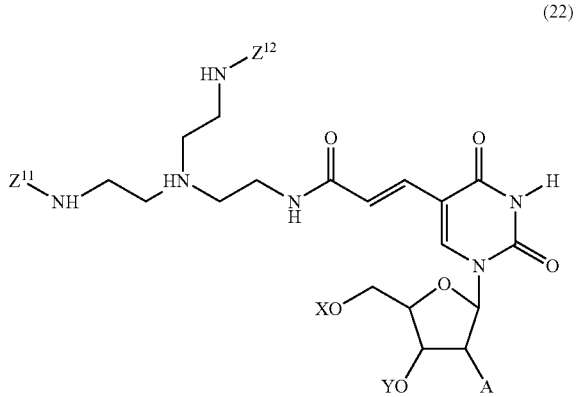

In the formula (22), A denotes a hydrogen atom or a hydroxy group. $Z^{11}$ and $Z^{12}$ are each independently an atomic group that exhibits fluorescence, a hydrogen atom, or a protecting group of an amino group, and particularly preferably a residue of an oxazole yellow derivative or a thiazole orange derivative. X denotes a hydrogen atom, a protecting group of a hydroxy group that can be deprotected with acid, a monophosphate group, a diphosphate group, or a triphosphate group. Y is a hydrogen atom, a protecting group of a hydroxy group, or a phosphoramidite group.

In the compound of the formula (21) or (22), when $Z^{11}$ and $Z^{12}$ are each a hydrogen atom or a protecting group of an amino group, two amino groups (or protected amino groups) are contained in one molecule, and therefore two labeled molecules can be introduced into one molecule using the amino groups. For example, when labeled nucleic acid is produced, with, for example, a fluorescent substance or a chemiluminescent substance being bound thereto, the nucleic acid detection sensitivity can be improved. Furthermore, as in the case where $Z^{11}$ and $Z^{12}$ are each an atomic group that exhibits fluorescence, labeling nucleic acid with a specific fluorescent substance makes it possible to detect it easily.

Furthermore, in the compound of the formula (21) or (22), a compound in which $Z^{11}$ and $Z^{12}$ are each an atomic group that exhibits fluorescence is nucleoside or nucleotide modified with two fluorescence molecules, for example, a thiazole orange derivative or an oxazole yellow derivative. A primer formed of a single-stranded nucleic acid containing such a compound emits very weak fluorescence, when the primer is used by itself, due to quenching caused by exciton coupling, but emits strong fluorescence by hybridizing with DNA or RNA. That is, for example, the fluorescence of the thiazole orange derivative or the oxazole yellow derivative is suppressed strongly by the distorted structure thereof, but when the thiazole orange derivative or oxazole yellow derivative binds to DNA, the structural distortion is cancelled and fixed and thereby strong fluorescence is emitted. The fluorescence can be detected by, for example, excitation performed using an Ar laser with a wavelength of 488 nm or 514 nm, but the detection method is not limited thereto.

The compound represented by the formula (1), (1b), or (1c) can be used for synthesizing, for example, a labeled primer (labeled nucleic acid) of the present invention. That is, the aforementioned compound can be used as a labeling substance (nucleic acid labeling reagent) for nucleic acid. For example, by using the compound represented by the formula (1), (1b), or (1c) as a nucleotide substrate and carrying out a nucleic acid synthesis reaction using a single-stranded nucleic acid as a template, or by synthesizing a single-stranded nucleic acid chemically (for example, a chemical synthesis method such as a phosphoramidite method that is carried out using an automated nucleic acid synthesizer) using a compound represented by the formula (1), (1b), or (1c), nucleic acid containing at least one molecule of the compound in one molecule can be produced. In this case, the atomic groups $Z^{11}$ and $Z^{12}$ may be each an atomic group that exhibits fluorescence but also may be a hydrogen atom or a protecting group. If the atomic groups $Z^{11}$ and $Z^{12}$ are each, for example, an atomic group that exhibits fluorescence, the labeled primer of the present invention can be produced, and if they are each a hydrogen atom or a protecting group, further substitution of those atoms or groups with atomic groups that exhibit fluorescence allows the labeled primer of the present invention to be produced.

The number of compounds represented by the formula (1), (1b), or (1c) that are contained in the labeled primer of the present invention is not particularly limited. It is, for example, approximately 1 to 100, and preferably approximately 1 to 20.

The compound or nucleic acid (the labeled primer of the present invention) may have, for example, a structure represented by any one of the following formulae (23) to (25). In this case, it can be used suitably as a fluorescence primer with a dye introduced therein. However, preferred compounds to be used as fluorescence primers are not limited thereto.

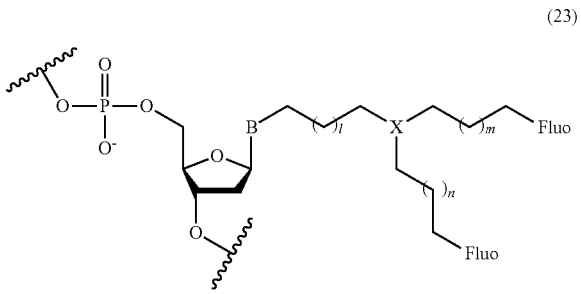
(23)

In the formula (23), two dyes (Fluo) are linked to a base B. The site at which the base B binds to a linker is not particularly limited. For example, the base B is linked to a linker in one position selected from the 4-position, the 5-position, and the 6-position of pyrimidine and the 2-position, the 3-position, the 6-position, the 7-position, and the 8-position of purine. The linker has one base linkage site, branches into at least two along the path, and is linked to dyes at the ends thereof. The method to be employed for linking it to a base or a dye is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linker, the lengths (l, m, and n) are arbitrary, and it may contain a single bond, a double bond, a triple bond, an amide bond, an ester bond, a disulfide bond, amine, imine, an ether bond, a thioether bond, or a thioester bond. Furthermore, it is preferable that the linker not prevent the exciton effect from being caused by dimerization. The branch (X) is each atom of carbon, silicon, nitrogen, phosphorus, and boron, and protonation (for example, $NH^+$) or oxidation (for instance, $P=O$) may occur. Preferably, the dye to be used is one that exhibits an exciton effect by dimerization. The site at which the dye is linked to a linker is any portion thereof. The formula (23) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

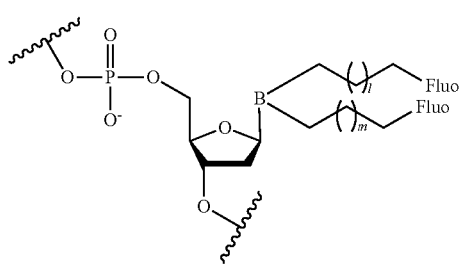
(24)

In the formula (24), two dyes (Fluo) are linked to base B. The sites by which the base B binds to linkers are not particularly limited. For example, the base B is linked to linkers in two positions selected from the 4-position, the 5-position, and the 6-position of pyrimidine and the 2-position, the 3-position, the 6-position, the 7-position, and the 8-position of purine. The two linkers each have one base linkage site and are linked to a dye at the other end thereof. The method to be employed for linking them to a base or dye is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linkers, the lengths (l and m) are arbitrary, and they may contain a single bond, a double bond, a triple bond, an amide bond, an ester bond, a disulfide bond, amine, imine, an ether bond, a thioether bond, or a thioester bond. Furthermore, it is preferable that the linkers not prevent the exciton effect from being caused by dimerization. Preferably, the dye to be used is one that exhibits an exciton effect by dimerization. The site at which the dye is linked to a linker is any portion thereof. The formula (24) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

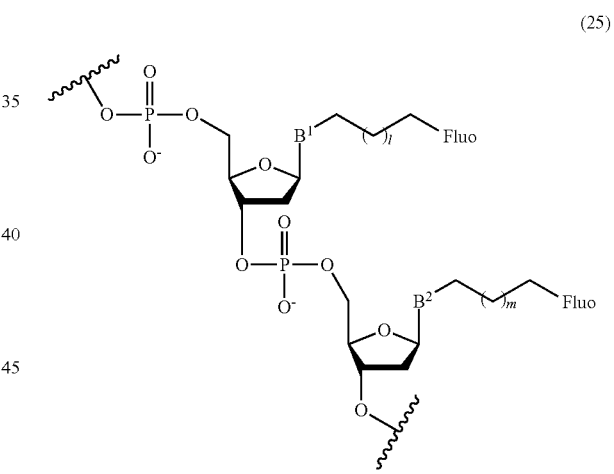
(25)

In the formula (25), the bases ($B^1$ and $B^2$) of contiguous nucleotides each are linked to one dye (Fluo). The site at which each base binds to a linker is not particularly limited. For example, each base is linked to a linker at one position selected from the 4-position, the 5-position, and the 6-position of pyrimidine and the 2-position, the 3-position, the 6-position, the 7-position, and the 8-position of purine. The two linkers each have one base linkage site and are linked to a dye at the other end thereof. The method to be employed for linking them to bases or dyes is not only a bond formed by, for example, a metal-catalyzed reaction, a ring formation condensation reaction, or a Michael addition reaction to a double bond or a triple bond but also, for example, an amide bond, an ester bond, a disulfide bond, or a bond formed by, for instance, an imine formation reaction. With respect to the linkers, the lengths (l and m) are arbitrary, and they may contain a single bond, a double bond, a triple bond, an amide bond, an ester bond, a disulfide bond, amine, imine, an ether bond, a thioether bond, or a thioester bond. Furthermore, it is preferable that the linkers not prevent the exciton effect from being caused by dimerization. Preferably, the dye to be used is one that exhibits an exciton effect by dimerization. The site at which the dye is linked to a linker is any portion thereof. The formula (25) shows deoxyribonucleotide, which is a partial structure of DNA, but instead of that, the nucleic acid skeleton may be ribonucleotide (RNA) as well as sugar-modified nucleic acid such as 2'O-methyl RNA or 2'-fluoro DNA, phosphoric acid modified nucleic acid such as phosphorothioate nucleic acid, or functional nucleic acid such as PNA or LNA (BNA).

When the aforementioned compound or nucleic acid (for instance, labeled nucleic acid of the present invention) has an isomer such as a tautomer or a stereoisomer (ex. a geometric isomer, a conformer, or an optical isomer), any isomer can be used for the present invention. The salt of the compound or nucleic acid may be an acid addition salt but may be a base addition salt. Furthermore, the acid that forms the acid addition salt may be an inorganic acid or an organic acid, and the base that forms the base addition salt may be an inorganic base or an organic base. The inorganic acid is not particularly limited. Examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodic acid, perfluoric acid, perchloric acid, perbromic acid, and periodic acid. The organic acid also is not particularly limited. Examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited. Examples thereof include ammonium hydroxide, alkali metal hydroxide, alkaline earth metal hydroxide, carbonate, and hydrogen carbonate. More specific examples include sodium hydroxide, potassium hydroxide, potassium carbonate, sodium carbonate, sodium bicarbonate, potassium hydrogencarbonate, calcium hydroxide, and calcium carbonate. The organic base also is not limited. Examples thereof include ethanolamine, triethylamine, and tris(hydroxymethyl)aminomethane. The method of producing salts thereof also is not particularly limited. They can be produced by a method in which, for example, the acids or bases as described above are added suitably to the electron donor/receptor binding molecule by a known method. Furthermore, when, for example, the substituent has an isomer, any isomer can be used. For instance, in the case of a "naphthyl group", it may be a 1-naphthyl group or a 2-naphthyl group.

Furthermore, in the present invention, the alkyl group is not particularly limited. Examples thereof include a methyl group, an ethyl group, an n-propyl group, an isopropyl group, an n-butyl group, an isobutyl group, a sec-butyl group, and a tert-butyl group, as well as groups (for example, an alkylamino group and an alkoxy group) containing alkyl groups in their structures. Moreover, the perfluoroalkyl group is not particularly limited. Examples thereof include perfluoroalkyl groups derived from a methyl group, an ethyl group, an n-propyl group, an isopropyl group, an n-butyl group, an isobutyl group, a sec-butyl group, and a tert-butyl group, as well as groups containing perfluoroalkyl groups in their structures (for example, a perfluoroalkylsulfonyl group and a perfluoroacyl group). In the present invention, the acyl group is not particularly limited. Examples thereof include a formyl group, an acetyl group, a propionyl group, an isobutyryl group, a valeryl group, an isovaleryl group, a pivaloyl group, a hexanoyl group, a cyclohexanoyl group, a benzoyl group, and an ethoxycarbonyl group, as well as groups containing acyl groups in their structures (for example, an acyloxy group and an alkanoyloxy group). In the present invention, carbonyl carbon is included in the carbon number of the acyl group. For example, an alkanoyl group (an acyl group) with a carbon number of 1 indicates a formyl group. Furthermore, in the present invention, "halogen" denotes an arbitrary halogen element, and examples thereof include fluorine, chlorine, bromine, and iodine. In the present invention, the protecting group of an amino group is not particularly limited. Examples thereof include a trifluoroacetyl group, a formyl group, a C1-6alkyl-carbonyl group (for example, acetyl and ethylcarbonyl), a C1-6alkyl sulfonyl group, a tert-butyloxycarbonyl group (hereinafter also referred to as "Boc"), a benzyloxycarbonyl group, an allyloxycarbonyl group, a fluorenylmethyloxy carbonyl group, an arylcarbonyl group (for example, phenylcarbonyl and naphthylcarbonyl), an arylsulfonyl group (for example, phenylsulfonyl and naphthylsulfonyl), a C1-6 alkyloxycarbonyl group (for example, methoxycarbonyl and ethoxycarbonyl), a C7-10 aralkylcarbonyl group (for example, benzylcarbonyl), a methyl group, and an aralkyl group (for example, benzyl, diphenylmethyl, and trityl group). These groups may be substituted with, for example, one to three halogen atoms (for example, fluorine, chlorine, or bromine) or nitro groups. Specific examples thereof include a p-nitrobenzyloxycarbonyl group, a p-chlorobenzyloxycarbonyl group, a m-chlorobenzyloxycarbonyl group, and a p-methoxybenzyloxycarbonyl group. In the present invention, the protecting group of a hydroxy group (including one capable of being deprotected with acid) is not particularly limited. Examples thereof include a dimethoxytrityl group, a monomethoxytrityl group, and a pixyl group.

Particularly preferred examples of the compound or nucleic acid (the labeled nucleic acid of the present invention) include those represented by chemical formulas, described later in the section of Example, 102 to 106, 110, 113, 114, 116 to 118, 120, 121, 122, 123, 124, ODN1, ODN2, ODN3, ODN4, ODN5, ODN6, ODN7, ODN8, ODN9, ODN10, ODN (anti4.5S), and ODN (antiB1), as well as geometric isomers, stereoisomers and salts thereof. Especially, compounds 110, 113, 114, 116~118, 120, 121, 122, 123, 124, ODN1, ODN2, ODN3, ODN4, ODN5, ODN6, ODN7, ODN8, ODN9, ODN10, ODN (anti4.5S), and ODN (antiB1) are particularly good in, for example, nucleic acid detection sensitivity since thiazole orange and DNA are covalently bonded with a unique structure. Furthermore, compounds 110, 113, 117, 118, 120, 121, 122, 123, 124, ODN1, ODN2, ODN3, ODN4, ODN5, ODN9, ODN (anti4.5S) and ODN (antiB1) that contain two thiazole orange structures in one molecule can be used further effectively as a fluorescence primer of a single-stranded DNA that suppresses the fluorescence in a single-stranded state and has fluorescence intensity that is increased by forming a double helix with a complementary DNA or RNA.

Next, the labeling substance of the present invention is described. The labeling substances mentioned below each can be used as the labeled primer (labeled nucleic acid) of the present invention.

That is, the labeling substance is:

(i) a labeling substance that emits fluorescence, with two planar chemical structures contained in one molecule, which exist not in the same plane but with a certain angle formed therebetween, being located so as to be arranged in the same plane when the molecule undergoes intercalation into or groove binding to nucleic acid, (ii) a labeling substance formed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to nucleic acid, or (iii) a complex labeling substance having, as a characteristic chemical structure, a chemical structure of at least two dye molecules contained in one molecule, with the at least two dye molecules not exhibiting fluorescence emission due to the exciton effect obtained when they aggregate in parallel to each other but exhibiting fluorescence emission, with the aggregation state being resolved when the molecules undergo intercalation into or groove binding to nucleic acid.

In the case of item (ii) or (iii), it is preferable that the dye molecules each be the molecule described in item (i). Furthermore, in the case of item (iii), it is preferable that the complex labeling substance have a structure in which at least two dye molecules are bonded to a linker molecule bonded to a nucleic acid to be labeled, with an additional linker molecule being interposed therebetween so as to have a branched structure, or are bonded directly thereto with no additional linker molecule being interposed therebetween.

The labeling substance of the present invention is preferably a compound of the present invention, where the atomic groups $Z^{11}$ and $Z^{12}$ exhibit fluorescence, a tautomer or stereoisomer thereof, or salts thereof, or nucleic acid of the present invention. For example, in the compound or nucleic acid of the present invention, since $Z^{11}$ and $Z^{12}$ are atomic groups that exhibit the exciton effect, the fluorescence increases when a double helix structure is formed and thereby the double helix structure can be detected further effectively. However, in the compound or nucleic acid of the present invention, even when $Z^{11}$ and $Z^{12}$ are not atomic groups that exhibit the exciton effect or even when only one atomic group (dye) that exhibits fluorescence has been introduced into one molecule, it can be used as a labeling substance, for example, for nucleic acid, and the double helix structure also can be detected effectively. Examples of the form of the labeling substance according to the present invention include the form of a fluorescence primer of a single-stranded nucleic acid. However, it is not limited thereto and it may have any form such as labeled mononucleotide, labeled oligonucleotide, or double-stranded nucleic acid.

The labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a nucleic acid of the present invention, a compound of the present invention, where $Z^{11}$ and $Z^{12}$ each are an atomic group that exhibits fluorescence, a tautomer or stereoisomer thereof, or a salt thereof.

A labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a nucleic acid of the present invention, a compound of the present invention, where $Z^{11}$ and $Z^{12}$ each are an atomic group that exhibits fluorescence, a tautomer or stereoisomer thereof, or a salt thereof with a linker molecule bonded to at least one base molecules or molecules forming the main chain that are contained in mononucleotide, oligonucleotide, nucleic acid, or a nucleic acid analog, or a labeling substance.

A labeling substance of the present invention is, for example, labeled mononucleotide, labeled oligonucleotide, labeled nucleic acid, or a labeled nucleic acid analog, wherein the labeling substance is a labeling substance labeled with any one of items (i) to (iii), a nucleic acid of the present invention, a compound of the present invention, where $Z^{11}$ and $Z^{12}$ each are an atomic group that exhibits fluorescence, a tautomer or stereoisomer thereof, or a salt thereof with a linker molecule bonded to a carbon atom in the 5-position of a pyrimidine nucleus or a carbon atom in the 8-position of a purine nucleus of at least one base molecule contained in mononucleotide, oligonucleotide, nucleic acid, or a nucleic acid analog.

[Method of Producing Compound and Labeled Primer]

In the present invention, the methods of producing the compound, nucleic acid, and labeled primer (labeled nucleic acid) are not particularly limited, and known synthesis methods (production methods) can be used suitably. In the case of a compound represented by the formula (21), as an example, it may be produced by a production method including: a step of reacting tris(2-aminoethyl)amine with a compound represented by the following formula (26) after the carboxyl group of the compound is activated; a step of protecting an amino group: and a step of carrying out a reaction for protecting the hydroxy group present in the compound obtained above with a protecting group and a reaction for adding phosphoric acid or a phosphoramidite group to the hydroxy group present in the compound obtained above.

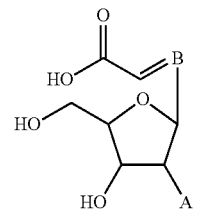

(26)

In the formula (26), A denotes a hydrogen atom or a hydroxy group and B denotes a residue of adenine, guanine, cytosine, thymine, or uracil.

For example, the following production method (synthesis method) can be used for the production of a compound, nucleic acid, or labeled primer (labeled nucleic acid) according to the present invention. That is, a method, in which an active amino group contained in DNA and an activated carboxyl group in a labeling agent are reacted with each other in a buffer solution, has been used widely as an easy DNA labeling method. This method can be used for the production of both the compound and the nucleic acid of the present invention, and can be used particularly for introduction of a linker or a dye. Examples of the method of introducing an amino group include a method using an amino modifier phosphoramidite available from GLEN RESEARCH.

The atomic groups $Z^{11}$ and $Z^{12}$ each can be converted, for example, from a protecting group to a hydrogen atom (i.e. a protecting group is removed), and further the hydrogen atom can be substituted with an atomic group (dye) having fluorescence. The method of removing the protecting group is not particularly limited, and a known method can be used suitably. The method of substituting with an atomic group (dye) having fluorescence also is not particularly limited. For example, a compound or nucleic acid of the present invention in which $Z^{11}$ and $Z^{12}$ are each a hydrogen atom may be reacted suitably with a fluorescence molecule (dye). For instance, it is preferable that at least one of $Z^{11}$ and $Z^{12}$ be an active amino group, since it tends to react with a fluorescence molecule (dye). More preferably, both of $Z^{11}$ and $Z^{12}$ are active amino groups. The fluorescence molecule (dye) also is not particularly limited and may be, for example, a compound represented by any one of the formulae (7) to (9) (where $R^{11}$ and $R^{12}$ are each a hydrogen atom or a lower alkyl group, or a carboxypolymethylene group). Furthermore, in the case of nucleic acid (polynucleotide, polynucleoside, oligonucleotide, or oligonucleoside), the step of removing a protecting group and the step of substituting with an atomic group (dye) having fluorescence may be carried out before polymerization (nucleic acid synthesis) or may be carried out after that. For example, from the viewpoint of preventing a dye portion from being damaged in the synthesis process, it is preferable that an atomic group (dye) having fluorescence be introduced after polymerization (nucleic acid synthesis).

As described above, the dye is not particularly limited and any dyes can be used. For example, it is preferably cyanine dye and particularly preferably thiazole orange. The cyanine dye has a chemical structure in which, for example, two heterocycles having hetero atoms are linked to each other with a methine linker. It is possible to synthesize fluorescent dyes with various excitation/emission wavelengths by, for example, changing the type of the heterocycles or the length of the methine linker, or introducing a substituent into the heterocycles. Furthermore, the introduction of a linker for introducing DNA also is relatively easy. Thiazole orange hardly emits fluorescence in water but emits strong fluorescence through an interaction with DNA or RNA. Conceivably, the interaction between dye molecules is prevented by an interaction with nucleic acid and the rotation around the methine linker located between the two heterocycles of dye molecules is prevented, which leads to an increase in fluorescence intensity. The method of using a thiazole orange dye is well known. It can be used with reference to, for example, H. S. Rye, M. A. Quesada, K. Peck, R. A. Mathies and A. N. Glazer, High-sensitivity two-color detection of double-stranded DNA with a confocal fluorescence gel scanner using ethidium homodimer and thiazole orange, Nucleic Acids Res., 1991, 19, 327-33; and L. G. Lee, C. H. Chen and L. A. Chiu, Thiazole orange: a new dye for reticulocyte analysis, Cytometry, 1986, 7, 508-17.

In the present invention, as described above, the basic skeleton of the compound, nucleic acid, or labeled primer (labeled nucleic acid) is not particularly limited. It may be, for example, any one of oligonucleotide, modified oligonucleotide, oligonucleoside, modified oligonucleoside, polynucleotide, modified polynucleotide, polynucleoside, modified polynucleoside, DNA, modified DNA, RNA, modified RNA, LNA, and PNA (peptide nucleic acid), or another structure. DNA, modified DNA, RNA, or modified RNA is preferable as the basic skeleton, since it makes synthesis easy and also makes, for instance, substitution with a dye (introduction of a dye molecule) easy. The method of introducing a dye molecule into LNA or PNA is not particularly limited and a known method can be used suitably. Specifically, for example, Analytical Biochemistry 2000, 281, 26-35. Svanvik, N., Westman, G., Wang, D., Kubista, M. (2000) Anal Biochem. 281, 26-35. Hrdlicka, P. J., Babu, B. R., Sorensen, M. D., Harrit, N., Wengel, J. (2005) J. Am. Chem. Soc. 127, 13293-13299 can be referred to.

A method of synthesizing nucleic acid having, as a basic skeleton, oligonucleotide, modified oligonucleotide, oligonucleoside, modified oligonucleoside, polynucleotide, modified polynucleotide, polynucleoside, modified polynucleoside, DNA, modified DNA, RNA, or modified RNA is well known. For example, it can be synthesized by a so-called phosphoramidite method. The phosphoramidite reagent to serve as a raw material thereof also can be synthesized easily by a known method. When the nucleic acid of the present invention is DNA, particularly short oligodeoxyribonucleotide, it can be synthesized easily with, for example, an automated DNA synthesizer. Furthermore, it also is possible to synthesize, for example, a long-chain nucleic acid (DNA) by, for instance, PCR. As described above, the position where DNA and a dye molecule are bonded to each other is not particularly limited, but, for example, the 5-position of thymidine is particularly preferable. Triphosphoric acid of a nucleotide derivative with various substituents being extended from the 5-position of thymidine is known to have relatively high efficiency of introduction carried out with DNA polymerase. Accordingly, nucleic acid of the present invention can be synthesized easily, for example, not only when it is short oligodeoxyribonucleotide but also when it is a long-chain DNA.

Particularly, a fluorescence primer (labeled nucleic acid) of the present invention, which is a single-stranded DNA, with, for example, thiazole orange used therein have the following advantages, for example: (1) it can be prepared merely by providing a dye for DNA synthesized with an automated DNA synthesizer, in a buffer solution, and is synthetically easy, and (2) it also is possible to produce a long-chain fluorescence primer by reacting a dye with long-chain DNA prepared enzymatically. Furthermore, it can be excited with light having a relatively long wavelength around, for example, 500 nm.

A primer set of the present invention may include, for example, at least two types of labeled primers of the present invention having fluorescent atomic groups that are different in detection wavelength from each other. With respect to at least two types of target nucleic acid sequences, when labeled primers of the present invention having different fluorescent atomic groups from each other are used together as primers for amplifying them, respectively, the amplification reaction can be carried out in the same reaction solution and amplification of the respective target nucleic acid sequences can be detected at detection wavelengths according to the respective fluorescent atomic groups.

When the primer set of the present invention is used for detecting a mutation site in a target nucleic acid sequence, it is preferable that the primer set include: a labeled primer of the present invention having a sequence completely complementary to a region containing the mutation site in the target nucleic acid sequence; and a primer having a sequence completely complementary to the region containing the mutation site except for the mutation site. A completely complementary primer is referred to as a full-match primer, and a primer complementary to the region except for the mutation site is referred to as a mismatch primer. In the present invention, the mismatch primer may have, for example, a sequence complementary to the region except for not only the mutation site but also several bases (the same applies below). As described above, when using a mismatch primer together, the full-match primer is prevented from, for example, hybridizing with a mismatch region in a template, and thereby amplification can be carried out with a higher specificity.

[Nucleic Acid Amplification Method]

The nucleic acid amplification methods of the present invention include the following first nucleic acid amplification method and second nucleic acid amplification method.

(1) First Nucleic Acid Amplification Method

The first nucleic acid amplification method of the present invention is a method of amplifying a target nucleic acid sequence in a nucleic acid sample and is characterized by including the following steps (A) and (B):

(A) a step of preparing the nucleic acid sample, and
(B) a step of amplifying the target nucleic acid sequence in the nucleic acid sample using a primer of the present invention or a primer set of the present invention.

The nucleic acid amplification methods of the present invention are not limited as long as a labeled primer of the present invention or a primer set of the present invention including the same is used, and other conditions or steps are not limited. For example, the conditions for nucleic acid amplification can be set suitably according to the type of the nucleic acid amplification method to be employed or the sequence information of the target nucleic acid sequence to be amplified.

According to the nucleic acid amplification methods of the present invention, since a labeled primer of the present invention or a primer set of the present invention including the same is used, the occurrence of amplification of a target nucleic acid sequence can be judged, for example, by merely detecting the fluorescence intensity of a nucleic acid amplification reaction solution. This is because of the following reasons, for example. When the primer hybridizes to, for example, DNA or RNA containing a target nucleic acid sequence, a double-stranded nucleic acid is formed and thereby the atomic group (dye) of the labeled primer is subjected to intercalation into or group binding to the double-stranded nucleic acid. In this case, since, for example, the exciton effect of the atomic group (dye) as described above does not occur, the atomic group emits fluorescence. On the other hand, since the exciton effect occurs when it does not hybridize, the atomic group does not emit fluorescence. Therefore, for example, when the primer does not hybridize to a template or when no amplification occurs, the atomic group emitting fluorescence is not found or the number thereof does not increase. Accordingly, when the fluorescence intensity is detected and has increased, it can be judged that the target nucleic acid sequence has been amplified, while when the fluorescence intensity is detected and has not increased, it can be judged that the target nucleic acid sequence has not been amplified.

The method of detecting the amplified target nucleic acid sequence can be illustrated conceptually with FIG. 1. FIG. 1(A) (the left diagram indicated with "Non-hybrid") shows a primer quenched by the exciton effect, and FIG. 1(B) (the right diagram indicated with "Hybrid") shows a primer that forms a double strand to be subjected to intercalation and emits fluorescence. In FIG. 1, numeral 1 denotes a primer (fluorescence primer) of the present invention, numeral 2 indicates an atomic group (dye) that exhibits fluorescence, numeral 1' denotes a complementary strand to the primer (fluorescence primer) 1, numeral 3 indicates a double-stranded nucleic acid formed of the primer 1 and the complementary strand 1'. In the upper part of FIG. 1, an electron transition diagram is shown. The term "Allowed" denotes allowable transition, while the term "Forbidden" denotes forbidden transition. The term "Emissive" denotes that fluorescence can be emitted, and the term "Non-emissive" denotes that theoretically, fluorescence cannot be emitted. That is, conceivably, in the single-stranded state (FIG. 1(A)), the dyes 2 in the ground state aggregate together to interact with each other according to the exciton coupling theory and the excitation state of the dye aggregate is divided into two energy levels, so that the emission is suppressed. Since the emission from a low energy level is prohibited theoretically, the singlet excitation state of the aggregate remains in a low emission state. On the other hand, conceivably, when the primer hybridizes to form a double strand (FIG. 1(B)), the dyes 2 undergo intercalation into or groove binding to double-stranded nucleic acid 3 and thereby the exciton coupling is dissolved, so that fluorescence is emitted. FIG. 1 is a schematic view that conceptually shows an example of a mechanism of detecting a target nucleic acid according to the present invention. The present invention is not limited by FIG. 1 and the description thereof. In the exciton effect, the fluorescence emission can be controlled by regulating the distance between two dyes. When this system is attached to DNA for discriminating a sequence, sequence-selective fluorescence emission can be obtained. In the nucleic acid amplification method, nucleic acid detection method, mutation detection method, or kits of the present invention, hybridization can be detected by, for example, irradiating a sample with visible light from the lower side thereof, and even visually it can be discriminated clearly. Furthermore, in the present invention, hybridization can be observed in a container such as a fluorescent cell, a microplate, a gel, a capillary, or a plastic tube. Moreover, in the present invention, for example, hybridization can be observed from immediately after mixing with the target nucleic acid.

The fluorescence intensity may be detected in parallel with the nucleic acid amplification reaction in step (B) continuously or intermittently or may be detected after completion of step (B). When the fluorescence intensity is to be detected after the reaction completion in step (B), it is preferable that it also be detected before the reaction start in step (B) as a background. The fluorescence intensity can be detected by, for example, irradiating a reaction solution with visible light, and it also is possible to observe it in a container such as a fluorescence cell, a microplate, a gel, a capillary, or a plastic tube. Furthermore, the fluorescence intensity may be detected visually or it also can be detected using, for example, a commercial fluorescence measuring device such as a real-time PCR apparatus.

Examples of the nucleic acid sample include a sample containing DNA or RNA. The DNA may be any one of, for example, genomic DNA, cDNA, and synthetic DNA. The RNA may be any one of, for example, whole RNA, mRNA, rRNA, siRNA, hnRNA, synthetic RNA, spliced RNA, and unspliced RNA.

These nucleic acids can be prepared from biologically derived samples, such as blood, tissues, or cells, or microbially derived samples separated from, for example, food, soil, or drainage. Examples of the biologically derived samples include animals and plants. The method of preparing a nucleic acid sample is not particularly limited and it can be prepared by a conventionally known method. Specific examples of the method include those employing a dissolution treatment using a surfactant, an ultrasonic treatment, shaking agitation using, for example, glass beads, or a French press. Moreover, when endogenous nuclease exists, it is preferable that isolated nucleic acid be purified. The nucleic acid can be purified by, for example, phenol extraction, chromatography, ion exchange, gel electrophoresis, or a density gradient centrifugation method.

In step (B) described above, the nucleic acid amplification method of the present invention can employ, for example, at least two types of labeled primers of the present invention having fluorescent atomic groups that differ in detection wavelength from each other. Specifically, when at least two types of target nucleic acid sequences are to be amplified, it is preferable that at least two types of labeled primers of the present invention having different fluorescent atomic groups from each other be used in combination as primers for amplifying the respective target nucleic acid sequences. This, for example, allows at least two types of target nucleic acid sequences to be amplified in one reaction solution and amplification of the respective target nucleic acid sequences to be detected at detection wavelengths according to the respective fluorescent atomic groups.

In the nucleic acid amplification reaction of the present invention, when amplification is performed for detecting a mutation site in a target nucleic acid sequence, it is preferable that, for example, a labeled primer (a labeled full-match primer) of the present invention and a mismatch primer be used in step (B). The labeled primer has a sequence completely complementary to the region containing the mutation site in the target nucleic acid sequence. The mismatch primer is a primer having a sequence completely complementary to the region containing the mutation site except for the mutation site. In this manner, when a mismatch primer is allowed to be present together, for example, the full-match primer is prevented from hybridizing to the mismatch region in a template, which makes it possible to perform amplification with higher specificity. The mismatch primer may be, for example, an unlabeled primer or a labeled primer of the present invention.

As described above, the nucleic acid amplification method of the present invention is not limited by the type of the nucleic acid amplification reaction to be employed. It can be used for, for example, a PCR method as well as isothermal amplification methods such as an SDA method, a modified SDA method, a NASBA method, a LAMP method, an ICAN method, a self-sustained sequence replication method, a TMA method, a Q-beta replicase method, and a SMAP method. Hereinafter, the nucleic acid amplification method of the present invention using an isothermal amplification method is referred to as an "isothermal amplification method of the present invention", and a nucleic acid amplification method of the present invention using PCR is referred to as a "PCR method of the present invention".

Isothermal Amplification Method

The isothermal amplification method of the present invention is a method of carrying out a nucleic acid amplification reaction isothermally as described above. The conditions for the nucleic acid amplification reaction in step (B) are not particularly limited and can be determined suitably by persons skilled in the art. Preferably, the reaction temperature is set at, for example, a temperature around the melting temperature (Tm) of the primer or lower. Further preferably, the stringency level is set in view of the melting temperature (Tm) of the primer. Specific examples of the reaction temperature include around 20° C. to around 75° C., preferably around 35° C. to around 65° C.

The isothermal amplification method of the present invention is described using, as examples, a method in which an asymmetric primer set is used and a method in which a symmetrical primer set is used, as described above. However, the present invention is not limited thereto.

SMAP Method

Among nucleic acid amplification methods, the SMAP method can amplify a target nucleic acid sequence with excellent specificity, for example. Accordingly, the SMAP method makes it possible to judge, for example, the presence or absence of a mutation in a gene, particularly the presence or absence of one base mutation or the presence or absence of base deletion or base insertion by gene amplification. Therefore it is considered that the use of the primer set of the present invention allows the SMAP method to be carried out with, for example, higher sensitivity and higher precision.

As described above, the primer set of the asymmetric type is a primer set having a pair of primers of an asymmetric type in which one of the primers is different in morphology from the other. Preferably, it is used particularly for the SMAP method. Hereinafter, this primer set also is referred to as a "SMAP primer set".

A specific example of the SMAP primer set includes a pair of primers of an asymmetric type that includes a first primer and a second primer, wherein the first primer contains, in its 3' end portion, a sequence (Ac') that hybridizes to a sequence (A) located in the 3' end portion of the target nucleic acid sequence, and also contains, on the 5' side of the sequence (Ac'), a sequence (B') that hybridizes to a complementary sequence (Bc) to a sequence (B) that is present on the 5' side with respect to the sequence (A) in the target nucleic acid sequence, and the second primer contains, in its 3' end portion, a sequence (Cc') that hybridizes to a sequence (C) located in the 3' end portion of a complementary sequence to the target nucleic acid sequence, and also contains, on the 5' side of the sequence (Cc'), a folded sequence (D-Dc') that contains, on the same strand, two nucleic acid sequences that hybridize to each other.

Figure 45:
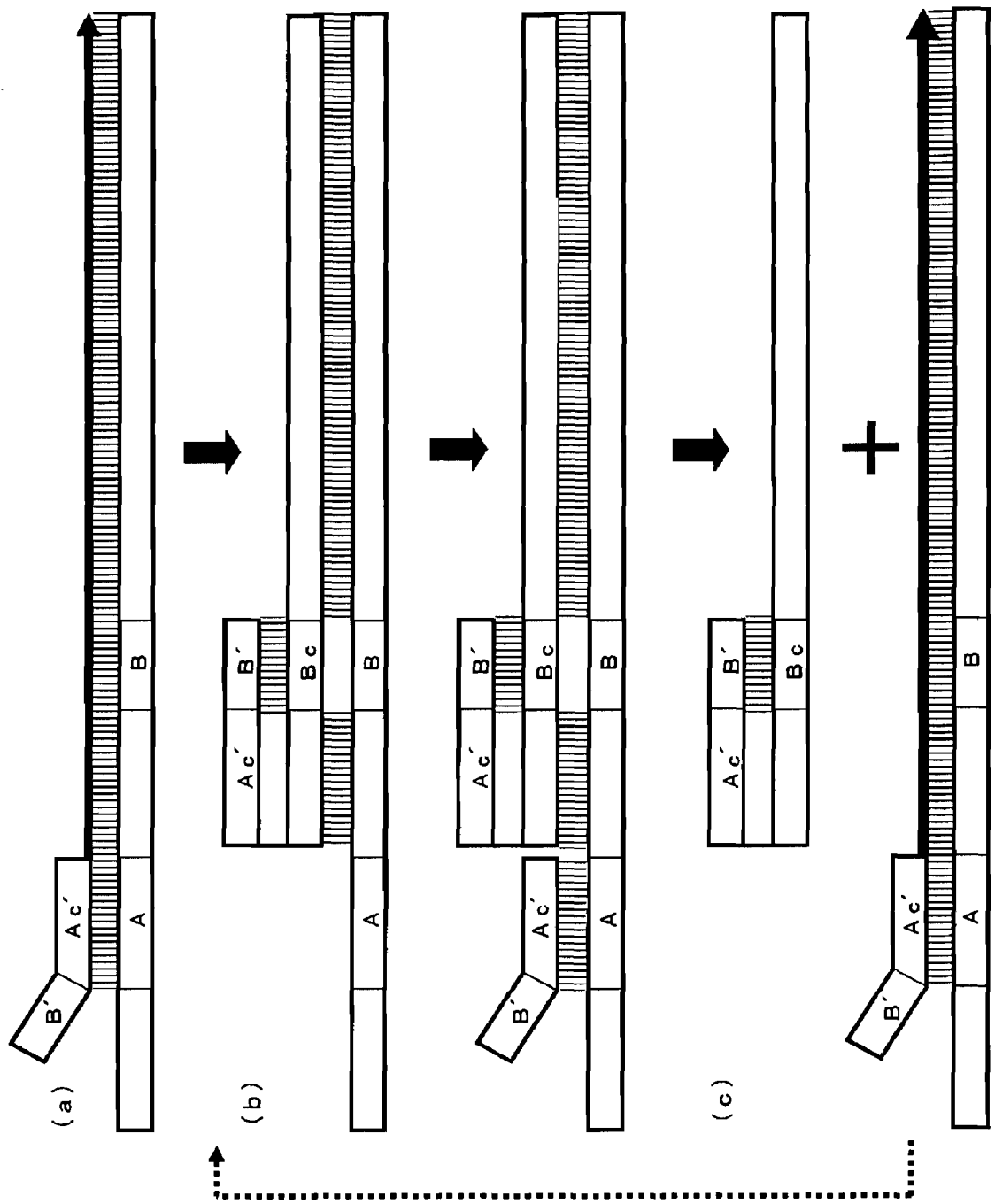
FIG. 45 is a schematic diagram showing the mechanism of action of nucleic acid synthesis using a first primer in the SMAP method of the present invention.

FIG. 45 schematically shows the action mechanism of nucleic acid synthesis to be conducted using the first primer. First, a target nucleic acid sequence contained in a nucleic acid to serve as a template is determined. Then the sequence (A) that is located in the 3' end portion of the target nucleic acid sequence as well as the sequence (B) that is present on the 5' side with respect to the sequence (A) are determined. The first primer contains the sequence (Ac') and further contains the sequence (B') on the 5' side thereof. The sequence (Ac') hybridizes to the sequence (A) while the sequence (B') hybridizes to the complementary sequence (Bc) to the sequence (B). In this case, the first primer may contain an intervening sequence that does not affect the reaction, between the sequence (Ac') and the sequence (B'). Annealing of such a primer to the template nucleic acid results in a state where the sequence (Ac') of the primer has hybridized to the sequence (A) of the target nucleic acid sequence (FIG. 45(a)). When a primer extension reaction occurs in this state, a nucleic acid containing the complementary sequence to the target nucleic acid sequence is synthesized. Then the sequence (B') that is present on the 5' end side of the nucleic acid thus synthesized hybridizes to the sequence (Bc) that is present in the nucleic acid. This allows a stem-loop structure to be formed in the 5' end portion of the nucleic acid synthesized as described above. As a result, the sequence (A) located on the template nucleic acid becomes a single strand and then another primer having the same sequence as that of the preceding first primer hybridizes thereto (FIG. 45(b)). Thereafter, an extension reaction occurs from the newly hybridized first primer due to the strand displacement reaction. At the same time, the nucleic acid synthesized previously is dissociated from the template nucleic acid (FIG. 45(c)).

In the action mechanism described above, the phenomenon that the sequence (B') hybridizes to the sequence (Bc) typically occurs due to the presence of the complementary regions on the same strand. Generally, when a double-stranded nucleic acid is dissociated into a single strand, partial dissociation starts from the ends thereof or from the relatively unstable portions other than the ends. In the double-stranded nucleic acid produced through the extension reaction caused by the above-mentioned first primer, base pairs located in the end portion are in a state of equilibrium between dissociation and binding at relatively high temperatures and thereby a double strand is retained as a whole. In such a state, when a sequence complementary to the dissociated portion located at the end is present on the same strand, a stem-loop structure can be formed in a metastable state. This stem-loop structure does not exist stably. However, another identical primer binds to the complementary strand portion (the sequence (A) on the template nucleic acid) exposed due to the formation of the stem-loop structure, and thereby a polymerase causes the extension reaction immediately. Accordingly, while the strand synthesized previously is displaced and thereby is released, a new double-stranded nucleic acid can be produced at the same time.

The design criteria for the first primer according to a preferred aspect of the present invention are as follows. First, in order for a new primer to anneal to the template nucleic acid efficiently after a complementary strand to the template nucleic acid is synthesized through the extension of the primer, it is necessary to allow the sequence (A) portion located on the template nucleic acid to be a single strand through the formation of the stem-loop structure at the 5' end of the complementary strand synthesized as described above. For that purpose, a ratio of (X−Y)/X is important. That is a ratio of the difference (X−Y) to the number X, wherein X denotes the number of bases contained in the sequence (Ac') and Y indicates the number of bases contained in the region flanked by the sequence (A) and the sequence (B) in the target nucleic acid sequence. However, the portion that is present on the 5' side with respect to the sequence (A) on the template nucleic acid and that is not associated with the hybridization of the primer is not required to be a single strand. Furthermore, in order for a new primer to anneal to the template nucleic acid efficiently, it also is necessary that the above-mentioned stem-loop structure be formed efficiently. For the efficient formation of the stem-loop structure, i.e. for efficient hybridization between the sequence (B') and the sequence (Bc), the distance (X+Y) between the sequence (B') and the sequence (Bc) is important. Generally, the optimal temperature for the primer extension reaction is a maximum of around 72° C. It is difficult to dissociate the extended strand over a long region at such low temperatures. Therefore, conceivably, in order for the sequence (B') to hybridize to the sequence (Bc) efficiently, it is preferable that a smaller number of bases exist between both the sequences. On the other hand, conceivably, in order for the sequence (B') to hybridize to the sequence (Bc) to allow the sequence (A) portion located on the template nucleic acid to be a single strand, it is preferable that a larger number of bases exist between the sequence (B') and the sequence (Bc).

From such factors as described above, the aforementioned first primer according to a preferred embodiment of the present invention is designed so that the ratio (X−Y)/X is preferably at least −1.00, more preferably at least 0.00, further preferably at least 0.05, and still preferably at least 0.10 but is preferably 1.00 or lower, more preferably 0.75 or lower, further preferably 0.50 or lower, and still further preferably 0.25 or lower, in the case where no intervening sequence is present between the sequence (Ac') and the sequence (B') that compose the primer. Moreover, the distance (X+Y) is preferably at least 15, more preferably at least 20, and further preferably at least 30 but is preferably 50 or less, more preferably 48 or less, and further preferably 42 or less.

When an intervening sequence (the number of bases contained therein is Y') is present between the sequence (Ac') and the sequence (B') that compose the primer, the first primer according to the preferred embodiment of the present invention is designed so that the ratio {X−(Y−Y')}/X is preferably at least −1.00, more preferably at least 0.00, further preferably at least 0.05, and still preferably at least 0.10 but is preferably 1.00 or lower, more preferably 0.75 or lower, further preferably 0.50 or lower, and still preferably 0.25 or lower. Moreover, the distance (X+Y+Y') is preferably at least 15, more preferably at least 20, and further preferably at least 30 but is preferably 100 or less, more preferably 75 or less, and further preferably 50 or less.

The aforementioned first primer has a strand length that enables base pairing with the target nucleic acid while allowing the necessary specificity to be maintained under given conditions. The strand length of this primer is preferably 15 to 100 nucleotides and more preferably 20 to 60 nucleotides. The lengths of the sequence (Ac') and the sequence (B') that compose the first primer each are preferably 5 to 50 nucleotides and more preferably 7 to 30 nucleotides. Furthermore, an intervening sequence that does not affect the reaction may be inserted between the sequence (Ac') and the sequence (B') if necessary.

Figure 46:
FIG. 46 is a schematic diagram showing an example of a second primer used in the SMAP method of the present invention.

As described above, the second primer included in the primer set according to the present invention contains, in its 3' end portion, a sequence (Cc') that hybridizes to a sequence (C) located in the 3' end portion of a complementary sequence (the strand located on the opposite side to the strand to which the first primer hybridizes) to the target nucleic acid sequence. The second primer also contains, on the 5' side of the sequence (Cc'), a folded sequence (D-Dc') that contains, on the same strand, two nucleic acid sequences that hybridize to each other. Such a second primer has a structure like the one shown in FIG. 46, for example. However, the sequence and the number of nucleotides of the second primer are not limited to those shown in FIG. 46. The length of the sequence (Cc') of the second primer is preferably 5 to 50 nucleotides and more preferably 10 to 30 nucleotides. On the other hand, the length of the folded sequence (D-Dc') is preferably 2 to 1000 nucleotides, more preferably 2 to 100 nucleotides, further preferably 4 to 60 nucleotides, and still further preferably 6 to 40 nucleotides. The number of nucleotides of the base pairs that are formed through hybridization that occurs in the folded sequence is preferably 2 to 500 bp, more preferably 2 to 50 bp, further preferably 2 to 30 bp, and still further preferably 3 to 20 bp. The nucleotide sequence of the folded sequence (D-Dc') may be any sequence and is not particularly limited. However, it is preferable that the nucleotide sequence be one that does not hybridize to the target nucleic acid sequence. In addition, an intervening sequence that does not affect the reaction may be inserted between the sequence (Cc') and the folded sequence (D-Dc') if necessary.

Figure 47A:
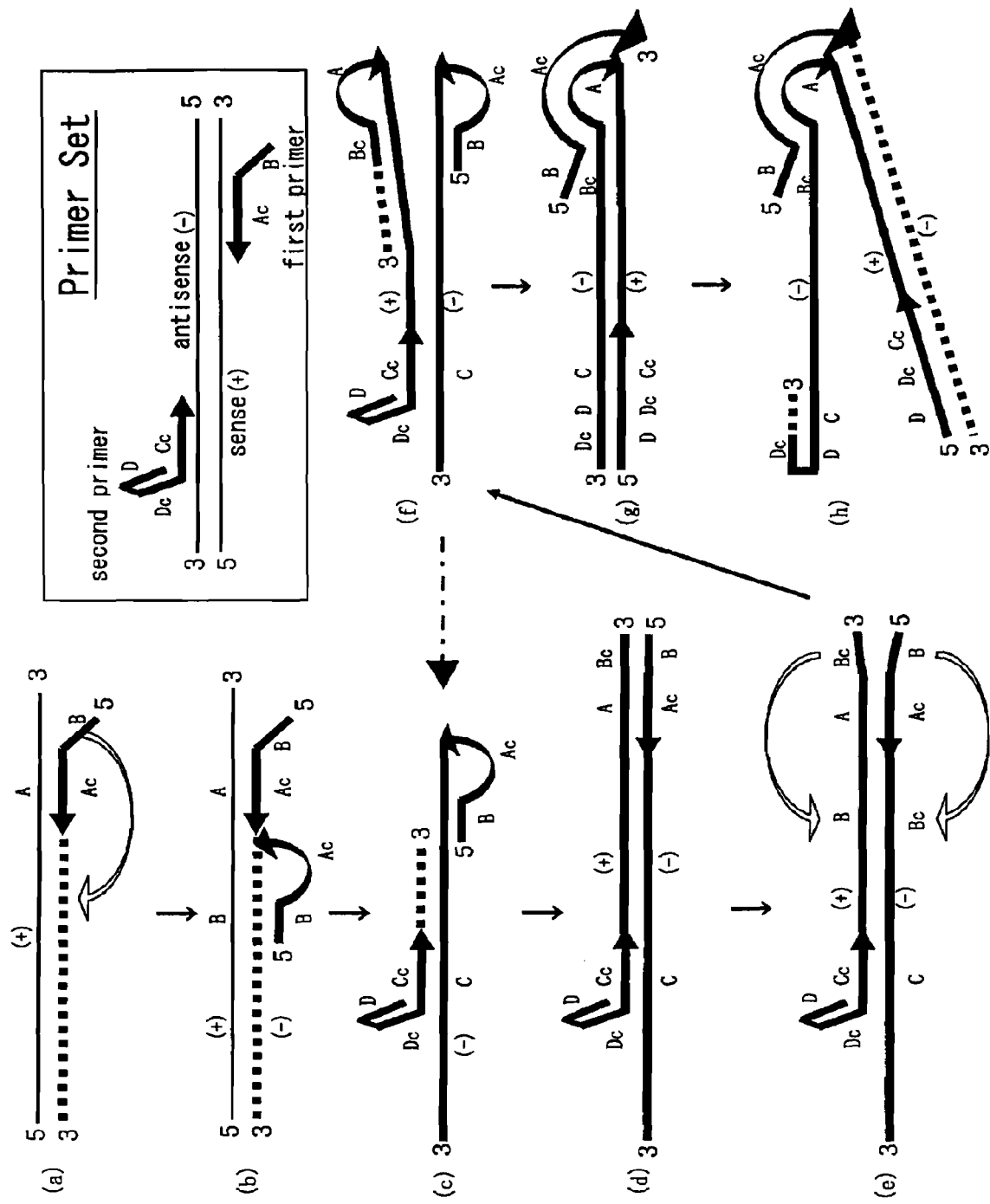
FIG. 47A is a schematic diagram showing the mechanism of action of the SMAP method according to the present invention.
Figure 47B:
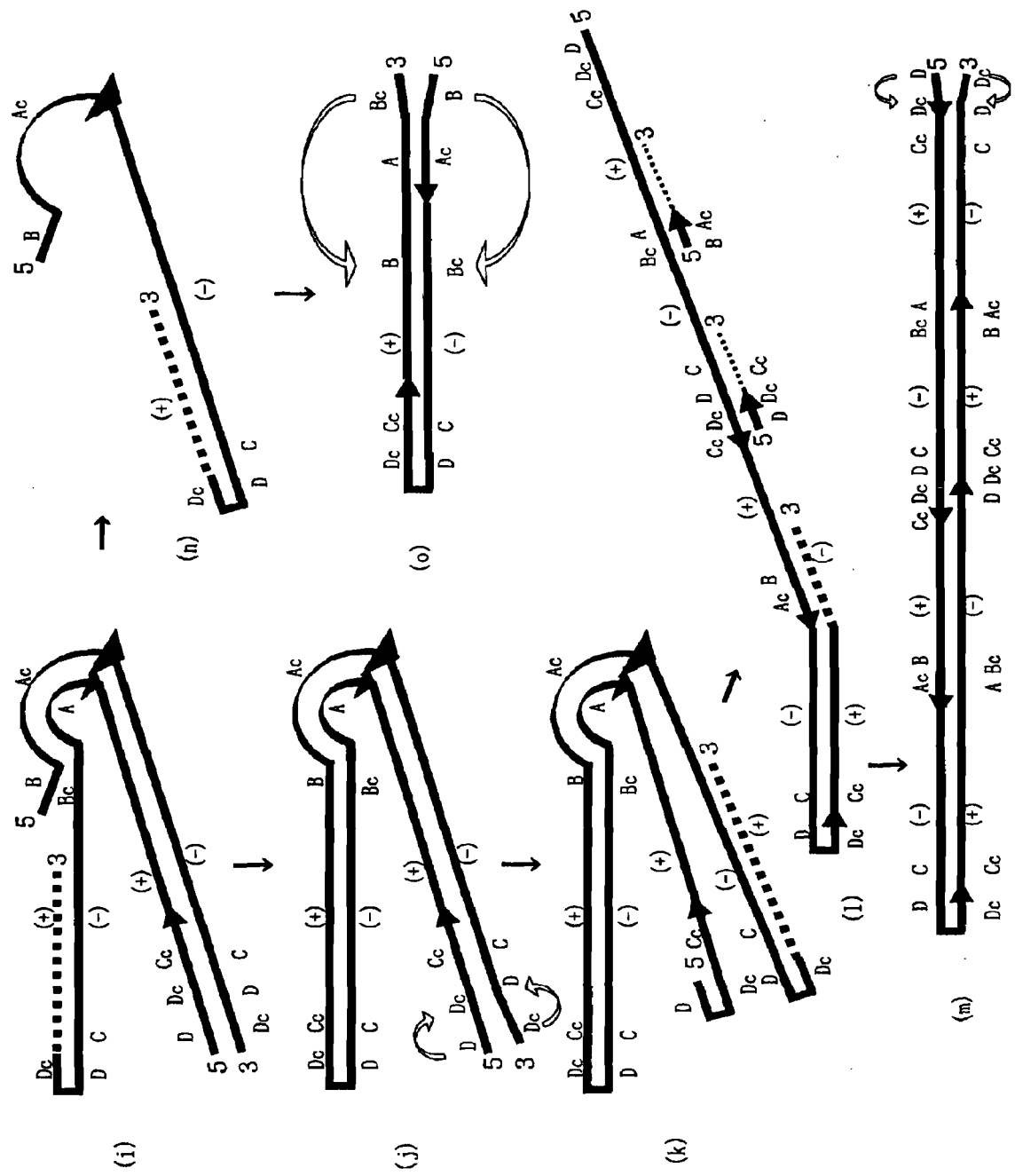
FIG. 47B is a schematic diagram showing the mechanism of action of the SMAP method according to the present invention.

A conceivable action mechanism of the nucleic acid amplification reaction that is caused by the above-mentioned first primer and second primer is described with reference to FIG. 47 (FIGS. 47A and 47B). In FIG. 47, in order to simplify the description, two sequences that hybridize to each other are described as sequences that are complementary to each other. However, the present invention is not limited thereby. First, the first primer hybridizes to a sense strand of a target nucleic acid and thereby the extension reaction of that primer occurs (FIG. 47A(a)). Subsequently, a stem-loop structure is formed on the extended strand (−) and thereby the sequence (A) on the target nucleic acid sense strand is allowed to be a single strand. Then a new first primer hybridizes to the sequence (A) (FIG. 47A(b)). This causes the extension reaction of the primer, and then the extended strand (−) synthesized previously is dissociated. Next, the second primer hybridizes to the sequence (C) located on the dissociated extended strand (−) (FIG. 47A(c)). This causes the extension reaction of the primer, and thereby an extended strand (+) is synthesized (FIG. 47A(d)). Stem-loop structures are formed at the 3' end of the extended strand (+) thus synthesized and at the 5' end of the extended strand (−) (FIG. 47A(e)). Then the extension reaction occurs from the loop end of the extended strand (+) that is the 3' end of the free form and at the same time, the extended strand (−) is dissociated (FIG. 47A(f)). The extension reaction that has occurred from the loop end results in production of a hairpin-type double-stranded nucleic acid to which the extended strand (−) has bound on the 3' side of the extended strand (+) through the sequence (A) and the sequence (Bc). Then the first primer hybridizes to the sequence (A) and the sequence (Bc) (FIG. 47A(g)), and the extension reaction caused thereby allows the extended strand (−) to be produced (FIGS. 47A(h) and 47(i)). Furthermore, the folded sequence that is present at the 3' end of the hairpin-type double-stranded nucleic acid provides the 3' end of the free form (FIG. 47A(h)). Then the extension reaction caused therefrom (FIG. 47B(i)) allows a single-stranded nucleic acid to be produced (FIG. 47B(j)). The single-stranded nucleic acid has the folded sequence at each end thereof and contains the extended strand (+) and the extended strand (−) alternately via the sequences derived from the first and second primers. In this single-stranded nucleic acid, the folded sequence that is present at the 3' end thereof provides the 3' end (the origin of complementary strand synthesis) of the free form (FIG. 47B(k)). Accordingly, the similar extension reaction is repeated and the strand length is doubled per extension reaction (FIGS. 47B(l) and 47B(m)). In the extended strand (−) synthesized from the first primer that has been dissociated in FIG. 47B(i), the folded sequence that is present at the 3' end thereof provides the 3' end (the origin of complementary strand synthesis) of the free form (FIG. 47B(n)). Accordingly, the extension reaction caused therefrom allows stem-loop structures to be formed at both ends and thereby a single-stranded nucleic acid is produced (FIG. 47B(o)). The single-stranded nucleic acid contains the extended strand (+) and the extended strand (−) alternately via the sequences derived from the primers. Similarly in this single-stranded nucleic acid, the formation of a loop at the 3' end provides the origin of complementary strand synthesis successively. Accordingly, the extension reaction therefrom occurs in succession. Thus in the single-stranded nucleic acid that is extended automatically in such a manner, the sequences derived from the first primer and the second primer are contained between the extended strand (+) and the extended strand (−). Therefore each primer can hybridize to cause the extension reaction. This allows the sense strand and the antisense strand of the target nucleic acid to be amplified considerably.

The SMAP primer set of the present invention may include a third primer in addition to the first primer and the second primer. The third primer hybridizes to, for example, the target nucleic acid sequence or the complementary sequence thereto. However, the third primer does not compete with other primers for hybridization to the target nucleic acid sequence or the complementary sequence thereto. In the present invention, the expression "does not compete" denotes that hybridization of the third primer to a target nucleic acid does not hinder other primers from providing origins for complementary strand synthesis.

When the target nucleic acid sequence has been amplified with the first primer and the second primer, the amplification product contains the target nucleic acid sequence and the complementary sequence thereto alternately as described above. The amplification product has, at its 3' end, a folded sequence or a loop structure. It provides the origin of complementary strand synthesis and thereby extension reactions occur successively therefrom. It is preferable that when such an amplification product becomes a single strand partially, the third primer can anneal to the target sequence that is present in the single strand portion. This allows the target nucleic acid sequence contained in the amplification product to be provided with a new origin of complementary strand synthesis. Then an extension reaction occurs therefrom. Thus the nucleic acid amplification reaction is performed much quicker.

The third primer is not limited and may be of one type, or for example, in order to improve the speed and specificity of the nucleic acid amplification reaction, at least two types of third primers may be used simultaneously. Typically, such third primers have, for example, different sequences from those of the first primer and the second primer. However, each of the third primers may hybridize to a region, a part of which is hybridized by the first or second primer, as long as they do not compete with the first or second primer. The strand length of the third primer is preferably 2 to 100 nucleotides, more preferably 5 to 50 nucleotides, and further preferably 7 to 30 nucleotides.

The third primer is intended mainly to provide an auxiliary function to advance the nucleic acid amplification reaction much quicker that is caused by the first primer and the second primer. Hence, it is preferable that the third primer have a lower Tm than that of each 3' end of the first primer and the second primer. Furthermore, it is preferable that the amount of the third primer to be added to the amplification reaction solution be smaller than that of each of the first primer and the second primer to be added thereto, for example.

The third primer to be used herein can be one that allows an origin of complementary strand synthesis to be provided for a loop portion, with a template having a structure capable of forming the loop, as described in, for example, WO 02/24902. The third primer, however, is not limited thereto. That is, it can be any primer that provides an origin of complementary strand synthesis for any site as long as the site is within the target nucleic acid sequence, for example.

In the SMAP primer set, for example, either one of the first primer or the second primer or both of them may be the labeled nucleic acid(s), or the third primer may be the labeled nucleic acid. Either the first primer or the second primer or both of them and the third primer may be the labeled nucleic acids.

When the SMAP method of the present invention is used, for example, for the mutation detection method to be described later, it is preferable that the SMAP primer be designed as follows. That is, preferably, the SMAP primer set is designed so that a nucleic acid sequence having a mutation at a target site (hereinafter referred to as a "mutated nucleic acid sequence") or a nucleic acid sequence having no mutation at the target site (hereinafter referred to as a "wildtype nucleic acid sequence") is a target nucleic acid sequence, and the site where the target mutation occurs is contained in the sequence (A), the sequence (B), or the sequence (C), or is located between the sequence (A) and the sequence (B) or between the sequence (A) and the sequence (C).

When using a primer set designed so that a nucleic acid sequence containing a mutation at the target site (mutated sequence) is a target nucleic acid sequence, for example, the presence of an amplification product after the nucleic acid amplification reaction indicates the presence of the mutated sequence, while the absence of or reduction in the amplification product indicates the absence of the mutated sequence. On the other hand, when using a primer set designed so that a nucleic acid sequence containing no mutation at the target site (wildtype sequence) is a target nucleic acid sequence, for example, the presence of an amplification product after the nucleic acid amplification reaction indicates the absence of the mutated sequence, while the absence of or reduction in the amplification product indicates the presence of the mutated sequence. In this case, the expression "reduction in the amplification product" denotes a reduction in amount of the amplification product obtained as compared to the amount of the amplification product that is obtained when the target nucleic acid sequence is present in the nucleic acid sample.

Preferably, the primer set is designed so that the target site is contained in the sequence (A). In the case of using such a primer set, for example, when the target nucleic acid sequence (for example, a wildtype sequence) is contained in the nucleic acid sample, the first primer anneals to the sequence (A) in the nucleic acid amplification reaction and thereby an amplification product is obtained. On the other hand, when a nucleic acid sequence (for example, a mutated sequence) that is different from the target nucleic acid sequence is contained in the nucleic acid sample, it is difficult for the first primer to anneal to the sequence (A) in the nucleic acid amplification reaction. Accordingly, in this case, no amplification product is obtained or a considerably reduced amount of amplification product is obtained. Preferably, the sequence (Ac') contained in the first primer is a sequence that is complementary to the sequence (A).

Preferably, the primer set is one designed so that, for example, the target site is contained in the sequence (C). In the case of using such a primer set, for example, when the target nucleic acid sequence (for example, a wildtype sequence) is contained in the nucleic acid sample, the second primer anneals to the sequence (C) in the nucleic acid amplification reaction and thereby an amplification product is obtained. On the other hand, when a nucleic acid sequence (for example, a mutated sequence) that is different from the target nucleic acid sequence is contained in the nucleic acid sample, it is difficult for the second primer to anneal to the sequence (C) in the nucleic acid amplification reaction. Therefore, in this case, no amplification product is obtained or a considerably reduced amount of amplification product is obtained. Preferably, the sequence (Cc') contained in the second primer is a sequence that is complementary to the sequence (C).

Preferably, the primer set is one designed so that, for example, the target site is contained in the sequence (B). In the case of using such a primer set, for example, when the target nucleic acid sequence (for example, a wildtype sequence) is contained in the nucleic acid sample, after the first primer anneals to the sequence (A) to cause an extension reaction, a sequence (B') that is contained in the primer hybridizes to a sequence (Bc) located on the extended strand in the nucleic acid amplification reaction. Therefore a stem-loop structure is formed efficiently. This efficient formation of the stem-loop structure allows another first primer to anneal to the template. Accordingly, the action mechanism shown in FIG. 45 proceeds efficiently and thereby an amplification product is obtained. On the other hand, when a nucleic acid sequence (for example, a mutated sequence) that is different from the target nucleic acid sequence is contained in the nucleic acid sample, it is difficult to form the above-mentioned stem-loop structure in the nucleic acid amplification reaction. Thus, the action mechanism shown in FIG. 45 is hindered. As a result, no amplification product is obtained or a considerably reduced amount of amplification product is obtained. Preferably, the sequence (B') contained in the first primer is a sequence identical to the sequence (B).

Preferably, the primer set is one designed so that, for example, the target site is located between the sequence (A) and the sequence (B). In the case of using such a primer set, when the target nucleic acid sequence (for example, a wildtype sequence) is contained in the nucleic acid sample, after the first primer anneals to the sequence (A) to cause an extension reaction, the sequence (B') that is contained in the primer hybridizes to the sequence (Bc) located on the extended strand and thereby a stem-loop structure is formed efficiently in the nucleic acid amplification reaction. This efficient formation of the stem-loop structure allows another first primer to anneal to the template. Accordingly, the action mechanism shown in FIG. 45 proceeds efficiently and thereby an amplification product is obtained. On the other hand, when a nucleic acid sequence (for example, a mutated sequence) that is different from the target nucleic acid sequence is contained in the nucleic acid sample, it is difficult to form the above-mentioned stem-loop structure in the nucleic acid amplification reaction since the distance maintained between the sequence (B') that is contained in the first primer and the sequence (Bc) located on the extended strand is not adequate. Thus, in this case, the action mechanism shown in FIG. 45 is hindered. As a result, no amplification product is obtained or a considerably reduced amount of amplification product is obtained.

Preferably, the primer set is one designed so that the target site is located between the sequence (A) and the sequence (C). In the case of using such a primer set, when the target nucleic acid sequence is contained in the nucleic acid sample (for example, a wildtype sequence), after the first primer anneals to the sequence (A) to cause an extension reaction, the sequence (B') that is contained in the primer hybridizes to the sequence (Bc) located on the extended strand and thereby a stem-loop structure is formed efficiently in the nucleic acid amplification reaction. This efficient formation of the stem-loop structure allows another first primer to anneal to the template. Accordingly, the action mechanism shown in FIG. 45 proceeds efficiently and thereby an amplification product is obtained. On the other hand, when a nucleic acid sequence (for example, a mutated sequence) that is different from the target nucleic acid sequence is contained in the nucleic acid sample, no amplification product is obtained or a considerably reduced amount of amplification product is obtained. For instance, when the nucleic acid sample contains a nucleic acid sequence that is different from the target nucleic acid sequence due to the insertion of a long sequence between the sequence (A) and the sequence (C), the rate (efficiency) of nucleic acid amplification decreases considerably. As a result, no amplification product is obtained or a considerably reduced amount of amplification product is obtained. Furthermore, when the nucleic acid sample contains a nucleic acid sequence that is different from the target nucleic acid sequence due to the deletion of a sequence between the sequence (A) and the sequence (C) and when a part or the whole of the sequence (B) has been lost due to the deletion, the sequence (B') contained in the first primer cannot hybridize onto the extended strand. Accordingly, a stem-loop structure cannot be formed or is difficult to form. Thus, the action mechanism shown in FIG. 45 is hindered. As a result, no amplification product is obtained or a considerably reduced amount of amplification product is obtained. Moreover, when the nucleic acid sample contains a nucleic acid sequence that is different from the target nucleic acid sequence due to the deletion of a sequence between the sequence (A) and the sequence (C) and even when no partial deletion of the sequence (B) is caused by the deletion, the rate (efficiency) of nucleic acid amplification decreases. As a result, no amplification product is obtained or a considerably reduced amount of amplification product is obtained.

LAMP Method

As described above, the primer set of a symmetrical type includes a pair of primers of a symmetrical type in which one of the primers is identical in morphology to the other. Particularly, it is preferable that the primer set be used for the LAMP method. Hereinafter, this primer set also is referred to as a "LAMP primer set".

In the LAMP method, for example, four types of primers are necessary. They recognize six regions, so that a target gene can be amplified. That is, in this method, a first primer anneals to a template strand to cause extension reaction first. Subsequently, the extended strand produced by the first primer separates from the template strand due to the strand displacement reaction caused by a second primer designed upstream from the first primer. At this time, a stem-loop structure is formed in the 5' end portion of the extended strand due to the structure of the first-primer extension product that has been removed. Similar reactions occur in the other strand of the double-stranded nucleic acid or on the 3' end side of the first-primer extension product that has been removed. These reactions are repeated and thereby the target nucleic acid is amplified. The template used in the LAMP method has, for example, at the 3' end and the 5' end on the same strand, regions composed of base sequences complementary to each other in the respective end regions. With this template (also referred to as a "dumbbell-type template nucleic acid"), loops are formed, in which base pairing can occur between the base sequences complementary to each other when they anneal to each other. The LAMP method can be performed according to, for example, WO 00/28082 or WO 01/034838.

PCR Method

In the PCR method, as described above, with the reaction temperature being changed, a target nucleic acid sequence can be amplified through, for example, dissociation of double-stranded nucleic acid, annealing of a primer to the dissociated single strand, and synthesis of nucleic acid from the primer. The conditions for the PCR method are not particularly limited and can be set suitably by persons skilled in the art.

The fluorescence intensity of the primer according to the present invention can be changed effectively by, for example, controlling the exciton interaction in the dye portions bonded thereto. In the present invention, an approach particularly utilizing the exciton interaction makes it possible to obtain sufficiently high quenching ability for serving as an on-off probe and, for example, a number of advantages that are clearly different as compared to conventional assays. The photophysical properties that the primer utilizing the exciton effect exhibits are not only very characteristic but also suitable for designing a new fluorescence DNA primer for DNA sequencing (sequence determination), genotyping (genotype analysis), and gene expression observation.

(2) Second Nucleic Acid Amplification Method

The second nucleic acid amplification method of the present invention is a method of amplifying a target nucleic acid sequence in a nucleic acid sample, wherein the method includes the following steps (A) and (B'):

(A) a step of preparing the nucleic acid sample, and
(B') a step including the following steps (B1') and (B2'):
(B1') a step of amplifying a target nucleic acid sequence in the nucleic acid sample using a primer or a primer set containing a pair of primers; and
(B2') a step of hybridizing a single-stranded nucleic acid sequence amplified in step (B1') to a probe made of a labeled nucleic acid containing at least one of the structures represented by the formulae (16), (16b), (17), (17b), (18), and (18b).

In the second nucleic acid amplification method of the present invention, the structure represented by the formula (16), (16b), (17), (17b), (18), or (18b) is the same labeled structure as those described above, and specific examples thereof also are as described above. In the second nucleic acid amplification method of the present invention, the labeled nucleic acid containing the labeled structure is referred to as a "labeled probe".

With respect to the labeled probe of the present invention, the structure thereof is not particularly limited, as long as it contains the nucleic acid structure. The labeled probe can be designed and produced, for example, in the same manner as in the case of the aforementioned labeled primer. The sequence of the probe is not particularly limited and can be set suitably according to, for example, the sequence of a target nucleic acid sequence to be detected, or information on the sequence around the target nucleic acid sequence in DNA or RNA.

The primer and primer set used in the second nucleic acid amplification method of the present invention are not particularly limited. They can be set suitably according to, for example, the target nucleic acid sequence to be detected or the type of the nucleic acid amplification reaction. Furthermore, the type of the nucleic acid amplification method of the present invention is not particularly limited. Examples thereof include the PCR method and various isothermal amplification methods such as the SMAP method and the LAMP method as described above. It can be carried out in the same manner as in the case of the first nucleic acid amplification method.

According to the second nucleic acid amplification method of the present invention, since the aforementioned labeled probe is used, the occurrence of amplification of, for example, a target nucleic acid sequence can be judged by merely detecting the fluorescence intensity of, for example, a nucleic acid amplification reaction solution. This is achieved, for example, for the following reasons. Since a double-stranded nucleic acid is formed when a probe hybridizes to a nucleic acid sequence complementary thereto, the atomic group (dye) of the labeled primer undergoes intercalation into or groove binding to the double-stranded nucleic acid. In this case, for example, the exciton effect of the atomic group (dye) as described above does not occur, and therefore the atomic group emits fluorescence. On the other hand, since the exciton effect occurs when the hybridization does not occur, the atomic group does not emit fluorescence. Therefore, when, for example, the probe does not hybridize to an amplification product obtained through the nucleic acid amplification reaction or amplification does not occur, no atomic group that emits fluorescence is observed or the number thereof does not increase. Accordingly, with detection of the fluorescence intensity, it can be judged that the target nucleic acid sequence was amplified when the fluorescence intensity increased, while it can be judged that, the target nucleic acid sequence was not amplified when the fluorescence intensity did not increase.

The labeled probe may be added to the reaction solution before the nucleic acid amplification reaction carried out in step (B1') or may be added to the reaction solution after the nucleic acid amplification reaction carried out in step (B1'), for example. In the case of the former, the fluorescence intensity may be detected in parallel with the nucleic acid amplification reaction in step (B1') continuously or intermittently, or may be detected after completion of step (B1'). When the fluorescence intensity is detected after completion of the reaction in step (B1'), it is preferable that it also be detected as a background before the start of the reaction in step (B1'). On the other hand, when step (B1') and step (B2') are carried out separately, it is preferable that, for example, the labeled probe be added to the reaction solution after the nucleic acid amplification reaction carried out in step (B1'). In this case, detection of the fluorescence intensity is carried out, for example, after step (B1'). In this case, it is preferable that the fluorescence intensity also be detected as a background, for example, after step (B1') but immediately before or after addition of the labeled probe. Specific examples of the detection method are as described above.

(1) The probe of the present invention can be used in a liquid phase homogeneous assay (using, for example, a 96-well microplate or capillary).

(2) The probe of the present invention can be used as a PCR probe. It can be used for detection of an amplification curve in a DNA amplification reaction (real-time PCR) or a low-cost method replaced with the TaqMan probe method. It can be used as a primer label or an internally labeled probe.

(3) The probe of the present invention can be used as a trapping probe or labeled probe in a DNA chip. This is a high-throughput system requiring no reagent, and the labeling process and washing process are not required. With this system, human errors can be avoided considerably. It makes it possible to carry out multiple simultaneous (high-throughput) analysis in glass or a solid-phase carrier material replaced therewith (a material to which many specimens can be attached, such as a substrate made of gold, ITO, or copper, diamond, or plastic).

(4) The probe of the present invention can be fixed to a bead, fiber, or hydrogel. It allows a gene to be detected under a semiliquid/semisolid environment. While it has a measurement environment like a liquid, it can be carried like a solid.

(5) The probe of the present invention can be used as a probe for blotting (for example, Southern blot, Northern blot, or dot blot). With the use thereof, only a target gene segment is allowed to emit light and thereby to be detected. According to the method of the present invention, washing is not required after the hybridization operation.

(6) The probe of the present invention can be used as a probe for detection and tracing of intracellular nucleic acid. This allows spatiotemporal analysis of intracellular DNA/RNA to be carried out. A fluorescence microscope and a cell sorter can be used. This can be used for DNA labeling, tracing of transcription/splicing to RNA, and RNAi functional analysis, for example. In the method of the present invention, since washing is not required, it is suitable for tracing of a living cell function.

(7) The probe of the present invention can be used as a probe for fluorescence in situ hybridization (FISH). The method of the present invention allows, for example, a tissue to be dyed. In the method of the present invention, washing is not required, which reduces human error. That is, the probe of the present invention serves as a fluorescent dye that does not emit fluorescence when not recognizing a target biomolecule. Therefore the use thereof can establish bioimaging that does not require a cumbersome washing step. This leads to highly reliable, real-time fluorescence observation with less work.

The effects of the fluorescent probe (labeling substance) of the present invention can include, for example, the following advantages as compared to conventional single-stranded quenching fluorescent probe (for example, a molecular beacon). However, they are mere examples and do not limit the present invention.

(1) It is easy to synthesize when only one type of dye is used.
(2) It is easy to use as a PCR probe when the DNA probe (labeling substance) of the present invention has a free end.
(3) It is not necessary to form a special conformation such as a hairpin structure and therefore sequences that are not associated with sequence recognition, such as a stem sequence, are not required (neither useless sequences nor restrained sequences are contained).
(4) Fluorescent dyes can be introduced into a plurality of sites (desired sites) in the probe.
(5) When at least two dye structures are contained in one molecule, the positional relationship between the dyes is restrained and thereby the S/N ratio (the fluorescence intensity ratio before and after hybridization) is high.

The fluorescence intensity of the probe according to the present invention can be changed effectively by, for example, controlling the exciton interaction in the dye portions bonded thereto. In the present invention, an approach particularly utilizing the exciton interaction makes it possible to obtain sufficiently high quenching ability for serving as an on-off probe and, for example, as described above, a number of advantages that are clearly different as compared to conventional assays. The design of such on-off fluorescence nucleotide is very important for establishment of a bioimaging assay that does not require washing, for example. The photophysical properties that the probe utilizing the exciton effect exhibits are not only very characteristic but also suitable for designing a new fluorescence DNA probe for DNA sequencing (sequence determination), genotyping (genotype analysis), monitoring of DNA conformational transition, and gene expression observation.

Furthermore, with the probe (nucleic acid) of the present invention, when, for example, a target nucleic acid sequence is determined quantitatively, it can be detected immediately that phenomena such as amplification, degradation, and protein binding of the sequence concerned occurred and the amounts of those phenomena also can be determined quantitatively. The following description is directed to such detection and quantitative determination but indicates examples and does not limit the present invention. That is, first, the probe (nucleic acid) of the present invention hybridizes with the target nucleic acid sequence at a certain substance amount ratio and thereby a double strand is formed. The substance amount of the double strand thus formed is directly proportional to the substance amount of the target nucleic acid sequence. Accordingly, measurement of the fluorescence intensity of the double strand allows a target nucleic acid sequence to be detected and the substance amount thereof to be determined quantitatively. In this case, since the probe (nucleic acid) of the present invention is prevented from emitting fluorescence, it does not hinder the measurement of the fluorescence intensity of the double strand, and thus it can be measured correctly.

[Mutation Detection Method]

The mutation detection method of the present invention is a method of detecting the presence or absence of a mutation in a target nucleic acid sequence contained in a nucleic acid sample, wherein the method includes the following steps (a) to (c):

(a) a step of amplifying the target nucleic acid sequence contained in the nucleic acid sample by a nucleic acid amplification method according to the present invention,
(b) a step of measuring fluorescence intensity before and after step (a), and
(c) a step of detecting the presence or absence of a mutation by comparing the fluorescence intensities to each other that are obtained before and after step (a) that have been measured in step (b).

In the mutation detection method of the present invention, as long as the target nucleic acid sequence is amplified by a nucleic acid amplification method using a primer or primer set of the present invention, other conditions and steps are not limited. The method and conditions for measuring the fluorescence intensity can be set suitably according to, for example, the type of the atomic group of the labeled primer according to the present invention. The method of measuring the fluorescence intensity in step (b) is not particularly limited and is the same as described above.

In the present invention, the term "mutation" denotes that a different base (a base pair in the case of double-stranded nucleic acid) as compared to a nucleic acid sequence that serves as a control is present in the nucleic acid sequence. Examples of the mutation include substitution, deletion, and insertion of a base. Example of the control includes a standard base sequence with respect to a specific base sequence, for example, a nucleic acid sequence of a wildtype (also called a normal type) that is considered as a standard genotype.

According to the mutation detection method of the present invention, since a labeled primer of the present invention or a primer set of the present invention including the same is used, the presence or absence of a mutation can be judged by merely detecting the fluorescence intensity of the nucleic acid amplification reaction solution and comparing the fluorescence intensities to each other that are obtained before and after the reaction, in steps (b) and (c). This is because of, for example, the following reasons. When the primer hybridizes to, for example, DNA or RNA containing a target nucleic acid sequence and thereby double-stranded nucleic acid is formed, the atomic group (dye) of the labeled primer undergoes intercalation into or group binding to the double-stranded nucleic acid. In this case, for example, since the exciton effect of the atomic group (dye) as described above does not occur, the atomic group emits fluorescence. On the other hand, when the primer does not hybridize, the exciton effect occurs and thereby the atomic group does not emit fluorescence. Therefore, for example, in the case where one primer is designed as a complementary sequence to a sequence containing a mutation to be detected, when the target nucleic acid sequence of a template has a mutation, the primer hybridizes to the target nucleic acid sequence and thereby nucleic acid synthesis proceeds. As a result, amplification occurs and fluorescence is emitted. However, when the target nucleic acid sequence does not include any mutation, the primer cannot hybridize to the target nucleic acid sequence. As a result, amplification does not occur and fluorescence is not emitted. Therefore when the fluorescence intensity is detected and has increased, it can be judged that a target mutation is present, while when it has not increased, it can be judged that no target mutation is present. On the contrary, in the case where the primer is designed as a complementary sequence to a wildtype, when the fluorescence intensity has increased, it can be judged that no target mutation is present, while when it has not increased, it can be judged that a target mutation is present.

In the present invention, any primer may be the labeled primer. Furthermore, the primer set of the present invention may include, for example, a primer (mutated primer) with a base to be detected being of a mutated form, and a primer (wildtype primer) with the base being of a wildtype. In this case, the mutated primer and the wildtype primer are preferably, for example, labeled primers having fluorescent atomic groups that are detected under different conditions, respectively. This makes it possible to carry out quantitative analysis of a mutated DNA and a wildtype DNA that are contained in a nucleic acid sample.

In the mutation detection method of the present invention, in step (a), at least two types of primers of the present invention can be used, with the primers having fluorescent atomic groups that are different in detection wavelength from each other. Specifically, when mutations of at least two types of target nucleic acid sequences are to be detected, it is preferable that in step (a), at least two types of labeled primers of the present invention having different fluorescent atomic groups from each other be used in combination as primers for amplifying the respective target nucleic acid sequences, respectively, and in step (c), the respective fluorescence intensities thereof be measured with respective detection wavelengths corresponding to the respective fluorescent atomic groups. Thus, for example, at least two types of target nucleic acid sequences are amplified in one reaction solution, and the amplification of mutations of the respective target nucleic acid sequences can be detected at detection wavelengths according to the respective fluorescent atomic groups.

In the mutation detection method of the present invention, when amplification is performed for detecting a mutated site in a target nucleic acid sequence, it is preferable that, for example, a labeled primer (a labeled full-match primer) of the present invention and a mismatch primer be used in step (a). The labeled primer has a sequence completely complementary to the region containing the mutation site in the target nucleic acid sequence. The mismatch primer is a primer having a sequence completely complementary to the region containing the mutation site except for the mutation site. In this manner, when a mismatch primer is allowed to be present together, for example, the full-match primer is prevented from hybridizing to the mismatch region in a template, which makes it possible to perform amplification with higher specificity. The mismatch primer may be, for example, an unlabeled primer or a labeled primer of the present invention.

[Method of Improving the Specificity]

The present invention further includes a method of improving the specificity of a primer to a target nucleic acid sequence. In a first specificity improvement method of the present invention, a labeled primer having a fluorescent atomic group of the present invention is used as the primer for amplifying the target nucleic acid sequence. That is, the primer structure is designed to be labeled nucleic acid containing at least one of the structures represented by the formulae (16), (16b), (17), (17b), (18), and (18b), and thereby the specificity of the primer to the target nucleic acid sequence can be improved as described above. In the present invention, when a labeled nucleic acid with the aforementioned structure is used, since the Tm value increases as compared to unlabeled nucleic acid that does not contain the structure, it also can be referred to as a method of improving the Tm value. Specific examples of the labeled primer and the method of using the same are as described above.

In a second specificity improvement method of the present invention, a labeled primer (a labeled full-match primer) of the present invention as the primer for amplifying the target nucleic acid sequence and a mismatch primer as a primer for improving the specificity of the primer are used in combination. The labeled primer has a sequence completely complementary to the region containing the mutation site in the target nucleic acid sequence. The mismatch primer is a primer having a sequence completely complementary to the region containing the mutation site except for the mutation site. In this manner, when the labeled full-match primer of the present invention and the mismatch primer are used in combination, for example, the labeled full-match primer is prevented from hybridizing to the mismatch region in a template and thereby the specificity of the labeled full-match primer can be improved. Specific examples of the labeled primer and the mismatch primer and the method of using the same are as described above.

[Kit]

A kit for nucleic acid amplification of the present invention is used for a nucleic acid amplification method for amplifying a target nucleic acid sequence, wherein the kit includes a primer or primer set of the present invention. As long as the kit for nucleic acid amplification of the present invention includes a primer or primer set of the present invention, for example, other structures or the ratio of contents are not limited. Furthermore, the nucleic acid amplification method that utilizes a kit for nucleic acid amplification of the present invention is not limited. As described above, it can be used, for example, for various isothermal amplification methods and the PCR method.

A mutation detection kit of the present invention is used for a mutation detection method for detecting the presence or absence of a mutation in the target nucleic acid sequence, wherein the mutation detection kit includes a kit for nucleic acid amplification of the present invention. As long as the mutation detection kit of the present invention includes the kit for nucleic acid amplification of the present invention, for example, other structures or the ratio of contents are not limited. Furthermore, the mutation detection method that utilizes a mutation detection kit of the present invention is not limited. As described above, it can be used for methods that utilize, for example, various isothermal amplification methods and the PCR method.

The kit for nucleic acid amplification and mutation detection kit of the present invention can be used for the nucleic acid amplification method and the mutation detection method of the present invention. The kit for nucleic acid amplification and mutation detection kit of the present invention further may include, for example, polymerase and/or mismatch binding protein as described above.

The kit for nucleic acid amplification and the mutation detection kit of the present invention further may include, for example, a nucleic acid synthesis unit and a fluorescence intensity measurement unit. The nucleic acid synthesis unit is not particularly limited and is, for example, a known automated nucleic acid synthesizer. The fluorescence intensity measurement unit also is not particularly limited and is, for example, a known fluorescence measuring device.

[System]

A nucleic acid amplification system of the present invention is a nucleic acid amplification system for carrying out the nucleic acid amplification method of the present invention, wherein the nucleic acid amplification system includes a reaction unit in which a nucleic acid amplification reaction is carried out, a temperature control unit for controlling temperature of the reaction unit, and a detection unit for detecting fluorescence intensity in the reaction unit. Furthermore, a mutation detection system of the present invention is a mutation detection system for carrying out a mutation detection method of the present invention, wherein the mutation detection system includes a reaction unit in which a nucleic acid amplification reaction is carried out, a temperature control unit for controlling temperature of the reaction unit, and a detection unit for detecting fluorescence intensity in the reaction unit. These respective systems may include as other components, for example, a reagent supply unit for supplying a reagent to the reaction unit and a reagent storage unit for storing the reagent.

The respective methods, kits, and systems of the present invention as described above are very useful in, for example, study, clinical use, and diagnosis.

EXAMPLES

The present invention is described in further detail using the following examples. However, the present invention is not limited by the following examples. In the description below, "ODN" denotes oligodeoxyribonucleotide (DNA oligomer).

[Measurement Conditions and Others]

The reagents and solvents used herein are commercially available. N-hydroxysuccinimidyl ester of biotin used herein was one available from PIERCE. The silica gel for purifying a compound used herein was Wako gel C-200 (Wako Pure Chemical Industries, Ltd.). $^1H$, $^{13}C$, and $^{31}P$ NMR spectra were measured with JNM-α400 (trade name) available from JEOL (JOEL Ltd.). The coupling constant (J value) is indicated in hertz (Hz). The chemical shift is indicated in ppm. Dimethylsulfoxide ($\delta$=2.48 in $^1$HNMR, $\delta$=39.5 in $^{13}$CNMR) and methanol ($\delta$=3.30 in $^1$HNMR, $\delta$=49.0 in $^{13}$CNMR) were used for internal standards. For $^{31}$PNMR measurement, $H_3PO_4$ ($\delta$=0.00) was used as an external standard. The ESI mass spectrum was measured using Bruker Daltonics APEC-II (trade name) available from Bruker Daltonics. The automated DNA synthesizer used herein was 392 DNA/RNA synthesizer (trade name) available from Applied Biosystems. In the reversed-phase HPLC, separation was carried out using Gilson Chromatograph, Model 305 (trade name), an apparatus available from Gilson, Inc. and CHEMCOBOND 5-ODS-H preparative column (trade name; 10×150 mm) available from Chemco Scientific Co., Ltd. and detection was carried out with a UV detector, Model 118 (trade name) at a wavelength of 260 nm. The mass of DNA was measured with MALDI-TOF MS. The MALDI-TOF MS used herein was PerSeptive Voyager Elite (trade name) available from Applied Biosystems. The mass was measured at an accelerating voltage of 21 kV in a negative mode, 2',3',4'-trihydroxyacetophenone was used as a matrix, and T8 ([M.H]. 2370.61) and T17 ([M.H]. 5108.37) were used as internal standards. UV and fluorescence spectrum were measured using a Shimadzu UV-2550 (trade name) spectrophotometer and a RF-5300PC (trade name) fluorescence spectrophotometer available from Shimadzu Corporation, respectively. Fluorescence lifetime was measured with a compact high-performance lifetime spectrofluometer system, HORIBA JOBIN YVON FluoroCube (trade name) equipped with NanoLED-05A (trade name) available from HORIBA, Ltd. The melting point (Tm) of double-stranded nucleic acid was measured in a 50 mM sodium phosphate buffer solution (pH=7.0) containing 100 mM sodium chloride, with the final double strand concentration being 2.5 μM. The absorbance of the sample was measured at a wavelength of 260 nm, and was traced in the range of 10° C. to 90° C. while being heated at a rate of 0.5° C./min. From the properties thus observed, the temperature at which a first change occurred was taken as the melting point Tm.

The absorption spectrum, fluorescence spectrum, and CD spectrum measurements were carried out at a strand concentration of 2.5 μM (single strand or double strand) in a 50 mM sodium phosphate buffer solution (pH=7.0) containing 100 mM sodium chloride using a measurement cell with an optical path length of 1 cm, unless otherwise described. The bandwidth of the excitation and fluorescence emission was 1.5 nm. The fluorescence quantum yield ($\Phi_F$) was calculated based on the quantum yield $\Phi_F$=0.95 of 9,10-diphenylanthracene in ethanol, using 9,10-diphenylanthracene as a control substance. The area of the emission spectrum was calculated by integration carried out using instrumentation software. The quantum yield ($\Phi_F$) was calculated by the following formula (1):

$$\Phi_{F(S)}/\Phi_{F(R)} = [A_{(S)}/A_{(R)}] \times [(Abs)_{(R)}/(Abs)_{(S)}] \times [n_{(S)}^2/n_{(R)}^2] \quad (1)$$

where $\Phi_{F(S)}$ is the fluorescence quantum yield of a sample, $\Phi_{F(R)}$ is the fluorescence quantum yield of a control substance (Reference), $A_{(S)}$ is the area of the fluorescence spectrum of the sample, $A_{(R)}$ is the area of the fluorescence spectrum of the control substance, $(Abs)_{(S)}$ is the optical density of the sample solution obtained at an excitation wavelength, $(Abs)_{(R)}$ is the optical density of the control substance solution obtained at an excitation wavelength, $n_{(S)}$ is the refractive index of the sample solution, $n_{(R)}$ is the refractive index of the control substance solution, and calculation was carried out with $n_{(S)}$=1.333 and $n_{(R)}$=1.383.

Examples 1 to 3

According to the following Scheme 1, compounds 102 and 103 including two active amino groups protected with trifluoroacetyl groups, respectively, were synthesized (produced), and further phosphoramidite 104 was synthesized.

Scheme 1

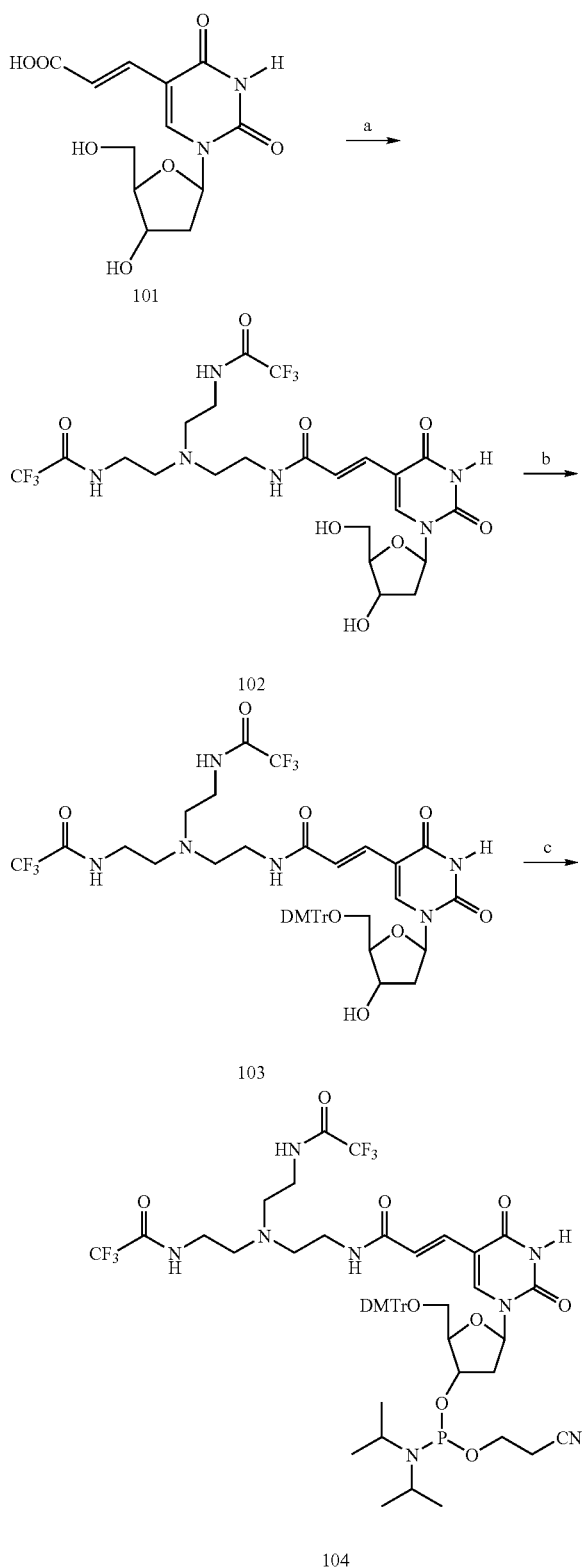

Scheme 1—Reaction Reagent and Reaction Conditions:
(a) (i) N-hydroxysuccinimide, EDC/DMF, (ii) tris(2-aminoethyl)-amine/CH$_3$CN, (iii) CF$_3$COOEt, Et$_3$N; (b) DMTrCl/pyridine; (c) 2-cyanoethyl-N,N,N',N'-tetraisopropyl phosphoramidite, 1H-tetrazole/CH$_3$CN.

Scheme 1 is described below in further detail.

Example 1

Synthesis of 2-[2-[N,N-bis(2-trifluoroacetamidoethyl)]-aminoethyl]carbamoyl-(E)-vinyl]-2'-deoxyuridine (Compound 102)

The starting material, (E)-5-(2-carboxyvinyl)-2'-deoxyuridine (Compound 101), was synthesized according to Tetrahedron 1987, 43, 20, 4601-4607. That is, first, 71 mL of 1,4-dioxane was added to 430 mg of palladium acetate (II) (FW 224.51) and 1.05 g of triphenylphosphine (FW 262.29), and further 7.1 mL of triethylamine (FW 101.19, d=0.726) was added thereto. This was heated and stirred at 70° C. After the reaction solution was changed from reddish brown to blackish brown, 14.2 g of 2'-deoxy-5-iodouridine (FW 354.10) and 7.0 mL of methyl acrylate (FW 86.09, d=0.956) that were suspended in 1,4-dioxane were added thereto. This was heat-refluxed at 125° C. for one hour. Thereafter, it was filtered while it was still hot, the residue was washed with methanol, and then the filtrate was recovered. After the solvent was evaporated from the filtrate under reduced pressure, the product thus obtained was purified with a silica gel column (5-10% methanol/dichloromethane). The solvent of the collected fraction was evaporated under reduced pressure, and the residual white solid was dried under reduced pressure. About 100 mL of ultrapure water was added to the dried solid, and 3.21 g of sodium hydroxide (FW 40.00) was added thereto. This was stirred at 25° C. throughout the night. Thereafter, concentrated hydrochloric acid was added thereto to acidize the solution. The precipitate thus produced was filtered, washed with ultrapure water, and then dried under reduced pressure. Thus, 8.10 g (with a yield of 68%) of target compound (Compound 101) was obtained as white powder. The white powder was confirmed to be the target compound 101 since the $^1$HNMR measured value agreed with the reference value. The $^{13}$CNMR measured value is described below.

(E)-5-(2-carboxy vinyl)-2'-deoxyuridine (Compound 101)

$^{13}$CNMR (DMSO-d6): δ168.1, 161.8, 149.3, 143.5, 137.5, 117.8, 108.4, 87.6, 84.8, 69.7, 60.8, 40.1.

Next, 1.20 g of (E)-5-(2-carboxy vinyl)-2'-deoxyuridine 101 (with a molecular weight of 298.25), 925 mg of N-hydroxysuccinimide (with a molecular weight of 115.09), and 1.54 g of 1-ethyl-3-(3-dimethylaminopropyl)carbodiimide (with a molecular weight of 191.70) were placed in a recovery flask containing a stirring bar, and 20 mL of DMF was added thereto, which was then stirred at 25° C. for 16 hours. About 1 mL of acetic acid was added thereto and 300 mL of methylene chloride and 100 mL of ultrapure water were added thereto, which was then stirred vigorously. The aqueous layer was removed and further 100 mL of ultrapure water was added, which then was washed twice in the same manner. The precipitate thus produced was filtered, washed with methylene chloride, and then dried under reduced pressure. The solvent was evaporated from the filtrate, methylene chloride was added to the precipitate thus produced, and the precipitate was then recovered in the same manner as described above. The precipitates thus recovered were collected and then suspended in 80 mL of acetonitrile. This was stirred vigorously. Then 3.0 mL of tris(2-aminoethyl)amine (with a molecular weight of 146.23, d=0.976) was added all at once, which further was stirred at 25° C. for 10 minutes. Thereafter, 4.8 mL of ethyl trifluoroacetate (with a molecular weight of 142.08, d=1.194) was added and further 5.6 mL of triethylamine (with a molecular weight of 101.19, d=0.726) was added thereto, which was stirred at 25° C. for three hours. The solvent was evaporated and the product thus obtained was purified with a silica gel column (5-10% MeOH/CH$_2$Cl$_2$). The solvent was evaporated, the product thus obtained was dissolved in a small amount of acetone, and ether was then added thereto. As a result, white precipitate was produced. This was filtered and then washed with ether. Thereafter, this was dried under reduced pressure. Thus 884 mg (33.5%) of target substance (Compound 102) was obtained.

The same synthesis as described above was carried out except for slight changes in the amounts of, for example, raw materials and solvents to be used, the reaction time, and the steps to be taken. As a result, the yield was improved up to 37%. That is, 597 mg (2.0 mmol) of (E)-5-(2-carboxy vinyl)-2'-deoxyuridine 101 (with a molecular weight of 298.25), 460 mg (4.0 mmol) of N-hydroxysuccinimide (with a molecular weight of 115.09), and 767 mg (4.0 mmol) of 1-ethyl-3-(3-dimethylaminopropyl)carbodiimide hydrochloride (with a molecular weight of 191.70) were placed in a recovery flask containing a stirring bar. Thereafter, 5.0 mL of DMF was added thereto, which was stirred at 25° C. for three hours. About 0.5 mL of acetic acid was added and 100 mL of methylene chloride and 100 mL of ultrapure water were added thereto, which was stirred vigorously. The precipitate thus produced was filtered, washed with water, and then dried under reduced pressure throughout the night. The resultant white residue was suspended in 50 mL of acetonitrile, which was stirred vigorously. Then, 3.0 mL (20 mmol) of tris(2-aminoethyl)amine (with a molecular weight of 146.23, d=0.976) was added thereto all at once, which further was stirred at 25° C. for 10 minutes. Thereafter, 4.8 mL of ethyl trifluoroacetate (with a molecular weight of 142.08, d=1.194) was added and further 5.6 mL (40 mmol) of triethylamine (with a molecular weight of 101.19, d=0.726) was added thereto, which was then stirred at 25° C. for 16 hours. The solvent was evaporated and the product thus obtained was purified with a silica gel column (5-10% MeOH/CH$_2$Cl$_2$). The solvent was evaporated, the product thus obtained was dissolved in a small amount of acetone, and ether was then added thereto. As a result, white precipitate was produced. This was filtered and then washed with ether. Thereafter, this was dried under reduced pressure. Thus 453 mg (37%) of target substance (Compound 102) was obtained as white powder. The instrumental analytical values of Compound 102 are indicated below. Further, a $^1$HNMR spectrum diagram is shown in FIG. 2.

2-[2-[N,N-bis(2-trifluoroacetamidoethyl)]-aminoethyl]carbamoyl-(E)-vinyl)-2'-deoxyuridine (Compound 102)

$^1$HNMR (CD$_3$OD): δ8.35 (s, 1H), 7.22 (d, J=15.6 Hz, 1H), 7.04 (d, J=15.6 Hz, 1H), 6.26 (t, J=6.6 Hz, 1H), 4.44-4.41 (m, 1H), 3.96-3.94 (m, 1H), 3.84 (dd, J=12.2, 2.9 Hz, 1H), 3.76 (dd, J=12.2, 3.4 Hz, 1H), 3.37-3.30 (m, 6H), 2.72-2.66 (m, 6H), 2.38-2.23 (m, 2H). $^{13}$CNMR (CD$_3$OD): δ169.3, 163.7, 159.1 (q, J=36.4 Hz), 151.2, 143.8, 134.3, 122.0, 117.5 (q, J=286 Hz), 110.9, 89.1, 87.0, 71.9, 62.5, 54.4, 53.9, 41.7, 38.9, 38.7. HRMS (ESI) calcd for C$_{22}$H$_{29}$F$_6$N$_6$O$_8$ ([M+H]$^+$) 619.1951, found 619.1943.

Example 2

Synthesis of 5'-O-DMTr-(2-[2-[N,N-bis(2-trifluoroacetamidoethyl)]-aminoethyl]carbamoyl-(E)-vinyl)-2'-deoxyuridine (Compound 103)

5'-hydroxy group of Compound 102 was protected with a DMTr group. Thus Compound 103 was obtained. That is, first, 618 mg of Compound 102 (with a molecular weight of 618.48) and 373 mg of 4,4'-dimethoxytritylchloride (with a molecular weight of 338.83) were placed in a recovery flask containing a stirring bar. Then 10 mL of pyridine was added thereto, which was stirred at 25° C. for 16 hours. A small amount of water was added thereto, the solvent was evaporated, and the product thus obtained was purified with a silica gel column (2-4% MeOH, 1% Et$_3$N/CH$_2$Cl$_2$). The solvent of the fraction containing the target Compound 103 was evaporated. Thus 735.2 mg (79.8%) of target substance (Compound 103) was obtained. The instrumental analytical values of Compound 103 are indicated below. Further, a $^1$HNMR spectrum diagram is shown in FIG. 3.

5'-O-DMTr-(2-[2-[N,N-bis(2-trifluoroacetamidoethyl)]-aminoethyl]carbamoyl-(E)-vinyl)-2'-deoxyuridine (Compound 103)

$^1$HNMR (CD$_3$OD): δ7.91 (s, 1H), 7.39-7.11 (m, 9H), 7.02 (d, J=15.6 Hz, 1H), 6.93 (d, J=15.6 Hz, 1H), 6.80-6.78 (m, 4H), 6.17 (t, J=6.6 Hz, 1H), 4.38-4.35 (m, 1H), 4.06-4.04 (m, 1H), 3.68 (s, 6H), 3.32-3.22 (m, 8H), 2.66-2.55 (m, 6H), 2.40 (ddd, J=13.7, 5.9, 2.9 Hz, 1H), 2.33-2.26 (m, 1H). $^{13}$CNMR (CD$_3$OD): δ168.9, 163.7, 160.1, 159.1 (q, J=36.9 Hz), 151.0, 146.1, 143.0, 137.0, 136.9, 134.1, 131.24, 131.16, 129.2, 128.9, 128.0, 122.5, 117.5 (q, J=286.7 Hz), 114.2, 110.9, 88.1, 87.9, 87.6, 72.6, 65.0, 55.7, 54.2, 53.9, 41.7, 38.9, 38.6. HRMS (ESI) calcd for C$_{43}$H$_{47}$F$_6$N$_6$O$_{10}$ ([M+H]$^+$) 921.3258, found 921.3265.

Example 3

Synthesis of 5'-O-DMTr-(2-[2-[N,N-bis(2-trifluoroacetamidoethyl)]-aminoethyl]carbamoyl-(E)-vinyl)-2'-deoxyuridine, 3'-[(2-cyanoethyl)-(N,N-diisopropyl)]-phosphoramidite (Compound 104)

First, 188 mg (0.20 mmol) of Compound 103 (with a molecular weight of 920.85) was allowed to form an azeotrope with CH$_3$CN, and 28.6 mg (0.40 mmol) of 1H-tetrazole (with a molecular weight of 70.05) was added thereto. This was vacuum-dried with a vacuum pump overnight. Then, 5.1 mL of CH$_3$CN was added thereto and thereby the product thus dried was dissolved therein, which was then stirred. Thereafter, 194 μmL (0.60 mmol) of 2-cyanoethylN,N,N',N'-tetraisopropylphosphoramidite (with a molecular weight of 301.41, d=0.949) was then added thereto all at once, which was stirred at 25° C. for two hours. After that, a mixture of 50 mL of ethyl acetate and 50 mL of saturated sodium bicarbonate water was added thereto, and liquid separation was carried out. After the organic layer thus obtained was washed with saturated saline, it was dried with magnesium sulfate. The magnesium sulfate was removed by filtration, and the solvent was then evaporated. The crude product obtained by this liquid separation was allowed to form an azeotrope with CH₃CN. Thereafter, assuming that the product (Compound 104) was obtained with a yield of 100%, 0.1 M of CH₃CN solution was prepared and was used for DNA synthesis. The fact that Compound 104 had been obtained was confirmed from $^{31}$PNMR (CDCl₃) and HRMS (ESI) of the crude product. The values thereof are indicated below.

Compound 104

$^{31}$PNMR (CDCl₃) δ 149.686, 149.430; HRMS (ESI) calcd for $C_{52}H_{64}F_6N_8O_{11}P$ ([M+H]⁺) 1121.4336, found 1121.4342.

Example 4

DNA Oligomer Synthesis

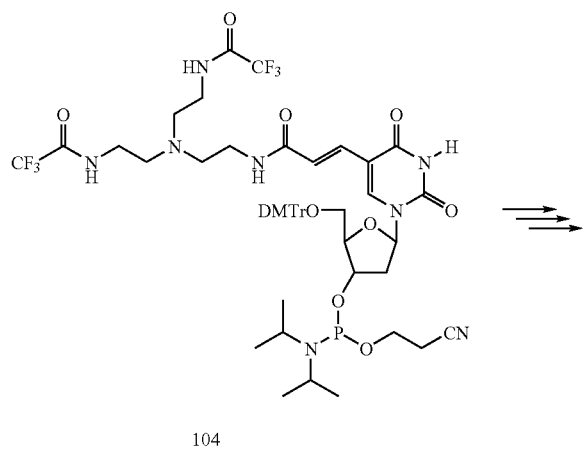

104

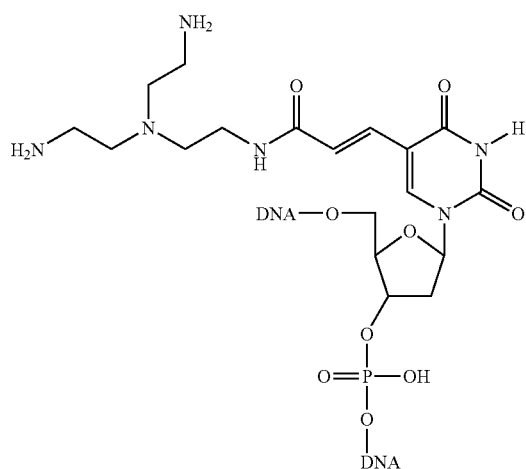

105

Figure 4:
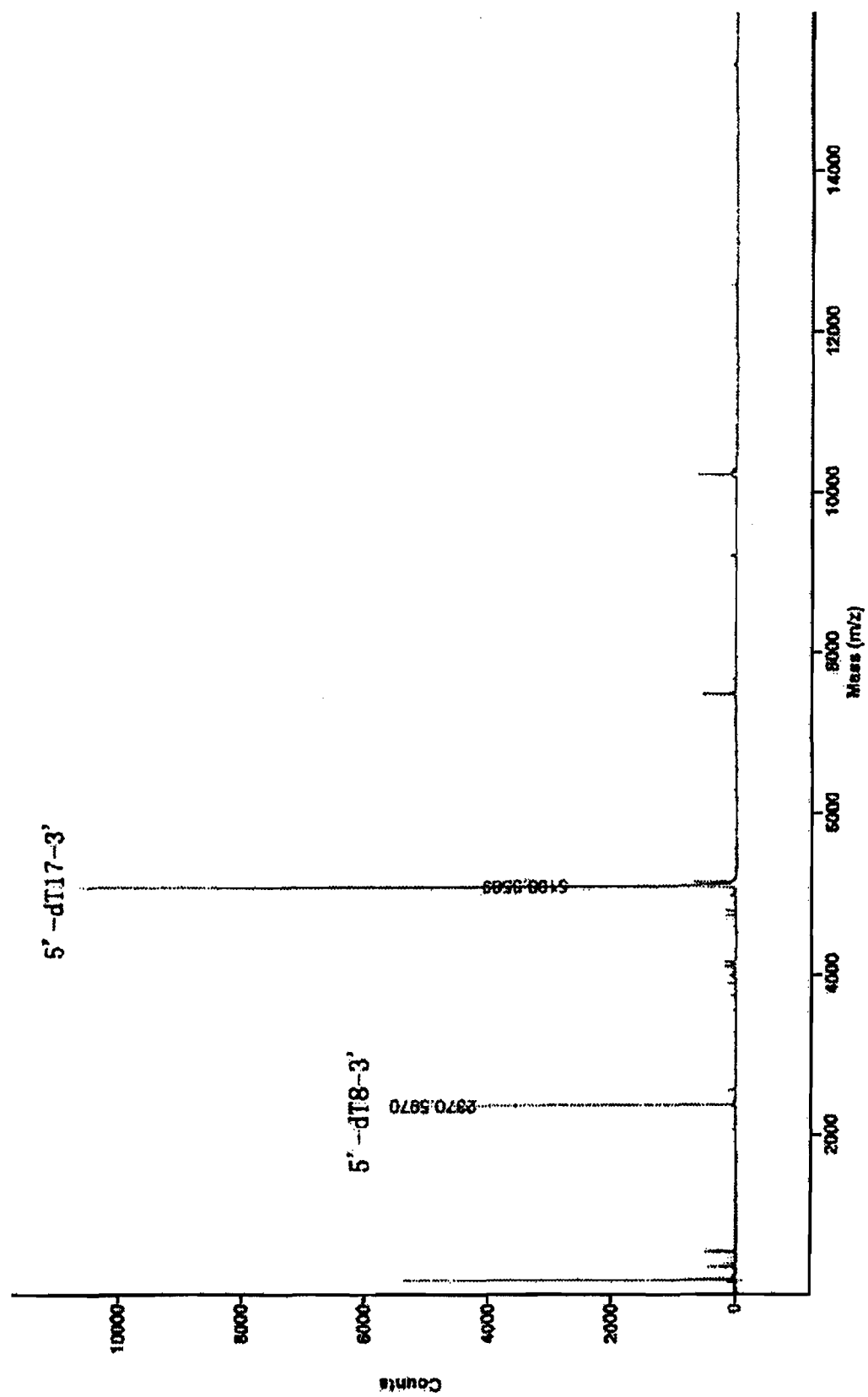
FIG. 4 shows a MALDI-TOF mass spectrum of purified DNA oligomer 5'-d(CGCAATXTAACGC)-3'; the arrow shows the mass peak (4101.9) derived from the purified product, and the calculated value of [M−H]⁻ is 4101.8 based on a calculated value of molecular weight of 4102.8 ($C_{134}H_{176}N_{52}O_{76}P_{12}$) and therefore matches therewith.

The synthesis of oligodeoxyribonucleotide with an automated DNA synthesizer using Compound 104 was carried out by a conventional phosphoramidite method (DMTr OFF) on a 1 μmol scale. Thus DNA oligomer with a sequence of 5'-d(CGCAATXTAACGC)-3' (13-mer, the structure of X is the same as that of Chemical Formula 105) (SEQ ID NO. 1) was synthesized. Deprotection was carried out with concentrated ammonia water (28 mass %) at 55° C. for 16 hours. Ammonia was volatilized with a speed vac, and the product thus obtained was passed through a 0.45-μm filter. Thereafter, DNA oligomer cut out therefrom was analyzed by reversed-phase HPLC, the peak that had appeared after about 10.5 minutes was purified (CHEMCOBOND 5-ODS-H (trade name); 10×150 mm, 3 mL/min, 5-30% CH₃CN/50 mM TEAA buffer pH 7 (20 minutes), detected at 260 nm). The molecular weight of the product thus purified was measured with a MALDI TOF mass spectrometer in its negative mode. As a result, it was confirmed that the product had the molecular weight (4102.8, which was a value calculated in terms of $C_{134}H_{176}N_{52}O_{76}P_{12}$) expected from the aforementioned sequence of 5'-d(CGCAATXTAACGC)-3' (13-mer, the structure of X is as shown in Chemical Formula 105) ([M−H]⁻ measured value: 4101.9, calculated value: 4101.8). FIG. 4 shows the spectrum obtained with the MALDI TOF mass spectrometer.

Further, 5'-d(CGCAATXTAACGC)-3' (13-mer, the structure of X is as shown in Chemical Formula 105) was synthesized in the same manner as described above except that the deprotection was carried out with the concentrated ammonia water at 55° C. for 4 hours and further at 25° C. for 16 hours, the concentration of the TEAA (triethylamine acetate) buffer (pH 7) was 0.1 M in the reversed-phase HPLC, and the development time was at least 30 minutes in the reversed-phase HPLC. Moreover, a DNA (containing nucleotide represented by Chemical Formula 105) that was used as a raw material for each ODN indicated in Table 1 was synthesized in the same manner.

In order to determine the concentration of each DNA thus synthesized, each purified DNA was digested completely at 25° C. over 16 hours using calf intestinal alkaline phosphatase (50 U/mL), snake venom phosphodiesterase (0.15 U/mL), and P1 nuclease (50 U/mL). The digested liquids thus obtained were analyzed by HPLC with a CHEMCOBOND 5-ODS-H (trade name) column (4.6×150 mm). In this analysis, 0.1 M TEAA (pH 7.0) was used as a developer and the flow rate was 1.0 mL/min. The concentration of the DNA synthesized as described above was determined as compared to the peak area of the standard solution containing dA, dC, dG, and dT, the concentration of each of which was 0.1 mM. Furthermore, the DNA synthesized as described above also was identified with a MALDI TOF mass spectrum. The mass spectrometry values thereof are indicated below, where [105] denotes that the nucleotide represented by Chemical Formula 105 is inserted in that site.

CGCAAT[105]TAACGC, calcd for $C_{134}H_{177}N_{52}O_{76}P_{12}$ ([M+H]⁺) 4103.8, found 4107.0;

TTTTTT[105]TTTTTT, calcd for $C_{138}H_{187}N_{30}O_{90}P_{12}$ ([M+H]⁺) 4077.8, found 4076.9;

TGAAGGGCTT[105]TGAACTCTG, calcd for $C_{205}H_{265}N_{77}O_{122}P_{19}$ ([M+H]⁺) 6348.2, found 6348.7;

GCCTCCT[105]CAGCAAATCC[105]ACCGGCGTG, calcd for $C_{285}H_{376}N_{108}O_{169}P_{27}$ ([M+H]⁺) 8855.0, found 8854.8;

CCTCCCAAG[105]GCTGGGAT[105]AAAGGCGTG, calcd for $C_{289}H_{376}N_{116}O_{168}P_{27}$ ([M+H]⁺) 8999.1, found 9002.2.

Example 5

Biotin Modification of DNA Oligomer Containing Nucleotide Having Two Amino Groups Scheme 3

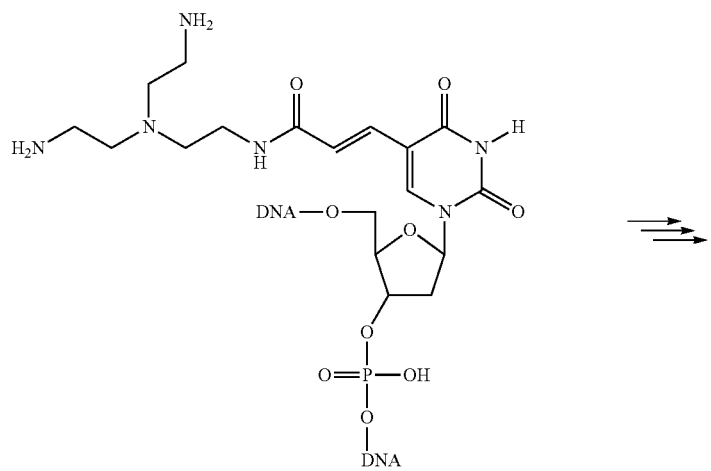

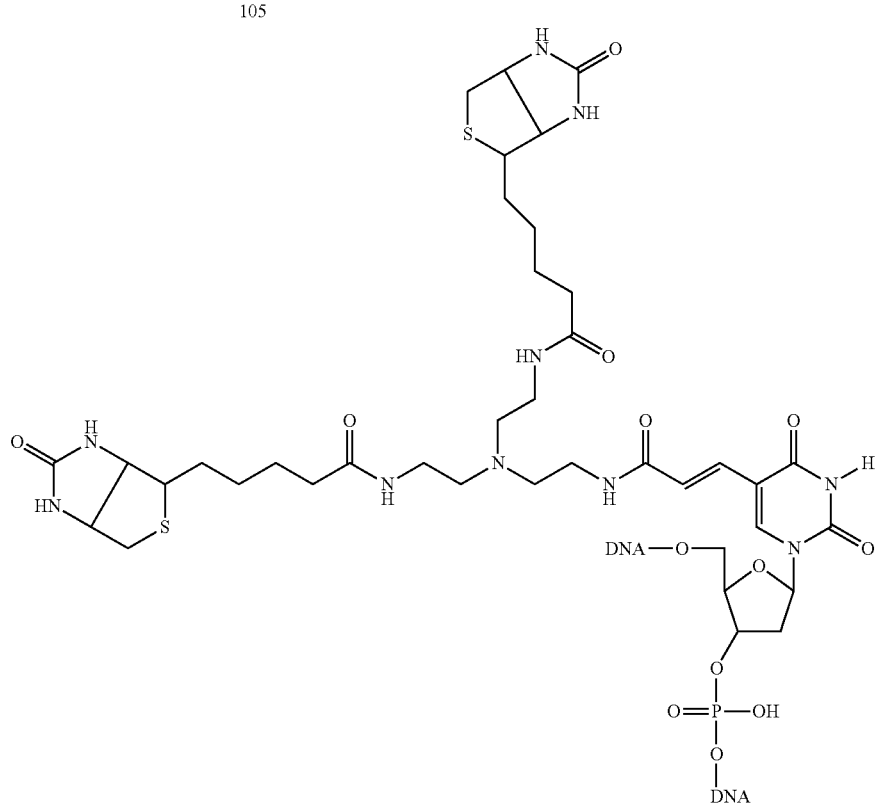

Figure 5:
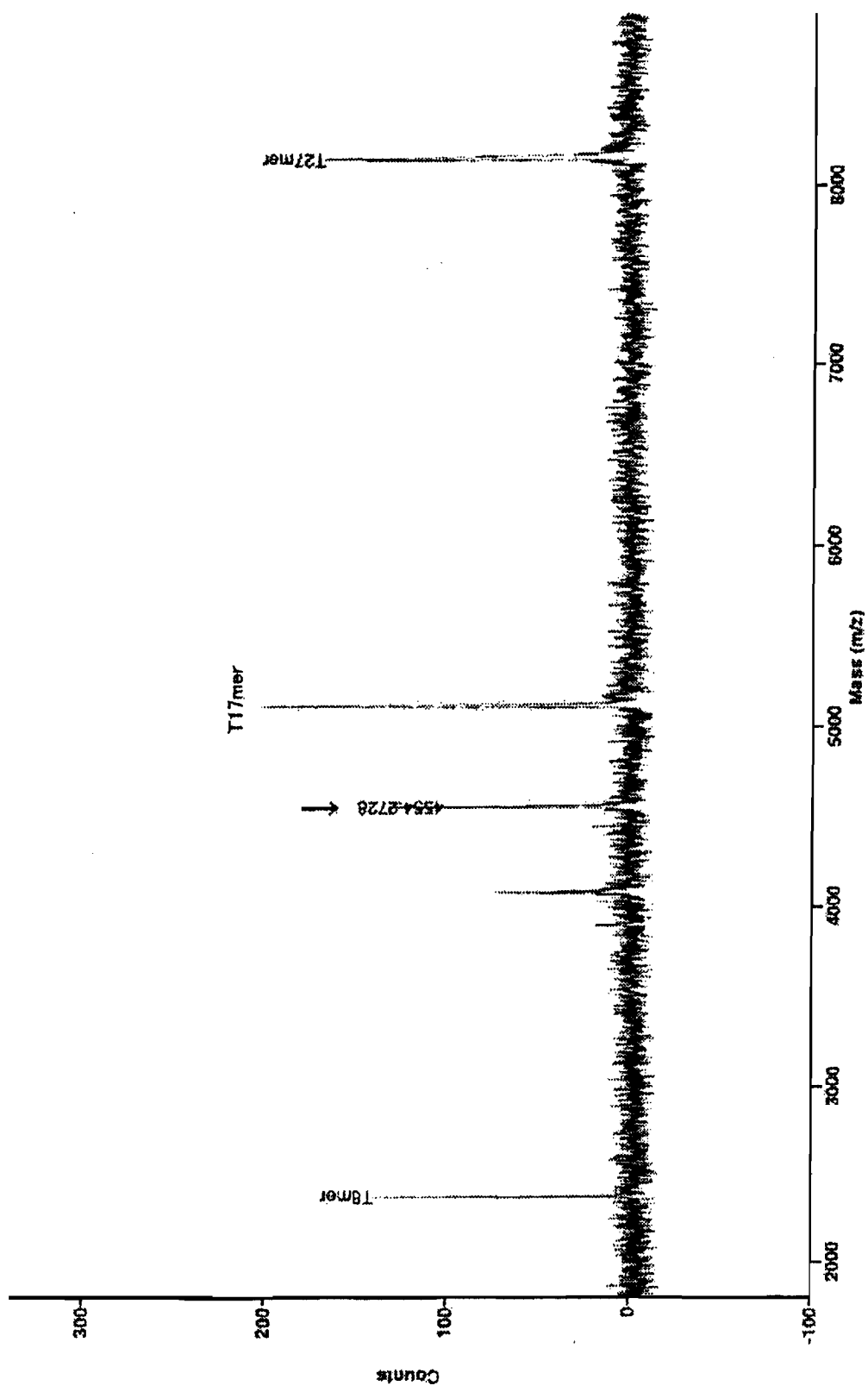
FIG. 5 shows a MALDI-TOF mass spectrum of a reaction product of DNA oligomer 5'-d(CGCAATXTAACGC)-3' and a biotin derivative; the arrow shows the mass peak (4554.3) derived from the purified product, and the calculated value of [M−H]⁻ is 4554.4 based on a calculated value of molecular weight of 4555.4 ($C_{134}H_{176}N_{52}O_{76}P_{12}$) and therefore matches therewith.

The synthesized DNA oligomer 5'-d(CGCAATX-TAACGC)-3' (Compound 105, where Compound 4 was used as X) was allowed to react with N-hydroxysuccinimidyl ester of biotin and thereby two amino groups were labeled with two 2 biotins (Scheme 3 shown above). That is, first, 30 μL of 5'-d(CGCAATXTAACGC)-3' (Compound 105, with a strand concentration of 320 μM), 10 μL of $Na_2CO_3/NaHCO_3$ buffer (1 M, pH 9.0), and 60 μL of $H_2O$ were mixed together. Then 100 μL of biotin N-hydroxysuccinimidyl ester DMF solution (20 mM) was added thereto, which was then mixed well. This was allowed to stand still at 25° C. for 16 hours. Thereafter, 800 μL of $H_2O$ was added thereto, which was passed through a 0.45-μm filter. The peak appeared in reversed-phase HPLC after about 14 minutes was purified (CHEMCOBOND 5-ODS-H 10×150 mm, 3 mL/min, 5-30% CH$_3$CN/50 mM TEAA buffer (20 minutes), detected at 260 nm). The product obtained by this HPLC purification was measured with the MALDI TOF mass spectrometer in its negative mode. As a result, the peak was observed at 4554.3. This peak value agreed with the calculated value of [M−H]$^-$, 4554.4, determined from the molecular weight of 4555.4 (a value calculated in terms of C$_{154}$H$_{204}$N$_{56}$O$_{80}$P$_{12}$S$_2$) of the target product 6 in which two biotin molecules reacted with two amino groups. FIG. 5 shows the spectrum obtained with the MALDI TOF mass spectrometer.

Using this compound 6 (in a single-stranded state), double-stranded DNA and RNA were synthesized, and the fluorescence intensity obtained in the single-stranded state was compared to that obtained in the double-stranded state. As a result, it was confirmed that the fluorescence emission of the fluorescence DNA oligomer (a primer (Compound 6)) was suppressed in the single-stranded state, while strong fluorescence emission was obtained when it formed a double helix together with a complementary nucleic acid.

In Examples 6 to 13 described below, thiazole orange derivatives having carboxymethylene linkers represented by the following chemical formulae b and c were synthesized. They were activated as N-hydroxysuccinic ester and were allowed to react with DNA oligomer (oligonucleotide) having active amino groups. Thus various oligonucleotides (fluorescence DNA oligomers) having fluorescence were prepared. That is, various oligonucleotides (fluorescence DNA oligomers) were produced that were different from one another in length of the methylene linker extended from a dye and in the linker containing the amino group extended from the 5-position of thymidine. As a result, in any of the various fluorescence DNA oligomers (fluorescence DNA primers), it was possible to suppress the fluorescence emission of the single-stranded DNA fluorescence primer and to obtain strong fluorescence emission when it formed a double helix together with a complementary nucleic acid. In the following Chemical Formula b and c, n denotes the linker length (the number of linking atoms).

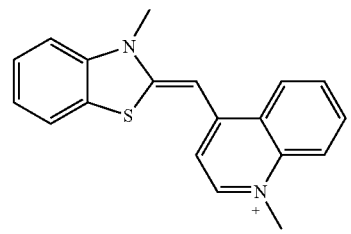

a

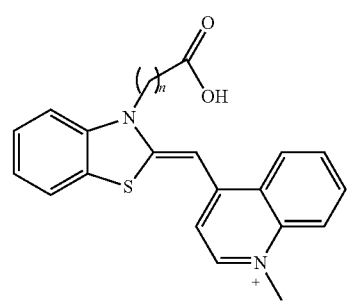

b

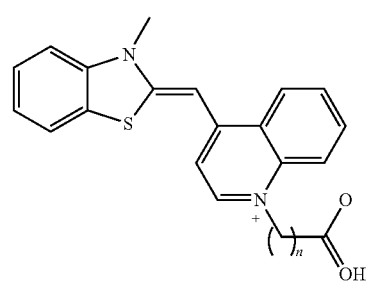

c

Example 6

Synthesis of Compound Having, in One Molecule, Structures Derived from Thiazole Orange in Two Places Scheme 4

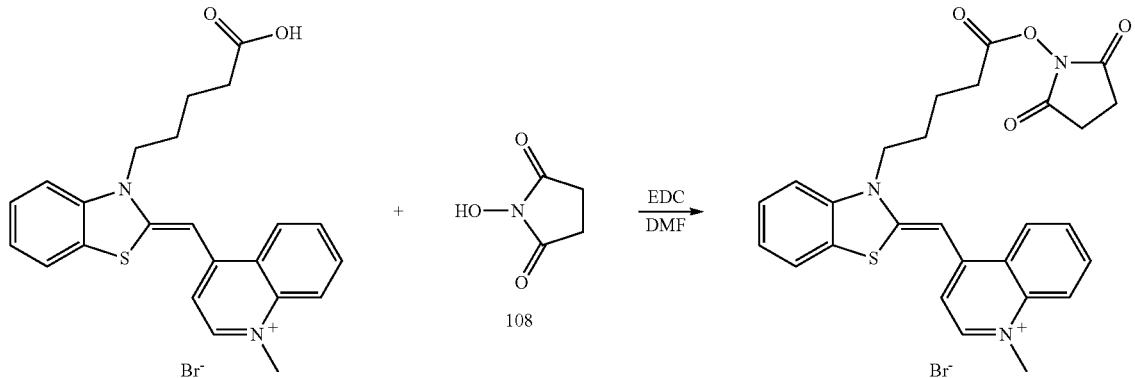

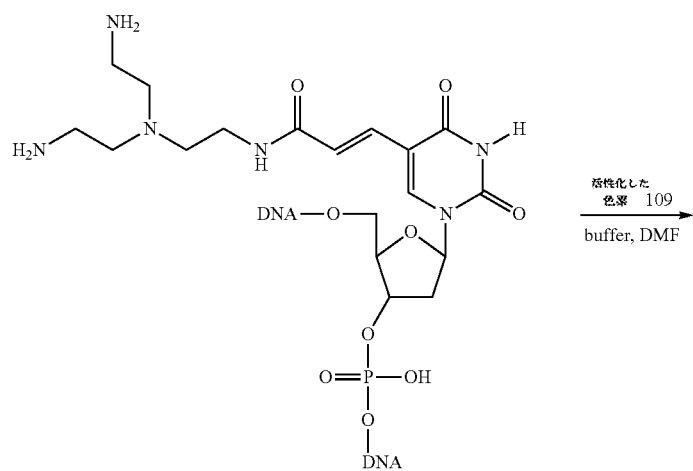
105
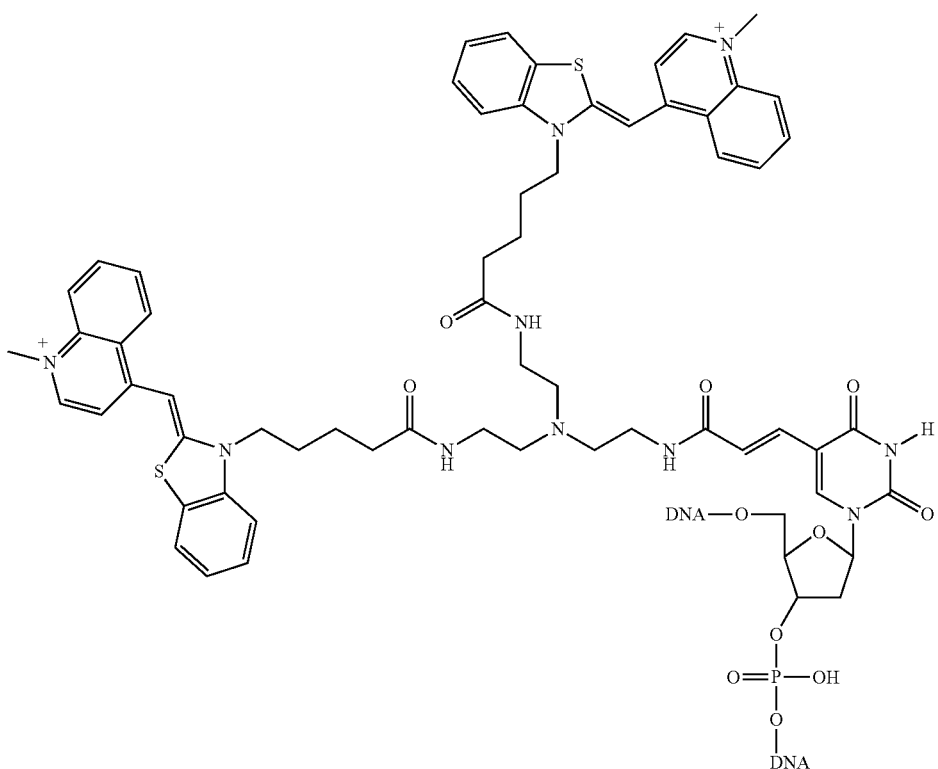
110

As shown in Scheme 4, DNA oligomer (oligonucleotide) 110 was synthesized that has, in one molecule, structures derived from thiazole orange in two places. A more specific description follows.

The thiazole orange derivative 107 was synthesized as indicated below in Scheme 5 with reference to Organic Letters 2000, 6, 517-519.

Scheme 5

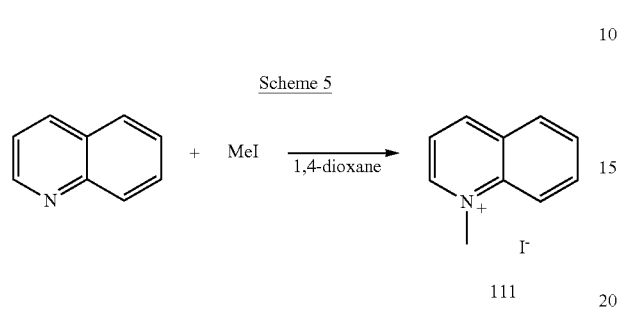

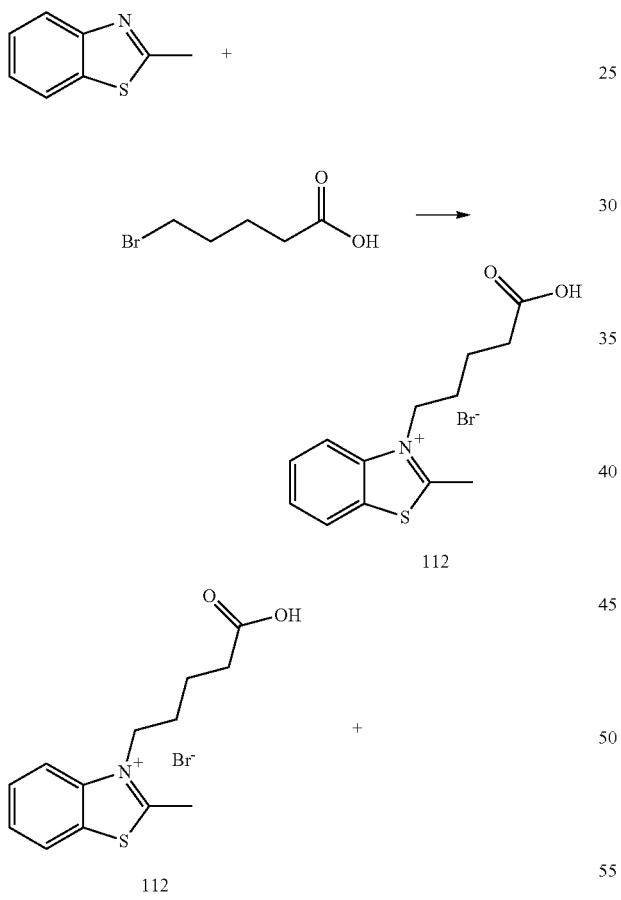

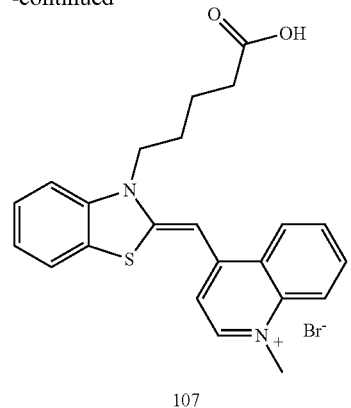

107

(1) Synthesis of N-methylquinolinium iodide Compound (111)

N-methylquinolinium iodide (Compound III) was synthesized according to the description in the aforementioned reference. Specifically, 2.4 mL of quinoline and 4 mL of methyl iodide were added to 42 mL of anhydrous dioxane, which was stirred at 150° C. for one hour. Thereafter, it was filtered and thereby a precipitate was collected and then washed with ether and petroleum ether. This was dried and thus N-methylquinolinium iodide (Compound III) was obtained.

(2) Synthesis of 3-(4-carboxybutyl)-2-methylbenzothiazolium bromide (Compound 112)

First, 8 mL of 2-methylbenzothiazole (FW 149.21, d=1.173) and 9.4 g of 5-bromovaleric acid (5-bromopentanoic acid) (FW 181.03) were stirred at 110° C. for 16 hours. The crude product was cooled to room temperature and a solid thus produced was suspended in 20 mL of methanol and further 40 mL of ether was added thereto. The precipitate thus produced was filtered and then washed with dioxane until the odor of 2-methylbenzothiazole was removed. This further was washed with ether and then dried under reduced pressure. Thus 9.8 g of white powder was obtained. Thereafter, $^1$HNMR of this white powder was measured. As a result, it was found to be a mixture of 3-(4-carboxybutyl)-2-methylbenzothiazolium bromide (Compound 112), which was the target substance whose 2-position had been alkylated, and 3-(4-carboxybutyl)-benzothiazolium bromide whose 2-position had not been alkylated. The peak ratio of proton was non-alkylated:alkylated=10:3. This crude product was used for the next reaction without further being treated.

(3) Synthesis of 1-methyl-4-[{3-(4-carboxybutyl)-2 (3H)-benzothiazolylidene}methyl]quinolinium bromide (Compound 107)

First, 2.18 g of crude product containing 3-(4-carboxybutyl)-2-methylbenzothiazolium bromide (Compound 112) obtained in (2) above and 700 mg of N-methylquinolinium iodide (Compound 111) (FW 271.10) were stirred in 10 mL of methylene chloride at 25° C. for two hours in the presence of 3.6 mL of triethylamine (FW 101.19, d=0.726). Thereafter, 50 mL of ether was added thereto and a precipitate produced thereby was filtered, washed with ether, and then dried under reduced pressure. The precipitate was suspended in 50 mL of ultrapure water, which was filtered, washed with ultrapure water, and then dried under reduced pressure. Further, the precipitate was dispersed in 50 mL of acetonitrile, which was filtered, washed with acetonitrile, and then dried under reduced pressure. Thus 307.5 mg of red powder was obtained (with a yield of 25.3%). This red powder was confirmed to be the target substance (Compound 107) through a comparison in $^1$HNMR spectrum with the reference value.

Moreover, it also was possible to synthesize 3-(4-carboxybutyl)-2-methylbenzothiazolium bromide (Compound 112) and 1-methyl-4-[{3-(4-carboxybutyl)-2(3H)-benzothiazolylidene}methyl]quinolinium bromide (Compound 107) as follows. That is, first, 11.7 mL (92 mmol) of 2-methylbenzothiazole (FW 149.21, d=1.173) and 13.7 g (76 mmol) of 5-bromovaleric acid (5-bromopentanoic acid) (FW 181.03) were stirred at 150° C. for one hour. The crude product was cooled to room temperature and the solid thus produced was suspended in 50 mL of methanol. Further, 200 mL of ether was added thereto. The precipitate thus produced was filtered, washed with ether, and then dried under reduced pressure. Thus 19.2 g of light purple powder was obtained. This powder was a mixture of a target compound 112 (3-(4-carboxybutyl)-2-methylbenzothiazolium bromide) and 2-methylbenzothiazolium bromide. This mixture was subjected to $^1$HNMR (in DMSO-d6) measurement, and the yield of the target compound 112 was calculated to be 9.82 g (14 mmol, 32%) from the peak area ratio between the peak at 8.5 ppm (derived from the target compound 112) and the peak at 8.0 ppm (derived from 2-methylbenzothiazolium bromide). This mixture (crude product) was used for the next reaction without being purified. In the same manner as described above except that the 5-bromovaleric acid (5-bromopentanoic acid) was replaced with 4-bromobutyric acid (4-bromobutanoic acid), 3-(4-carboxypropyl)-2-methylbenzothiazolium bromide with a linker (a polymethylene chain linked to a carboxyl group) having a carbon number n of 3 was synthesized, which was obtained with a yield of 4%. Furthermore, in the same manner as described above except that 5-bromovaleric acid (5-bromopentanoic acid) was replaced with 6-bromohexanoic acid, 3-(4-carboxypentyl)-2-methylbenzothiazolium bromide with a linker (a polymethylene chain linked to a carboxyl group), having a carbon number n of 5 was synthesized, which was obtained with a yield of 35%. Moreover, in the same manner as described above except that 5-bromovaleric acid (5-bromopentanoic acid) was replaced with 7-bromoheptanoic acid, 3-(4-carboxypropyl)-2-methylbenzothiazolium bromide with a linker (a polymethylene chain linked to a carboxyl group) having a carbon number n of 6 was synthesized, which was obtained with a yield of 22%.

Figure 6:
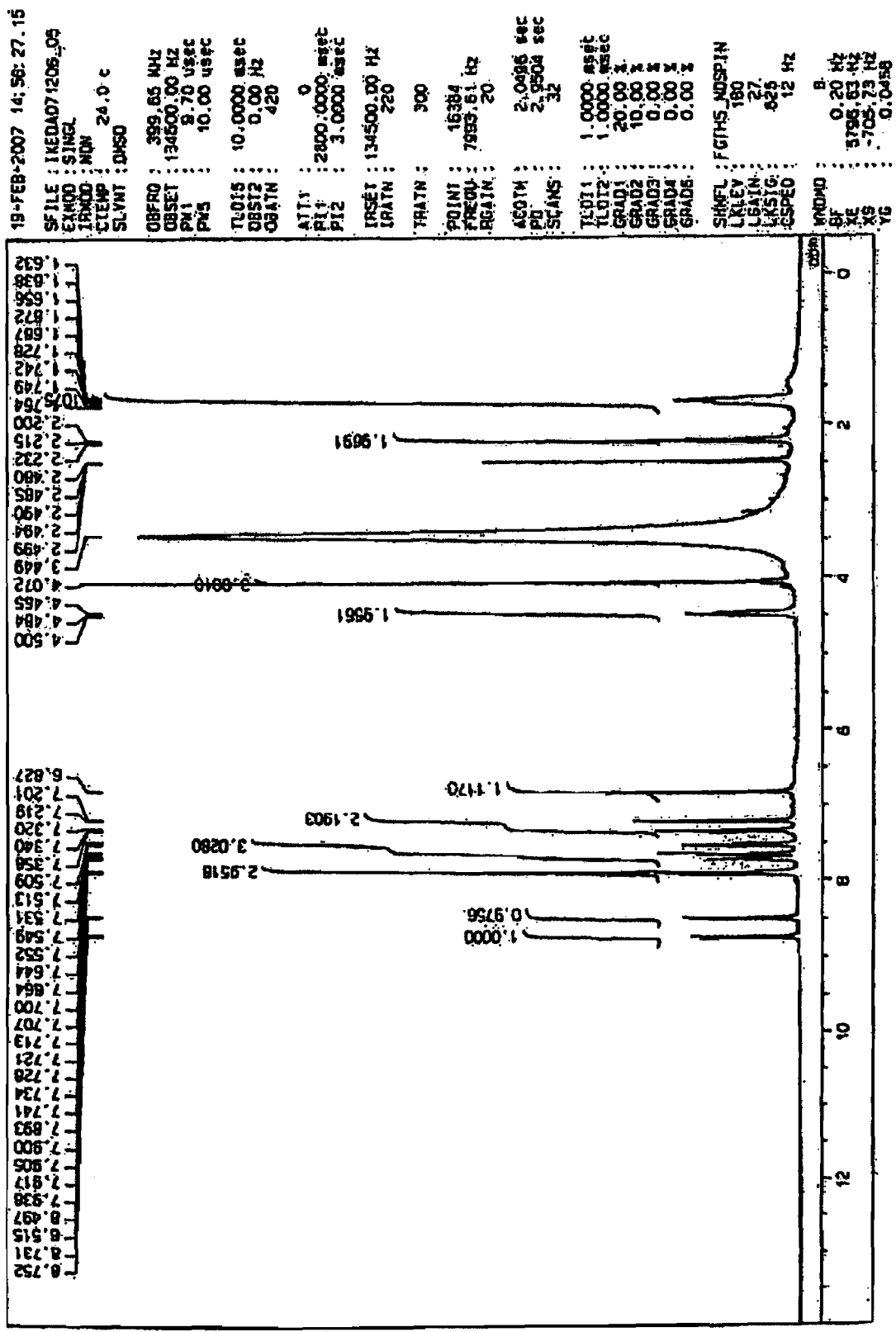
FIG. 6 shows a $^1$HNMR spectrum (DMSO-d6) of a compound (DNA labeled with a dye) of an example.

Next, 1.36 g (5.0 mmol) of N-methylquinolinium iodide (Compound III) (FW 271.10), 7.0 mL (50 mmol) of triethylamine (FW 101.19, d=0.726), and 100 mL of methylene chloride were added to 3.24 g of mixture (crude product) containing Compound 112 (3-(4-carboxybutyl)-2-methylbenzothiazolium bromide) and 2-methylbenzothiazolium bromide. As a result, a transparent solution was obtained. This solution was stirred at 25° C. for 16 hours. Thereafter, the solvent was evaporated under reduced pressure. Acetone (200 mL) was then added to the residue and the precipitate obtained thereby was filtered, which then was washed with acetone. The residue thus obtained was dried under reduced pressure, and the red residue obtained after drying was washed with distilled water (50 mL). This further was filtered, which was washed with distilled water and then dried under reduced pressure. Thus a target substance (Compound 107) was obtained as red powder (654 mg, 1.39 mmol, 28%). This red powder was confirmed to be the target substance (Compound 107) through a comparison in $^1$HNMR spectrum with the reference value. Peak values from $^1$HNMR and $^{13}$CNMR (DMSO-d6) and the measured values of HRMS (ESI) are indicated below. Furthermore, FIG. 6 shows the $^1$HNMR spectrum (DMSO-d6) of Compound 107. Compound 107: $^1$HNMR (DMSO-d6): δ 8.74 (d, J=8.3 Hz, 1H), 8.51 (d, J=7.3 Hz, 1H), 7.94-7.89 (m, 3H), 7.74-7.70 (m, 1H), 7.65 (d, J=8.3 Hz, 1H), 7.55-7.51 (m, 1H), 7.36-7.32 (m, 1H), 7.21 (d, J=7.3 Hz, 1H), 6.83 (s, 1H), 4.47 (t, J=7.1 Hz, 2H), 4.07 (s, 3H), 2.22 (t, J=6.6 Hz, 1H), 1.77-1.63 (m, 4H);
$^{13}$CNMR (DMSO-d6, 60° C.) δ 174.6, 158.8, 148.4, 144.5, 139.5, 137.6, 132.7, 127.9, 126.8, 125.5, 124.1, 123.7, 123.6, 122.4, 117.5, 112.6, 107.6, 87.4, 45.6, 42.0, 35.5, 26.2, 22.3; HRMS (ESI) calcd for $C_{23}H_{23}N_2O_2S$ ([M.Br]$^+$) 391.1480, found 391.1475.

4-((3-(3-carboxypropyl)benzo[d]thiazole-2(3H)-ylidene) methyl)-1-methylquinoliniumbromide with a linker (a polymethylene chain linked to a carboxyl group) having a carbon number n of 3 was synthesized from the mixture of 3-(4-carboxypropyl)-2-methylbenzothiazolium bromide and 2-methylbenzothiazolium bromide by the same method as that used for Compound 107, which was obtained with a yield of 43%. The instrumental analytical values are indicated below.

4-((3-(3-carboxypropyl)benzo[d]thiazole-2(3H)-ylidene)methyl)-1-methylquinoliniumbromide $^1$HNMR (DMSO-d6) δ 8.85 (d, J=8.3 Hz, 1H), 8.59 (d, J=7.3 Hz, 1H), 8.02.7.93 (m, 3H), 7.78.7.70 (m, 2H), 7.61.7.57 (m, 1H), 7.42.7.38 (m, 1H), 7.31 (d, J=6.8 Hz, 1H), 7.04 (s, 1H), 4.47 (t, J=8.1 Hz, 2H), 4.13 (s, 3H), 2.52.2.48 (m, 2H), 1.99.1.92 (m, 2H); $^{13}$CNMR (DMSO-d6, 60° C.) δ 174.3, 158.9, 148.6, 144.5, 139.5, 137.7, 132.7, 127.9, 126.7, 125.6, 124.1, 124.0, 123.7, 122.5, 117.5, 112.5, 107.6, 87.7, 45.6, 42.0, 31.6, 22.4; HRMS (ESI) calcd for $C_{22}H_{21}N_2O_2S$ ([M.Br]$^+$) 377.1324, found 377.1316.

Furthermore, 4-((3-(3-carboxypentyl)benzo[d]thiazole-2(3H)-ylidene) methyl)-1-methylquinoliniumbromide with a linker (a polymethylene chain linked to a carboxyl group) having a carbon number n of 5 was synthesized from the mixture of 3-(4-carboxypentyl)-2-methylbenzothiazolium bromide and 2-methylbenzothiazolium bromide by the same method as that used for Compound 107, which was obtained with a yield of 26%. The instrumental analytical values are indicated below.

4-((3-(3-carboxypentyl)benzo[d]thiazole-2(3H)-ylidene)methyl)-1-methylquinoliniumbromide $^1$HNMR (DMSO-d6) δ 8.70 (d, J=8.3 Hz, 1H), 8.61 (d, J=6.8 Hz, 1H), 8.05.8.00 (m, 3H), 7.80.7.73 (m, 2H), 7.60.7.56 (m, 1H), 7.41.7.35 (m, 2H), 6.89 (s, 1H), 4.59 (t, J=7.3 Hz, 2H), 4.16 (s, 3H), 2.19 (t, J=7.3 Hz, 1H), 1.82.1.75 (m, 2H), 1.62.1.43 (m, 4H); $^{13}$CNMR (DMSO-d6, 60° C.) δ 174.5, 159.0, 148.6, 144.7, 139.7, 137.8, 132.9, 127.9, 126.9, 125.2, 124.2, 123.8, 123.6, 122.6, 117.8, 112.6, 107.7, 87.4, 45.6, 42.1, 36.0, 26.3, 25.9, 24.9; HRMS (ESI) calcd for $C_{24}H_{25}N_2O_2S$ ([M.Br]$^+$) 405.1637, found 405.1632.

Furthermore, 4-((3-(3-carboxyhexyl)benzo[d]thiazole-2(3H)-ylidene) methyl)-1-methylquinoliniumbromide with a linker (a polymethylene chain linked to a carboxyl group) having a carbon number n of 6 was synthesized from the mixture of 3-(4-carboxyhexyl)-2-methylbenzothiazolium bromide and 2-methylbenzothiazolium bromide by the same method as that used for Compound 107, which was obtained with a yield of 22%. The instrumental analytical values are indicated below.

4-((3-(3-carboxyhexyl)benzo[d]thiazole-2(3H)-ylidene)methyl)-1-methylquinoliniumbromide $^1$HNMR (DMSO-d6) δ 8.72 (d, J=8.3 Hz, 1H), 8.62 (d, J=6.8 Hz, 1H), 8.07.8.01 (m, 3H), 7.81.7.75 (m, 2H), 7.62.7.58 (m, 1H), 7.42.7.38 (m, 2H), 6.92 (s, 1H), 4.61 (t, J=7.3 Hz, 2H), 4.17 (s, 3H), 2.18 (t, J=7.3 Hz, 1H), 1.82.1.75 (m, 2H), 1.51.1.32 (m, 6H); $^{13}$CNMR (DMSO-d6, 60° C.) δ 174.0, 159.1, 148.6, 144.7, 139.8, 137.8, 132.9, 127.9, 126.8, 125.0, 124.2, 123.8, 123.6, 122.6, 118.0, 112.7, 107.8, 87.4, 45.5, 42.1, 33.4, 27.9, 26.4, 25.5, 24.1; HRMS (ESI) calcd for $C_{25}H_{27}N_2O_2S$ ([M.Br]$^+$) 419.1793, found 419.1788.

(4) Synthesis of N-hydroxysuccinimidyl ester 109

9.4 mg (20 μmol) of 1-methyl-4-[{3-(4-carboxybutyl)-2(3H)-benzothiazolylidene}methyl]quinolinium bromide (Compound 107) (FW 471.41), 4.6 mg (40 μmol) of N-hydroxysuccinimide (Compound 108) (FW 115.09), and 7.6 mg (40 μmol) of EDC (1-ethyl-3-(3-dimethylaminopropyl) carbodiimide hydrochloride) (FW 191.70) were stirred in 1 mL of DMF at 25° C. for 16 hours. Thus N-hydroxysuccinimidyl ester (Compound 109) was obtained, in which the carboxy group of a dye (Compound 107) had been activated. This reaction product was not purified and the reaction solution (20 mM of a dye) was used for the reaction with oligomeric DNA (oligonucleotide) 105 without further being treated.

Furthermore, 4-((3-(4-(succinimidyloxy)-4-oxobutyl)benzo[d]thiazole-2(3H)-ylidene)methyl)-1-methylquinolinium bromide with a linker (a polymethylene chain) having a carbon number n of 3 was synthesized by the same method as that used for Compound 109 except for a compound with a linker (a polymethylene chain) having a different carbon number was used instead of Compound 107 as a raw material. Moreover, 4-((3-(4-(succinimidyloxy)-4-oxohexyl)benzo[d]thiazole-2(3H)-ylidene)methyl)-1-methylquinolinium bromide with a linker (a polymethylene chain) having a carbon number n of 5 and 4-((3-(4-(succinimidyloxy)-4-oxoheptyl)benzo[d]thiazole-2(3H)-ylidene)methyl)-1-methylquinolinium bromide with a linker (a polymethylene chain) having a carbon number n of 6 were synthesized in the same manner.

Figure 7:
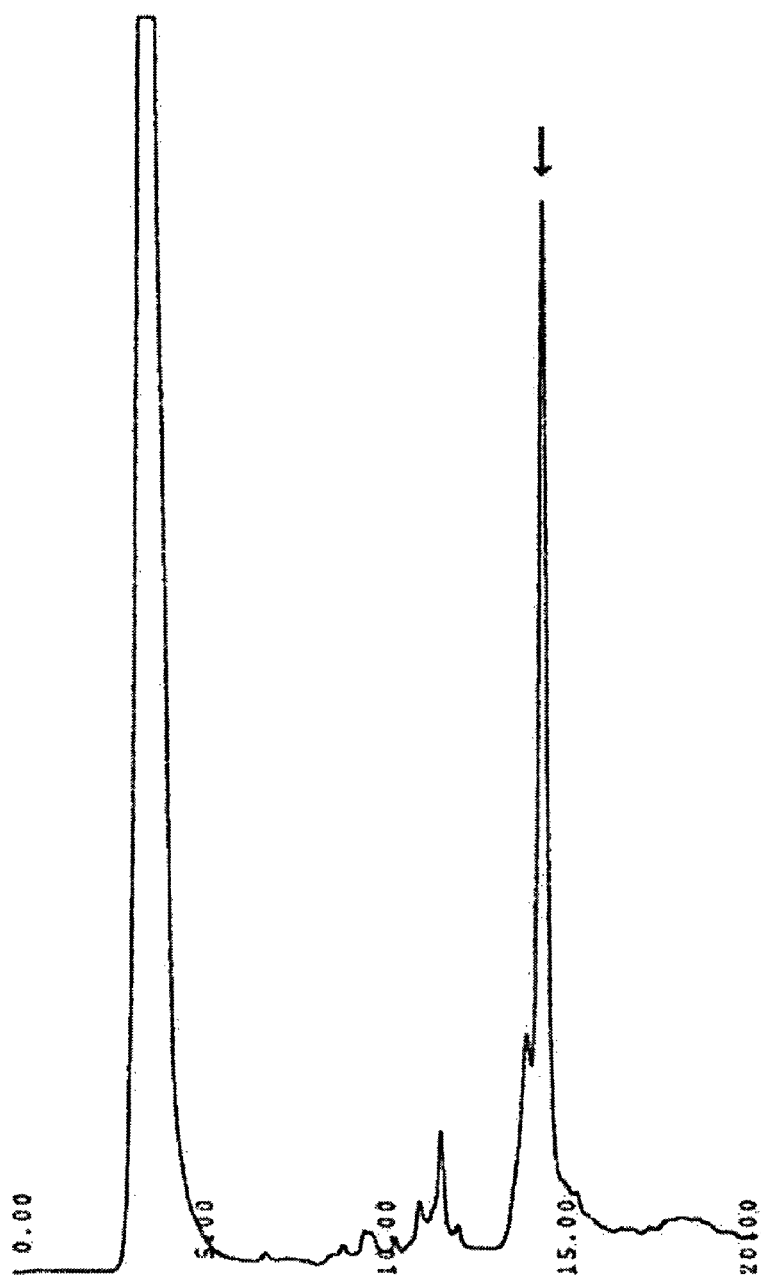
FIG. 7 shows a chart of reversed-phase HPLC of the compound (DNA labeled with a dye) shown in FIG. 6.
Figure 8:
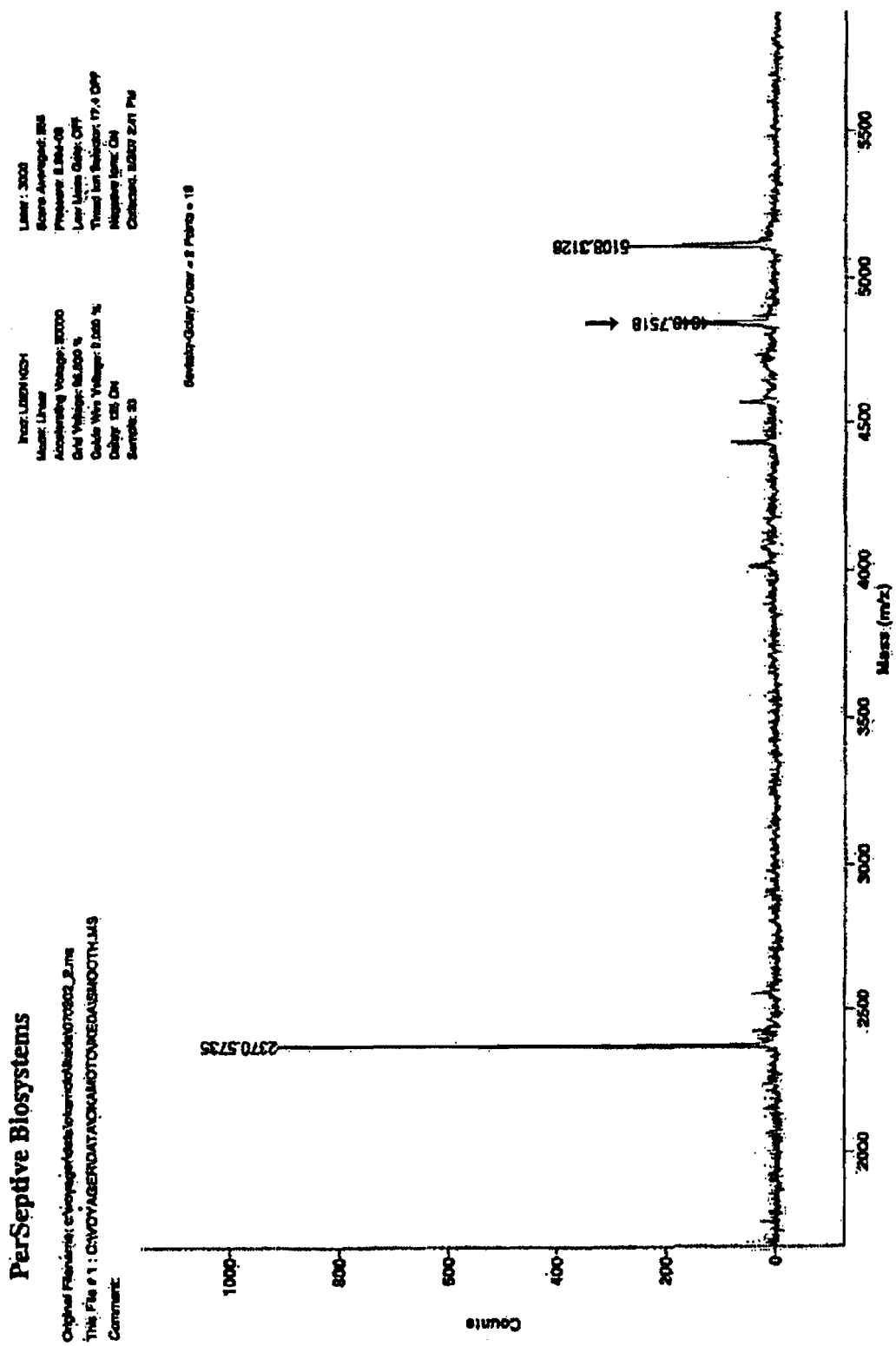
FIG. 8 shows a MALDI-TOF mass spectrum of the compound (DNA labeled with a dye) shown in FIG. 6.

(5) Synthesis of DNA Oligomer (oligonucleotide 110) Modified with 2 Molecules of Thiazole Orange A DNA oligomer (oligonucleotide) 105 having two active amino groups was synthesized by a conventional method with an automated DNA synthesizer in the same manner as in Example 4. The sequence of Compound 105 used herein was the same as that used in Example 4, specifically, 5'-d(CGCAATXTAACGC)-3' (X was Compound 104). Next, this DNA oligomer (oligonucleotide) 105 was reacted with N-hydroxysuccinimidyl ester (Compound 109) and thereby DNA oligomer (oligonucleotide) 110 was synthesized having, in one molecule, structures derived from thiazole orange in two places. That is, first, 30 μL of 5'-d(CGCAATXTAACGC)-3' (Compound 105, with a strand concentration of 320 μM), 10 μL of $Na_2CO_3$/$NaHCO_3$ buffer (1 M, pH 9.0), and 60 μL of $H_2O$ were mixed together. Thereafter, 100 μL of DMF solution (20 mM) of N-hydroxysuccinimidyl ester (Compound 109) was added thereto and mixed well. This was allowed to stand still at 25° C. for 16 hours. Thereafter, 800 μL of $H_2O$ was added thereto, which was then passed through a 0.45-μm filter. The peak that appeared after about 14.5 minutes in reversed-phase HPLC was purified (CHEMCOBOND 5-ODS-H 10×150 mm, 3 mL/min, 5-30% $CH_3CN$/50 mM TEAA buffer (20 minutes), detected at 260 nm). FIG. 7 shows the chart of the reversed-phase HPLC. The fraction indicated with the peak marked with an arrow was fractionated and purified. The product thus obtained by HPLC purification was measured with a MALDI TOF mass spectrometer in its negative mode. As a result, a peak was observed at 4848.8, and it was confirmed to be DNA oligomer (oligonucleotide) 110. FIG. 8 shows the MALDI TOF MASS spectrum of the DNA oligomer (oligonucleotide) 110. In FIG. 8, the arrow indicates the mass peak (4848.8) derived from the purified product. This peak value agreed with a calculated value of 4848.8 of $[M^{2+}-3H^+]^-$ in which three protons were removed from a molecule $M(C_{180}H_{220}N_{56}O_{78}P_{12}S_2)$ of DNA oligomer (oligonucleotide) 110 having two positive charges. The peaks located on the left and right sides thereof are derived from T8-mer and T18-mer of DNA that were added as standard substances.

Example 7

Use of DNA Oligomer (Oligonucleotide) 110 as Fluorescence Primer

Figure 9:
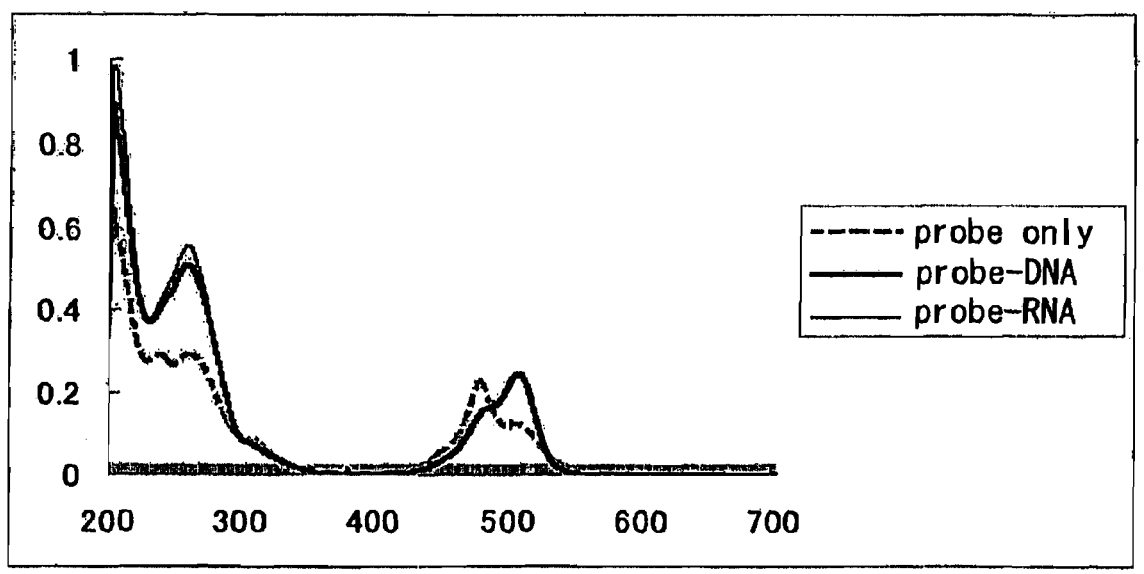
FIG. 9 shows UV spectra of three samples of a fluorescent DNA oligomer according to an example that were in a single strand state, a DNA-DNA double helix state, and a DNA-RNA double helix state, respectively.

DNA oligomer (oligonucleotide) 110 (DNA with two molecules of dye) purified in Example 6 was desalted and lyophilized. Thereafter, an aqueous solution thereof was prepared, and the concentration thereof was determined according to UV absorption (X was approximated by T). Thereafter, UV measurement was carried out with respect to the fluorescence primer (DNA oligomer 110) under conditions including a strand concentration of 2.5 μM, 50 mM phosphoric acid buffer (pH 7.0), and 100 mM NaCl, with the fluorescence primer being in a single strand state, a DNA-DNA double helix state, and a DNA-RNA double helix state. FIG. 9 shows spectra of those three samples. As shown in FIG. 9, the maximum wavelength of UV absorption around 500 nm moved when the double helices were formed.

Figure 10:
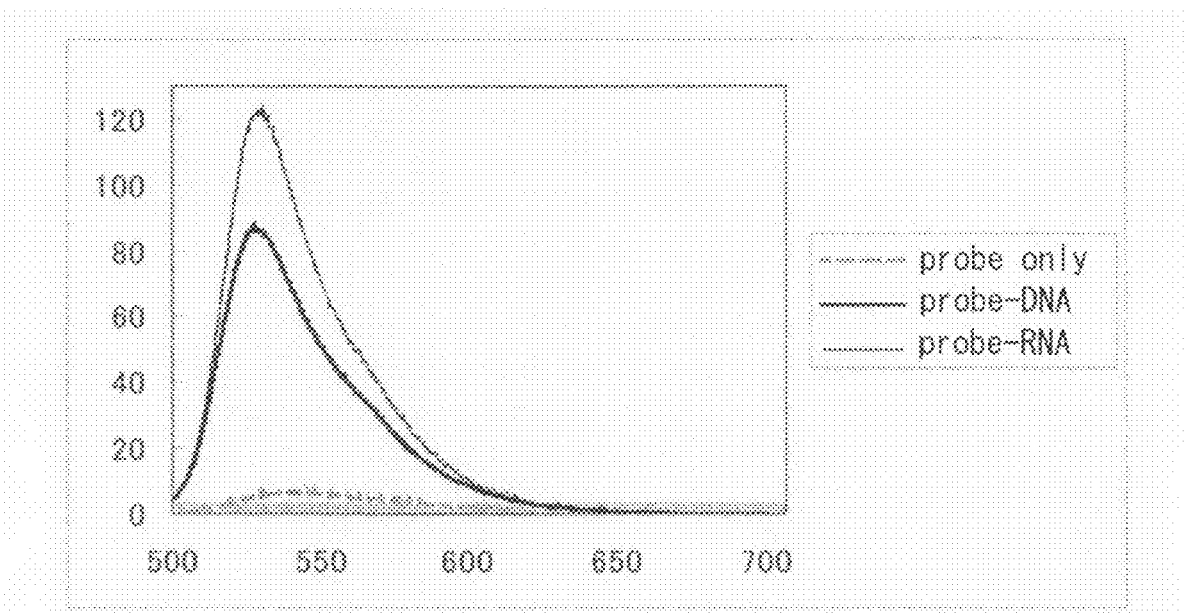
FIG. 10 shows fluorescence spectra of the three samples of the fluorescent DNA oligomer shown in FIG. 9 that were in a single strand state, a DNA-DNA double helix state, and a DNA-RNA double helix state, respectively, which were obtained using excitation light with a wavelength of 488 nm.

Next, the fluorescence primer was excited with excitation light (bandwidth: 1.5 nm) with a wavelength of 488 nm under the same conditions including a strand concentration of 2.5 μM, 50 mM phosphoric acid buffer (pH 7.0), and 100 mM NaCl. Thereafter, fluorescence measurement was carried out. FIG. 10 shows spectra of three samples of the fluorescence primer (the fluorescence DNA oligomers) in a single strand state, a DNA-DNA double helix state, and a DNA-RNA double helix state, respectively. As shown in FIG. 10, when compared with the fluorescence intensity of the single-stranded fluorescence primer obtained at 530 nm, the fluorescence intensity increased 15 times in the case of the DNA-DNA double helix and 22 times in the case of the DNA-RNA double helix.

Figure 11:
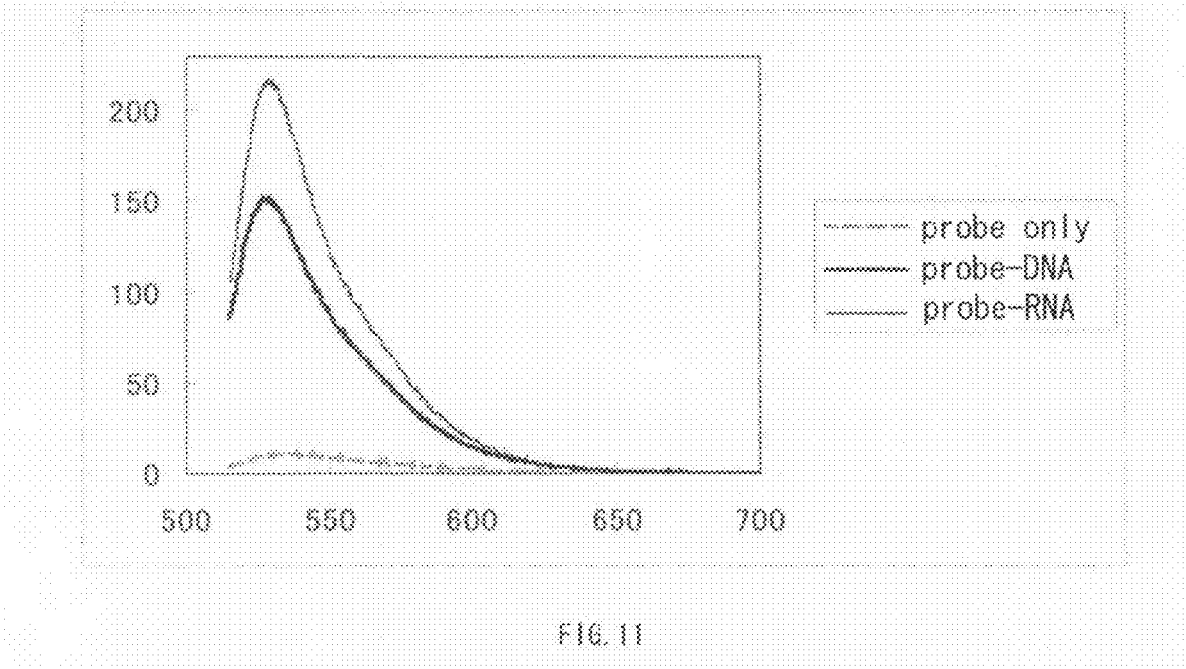
FIG. 11 shows fluorescence spectra of the three samples of the fluorescent DNA oligomer shown in FIG. 9 that were in a single strand state, a DNA-DNA double helix state, and a DNA-RNA double helix state, respectively, which were obtained using excitation light with a wavelength of 510 nm.

Furthermore, the same results were obtained when excitation light with a wavelength of 510 nm was used instead of the excitation light with a wavelength of 488 nm. FIG. 11 shows the spectra thereof.

Example 8

Synthesis of Compounds with Linkers Having Lengths Changed Variously and Use Thereof as Fluorescence Primer Compounds (DNA oligomers) represented by Chemical Formula 113 shown below were synthesized with the linker lengths n being changed variously. The compounds were synthesized in the same manner as in Examples 1 to 4 and 6 except that the compounds were prepared, in each of which the carbon number (chain length) of 5-bromovaleric acid (5-bromopentanoic acid) used as a raw material was changed according to the linker length. In this example, the sequence of Compound 113 was 5'-d(CGCAATXTAACGC)-3' (X was the site where a dye was introduced). Furthermore, each compound was used as a fluorescence primer in the same manner as in Example 7, and the performance thereof was evaluated through fluorescence measurement. As a result, it was proved that when the primer hybridizes with a target nucleic acid, the fluorescence increased approximately 10 times or more than that of a single-stranded primer, as long as the linker has a length in the range indicated below. Moreover, the double strand formed of the primer and target nucleic acid exhibited higher thermal stability than that of a double strand with a native sequence.

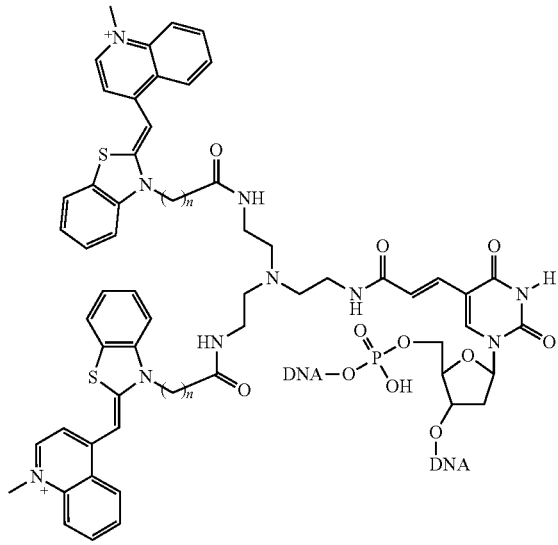

113

Measurement conditions: 2.5 μM primer (Compound 113), 50 mM phosphoric acid buffer (pH 7.0), 100 mM NaCl, 2.5 μM complementary strand The maximum wavelength of fluorescence was the value obtained when excitation was carried out with a light having a wavelength of 488 nm (1.5 nm width).

The quantum yield was calculated with 9,10-diphenylanthracene being used as a reference substance.

Figure 12:
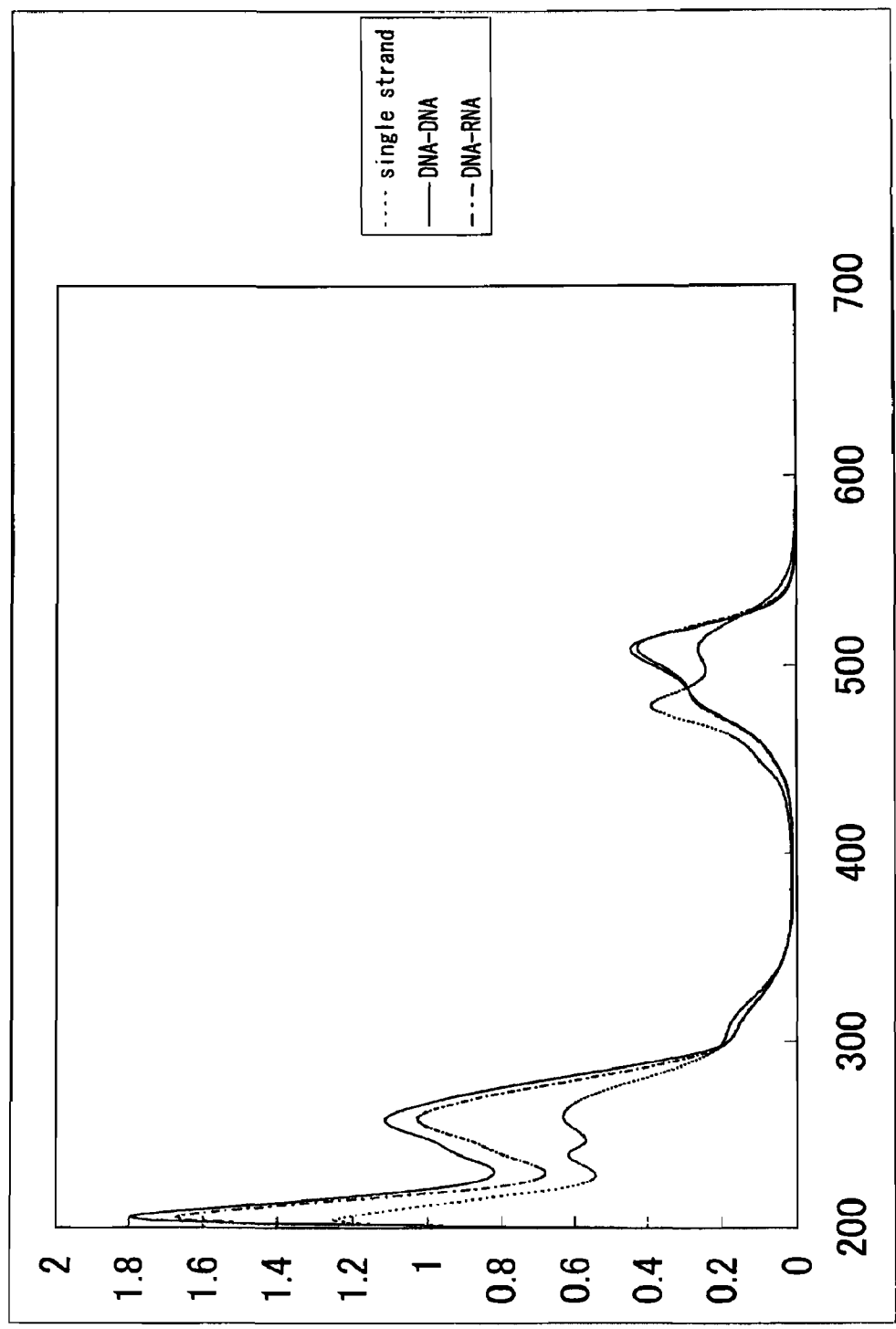
FIG. 12 shows UV spectra of three samples of a fluorescent DNA oligomer according to another example that were in a single strand state, a DNA-DNA double helix state, and a DNA-RNA double helix state, respectively.

FIG. 12 shows absorption spectra obtained with the linker length n being 4 in Example 8. When attention is drawn to absorption that occurred at 400 to 600 nm, the absorption band obtained in the single-stranded state appeared on the shorter wavelength side as compared to the absorption band obtained after hybridization. This clearly indicates the formation of an H-aggregate of dye dimer in the single-stranded state.

Figure 13:
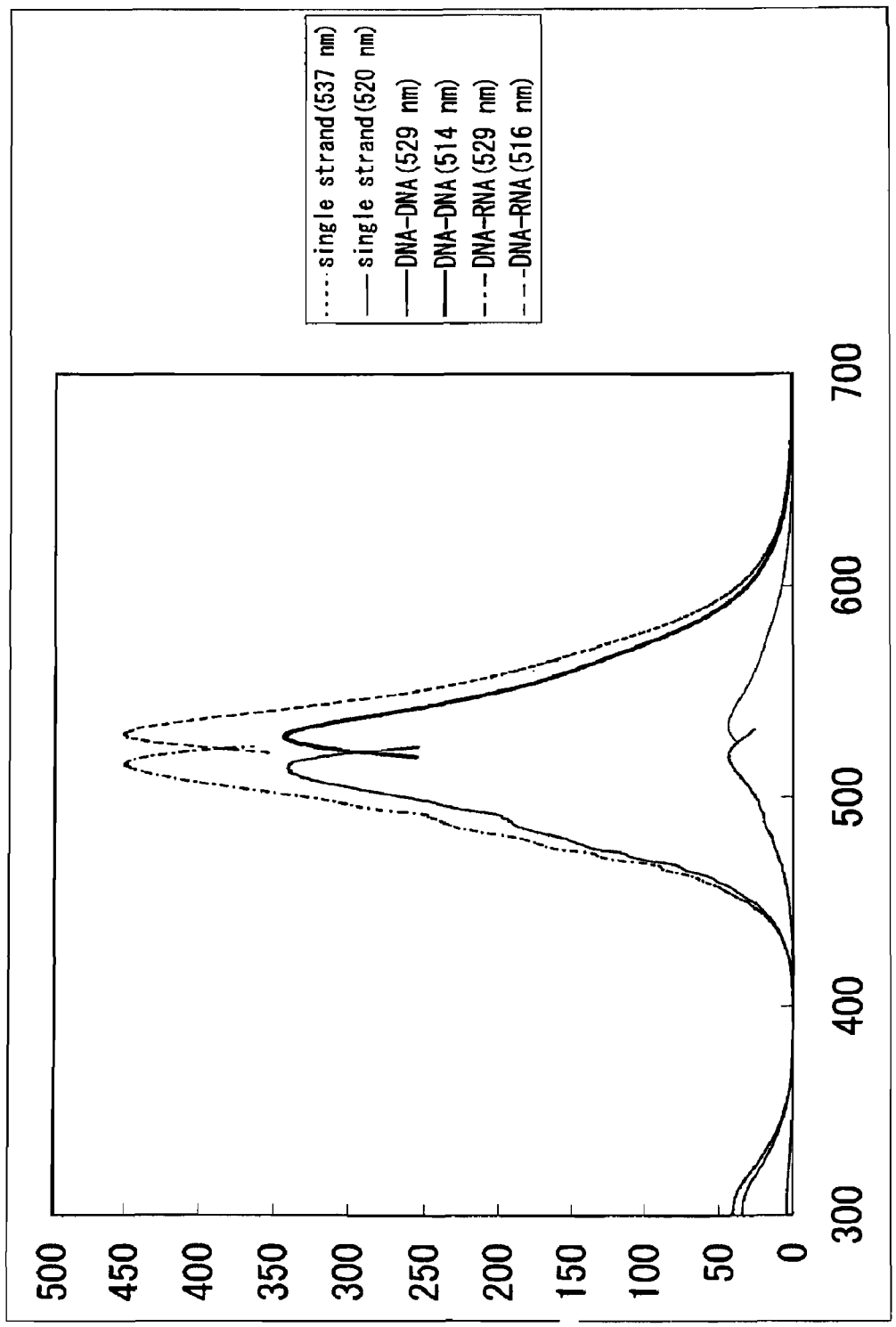
FIG. 13 shows fluorescence spectra of the three samples of the fluorescent DNA oligomer shown in FIG. 12 that were in a single strand state, a DNA-DNA double helix state, and a DNA-RNA double helix state, respectively.

FIG. 13 shows both the fluorescence emission spectra and excitation spectra obtained with a linker length n being 4 in Example 8. In FIG. 13, the curves located on the left side (the shorter wavelength side) indicate the excitation spectra while the curves located on the right side (the longer wavelength side) indicate the fluorescence emission spectra. In FIG. 13, the wavelength of reference fluorescence emission with respect to the excitation spectra and the excitation wavelength with respect to the fluorescence emission spectra are indicated in parentheses in the explanatory note. From the excitation spectra, it was proved that the absorption associated with fluorescence emission was only that in the absorption band on the longer wavelength side shown in FIG. 12 and the absorption on the shorter wavelength side was not associated with fluorescence emission. That is, it clearly indicates that the fluorescence emission was suppressed by the exciton effect. Accordingly, fluorescence emission was strong after hybridization, while it was very weak in the single-stranded state. This allows the states before and after hybridization to be differentiated clearly from each other.

TABLE 1

|  |  | $\lambda_{max}$ (nm) of UV and absorption coefficient | $\lambda_{max}$ (nm) of fluorescence | Quantum yield $\Phi_F$ | Fluorescence intensity ratio $I_{ds}/I_{ss}$ between double strand and single strand | Tm (° C.) |
|---|---|---|---|---|---|---|
| n = 3 | Primer Single strand | 480(117000) 510(93800) | 537 | 0.0193 | — | None |
|  | Primer-DNA Double strand | 505(145000) | 529 | 0.137 | 7.1 | 66 |
|  | Primer-RNA Double strand | 506(139000) | 529 | 0.161 | 8.3 | 54 |
| n = 4 | Primer Single strand | 479(156000) 509(104000) | 537 | 0.0105 | — | None |
|  | Primer-DNA Double strand | 509(179000) | 529 | 0.110 | 10.5 | 65 |
|  | Primer-RNA Double strand | 509(171000) | 529 | 0.116 | 11.0 | 52 |
| n = 5 | Primer Single strand | 480(139000) 510(107000) | 538 | 0.0131 | — | None |
|  | Primer-DNA Double strand | 508(172000) | 529 | 0.123 | 9.4 | 67 |
|  | Primer-RNA Double strand | 508(162000) | 529 | 0.126 | 9.6 | 51 |
| n = 6 | Primer Single strand | 479(139000) 509(93300) | 536 | 0.0122 | — | None |
|  | Primer-DNA Double strand | 509(164000) | 528 | 0.122 | 10.0 | 65 |
|  | Primer-RNA Double strand | 511(162000) | 530 | 0.129 | 10.6 | 52 |

5'-d(CGCAATTTAACGC)-3'/5'-d(GCGTTAAATTGCG)-3' Tm(° C.) 58
5'-d(CGCAATTTAACGC)-3'/5'-r(GCGUUAAAUUGCG)-3' Tm(° C.) 46

Example 9

Compounds (DNA oligomers) represented by Chemical Formula 114 below, each of which contained, in one molecule, one dye structure alone, were synthesized with the linker lengths n being changed variously. The compounds were synthesized in the same manner as in Example 1 to 4 and 6 except that the compounds were prepared, in each of which the carbon number (chain length) of 5-bromovaleric acid (5-bromopentanoic acid) used as a raw material was changed according to the linker length, and bis(2-aminoethyl)methylamine was used instead of tris(2-aminoethyl)amine used in synthesizing Compound 102. Compounds with n being 3, 4, 5, and 6, were synthesized in the same method.

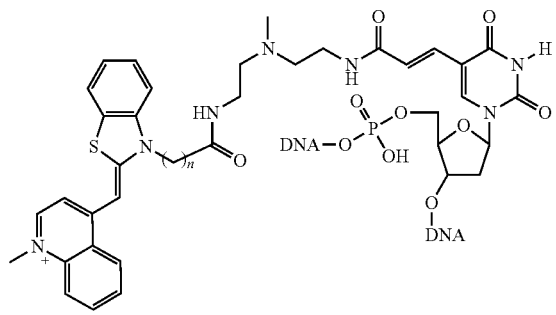

114

More specifically, the synthesis was carried out according to the following scheme. The following scheme shows the case where n=4, but the synthesis was carried out in the same manner even when n was another numerical value.

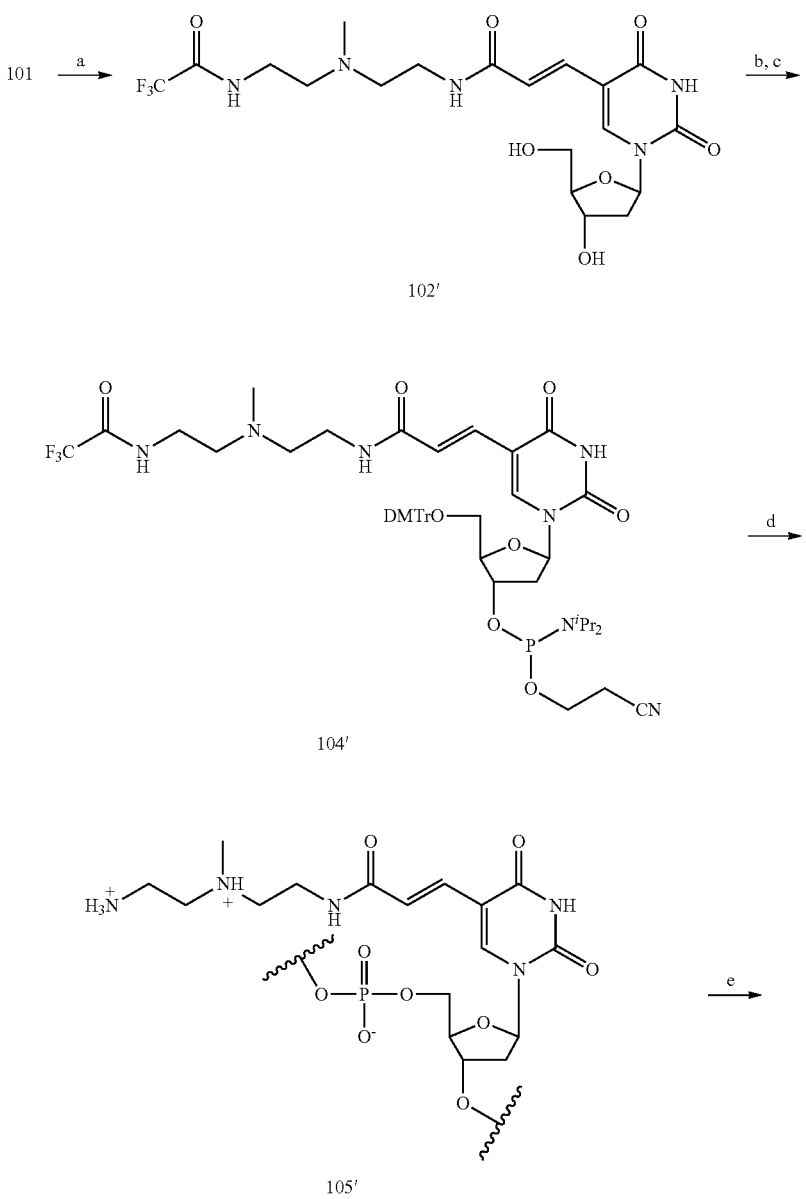

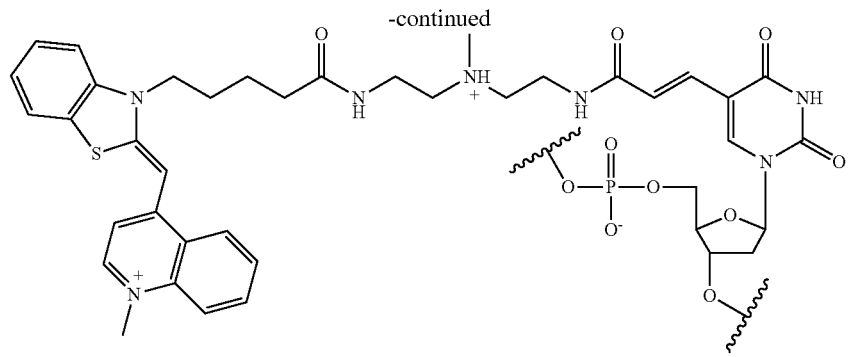

114(4)

Synthesis of (E)-5-(3-(2-(N-Methyl-N-(2-(2,2,2-trifluoroacetamido)ethyl)amino)ethylamino)-3-oxo-prop-1-enyl)-2'-deoxyuridine (102')

First, 1.19 g (4.0 mmol) of (E)-5-(2-carboxyvinyl)-2'-deoxyuridine 101 (with a molecular weight of 298.25), 921 mg (8.0 mmol) of N-hydroxysuccinimide (with a molecular weight of 115.09), and 1.53 g (8.0 mmol) of 1-ethyl-3-(3-dimethylaminopropyl)carbodiimide (with a molecular weight of 191.70) were placed in a recovery flask containing a stirring bar. Thereafter, 1.0 mL of DMF was added thereto, which was stirred at 25° C. for eight hours. Approximately 1 mL of acetic acid was added thereto, and 250 mL of methylene chloride and 250 mL of ultrapure water further were added thereto, which was then stirred vigorously. The precipitate produced thereby was filtered, washed with water, and dried under reduced pressure throughout the night. The white residue thus obtained was suspended in 100 mL of acetonitrile, which was stirred vigorously. Subsequently, 2.34 g (20 mmol) of N-methyl-2,2'-diaminodiethylamine (with a molecular weight of 146.23, d=0.976) was added thereto all at once, which further was stirred at 25° C. for 10 minutes. Thereafter, 4.8 mL (40 mmol) of ethyl trifluoroacetate (with a molecular weight of 142.08, d=1.194), 5.6 mL (40 mmol) of triethylamine (with a molecular weight of 101.19, d=0.726), and 50 mL of ethanol were added thereto, which was stirred at 25° C. for 16 hours. From the mixture thus obtained, the solvent was evaporated under reduced pressure, which was then purified in a silica gel column (10-20% MeOH/CH$_2$Cl$_2$). From the fraction containing the target substance, the solvent was evaporated under reduced pressure. The product produced thereby was dissolved in a small amount of acetone, and ether was then added thereto. As a result, white precipitate was produced. This was filtered, washed with ether, and then dried under reduced pressure. Thus 750 mg (76%) of target substance (Compound 102') was obtained as white powder. The instrumental analytical values are indicated below.

Compound 102'

$^1$HNMR (CD$_3$OD) δ 8.29 (s, 1H), 7.17 (d, J=15.6 Hz, 1H), 6.97 (d, J=15.6 Hz, 1H), 6.21 (t, J=6.3 Hz, 1H), 4.40.4.36 (m, 1H), 3.92.3.90 (m, 1H), 3.80 (dd, J=11.7, 2.9 Hz, 1H), 3.72 (dd, J=11.7, 3.4 Hz, 1H), 3.37.3.25 (m, 5H), 2.60.2.53 (m, 5H), 2.33.2.19 (m, 5H); $^{13}$CNMR (CD$_3$OD) δ 169.2, 158.7 (q, J=36.4 Hz), 151.2, 143.7, 143.6, 134.1, 122.2, 117.5 (q, J=286.2 Hz), 111.0, 89.2, 87.0, 72.1, 62.6, 57.4, 56.7, 42.4, 41.8, 38.5, 38.3; HRMS (ESI) calcd for C$_{19}$H$_{27}$F$_3$N$_5$O$_7$ ([M+H]$^+$) 494.1863, found 494.1854.

Synthesis of (E)-5-(3-(2-(N-Methyl-N-(2-(2,2,2-trifluoroacetamido)ethyl)amino)ethylamino)-3-oxo-prop-1-enyl)-5'O-(4,4'-dimethoxytrityl)-2'-deoxyuridine 3'O-(2-cyanoethyl)-N,N-disopropylphosphoramidite (Compound 104')

First, 296 mg (0.60 mmol) of Compound 102' (with a molecular weight of 494.19) and 224 mg (0.66 mmol) of 4,4'-dimethoxytritylchloride (with a molecular weight of 338.83) were placed in a recovery flask containing a stirring bar. Thereafter, 4 mL of pyridine was added thereto, which was stirred at 25° C. for two hours. Subsequently, 1 mL of water was added thereto, and the solvent was then evaporated under reduced pressure. The product obtained thereby was purified in a silica gel column (1.5% MeOH and 1% Et$_3$N/CH$_2$Cl$_2$). A fraction containing tritylide (an intermediate of Compound 104') of the target compound 102' was concentrated, and a saturated sodium bicarbonate aqueous solution was added to the residue. The mixture was extracted with ethyl acetate, washed with saturated saline, and dried under reduced pressure. Thus white foamy tritylide (366 mg, 77%) was obtained.

$^1$HNMR (CD$_3$OD) δ 7.94 (s, 1H), 7.42.7.17 (m, 9H), 7.01 (d, J=15.6 Hz, 1H), 6.95 (d, J=15.6 Hz, 1H), 6.86.6.83 (m, 4H), 6.21 (t, J=6.3 Hz, 1H), 4.41.4.38 (m, 1H), 4.09.4.06 (m, 1H), 3.75 (s, 6H), 3.40.3.30 (m, 6H), 2.59 (t, J=6.8 Hz, 2H), 2.53 (t, J=6.8 Hz, 2H), 2.46.2.31 (m, 5H); $^{13}$CNMR (CD$_3$OD) δ 169.2, 158.7 (q, J=36.4 Hz), 151.2, 143.7, 143.6, 134.1, 122.2, 117.5 (q, J=286.2 Hz), 111.0, 89.2, 87.0, 72.1, 62.6, 57.4, 56.7, 42.4, 41.8, 38.5, 38.3; HRMS (ESI) calcd for C$_{40}$H$_{45}$F$_3$N$_5$O$_9$ ([M+H]$^+$) 796.3169, found 796.3166.

In a round-bottom flask were placed 159 mg (0.20 mmol) of tritylide (with a molecular weight of 920.85) of Compound 102' and 28.6 mg (0.40 mmol) of 1H-tetrazole (with a molecular weight of 70.05). This was vacuum-dried with a vacuum pump overnight. Then, 4.0 mL of CH$_3$CN was added thereto and thereby the product thus dried was dissolved therein, which was then stirred. Thereafter, 191 μL (0.60 mmol) of 2-cyanoethyl N,N,N',N'-tetraisopropylphosphoramidite (with a molecular weight of 301.41, d=0.949) was added thereto all at once, which was stirred at 25° C. for two hours. After reaction completion was confirmed by TLC, saturated sodium bicarbonate water was added thereto, which was extracted with ethyl acetate. The organic layer obtained thereby was washed with saturated saline and then dried with magnesium sulfate. After the magnesium sulfate was removed by filtration, the solvent was evaporated under reduced pressure. Thus a crude product containing the target compound 104' was obtained. This composition was used for DNA synthesis without being purified or further treated. From $^{31}$PNMR (CDCl$_3$) and HRMS (ESI) of the crude product, it was confirmed that Compound 104' had been obtained. Those values are indicated below.

Compound 104'

$^{31}$PNMR (CDCl$_3$) δ 149.686, 149.393; HRMS (ESI) calcd for C$_{49}$H$_{61}$F$_3$N$_7$O$_{10}$P ([M+H]$^+$) 996.4248, found 996.4243.

DNA 105' was synthesized in the same manner as in the case of Compound 105. The instrumental analytical values are indicated below.

DNA 105'

CGCAAT[105']TAACGC, calcd for C$_{133}$H$_{174}$N$_{51}$O$_{76}$P$_{12}$ ([M+H]$^+$) 4074.8, found 4072.0; CGCAAT[105'][105'] AACGC, calcd for C$_{140}$H$_{187}$N$_{54}$O$_{77}$P$_{12}$ ([M+H]$^+$) 4230.0, found 4228.9.

DNA 114 containing thiazole orange introduced therein was synthesized in the same manner as in the case of Compound 113. The instrumental analytical values are indicated below.

CGCAAT[114]$_{(4)}$TAACGC, calcd for C$_{156}$H$_{194}$N$_{53}$O$_{77}$P$_{12}$S(M$^+$) 4447.3, found 4445.6; CGCAAT [114]$_{(4)}$[114]$_{(4)}$AACGC, calcd for C$_{18}$6H$_{228}$N$_{58}$O$_{79}$P$_{12}$S$_2$ ([M.H]$^+$) 4976.0, found 4976.9.

Figure 14:
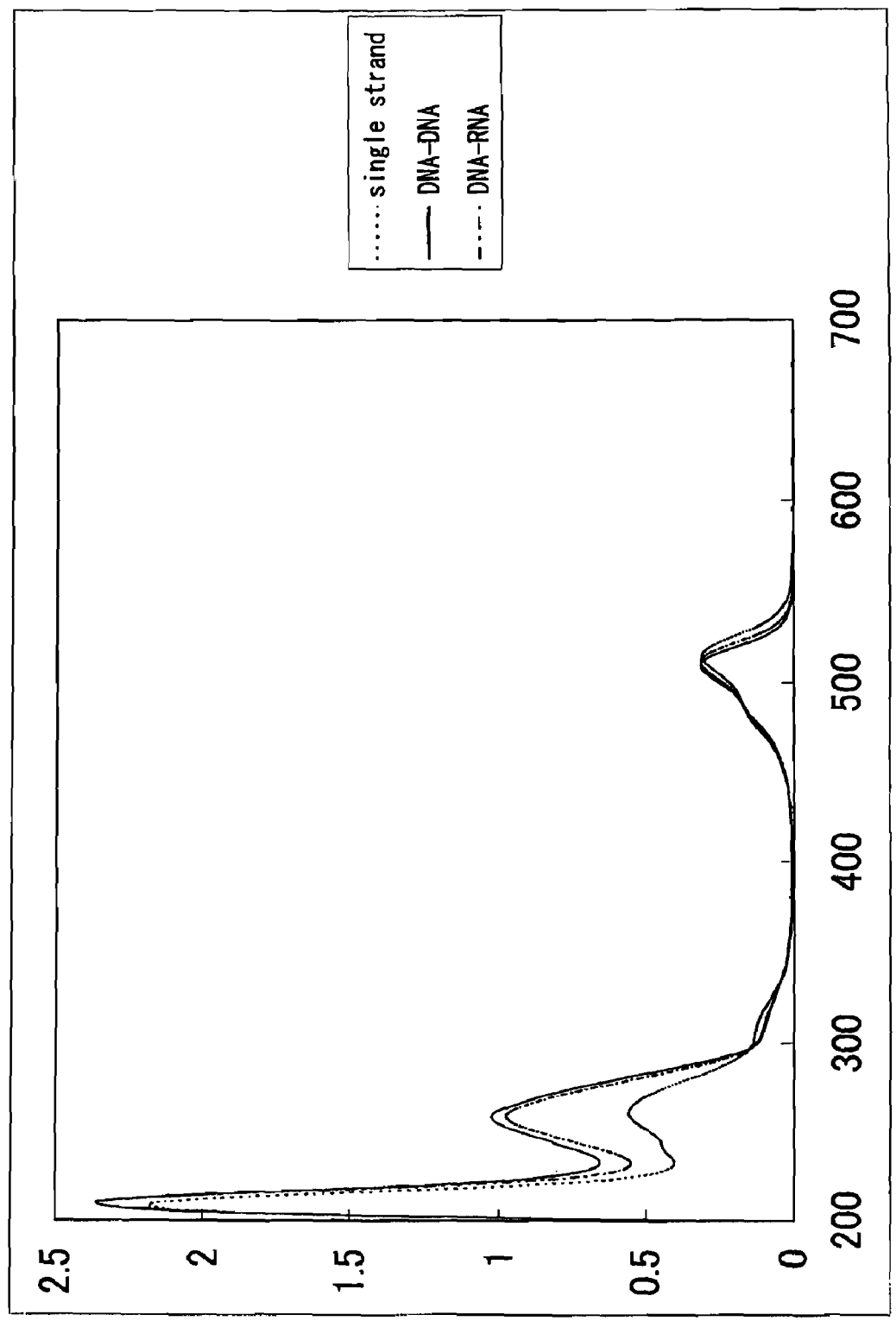
FIG. 14 shows UV spectra of three samples of a fluorescent DNA oligomer according to still another example that were in a single strand state, a DNA-DNA double helix state, and a DNA-RNA double helix state, respectively.
Figure 15:
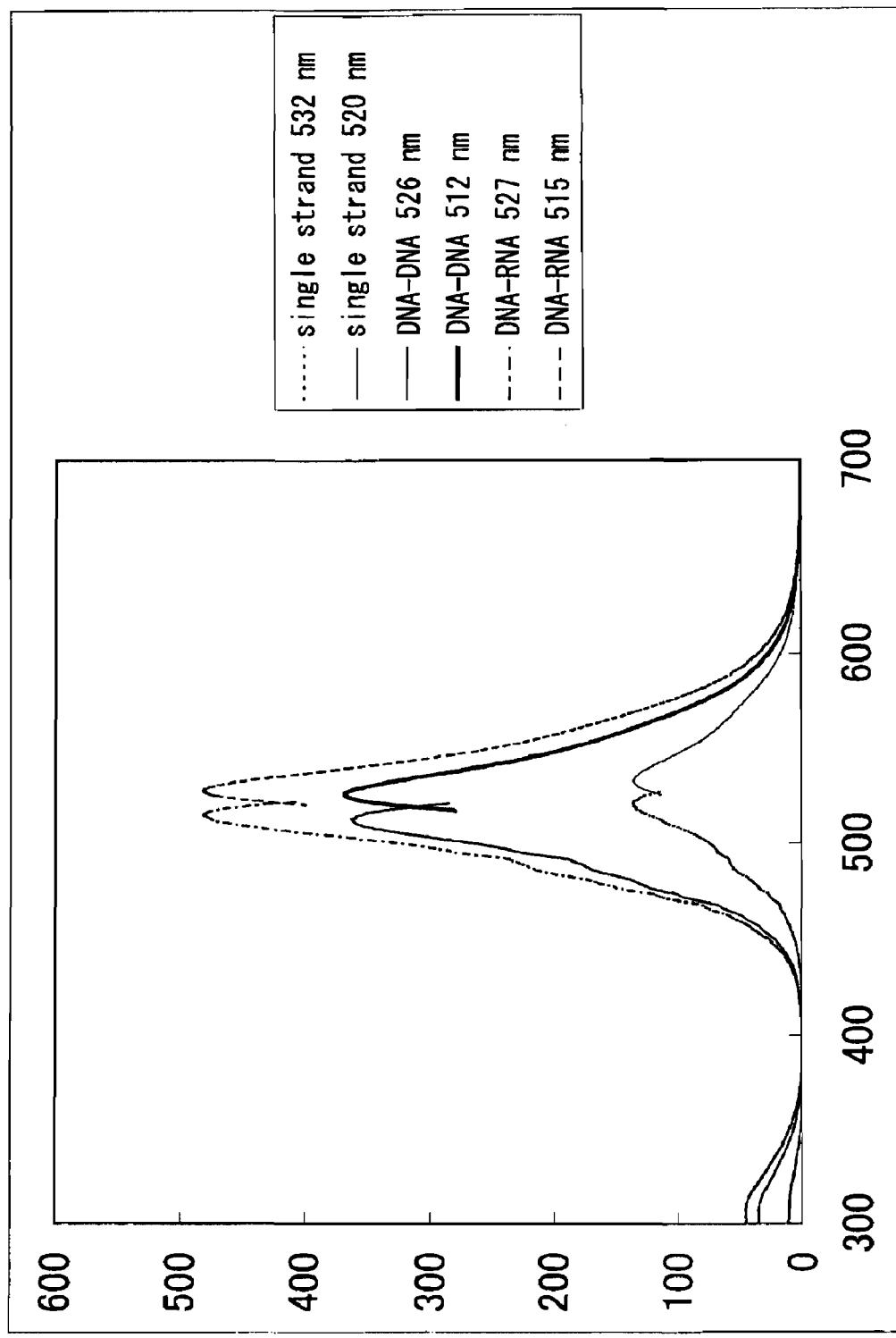
FIG. 15 shows fluorescence spectra of the three samples of the fluorescent DNA oligomer shown in FIG. 14 that were in a single strand state, a DNA-DNA double helix state, and a DNA-RNA double helix state, respectively.

With respect to ODN (a primer containing only one dye) having a sequence of 5'-d(CGCAAT[114]$_{(n)}$TAACGC)-3' selected from the synthesized DNA oligomers (ODNs), fluorescence behavior was observed in the same manner as in Examples 7 and 8. The results are indicated in Table 2 below and FIGS. 14 and 15. FIG. 14 shows the absorption spectra, and FIG. 15 shows the excitation spectra and emission spectra. In FIG. 15, the curves located on the left side (the shorter wavelength side) indicate the excitation spectra while the curves located on the right side (the longer wavelength side) indicate the fluorescence emission spectra. In FIG. 15, the wavelengths indicated in the explanatory note denote the wavelength of reference fluorescence emission with respect to the excitation spectra and the excitation wavelength with respect to the fluorescence emission spectra, respectively. As shown in FIGS. 14 and 15, Compound 114 has, in one molecule, only one dye structure and therefore no H-aggregate is formed. Thus the exciton effect does not occur (no shift towards the shorter wavelength side is observed in the absorption spectrum). Accordingly, fluorescence quenching was weaker in the single-stranded state as compared to the compounds containing two dye structures, and the fluorescence intensity ratio I$_{ds}$/I$_{ss}$ between the double strand and the single strand is relatively low. However, since the intercalation of dye through formation of a double strand planarizes the dye structure, higher fluorescence intensity was obtained in the double-stranded state as compared to the single strand as indicated in Table 2 below. In the single strand, when the excitation wavelength was changed from 488 nm to λ$_{max}$ (one on the longer wavelength side if there are two λ$_{max}$) in the UV absorption spectrum, a quantum yield Φ$_F$ of 0.120 was obtained as a measurement result. Furthermore, in the DNA-DNA double strand, when the excitation wavelength was changed from 488 nm to λ$_{max}$ (one on the longer wavelength side if there are two λ$_{max}$) in the UV absorption spectrum, a quantum yield Φ$_F$ of 0.307 and a fluorescence intensity ratio I$_{ds}$/I$_{ss}$ between the double strand and the single strand of 3.4 were obtained as measurement results.

Measurement conditions: 2.5 µM primer, 50 mM phosphoric acid buffer (pH 7.0), 100 mM NaCl, 2.5 µM complementary strand The maximum wavelength of fluorescence is a value obtained when excitation was carried out with light having a wavelength of 488 nm (with a width of 1.5 nm).

The quantum yield was calculated with 9,10-diphenylanthracene being used as a reference substance.

Example 10

Compounds (DNA oligomers), each of which contains only one dye structure in one molecule, were synthesized in the same manner as in Example 9 except that a compound represented by Chemical Formula 115 was used as a dye instead of Compound 107. The synthesis was carried out with the linker length n being changed variously from 1 to 4. The sequence was 5'-d(CGCAATXTAACGC)-3' (X was the site where a dye was introduced) as in Compound 105.

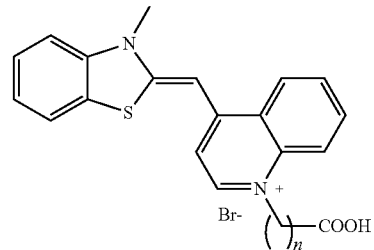

115

Compound 116 indicated below is obtained when n=2. Fluorescence intensity of Compound 116 was evaluated in the same manner as in Examples 7 to 9. As a result, in the case of the DNA-RNA double strand, the increase in fluorescence intensity was observed as compared to the case of the single strand.

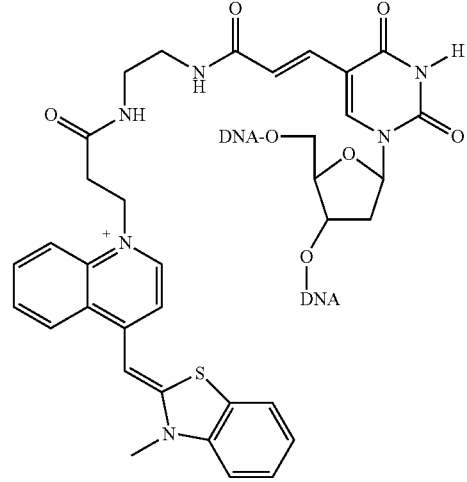

116

TABLE 2

| | | λ$_{max}$ (nm) of UV and absorption coefficient | λ$_{max}$ (nm) of fluorescence | Quantum yield | Ratio | Tm (° C.) |
|---|---|---|---|---|---|---|
| n = 4 | Single strand | 515(123000) | 532 | 0.0681 | — | None |
| | DNA-DNA Double strand | 509(125000) | 526 | 0.180 | 2.64 | 65 |
| | DNA-RNA Double strand | 511(125000) | 527 | 0.244 | 3.58 | 55 |

[Fluorescence Lifetime Measurement]

With respect to the DNA oligomers (oligonucleotides) of Example 8 (two dyes) and Example 9 (one dye), fluorescence lifetime was measured in the case of the single strand and in the case of the double-strand DNA, respectively. The DNA oligomer used as a measurement control contains, in the site X in the following sequence, a nucleotide containing a dye introduced therein.

```
5'-d(CGCAATXTAACGC)-3'     (SEQ ID NO. 1)

5'-d(GCGTTAAATTGCG)-3'     (SEQ ID NO. 2)
```

The results of the fluorescence lifetime measurement are indicated in Table 3 below. In Table 3, T is fluorescence lifetime (ns). CHISQ denotes a measurement error. T1 indicates the time elapsed from immediately after completion of excitation. T2 indicates the time further elapsed after time T1 has elapsed in the case of the primer containing two dyes of Example 8 while being the time elapsed from immediately after completion of excitation in the case of the primer containing one dye of Example 9. T3 indicates the time further elapsed after time T2 has elapsed. In Table 3, the numerical value expressed in "%" is the fluorescence decay rate (with the fluorescence intensity obtained immediately after completion of excitation being taken as 100%) during the passage of time T1, T2, or T3, and the sum total is 100% with respect to each primer (DNA oligomer). As indicated in Table 3, the primer containing two dyes (Example 8) undergoes a very short quenching process (the fluorescence decay rate obtained 0.0210 ns after excitation was 81.54%) in the single-stranded state, which indicates the presence of an exciton effect. This was not observed in other cases. The fluorescence quenching of this ODN labeled with two dyes, in the single-stranded state, plays an important role in sharp and hybridization-specific change in fluorescence intensity. Furthermore, as can be seen in Table 3, the fluorescence quenching properties agreed with quadratic or cubic function properties. With respect to the double strand with two dyes indicated in Table 3 below, measurement was carried out again under the same conditions (however, measurement of Ti was omitted). As a result, the fluorescence decay rate when T2=2.05 was 44%, the fluorescence decay rate when T3=4.38 was 56%, T was 3.33 (ns), and CHISQ was 1.09. Thus values that were very close to those indicated in Table 3 below were obtained. That is, it is indicated that the primer of this example has excellent reproducibility in this fluorescence lifetime measurement.

TABLE 3

|  | One dye Single strand | One dye Double strand | Two dyes Single strand | Two dyes Double strand |
|---|---|---|---|---|
| T1 | — | — | 0.0210 ns (81.54%) | 0.551 ns (2.73%) |
| T2 | 0.934 ns (39.19%) | 1.58 ns (24.63%) | 1.28 ns (8.99%) | 2.33 ns (50.30%) |
| T3 | 3.12 ns (60.81%) | 3.60 ns (75.37%) | 3.76 ns (9.48%) | 4.57 ns (46.97%) |
| T | 2.26 | 3.10 | 0.489 | 3.33 |
| CHISQ | 1.32 | 0.96 | 1.11 | 1.04 |

2.5 µM strand
50 mM phosphoric acid buffer (pH 7.0)
100 mM NaCl
Measured at 455 nm (prompt) and 600 nm (decay).

Example 11

A DNA oligomer represented by Chemical Formula 117 below was synthesized in the same manner as in Example 8 except that a compound represented by Chemical Formula 115' below was used as a dye instead of Compound 107. Compounds with n being 3, 4, 5, and 6, were synthesized in the same method. Furthermore, it was used as a fluorescence primer in the same manner as in Example 8, and the performance thereof was evaluated by fluorescence measurement. The result is indicated in Table 4 below. As indicated in Table 4, Compound 117 is different in absorption band from the DNA oligomer (Compound 113) of Example 8, but similarly it exhibited a good exciton effect. This indicates that in the present invention, multicolor detection can be carried out using fluorescence primers with different absorption bands from each other.

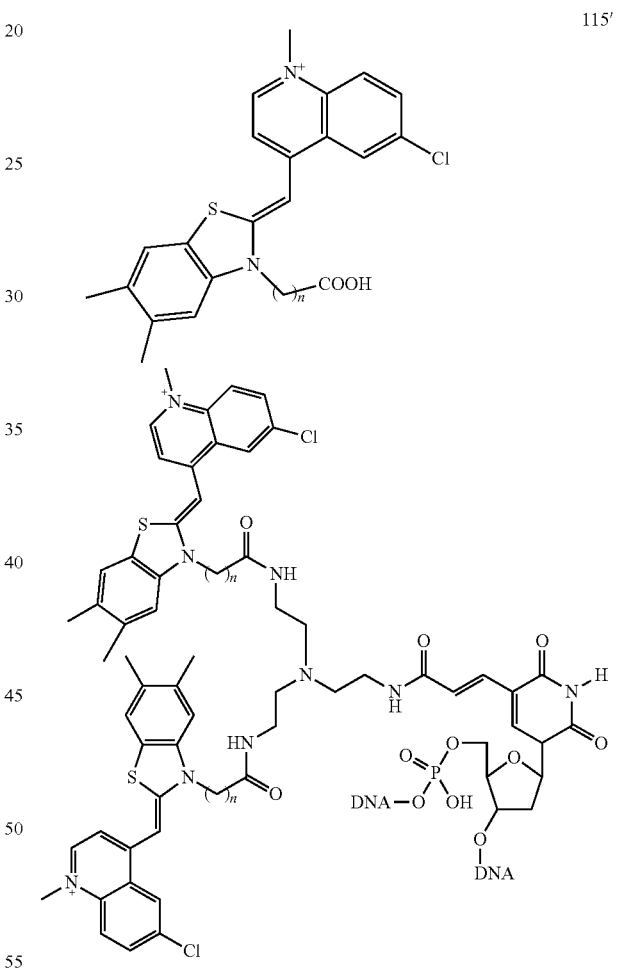

115'

TABLE 4

|  |  | $\lambda_{max}$ (nm) of UV and absorption coefficient | $\lambda_{max}$ (nm) of fluorescence | Quantum yield | Ratio |
|---|---|---|---|---|---|
| n = 4 | Primer Single strand | 499(135000) 532(86000) | 553 | 0.00911 | — |
|  | Primer-DNA Double strand | 505(111000) 530(148000) | 550 | 0.0706 | 7.7 |

Example 12

A DNA oligomer (Compound 118) expressed by the sequence described below was synthesized. X is a nucleotide (represented by the formula described below, referred to as Chemical Formula 118) having the same dye structure as that of Example 9. As indicated in the sequence described below, this DNA oligomer contains two successive nucleotides sequenced, each of which contains a dye introduced therein. Introduction of the dye and synthesis of the DNA oligomer were carried out in the same manners as in the respective examples described above.

5'-d(TTTTTTXXTTTTT)-3'          (SEQ ID NO. 3)

X =

Furthermore, this DNA oligomer was used as a fluorescence primer in the same manner as in the respective examples described above, and the performance thereof was evaluated through fluorescence measurement.
2.5 μM primer (strand concentration)
50 mM phosphoric acid buffer (pH 7.0)
100 mM NaCl
2.5 μM complementary strand (strand concentration)

Figure 16:
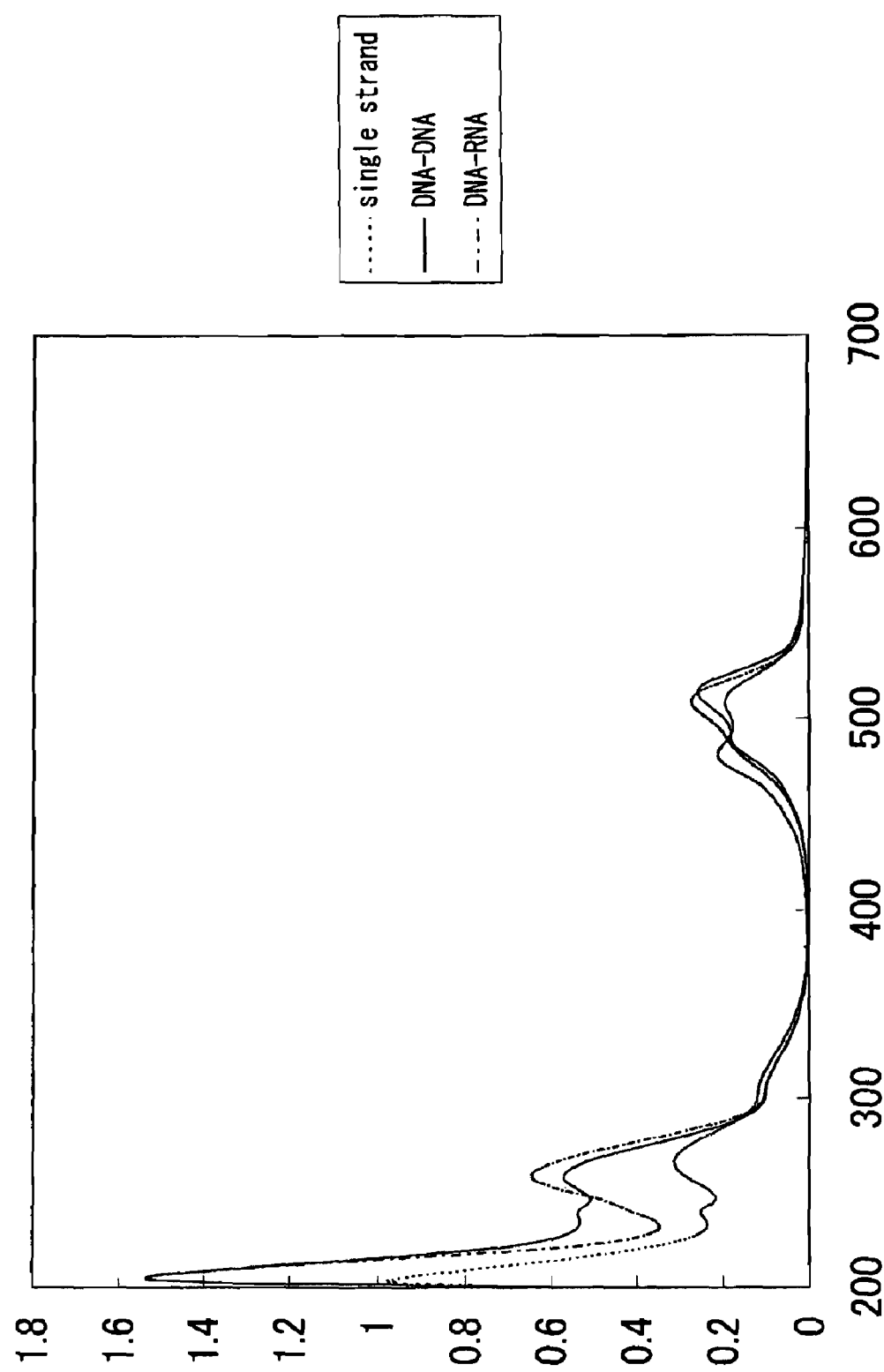
FIG. 16 shows UV spectra of three samples of a fluorescent DNA oligomer according to yet another example that were in a single strand state, a DNA-DNA double helix state, and a DNA-RNA double helix state, respectively.
Figure 17:
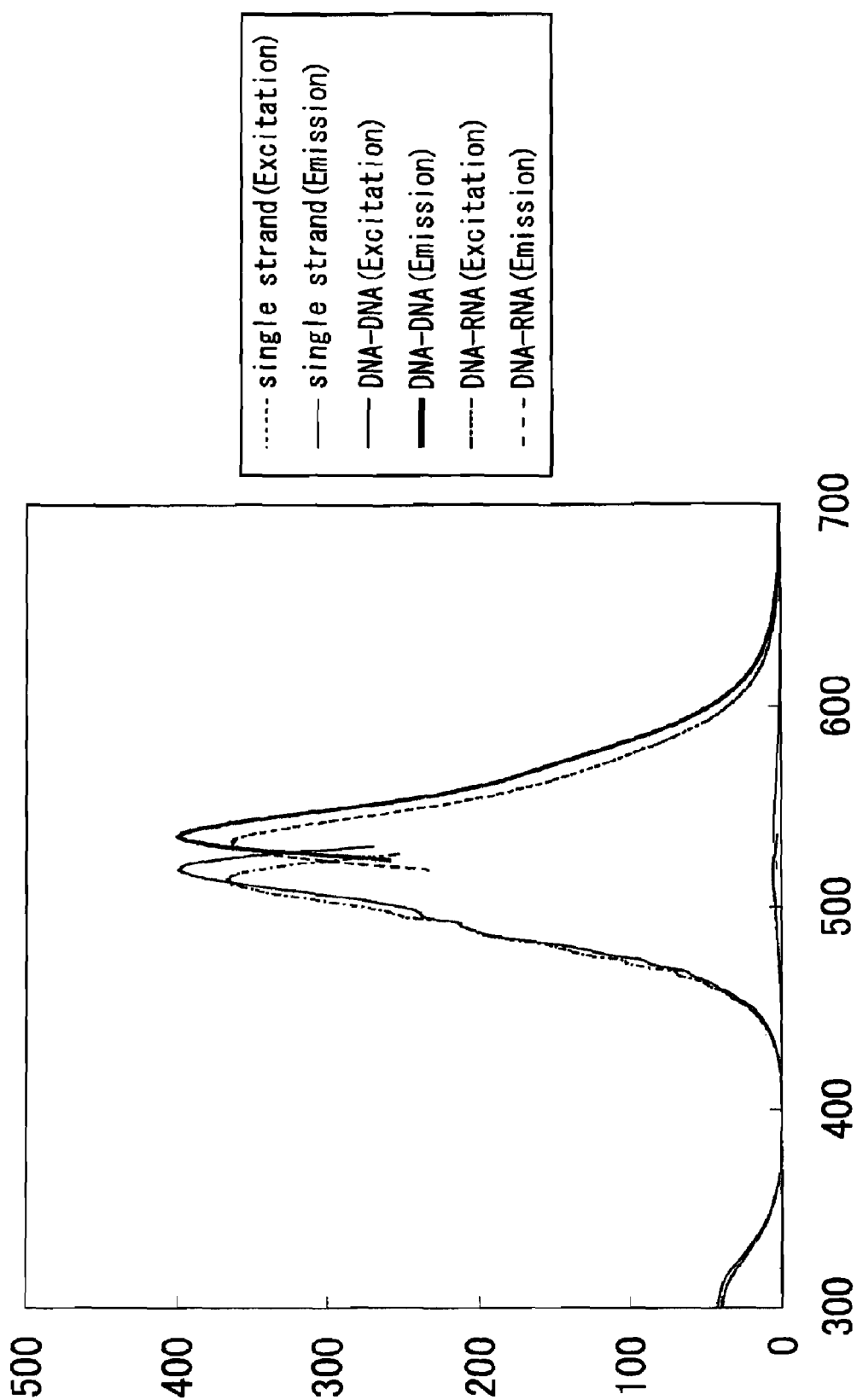
FIG. 17 shows fluorescence spectra of the three samples of the fluorescent DNA oligomer shown in FIG. 16 that were in a single strand state, a DNA-DNA double helix state, and a DNA-RNA double helix state, respectively.

The results are shown in FIGS. 16 and 17. FIG. 16 is a diagram showing absorption spectra, and FIG. 17 is a diagram showing both excitation spectra and fluorescence emission spectra. In FIG. 17, the curves located on the left side (the shorter wavelength side) indicate the excitation spectra while the curves located on the right side (the longer wavelength side) indicate the fluorescence emission spectra. As shown in FIGS. 16 and 17, even when two successive nucleotides, each of which contains a dye introduced therein, are sequenced, an exciton effect was exhibited because it was possible to locate the dyes at a short distance, and the states before and after hybridization with target nucleic acid can be differentiated clearly from each other by fluorescence intensity.

Example 13

Compounds (DNA oligomers) represented by Chemical Formula 113 or 114, i.e. the respective ODNs indicated in Table 5 below, were synthesized with the linker length n and nucleic acid sequence being changed variously. The "ODN" denotes oligodeoxyribonucleotide (DNA oligomer) as described above. The synthesis was carried out in the same manner as in Examples 1 to 4, 6, 8, 9, and 12 except that the compounds were prepared in each of which the carbon number (chain length) of 5-bromovaleric acid (5-bromopentanoic acid) used as a raw material was changed according to the linker length, and the sequence was changed suitably in the synthesis of oligodeoxyribonucleotide. ODN1 is identical to oligodeoxyribonucleotide (DNA oligomer) synthesized in Example 8, and ODN4 and ODN5 are identical to oligodeoxyribonucleotide (DNA oligomer) synthesized in Example 9. In the synthesis, N-hydroxysuccinimidyl ester (Compound 109) of thiazole orange used herein was at least 50 equivalents of active amino group. After the synthesis, the development time in reversed-phase HPLC was 20 to 30 minutes or longer as required. In Table 5 indicated below, for example, [113](n) or [114](n) denotes that a nucleotide represented by Chemical Formula 113 or 114 has been inserted in that site, and n denotes a linker length. In Table 5, ODN1' indicates a DNA strand complementary to ODN1. Similarly, ODN2' denotes a DNA strand complementary to ODN2, and ODN3' indicates a DNA strand complementary to ODN3.

TABLE 5

| | Sequence (5'→3') | |
|---|---|---|
| ODN1 | CGCAAT[113]$_{(n)}$TAACGC | SEQ ID NO. 1 |
| ODN1' | GCGTTAAATTGCG | SEQ ID NO. 2 |
| ODN2 | TTTTTT[113]$_{(4)}$TTTTTT | SEQ ID NO. 4 |
| ODN2' | AAAAAAAAAAAA | SEQ ID NO. 5 |

TABLE 5-continued

| | Sequence (5'→3') | |
|---|---|---|
| ODN3 | TGAAGGGCTT[113]$_{(4)}$TGAACTCTG | SEQ ID NO. 6 |
| ODN3' | CAGAGTTCAAAAGCCCTTCA | SEQ ID NO. 7 |
| ODN4 | CGCAAT[114]$_{(4)}$TAACGC | SEQ ID NO. 1 |
| ODN5 | CGCAAT[114]$_{(4)}$[114]$_{(4)}$AACGC | SEQ ID NO. 8 |
| ODN(anti4.5S) | GCCTCCT[113]$_{(4)}$CAGCAAATCC[113]$_{(4)}$ACCGGCGTG | SEQ ID NO. 9 |
| ODN(antiB1) | CCTCCCAAG[113]$_{(4)}$GCTGGGAT[113]$_{(4)}$AAAGGCGTG | SEQ ID NO. 10 |

With respect to each ODN synthesized as described above, the concentration was determined through enzymatic digestion in the same manner as in Example 4. Furthermore, each ODN synthesized as described above was identified with a MALDI TOF mass spectrum. The mass spectrometry values are indicated below.

ODN1 (n=3), CGCAAT[113]$_{(3)}$TAACGC, calcd for $C_{178}H_{213}N_{56}O_{78}P_{12}S_2$ ([M.H]$^+$) 4820.7, found 4818.9;
ODN1 (n=4), CGCAAT[113]$_{(4)}$TAACGC, calcd for $C_{180}H_{217}N_{56}O_{78}P_{12}S_2$ ([M.H]$^+$) 4848.8, found 4751.4;
ODN1 (n=5), CGCAAT[113]$_{(5)}$TAACGC, calcd for $C_{182}H_{221}N_{56}O_{78}P_2S_2$ ([M.H]$^+$) 4876.8, found 4875.6;
ODN1 (n=6), CGCAAT[113]$_{(6)}$TAACGC, calcd for $C_{184}H_{225}N_{56}O_{78}P_{12}S_2$ (([M.H]$^+$) 4904.9, found 4903.6;
ODN2, TTTTTT[113]$_{(4)}$TTTTTT, calcd for $C_{184}H_{227}N_{34}O_{92}P_{12}S_2$ ([M.H]$^+$) 4822.8, found 4821.4;
ODN3, TGAAGGGCTT[113]$_{(4)}$TGAACTCTG, calcd for $C_{251}H_{305}N_{81}O_{124}P_{19}S_2$ ([M.H]$^+$) 7093.2, found 7092.3;
ODN (anti4.5S), GCCTCCT[113]$_{(4)}$CAGCAAATC-C[113]$_{(4)}$ACCGGCGTG, calcd for $C_{377}H_{456}N_{116}O_{173}P_{27}S_4$ ([M.3H]$^+$) 10344.9, found 10342.7;
ODN (antiB1), CCTCCCAAG[113]$_{(4)}$GCTGGGAT[113]$_{(4)}$AAAGGCGTG, calcd for $C_{381}H_{456}N_{124}O_{172}P_{27}S_4$ ([M.3H]$^+$) 10489.0, found 10489.8.

Among ODNs indicated in Table 5, with respect to each of ODNs (ODN1, ODN2, and ODN3) containing [113](n) that were obtained with the sequence and linker length being changed variously, the absorption spectrum, excitation spectrum, and emission spectrum were measured before and after hybridization with a complementary strand. The results are indicated together in Table 6 below as well as FIGS. 18 and 19.

TABLE 6

| | $\lambda_{max}$/nm (ε) | $\lambda_{em}$/nm$^b$ | $\Phi_f^c$ | $I_{ds}/I_{ss}^d$ | Tm/°C. |
|---|---|---|---|---|---|
| ODN1 (n = 3) | 480(117000) 510(93800) | 537 | 0.096 | — | — |
| ODN1 (n = 3)/ODN1' | 505(145000) | 529 | 0.298 | 7.6 | 66 |
| ODN1 (n = 4) | 479(156000) 509(104000) | 538 | 0.059 | — | — |
| ODN1 (n = 4)/ODN1' | 509(179000) | 528 | 0.272 | 14.4 | 65 |
| ODN1 (n = 5) | 480(139000) 510(107000) | 538 | 0.043 | — | — |
| ODN1 (n = 5)/ODN1' | 508(172000) | 529 | 0.208 | 8.1 | 67 |
| ODN1 (n = 6) | 479(139000) 509(93300) | 536 | 0.053 | — | — |
| ODN1 (n = 6)/ODN1' | 509(164000) | 528 | 0.265 | 10.9 | 65 |
| 5'-CGCAATTTAACGC-3'/ODN1' | — | — | — | — | 58 |
| ODN2 | 478(221000) 505(115000) | 545 | 0.010 | — | — |
| ODN2/ODN2' | 513(209000) | 536 | 0.469 | 160 | 62 |
| ODN3 | 482(146000) 510(145000) | 535 | 0.074 | — | — |
| ODN3/ODN3' | 509(191000) | 530 | 0.232 | 4.5 | 74 |

Measurement conditions: 2.5 μM DNA, 50 mM sodium phosphate buffer solution (pH = 7.0), 100 mM sodium chloride
$^b$Excitation at 488 nm
$^c$Excitation at $\lambda_{max}$ (excitation at $\lambda_{max}$ on the longer wavelength side when there are two $\lambda_{max}$)
$^d$Fluorescence intensity ratio at $\lambda_{em}$ between a double-stranded state and a single-stranded state In Table 6, ODN1 (n=3 to 6) has the same structure as that of oligodeoxyribonucleotide (5'-d(CGCAATXTAACGC)-3', where X was the site where a dye 113 had been introduced) of Example 8. In Example 8, the fluorescence quantum yield $\Phi_F$ and the fluorescence intensity ratio ($I_{ds}/I_{ss}$) between the double-stranded state and a single-stranded state were measured through excitation carried out at a wavelength of 488 nm. However, in this example (Example 13), as described above, they were measured through excitation carried out at $\lambda_{max}$ in the UV absorption spectrum. Therefore Table 1 (Example 8) and Table 6 (Example 13) indicate the same substance with different fluorescence quantum yield $\Phi_F$ and fluorescence intensity ratio ($I_{ds}/I_{ss}$).

Figure 18:
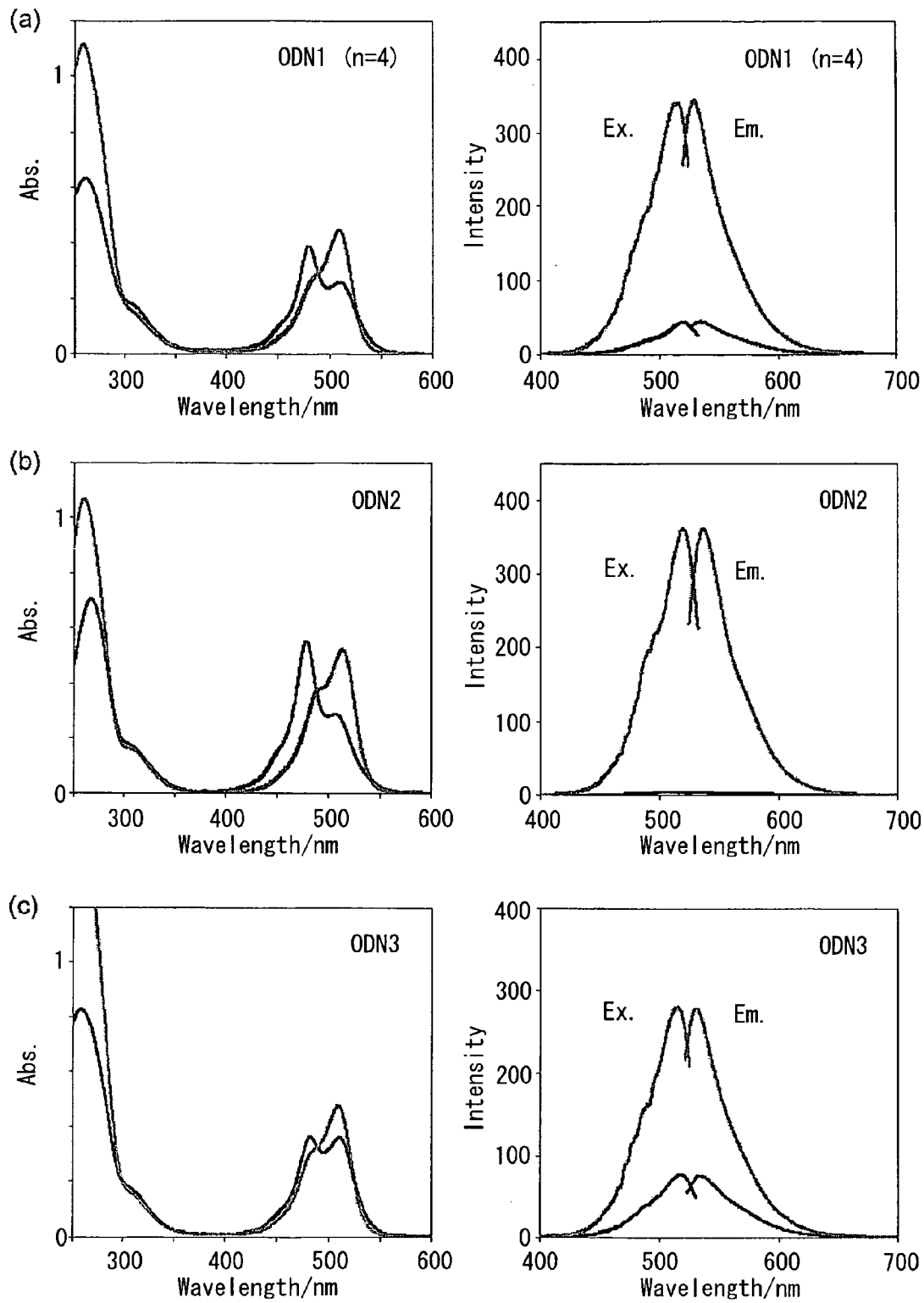
FIG. 18 shows graphs illustrating absorption spectra, excitation spectra, and emission spectra of several types of fluorescent DNA oligomer according to an example.

FIG. 18 shows graphs, each of which illustrates the absorption spectrum, excitation spectrum, and emission spectrum of [113]$_{(4)}$-containing ODN. In each of FIGS. 18(*a*), (*b*), and (*c*), the graph shown on the left side illustrates the absorption spectrum, with the horizontal axis indicating the wavelength and the vertical axis indicating the absorbance. The graph shown on the right side illustrates the excitation spectrum and the emission spectrum, with the horizontal axis indicating the wavelength and the vertical axis indicating the emission intensity. Each measurement was carried out at 25° C. using, as a sample, [113]$_{(4)}$-containing ODN in a 50 mM sodium phosphate buffer solution (pH=7.0) containing 100 mM sodium chloride. In each graph shown in FIG. 18, the black line indicates the measurement result with respect to the single-stranded ODN (ss), and the gray line indicates the measurement result with respect to ODN (ds) hybridized with a corresponding complementary strand DNA.

FIG. 18(*a*) shows the measurement result with respect to ODN1 (n=4) (2.5 μM). With respect to the excitation spectrum, the emission intensity at a wavelength of 534 nm was measured with respect to the ss, and the emission intensity at a wavelength of 528 nm was measured with respect to the ds. The emission spectra were measured, with the ss being excited at a wavelength of 519 nm and the ds being excited at a wavelength of 514 nm.

FIG. 18(*b*) shows the measurement result with respect to ODN2. The strand concentration was 2.5 µM in the graph shown on the left side, and it was 1 µM in the graph shown on the right side. With respect to the excitation spectrum, the emission intensity at a wavelength of 534 nm was measured with respect to the ss, and the emission intensity at a wavelength of 537 nm was measured with respect to the ds. The emission spectra were measured, with the ss being excited at a wavelength of 517 nm and the ds being excited at a wavelength of 519 nm.

FIG. 18(*c*) shows the measurement result with respect to ODN3. The strand concentration was 2.5 µM. With respect to the excitation spectrum, the emission intensity at a wavelength of 535 nm was measured with respect to the ss, and the emission intensity at a wavelength of 530 nm was measured with respect to the ds. The emission spectra were measured with the ss being excited at a wavelength of 518 nm and the ds being excited at a wavelength of 516 nm.

Figure 19:
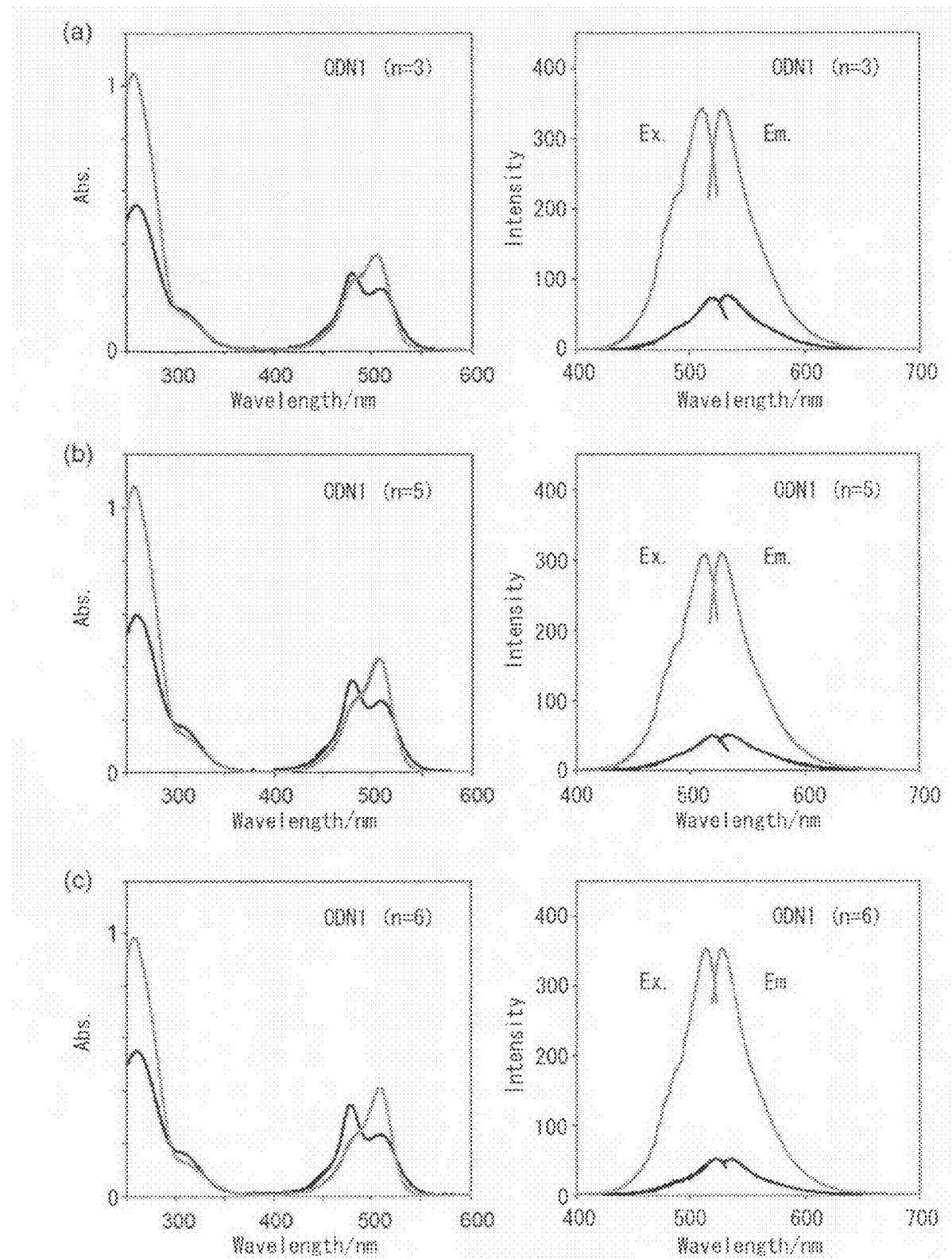
FIG. 19 shows graphs illustrating absorption spectra, excitation spectra, and emission spectra of other fluorescent DNA oligomer according to an example.

FIG. 19 shows graphs, each of which illustrates the absorption spectrum, excitation spectrum, and emission spectrum of ODN1 (n=3, 5, and 6). In each of FIGS. 19(*a*), (*b*), and (*c*), the graph shown on the left side illustrates the absorption spectrum, with the horizontal axis indicating the wavelength and the vertical axis indicating the absorbance. The graph shown on the right side illustrates the excitation spectrum and the emission spectrum, with the horizontal axis indicating the wavelength and the vertical axis indicating the emission intensity. Each measurement was carried out at 25° C. using, as a sample, ODN1 (n=3, 5, or 6) in a 50 mM sodium phosphate buffer solution (pH=7.0) containing 100 mM sodium chloride. In each graph shown in FIG. 19, the black line indicates the measurement result with respect to the single-stranded ODN (ss), and the gray line indicates the measurement result with respect to ODN (ds) hybridized with a corresponding complementary strand DNA.

FIG. 19(*a*) shows the measurement result with respect to ODN1 (n=3) (2.5 µM). With respect to the excitation spectrum, the emission intensity at a wavelength of 537 nm was measured with respect to the ss, and the emission intensity at a wavelength of 529 nm was measured with respect to the ds. The emission spectra were measured, with the ss being excited at a wavelength of 521 nm and the ds being excited at a wavelength of 511 nm.

FIG. 19(*b*) shows the measurement result with respect to ODN1 (n=5) (2.5 µM). With respect to the excitation spectrum, the emission intensity at a wavelength of 538 nm was measured with respect to the ss, and the emission intensity at a wavelength of 529 nm was measured with respect to the ds. The emission spectra were measured, with the ss being excited at a wavelength of 520 nm and the ds being excited at a wavelength of 512 nm.

FIG. 19(*c*) shows the measurement result with respect to ODN1 (n=6). The strand concentration was 2.5 µM. With respect to the excitation spectrum, the emission intensity at a wavelength of 536 nm was measured with respect to the ss, and the emission intensity at a wavelength of 528 nm was measured with respect to the ds. The emission spectra were measured with the ss being excited at a wavelength of 523 nm and the ds being excited at a wavelength of 514 nm.

As shown in Table 6 as well as FIGS. 18 and 19, two absorption bands were observed in the range of 400 to 550 nm with respect to the respective $[113]_{(n)}$-containing ODN samples. The absorption band on the shorter wavelength side (up to 480 nm) was increased when the 1(n)-containing ODN sample was in the single-stranded state, while the absorption band on the longer wavelength side (up to 510 nm) appeared prominently (dominantly) when the 1(n)-containing ODN sample hybridized with a complementary strand. The absorption band on the longer wavelength side (up to 510 nm) is a typical absorption band of thiazole orange alone. In the emission spectrum, a single broad absorption band was observed up to 530 nm. With the hybridization of a $[113]_{(n)}$-containing ODN sample with a complementary strand, the emission intensity was changed clearly. That is, the $[113]_{(n)}$-containing ODN sample hybridized to a target DNA strand exhibited strong fluorescence, but the $[113]_{(n)}$-containing ODN sample before being hybridized exhibited only very weak fluorescence as compared to that exhibited after hybridization. Particularly, the fluorescence of ODN2 formed of a polypyrimidine sequence was quenched almost completely in the single-stranded state. The fluorescence intensity ratio ($I_{ds}/I_{ss}$) between the double-stranded state and the single-stranded state of ODN2 reached 160 at the maximum emission wavelength. When the common 20-mer ODN3' chain and the ODN3 chain, were hybridized with each other, the emission intensity was clearly different before and after hybridization. Furthermore, as can be seen from Table 6 as well as FIG. 18(*a*) and FIG. 19, when the linker length n was changed from 3 to 6 in ODN1 of this example, a large $I_{ds}/I_{ss}$ value was obtained with any linker length. As described above, all the ODNs indicated in Table 6 exhibited high quenching ability although there was a difference in quenching ability depending on the linker length and the sequence of the primer.

As indicated in Table 6 above, the melting point (Tm) of ODN1 (n=4)/ODN1' increased by 7 to 9° C. as compared to the native double strand, 5'-CGCAATTAACGC-3'/ODN1'. This increase in $T_m$ value implies that two cationic dyes contained in the primer were bonded effectively to a double strand formed together with the target sequence. Furthermore, as can be seen from FIGS. 18 and 19, the excitation spectrum indicated a single broad peak around 510 nm regardless of the structure of the compound. This wavelength agreed well with one wavelength in the absorption band. That is, conceivably, the absorption associated with fluorescence emission occurs only in the absorption band around 510 nm, and the absorption band around 480 nm hardly affects the emission. Furthermore, the exciton coupling energy was estimated to be 1230 cm$^{-1}$ based on the absorption band shift from 510 nm to around 480 nm that was caused by dye aggregation. This is equivalent to the coupling energy that has been reported for the H-aggregate of cyanine dyes. However, these theoretical considerations do not limit the present invention.

[Absorption Spectrum]

Figure 20:
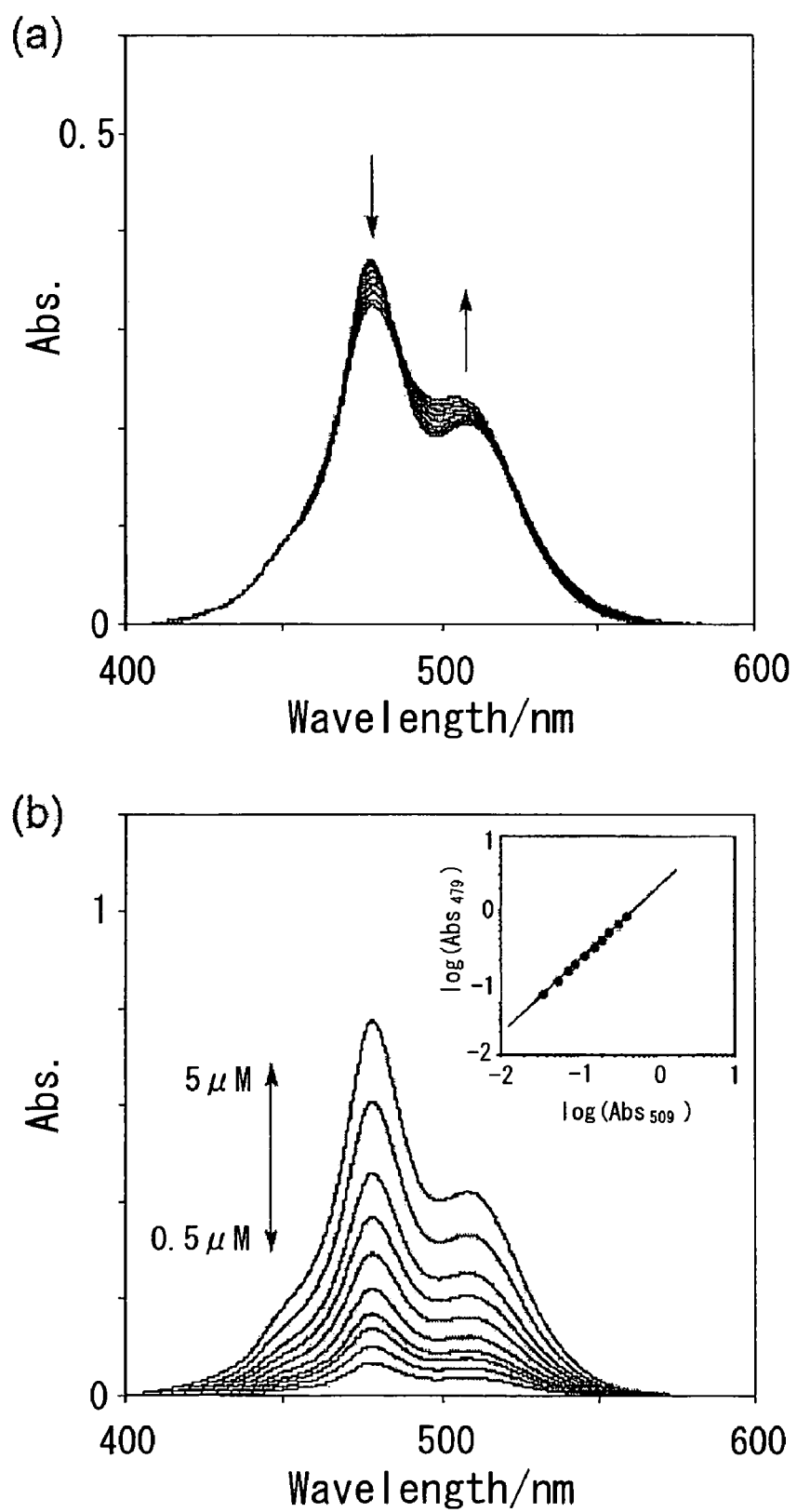
FIG. 20 shows diagrams illustrating absorption spectra obtained by measuring the absorption spectra of a fluorescent DNA oligomer according to an example at various temperatures and concentrations.

The absorption spectra of the ODN1 (n=4) were determined at various temperatures and concentrations, and the effects of the temperature and concentration on the absorption band were checked. The results are shown in the absorption spectrum diatram in FIG. 20. In FIGS. 20(*a*) and 20(*b*), the horizontal axis indicates the wavelength, and the vertical axis indicates the absorbance. Each measurement was carried out using, as a sample, ODN1 (n=4) contained in 50 mM sodium phosphate buffer solution (pH=7.0) containing 100 mM sodium chloride.

FIG. 20(*a*) shows a change in absorption spectrum obtained when the solution temperature was changed. The ODN concentration was 2.5 µM. The spectrum was measured at 10° C. intervals from 10° C. to 90° C.

FIG. 20(*b*) shows a change in absorption spectrum obtained when the solution concentration was changed. The measurement temperature was 25° C. The ODN concentrations were 0.5, 0.75, 1.0, 1.2, 1.5, 2.0, 2.5, 3.0, 4.0, and 5.0 µM.

The inset is a graph showing the relationship between the logarithm of the absorbance at a wavelength of 479 nm (vertical axis) and the logarithm of the absorbance at a wavelength of 509 nm (horizontal axis).

As shown in FIG. 20(*a*), the absorbance ratio between the two absorption bands was changed slightly when the measurement was carried out with the sample temperature being changed. That is, with the increase in sample temperature, absorbance in the absorption band of 479 nm decreased gradually, and absorbance in the absorption band of 509 nm increased. However, as can be seen from FIG. 20(a), the change was very small. This indicates that in the primer of the present invention, ODN1 (n=4), the structure change caused according to the temperature change is very small, and therefore it can be used while hardly being affected by temperature. As shown in FIG. 20(a), an isosbestic point that indicated the presence of two spectrum components was observed at 487 nm.

On the other hand, as shown in FIG. 20(b), when the concentration of the sample, ODN1 (n=4), was increased, an increase in absorbance was observed in both the absorption bands. Furthermore, as shown in the inset, the plot of log (Abs$_{479}$) versus log(Abs$_{509}$), i.e. the ratio between logarithms of the absorbances in the respective absorption bands, showed a straight line. This indicates that the ratio between the two spectrum components was almost constant regardless of the ODN concentration. In other words, the primer of the present invention, ODN1 (n=4), can be used without being affected by the concentration thereof, since the structure thereof hardly is changed even when its concentration in the solution is changed.

The cause of the spectrum changes shown in FIGS. 20(a) and (b) can be described, for example, as follows. However, these descriptions are examples of theoretical considerations and do not limit the present invention. That is, first, ODN1 (n=4) forms an intramolecular H-aggregate according to the dichroic system. Presumably, the spectrum change shown in FIG. 20(a) was caused because the structure of the H-aggregate had been loosened slightly due to increase in temperature. Conceivably, since the intramolecular H-aggregate completes intramolecularly (H-aggregate does not form in intermolecular), the structure hardly is changed by, for example, an intermolecular interaction even when the concentration increases, and therefore the ratio between the two spectrum components is almost constant as shown in FIG. 20(b) and the inset. Conceivably, two conformation modes of an intramolecular H-aggregate and dye monomers (the dye portions have not been aggregated) exist in the sample solution of ODN1 (n=4). It is surmised that the absorption band located on the shorter wavelength side (479 nm) is derived from the intramolecular H-aggregate. On the other hand, it is surmised that the absorption band (509 nm) located on the longer wavelength side is derived from the dye monomers since it increased by heating.

[CD Spectrum]

Figure 21:
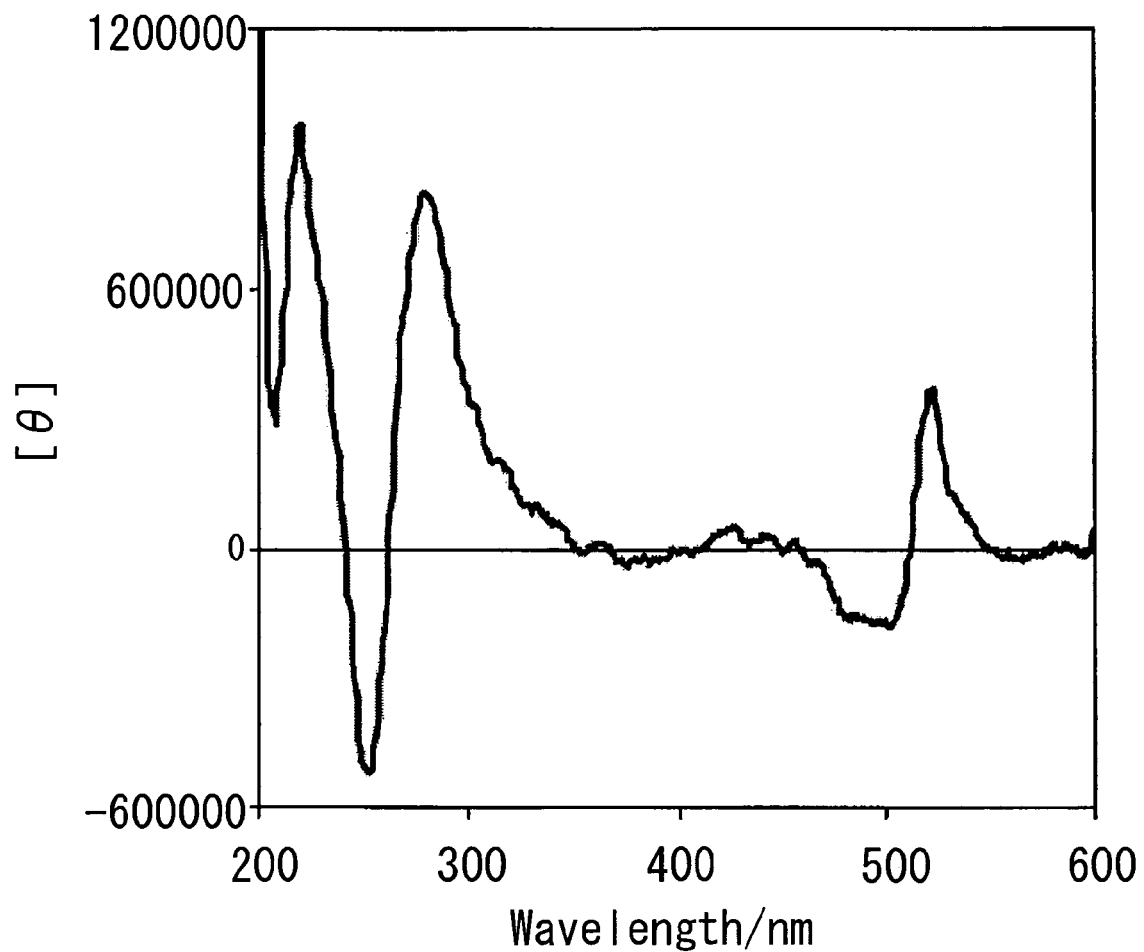
FIG. 21 is a CD spectrum diagram of a double strand obtained through hybridization of a fluorescent DNA oligomer of an example.

The CD spectrum of ODN1 (n=4)/ODN1' was measured. The measurement was carried out at 25° C. in a 50 mM sodium phosphate buffer solution (pH=7.0) containing 100 mM sodium chloride, with the strand concentration being 2.5 µM. The measurement result is shown in the CD spectrum diagram in FIG. 21. In FIG. 21, the horizontal axis indicates the wavelength (nm), and the vertical axis indicates the angle θ. As shown in FIG. 21, the ODN1 (n=4)/ODN1' double strand exhibited a split-Cotton effect between 450 and 550 nm. That is, a measured CD pair showed a typical pattern observed when a thiazole orange dye intercalated into a DNA double strand. Conceivably, in other words, the dye portions of the ODN1 (n=4) intercalated into a double-stranded DNA that had been formed, and thereby a dichroic aggregate (H-aggregate) was prevented strongly from being formed. This CD measurement result implies, together with the T$_m$ measurement result, that when the dye portions of the ODN1 (n=4) bind to the double-stranded DNA, both the two dye portions intercalate into the major groove and thereby a thermally stable double strand structure is formed. However, this theoretical consideration does not limit the present invention. The fact that the double-stranded structure to be formed is thermally stable indicates that the primer (nucleic acid) of the present invention can be used effectively for detecting the complementary sequence.

Example 14

With respect to the ODN5 (CGCAAT[114]$_{(4)}$[114]$_{(4)}$ AACGC), the absorption spectrum, excitation spectrum, and emission spectrum were measured in the double-stranded state and the single-stranded state. The results are shown in Table 7 below and FIG. 22.

TABLE 7

|  | $\lambda_{max}$/nm (ε) | $\lambda_{em}$/nm[b] | $\Phi_f$[c] | $I_{ds}/I_{ss}$[d] | Tm/° C. |
|---|---|---|---|---|---|
| ODN5 | 483(123000) | 545 | 0.059 | — | — |
|  | 511(118000) |  |  |  |  |
| ODN5/ODN1' | 509(180000) | 528 | 0.275 | 10.3 | 71 |

Figure 22:
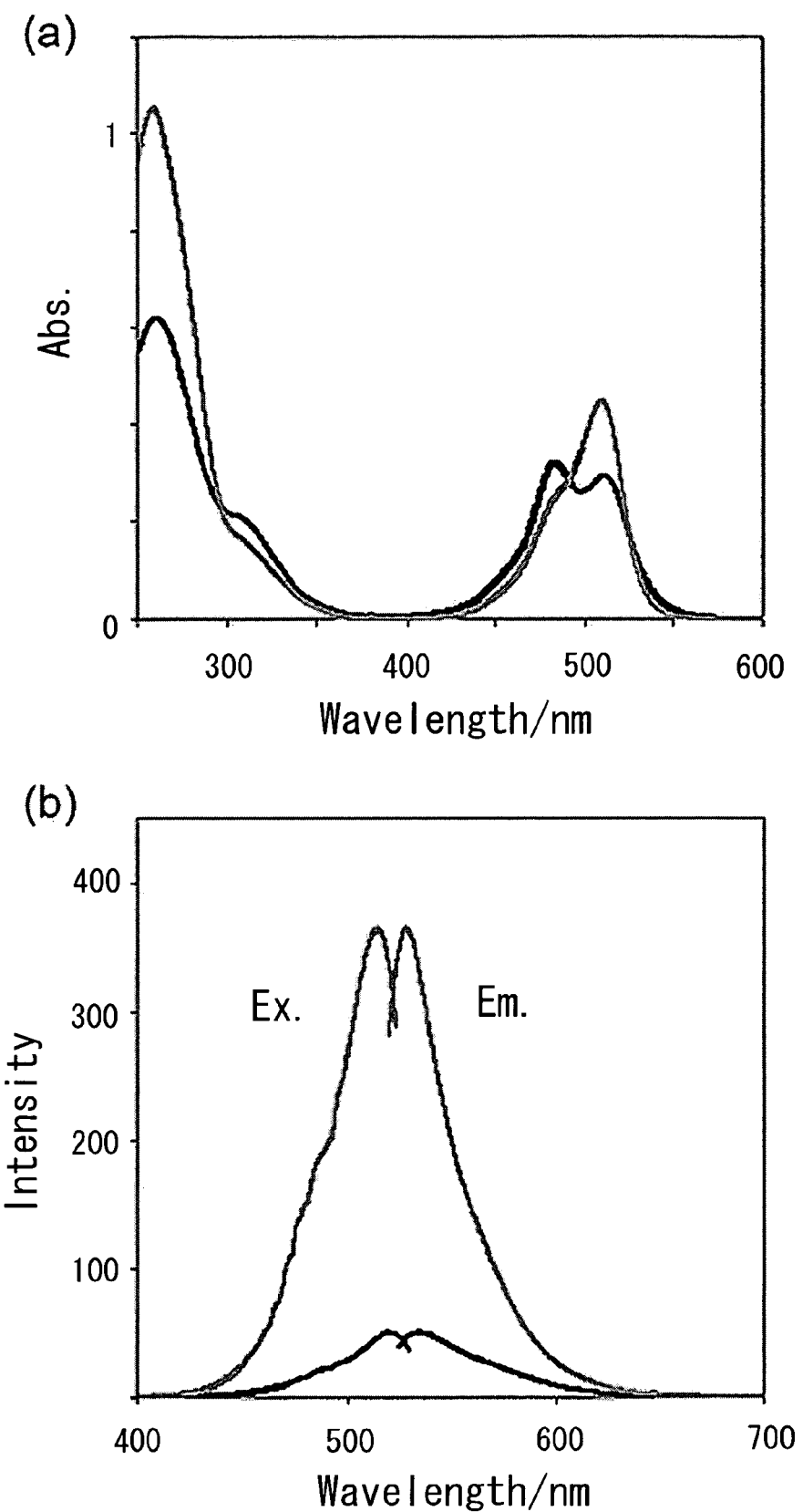
FIG. 22 shows graphs illustrating absorption spectra, excitation spectra, and emission spectra of another fluorescent DNA oligomer according to an example.

Measurement conditions: 2.5 µM DNA, 50 mM sodium phosphate buffer solution (pH = 7.0), 100 mM sodium chloride
[b]Excitation at 488 nm
[c]Excitation at $\lambda_{max}$ (excitation at $\lambda_{max}$ on the longer wavelength side when there are two $\lambda_{max}$)
[d]Fluorescence intensity ratio at $\lambda_{em}$ between the double-stranded state and the single-stranded state FIG. 22 shows graphs illustrating the absorption spectrum, excitation spectrum, and emission spectrum of ODN5, specifically, [114]$_{(4)}$-containing ODN. The measurement was carried out at 25° C. in a 50 mM sodium phosphate buffer solution (pH=7.0) containing 100 mM sodium chloride, with the strand concentration of ODN5 being 2.5 µM. The black line indicates the measurement result with respect to the single-stranded ODN5 (ss), and the gray line indicates the measurement result with respect to the double-stranded ODN5 (ds) hybridized with ODN1'. FIG. 22(a) shows the absorption spectrum, with the horizontal axis indicating the wavelength and the vertical axis indicating the absorbance. FIG. 22(b) shows the excitation spectrum and emission spectrum, with the horizontal axis indicating the wavelength and the vertical axis indicating the emission intensity. With respect to the excitation spectrum, the emission intensity at a wavelength of 534 nm was measured with respect to the ss, and the emission intensity at a wavelength of 514 nm was measured with respect to the ds. The emission spectra were measured, with the ss being excited at a wavelength of 528 nm and the ds being excited at a wavelength of 519 nm.

As shown in Table 7 and FIG. 22, the ODN 5 having a sequence containing two successive [114]$_{(4)}$ nucleotides exhibited further effective fluorescence quenching as compared to the emission suppression (Table 2 in Example 9) of the single-stranded ODN4 containing only one [114]$_{(4)}$ nucleotide. With respect to the absorption spectrum of ODN5, the absorption band was shifted to the shorter wavelength side in the single-stranded state. This implies that two [114]$_{(4)}$ nucleotides contained in the ODN5 formed an intramolecular H-aggregate. This aggregation resulted in quenching of the single-stranded ODN5 as is observed in the [113]$_{(n)}$-containing ODN. That is, conceivably, the cause of the fluorescence emission suppression (quenching) is that the dye portions of the two [114]$_{(4)}$ nucleotides contained in the ODN5 formed an H-aggregate and thereby an exciton coupling occurred between the dyes. This confirmed that the ODN5 containing two [114]$_{(4)}$ nucleotides was useful for detecting the complementary strand as in the case of the [113]$_{(n)}$-containing ODN.

Example 15

Figure 23:
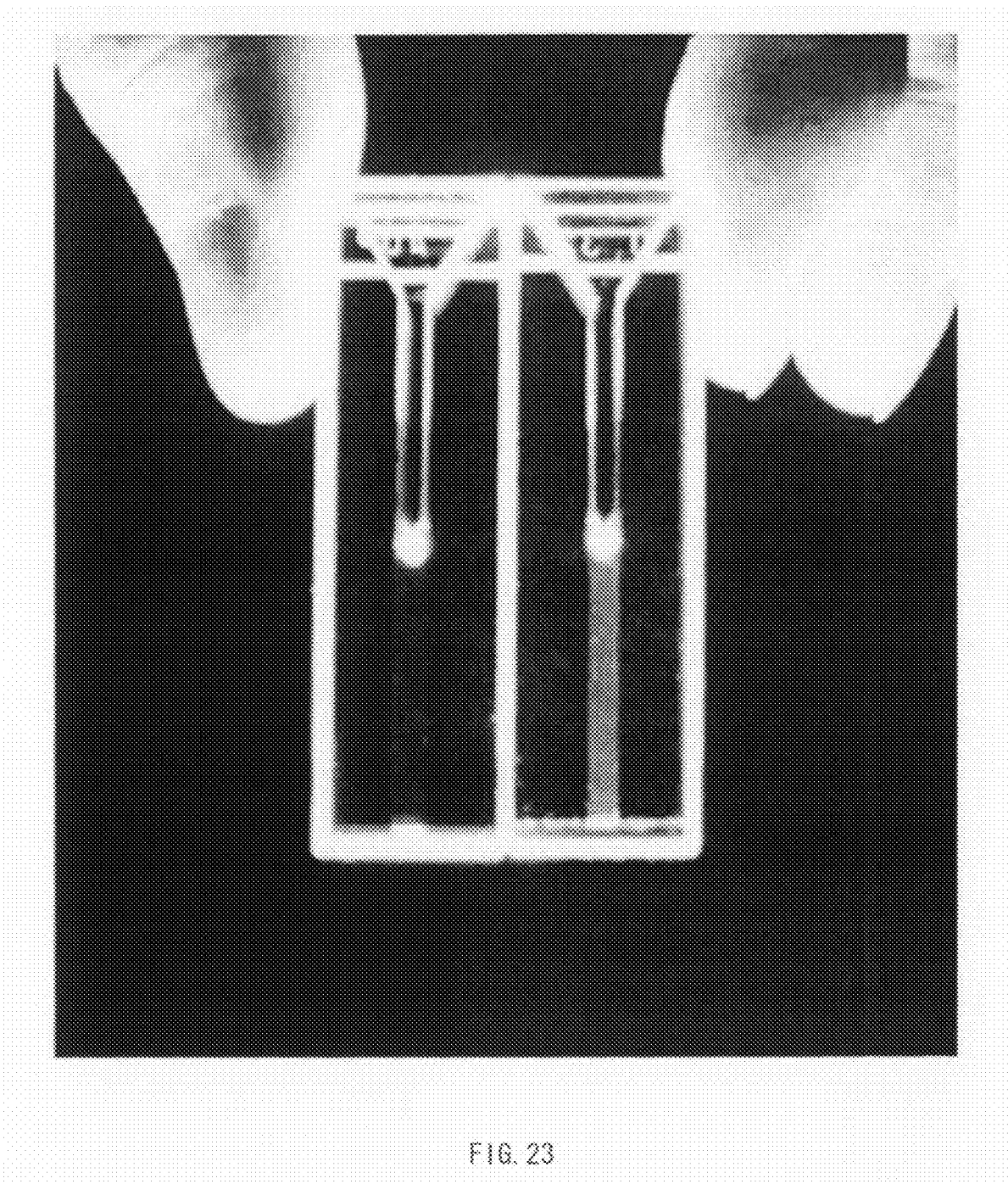
FIG. 23 is a diagram showing fluorescence emission of a double strand obtained through hybridization of another fluorescent DNA oligomer of an example.

The fluorescence obtained when ODN1 (n=4) was hybridized with a complementary ODN1' was determined by the naked eye. The measurement result is shown in FIG. 23. In FIG. 23, the left cell is a cell containing an ODN1 (n=4) single strand, and the right cell is a cell containing an ODN1 (n=4)/ODN1' double strand. The respective cells show the states thereof obtained after irradiation with 150 W halogen lamp. Each cell has a strand concentration of 2.5 µM and contains a 50 mM phosphoric acid buffer (sodium phosphate buffer solution) (pH 7.0) and 100 mM NaCl. As shown in FIG. 23, the left cell containing the ODN1 (n=4) single strand hardly emitted fluorescence after irradiation with a 150 W halogen lamp, but the right cell containing the ODN1 (n=4)/ODN1' double strand emitted light green fluorescence very clearly. Furthermore, the same result was obtained even when the complementary DNA strand ODN1' was replaced with a corresponding complementary RNA strand. Moreover, the same result was obtained in the cases of ODN2 and ODN2'. Furthermore, in the cases of ODN2 and ODN2', the same result was obtained even when ODN2' was replaced with a corresponding complementary RNA (A13-mer). In those cases, the strand concentration was 5 µM. In addition, the same results were obtained with respect to all ODNs indicated in Table 6 above. Thus, since the ODN of this example allows the fluorescence intensity to be changed clearly depending on hybridization, it was easy to determine the hybridizable target sequence by the naked eye. This indicates that those ODNs are useful for visible gene analysis.

Example 16

A DNA oligomer represented by Chemical Formula 120 below was synthesized in the same manner as in Example 8 except that a compound represented by Chemical Formula 119 below was used, as a dye, instead of compound 107.

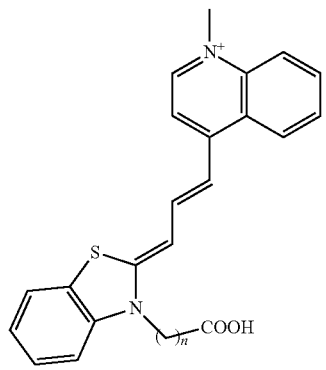

119

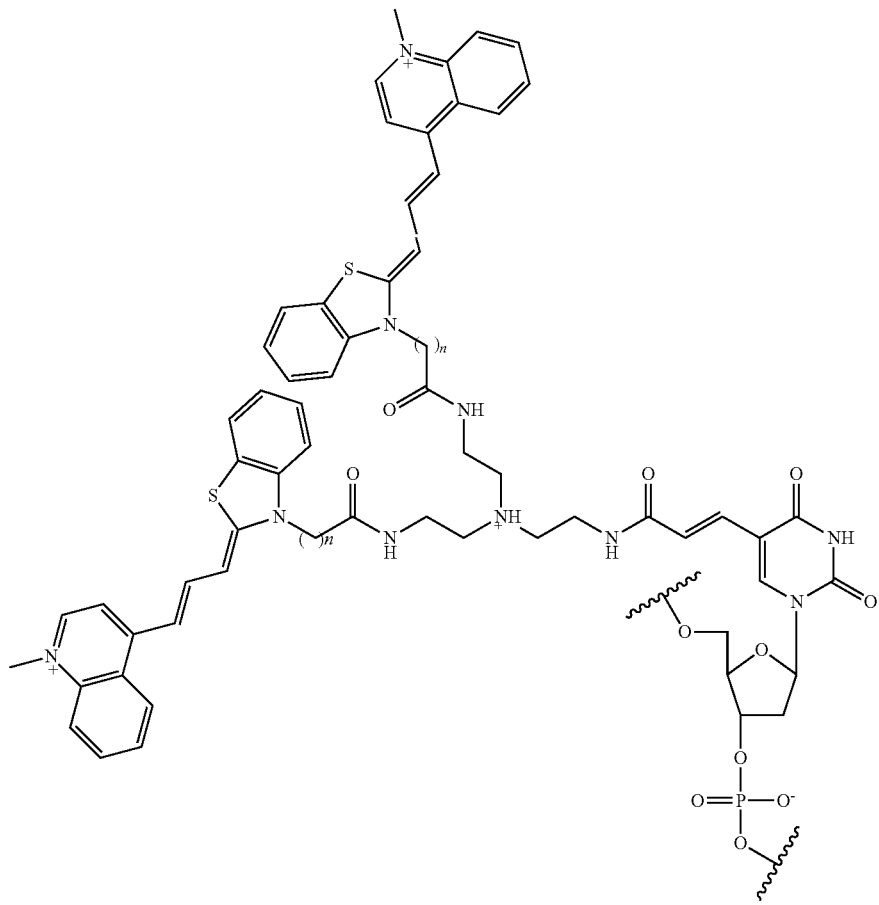

120

Compounds (oligodeoxyribonucleotides) represented by Formula 120, with n being 3, 4, 5, and 6, were synthesized in the same method. Furthermore, using ODN (referred to as ODN6 (n=5)) expressed by a sequence of 5'-d(CGCAAT

[120]$_{(5)}$TAACGC)-3' as a fluorescence primer, the absorption spectrum and fluorescence emission spectrum were determined and the performance thereof was evaluated. The measurement conditions were the same as those employed in Example 7. FIG. 24 shows the measurement results. FIG. 24(a) shows the absorption spectra, with the horizontal axis indicating the wavelength (nm) and the vertical axis indicating the absorbance. FIG. 24(b) shows the fluorescence emission spectra, with the horizontal axis indicating the wavelength (nm) and the vertical axis indicating the emission intensity. The black line indicates the spectrum of the single-stranded ODN, and the gray line indicates the spectrum of the double-stranded ODN hybridized with a complementary ODN. As shown in FIG. 24(a), in the double-stranded ODN, the maximum wavelength of UV absorption around 600 nm was shifted through the formation of a double helix. Furthermore, as shown in FIG. 24(b), in the double-stranded ODN, the fluorescence intensity increased considerably as compared to that of a single strand. Thus, it is conceivable that an exciton effect is exhibited in the single-stranded state. That is, although the ODN (Compound 120) of this example is different in absorption band from the ODN (Compound 113) of Example 8 and the ODN (Compound 117) of Example 11, it also exhibited a good exciton effect. This indicates that multicolor detection can be carried out using fluorescence primers that are different in absorption band from each other in the present invention.

Example 17

Formation of Double Strand with RNA

Figure 25:
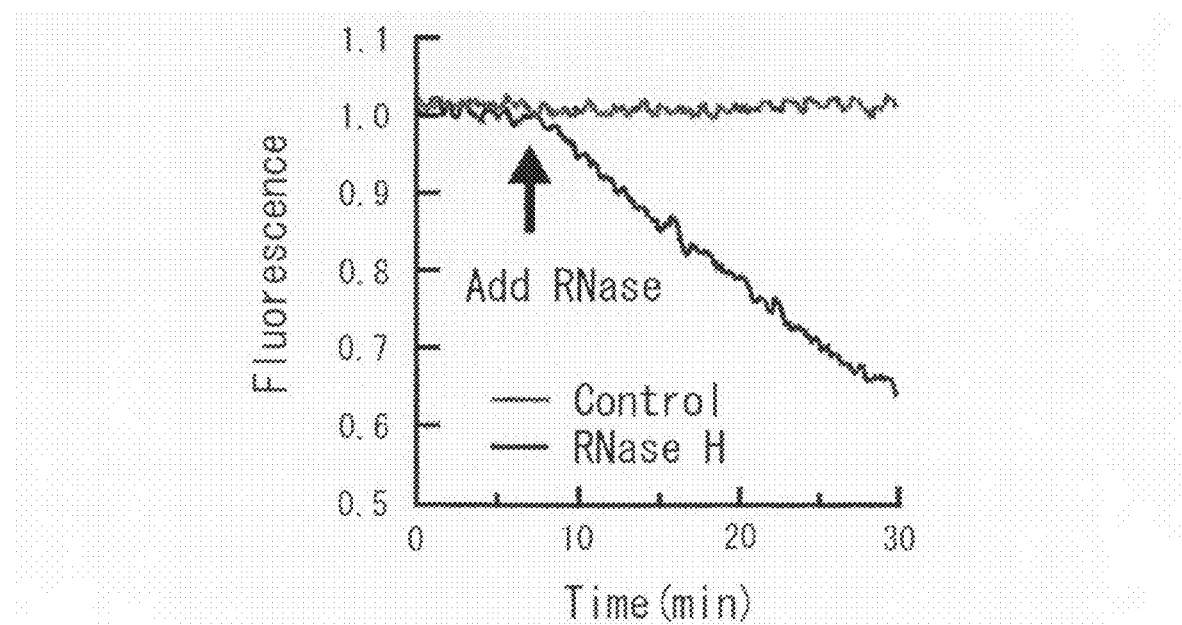
FIG. 25 is a diagram showing the change in fluorescence obtained when a RNA strand hybridized with a fluorescent DNA oligomer of an example was digested with RNase H.

In a cuvette, a double-stranded ODN was formed with the ODN2 (with a sequence of 5'-d(TTTTTT[113]$_{(4)}$TTTTTT)-3') and a corresponding complementary RNA strand (RNA A13-mer), and the fluorescence emission spectrum thereof was measured. Furthermore, RNase H was added thereto, and the change in spectrum was observed. FIG. 25 shows the result. In FIG. 25, the horizontal axis indicates the time, and the vertical axis indicates the fluorescence intensity. In FIG. 25, the black line indicates the spectrum change of the double-stranded ODN to which RNase H was added during the measurement, and the gray line indicates the spectrum change of a control, i.e. the double-stranded ODN to which the RNase H was not added. The measurement was carried out using the fluorospectrometer, with stirring being performed at 37° C. As shown in FIG. 25, when the RNase H was added, the RNA that had been hybridized to the ODN2 was digested and thereby the ODN2 returned to a single strand, which resulted in a gradual decrease in fluorescence intensity.

Example 18

Figure 26:
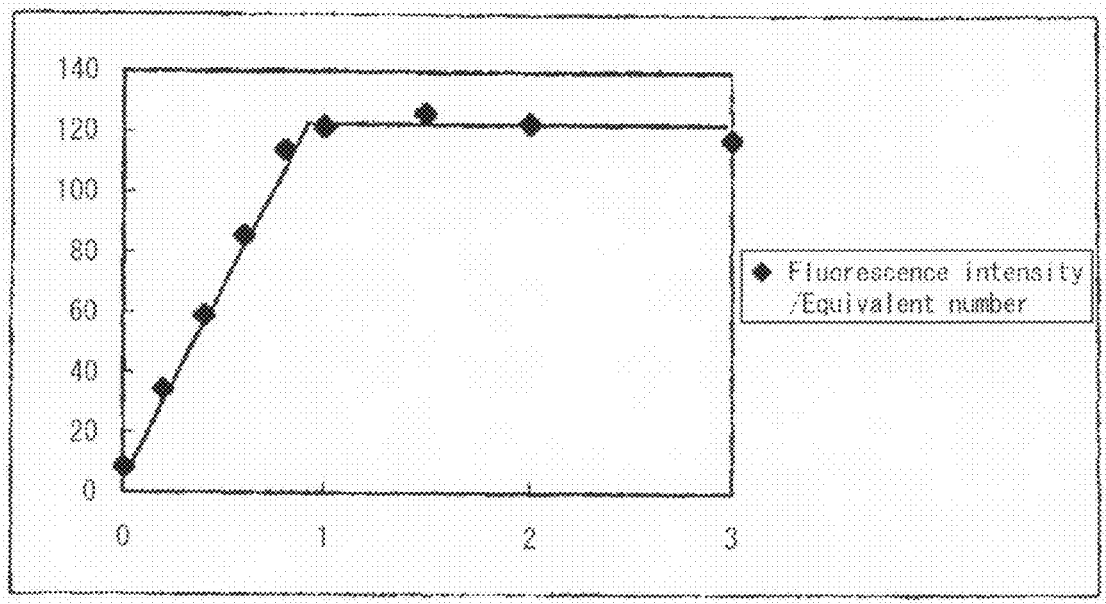
FIG. 26 is a diagram showing the results of observation of the change in fluorescence emission intensity obtained by changing the concentration ratio of the complementary DNA strand to a fluorescent DNA oligomer according to an example.

The change in fluorescence emission intensity was observed with the concentration ratios of the ODN1' (with a sequence, 5'-d(GCGTTAAATTGCG)-3') being changed, where the ODN1' was a complementary DNA strand to the ODN1 (n=4) (with a sequence of 5'-d(CGCAAT[113]$_{(4)}$TAACGC)-3'). The measurement conditions were as follows. That is, the strand concentration of the ODN1 (n=4) was fixed at 1.0 μM, a 50 mM phosphoric acid buffer (pH 7.0) and 100 mM NaCl were used, and an excitation wavelength of 488 nm (with a width of 1.5 nm) was employed. The measurement was carried out, with the concentration of the complementary strand ODN1' being 0, 0.2, 0.4, 0.6, 0.8, 1.0, 1.5, 2.0, and 3.0 μM. The measurement results thereof are shown in FIG. 26. In FIG. 26, the horizontal axis indicating the equivalent number of the ODN1' with respect to the ODN1 (n=4), and the vertical axis indicates the fluorescence emission intensity (relative value) at $\lambda_{max}$ (529 nm) of fluorescence. As shown in FIG. 26, the fluorescence emission intensity indicated a directly proportional relationship with very high accuracy with respect to the equivalent number when the equivalent number of ODN1' was 1 or smaller, but it did not change after the equivalent number exceeded 1. This indicates that the ODN1 (n=4) hybridized with the ODN1' at an exact ratio of substance amounts (number ratio of molecules) of 1:1.

As described above, when the substance amount of the ODN1' (target DNA) is equal to or smaller than that of the ODN1 (n=4), the fluorescence intensity increases in proportion to the concentration of the target DNA. Since the ODN1 (n=4) also can be used as, for example, a probe, it is possible to determine the quantity of the target DNA by measuring the fluorescence intensity when an excess of ODN1 (n=4) (probe) is added to the system where the ODN1' (target DNA) exists. Furthermore, it also is possible to determine the increase or decrease in the target DNA by tracing the increase or decrease in the fluorescence intensity.

In order to determine the quantity of the target DNA in the system, for example, a calibration curve may be prepared beforehand as shown in FIG. 26. For example, when a sample in which the concentration of ODN1' (target DNA) was unknown was measured under the same conditions as those employed in this example, if the fluorescence intensity obtained thereby was 80, the ODN1' (target DNA) concentration can be determined to be approximately 0.55 μM from FIG. 26.

In fact, when the quantity of the ODN1' (target DNA) sequence contained in nucleic acid was determined by the aforementioned method, it was possible not only to immediately detect the occurrence of phenomena such as amplification, degradation, and protein binding of the sequence concerned, but also to quantify such phenomena.

Reference Example 1

Dot Blotting Analysis

With respect to a new fluorescence DNA oligomer synthesized this time, in order to observe the change in fluorescence properties that was caused by hybridization, a DNA analysis was carried out by dot blotting using the ODN (antiB1) and ODN (anti4.5S). For the target DNA sequence, a short-stranded DNA fragment containing the B1 RNA sequence was used. This sequence is one of the short interspersed nuclear elements of the rodent genome. Furthermore, the short-stranded DNA fragment contains the 4.5S RNA sequence. This sequence is one of the small nuclear RNAs isolated from a rodent cell and has extensive homology to the B1 family. In this reference example, the ODN (antiB1) and ODN (anti4.5S) were prepared as DNA oligomers for blotting and two [113]$_{(4)}$ nucleotides were integrated thereinto, so that they were provided with a high sensitivity and a high fluorescence intensity. The structures of the ODN (antiB1) and ODN (anti4.5S), which were DNA oligomers, were as indicated in Table 5 in Example 13.

More specifically, the dot blotting analysis in this reference example was carried out as follows. That is, first, the following two DNA fragments (1) and (2) were prepared with the automated DNA synthesizer.

(1) DNA double strand containing 4.5S RNA sequence and complementary DNA thereto as follows:

(SEQ ID NO. 11)
5'-d(GCCGGTAGTGGTGGCGCACGCCGGTAGGATTTGCTGAAGGAGGCA

GAGGCAGGAGGATCACGAGTTCGAGGCCAGCCTGGGCTACACATTTTTT

T)-3'

(2) DNA double strand containing B1 RNA sequence and complementary DNA thereto as follows:

(SEQ ID NO. 12)
5'-d(GCCGGGCATGGTGGCGCACGCCTTTAATCCCAGCACTTGGGAGGC

AGAGGCAGGCGGATTTCTGAGTTCGAGGCCAGCCTGGTCTACAGAGTGA

G)-3'

The DNA double strand was denatured with an aqueous solution containing 0.5 M sodium hydroxide and 1 M sodium chloride. An aliquot of this DNA thus denatured was dotted (spotted) on a positively charged nylon membrane (available from Roche). This positively charged nylon membrane sheet was moistened with an aqueous solution containing 0.5 M sodium phosphate and 1 M sodium chloride. Thereafter, it was incubated at 50° C. for 30 minutes in an aqueous solution containing 0.5 M sodium phosphate, 1 M sodium chloride, and 100 µg/mL salmon sperm DNA. Thereafter, the positively charged nylon membrane sheet was incubated at 50° C. for one hour in a DNA oligomer aqueous solution (the DNA oligomer was 150 µmol of ODN (anti4.5S) or ODN (antiB1)) containing 0.5 M sodium phosphate and 1 M sodium chloride. After this was cooled to room temperature, the hybridization buffer solution was removed, a new phosphoric acid buffer solution was added thereto, and fluorescence emitted by the positively charged nylon membrane sheet was observed with a VersaDoc imaging system (trade name) available from BioRad. The excitation light used herein was light obtained by converting light emitted from an UV transilluminator Model-2270 (trade name) available from WAKENYAKU CO., LTD. by passing it through a UV/blue light converter plate (UVP).

FIG. 27 shows the measurement results.

FIG. 27(a) is a schematic view showing the state where DNAs having different sequences from each other were blotted on a nylon membrane. The four spots in the upper row indicate 4.5S RNA sequence-containing DNA, and the four spots in the lower row indicate B1 RNA-containing DNA.

FIG. 27(b) is a diagram showing the fluorescence emission obtained after incubation was carried out in the ODN (anti4.5S)-containing solution.

FIG. 27(c) is a diagram showing the fluorescence emission obtained after incubation was carried out in the ODN (antiB1)-containing solution.

As shown in FIG. 27, it was possible to read the fluorescence of the blotted spots at room temperature with a fluorescence imaging system without carrying out washing repeatedly after the blotting assay. As a result of the incubation with the probes, when the ODN (anti4.5S) had been added, strong fluorescence emission derived from the spots of 4.5S sequence was obtained, but the fluorescence emission derived from the spots of B1 sequence was ignorable. By contrast, when the ODN (antiB1) had been added, the B1 spots exhibited strong fluorescence but only very weak fluorescence was observed from the 4.5S spots. Thus, the DNA oligomers prepared in this reference example can realize an assay that is clearly different from a conventional blotting assay in requiring neither a cumbersome multistep washing process nor an antibody or enzyme treatment process after blotting. Furthermore, unlike the on-off oligomer such as a molecular beacon, the DNA oligomers of the present invention allows a plurality of fluorochrome-labeled portions to be introduced easily thereinto and thereby allows fluorescence intensity further to be increased. This is a great advantage of the present invention. The fluorochrome-labeled portions each may be, for example, one contained in $[113]_{(4)}$ nucleotide as in this reference example. As described above, with respect to DNA oligomers with two $[113]_{(4)}$ nucleotides incorporated therein, the change in fluorescence properties caused by hybridization with a target DNA fragment was confirmed in this reference example. Thus, it also is clear that DNA oligomers with two $[113]_{(4)}$ nucleotides incorporated therein can be used as primers.

Reference Example 2

Figure 28:
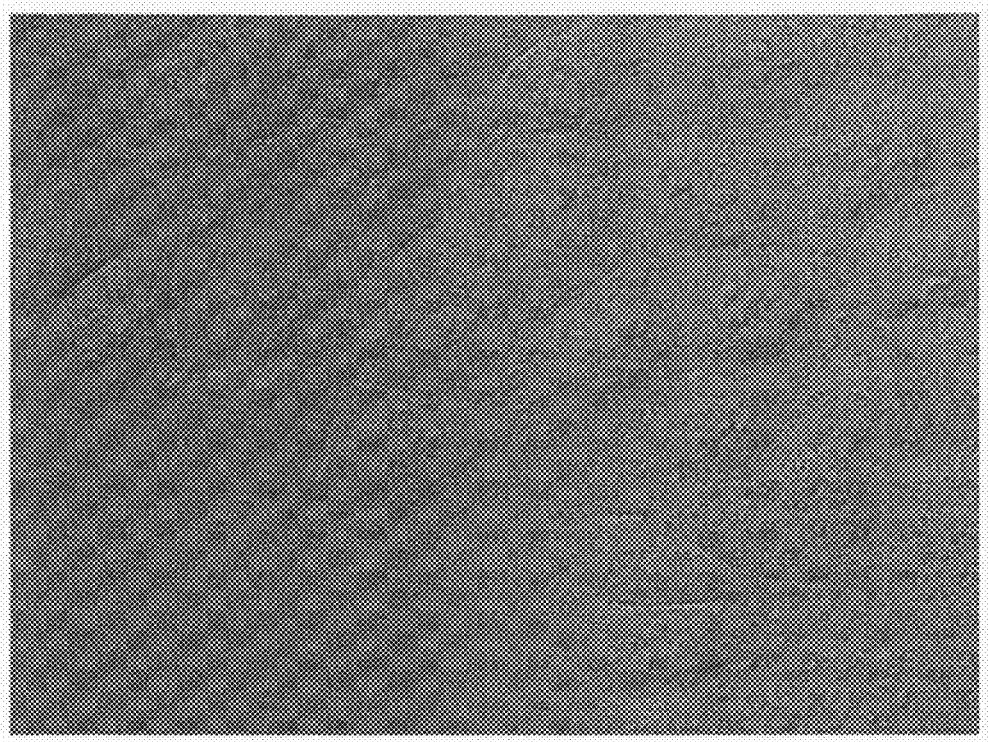
FIG. 28 is a photograph showing differential interference measured when a fluorescent DNA oligomer of a reference example was introduced into a cell.
Figure 29:
FIG. 29 is a photograph taken while fluorescence was observed when a fluorescent DNA oligomer of a reference example was introduced into a cell.
Figure 30:
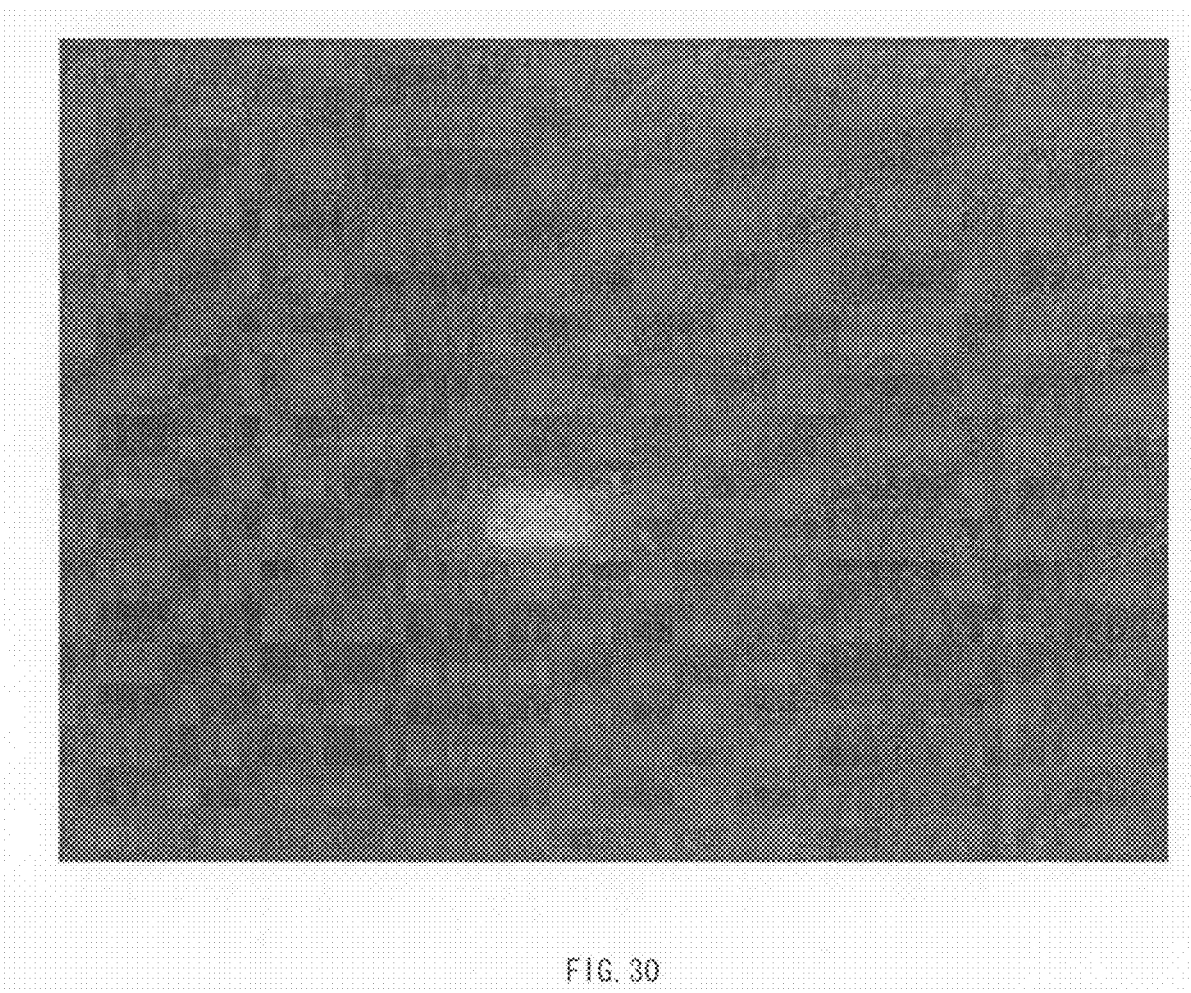
FIG. 30 is a photograph showing FIGS. 28 and 29 that were superimposed on each other.

Poly T DNA oligomer (the ODN2 described above) containing a dye with a linker length n of 4 used in Example 8 was introduced into a cell by microinjection technique using a micro glass tube, and the fluorescence emission was then measured with an inverted microscope equipped with a mercury lamp, a cooled CCD camera, and a fluorescence filter set (for YFP). FIGS. 28 to 30 show the results. FIG. 28 is a photograph taken in differential interferometry, FIG. 29 is a photograph taken during fluorescence observation, and FIG. 30 shows FIGS. 28 and 29 that were superimposed on each other. As shown in the figures, the fluorescence DNA oligomer (labeling substance) of the present invention was bonded to a poly(A) end sequence of mRNA that was expressed intracellularly, and thereby emitted light. That is, the labeled DNA oligomer of the present invention is effective for not only in vitro gene detection but also in vivo gene detection.

Reference Example 3

Figure 31A:
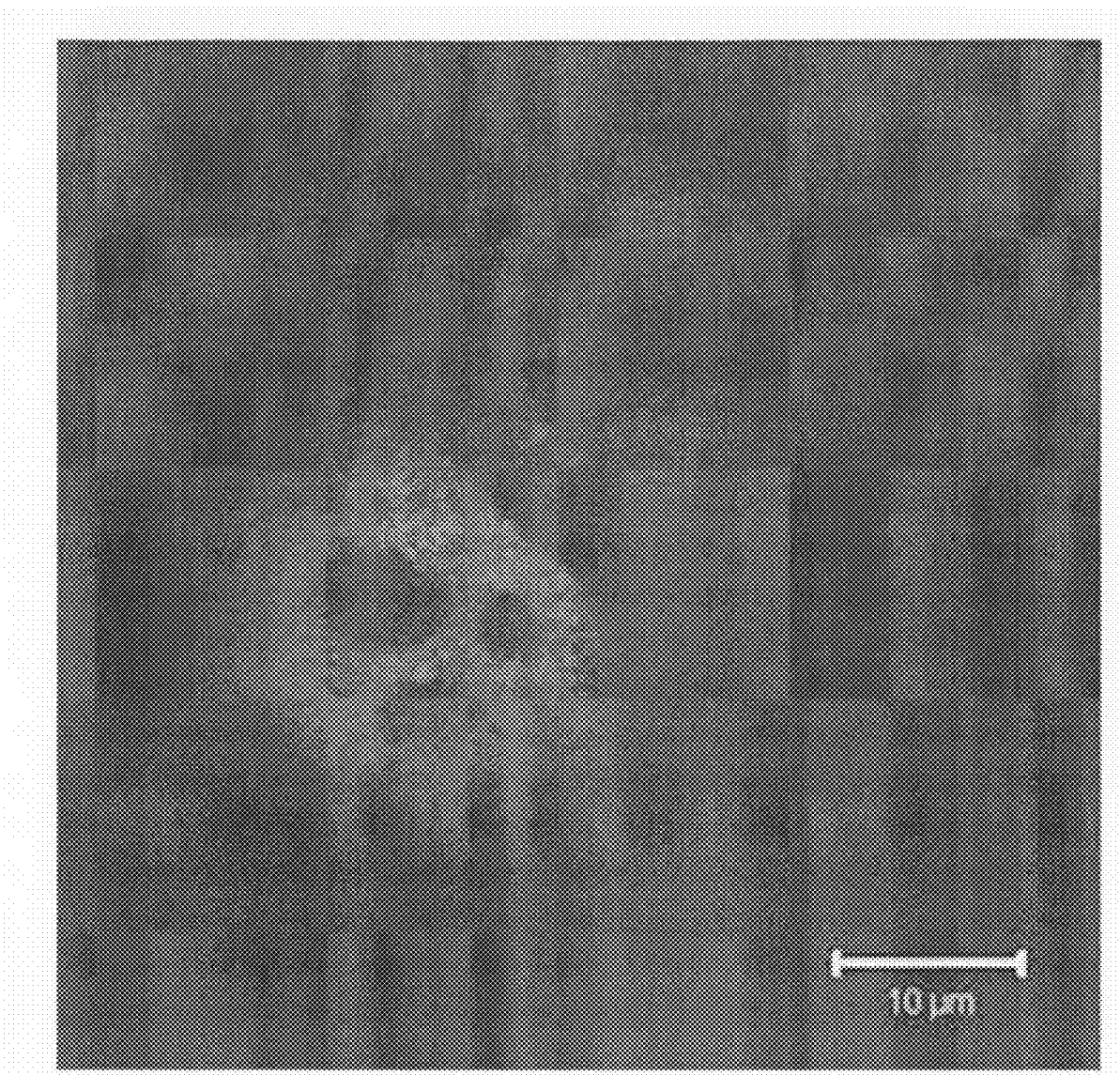
FIG. 31A is a photograph taken while fluorescence was observed when another fluorescent DNA oligomer of a reference example was introduced into a cell.
Figure 31B:
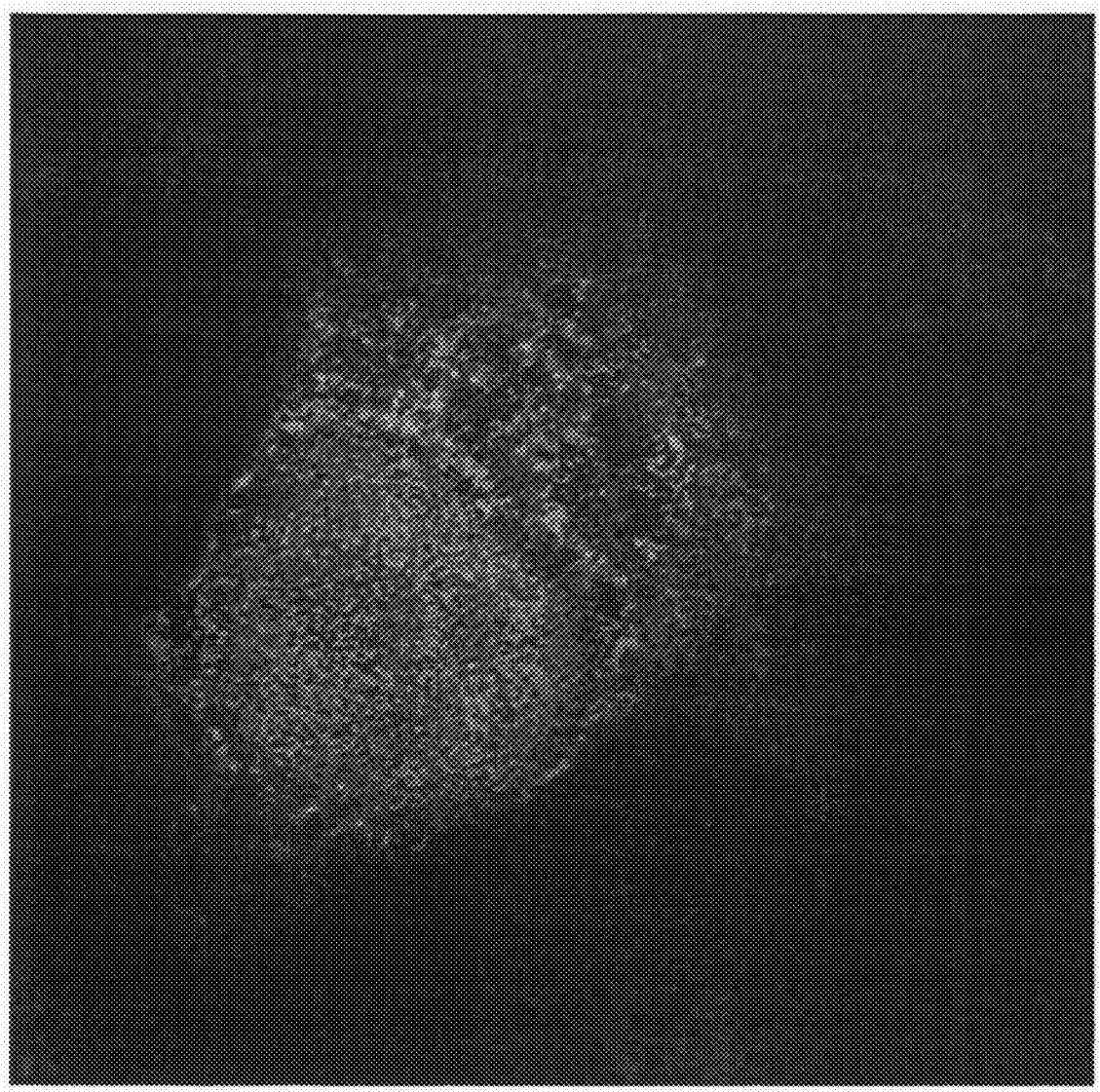
FIG. 31B is a photograph taken while fluorescence was observed when another fluorescent DNA oligomer of a reference example was introduced into a cell.

Further, a common fluorescent dye, Cy5, was bonded to the ODN2 (with a sequence of 5'-d(TTTTTT[113]$_{(4)}$TTTTTT)-3') by a conventional method, which further was introduced into a cell by the aforementioned method. In this case, Cy5 was added to the 5' end of the ODN2 with an automated DNA synthesizer to be bonded thereto in the process of synthesizing the ODN2 (with a sequence of 5'-Cy5-d(TTTTTT[113]$_{(4)}$TTTTTT)-3'). The fluorescence emission was measured with a laser scanning confocal microscope. FIG. 31 shows the result. FIG. 31A shows fluorescence derived from Cy5, with the fluorescence with a wavelength of at least 650 nm being obtained by excitation at 633 nm. FIG. 31B shows fluorescence derived from two thiazole orange portions, with the fluorescence between 505 nm and 550 nm being obtained by excitation at 488 nm. As shown in the figures, the ODN2 was bonded to the poly(A) end sequence of mRNA that was expressed intracellularly, and thereby emitted light. This allowed the distribution of intracellular mRNAs to be traced. As described above, a plurality of types of dyes (atomic groups that exhibit fluorescence) may be introduced into the compound or nucleic acid of the present invention. This also allows multicolor detection to be carried out, since, for example, respective dyes are different in $\lambda_{max}$ of fluorescence from each other.

Reference Example 4

Figure 32:
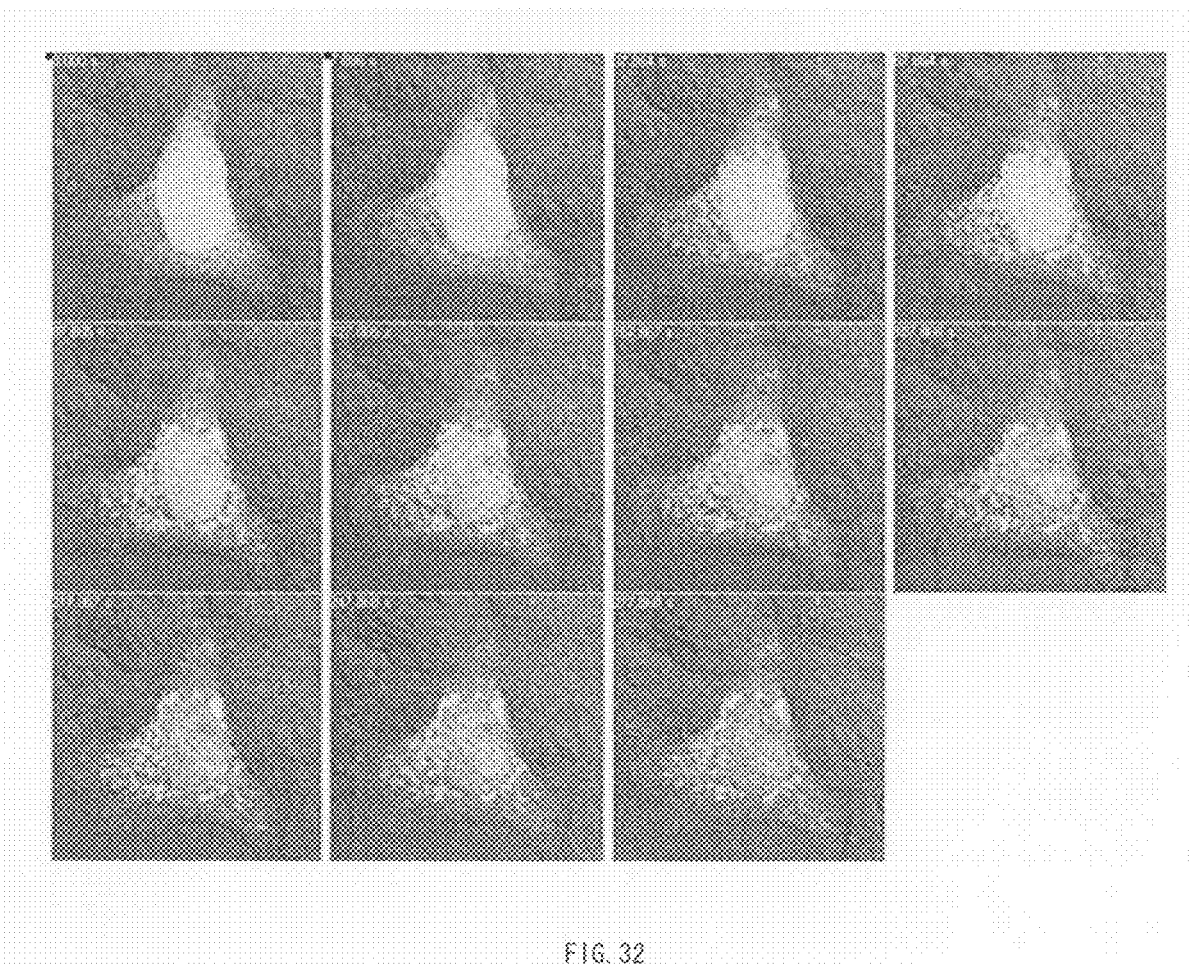
FIG. 32 shows diagrams illustrating the change in fluorescence with time after an identical DNA oligomer to that shown in FIGS. 28 to 30 was injected into a cell nucleus.

The aforementioned ODN2 (with a sequence of 5'-d(TTTTTT[113]$_{(4)}$TTTTTT)-3') was injected into a cell nucleus by the aforementioned method, and the fluorescence emission was traced with the laser scanning confocal microscope from immediately after injection (0 second) to approximately 4.5 minutes (excitation at 488 nm, and fluorescence obtained between 505 nm and 550 nm). FIG. 32 shows the result. FIG. 32 include 11 diagrams that show the progress after injection of the ODN2, from left to right and from upper row toward lower row. In each diagram, the elapsed time (after injection of the ODN2) is as indicated in Table 8 below. As shown in FIG. 32, it was confirmed that the ODN2 was concentrated in the cell nucleus immediately after injection thereof but was dispersed gradually throughout the cell together with mRNA (poly A) hybridized therewith. According to the present invention, it also is possible to trace mRNA in the manner as described above.

TABLE 8

| 0 sec | 8 sec | 38 sec | 68 sec |
|---|---|---|---|
| 98 sec | 128 sec | 158 sec | 188 sec |
| 218 sec | 248 sec | 278 sec | — |

Reference Example 5

Figure 33:
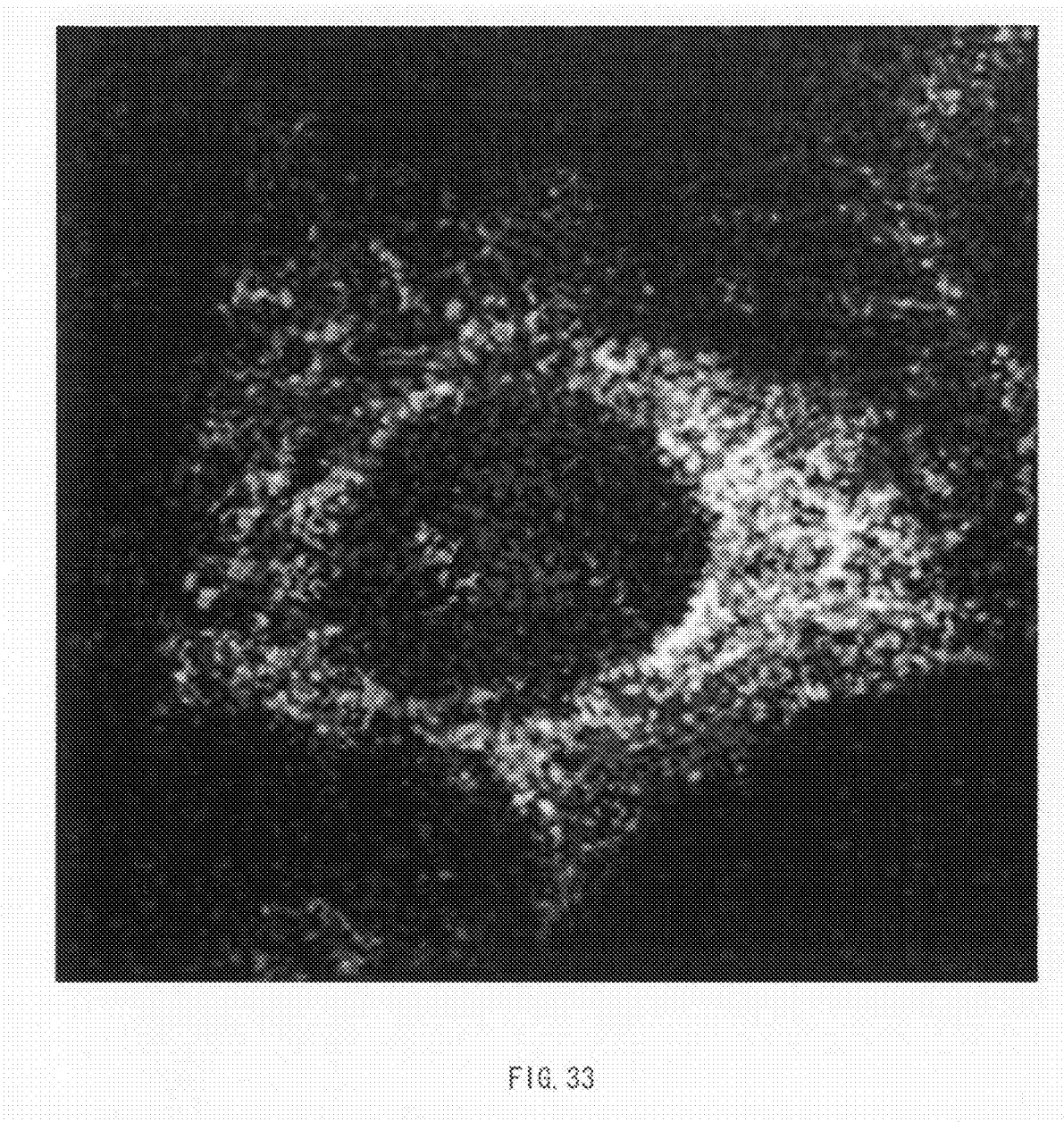
FIG. 33 is a photograph taken while fluorescence was observed when another fluorescent DNA oligomer of a reference example was introduced into a cell.

An ODN was synthesized, in which the number of Ts located on each side of [113]$_{(4)}$ of the ODN2 was increased to 24. This is referred to as "ODN7". This was synthesized by the same method as that of synthesizing the ODN2. The sequence of the ODN7 is: 5'-d(TTTTTTTTTTTTTTTTTTTTTTTT[113]$_{(4)}$TTTTTTTTTTTTTTTTTTTTTTTT)-3') (SEQ ID NO. 13). This was injected into a cell nucleus by the same method as that employed in Example 22, and the fluorescence intensity was measured. FIG. 33 shows a fluorescence photograph taken after a lapse of a certain period of time. The ODN7 was concentrated in the cell nucleus immediately after injection but was dispersed gradually throughout the cell together with mRNA (poly A) hybridized therewith, as in Example 22, and finally, it was dispersed around the cell nucleus as shown in FIG. 33.

Reference Example 6

Multicolor Detection

As described in, for instance, Examples 11 and 16, the fluorescence DNA oligomers of the present invention allow multicolor detection of complementary strands by having, for example, different absorption wavelengths and emission wavelengths from each other. This multicolor detection can be achieved by using dye (atomic group exhibiting fluorescence) portions having different structures as in the cased of Compounds 113, 117, and 120. In this reference example, further various fluorescence DNA oligomers were synthesized (produced) and multicolor detection of complementary strands was carried out.

First, DNA strands (fluorescence DNA oligomers), each of which contained a nucleotide structure represented by the following formula (121), were synthesized, with the structures of dye (atomic group exhibiting fluorescence) portions being varied. In the following formula (121), "Dye" denotes the dye portion.

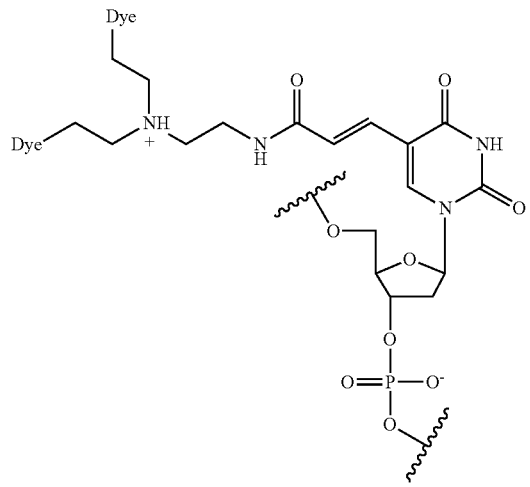

Specifically, compounds (DNA strands) 113, 120, 122, 123, and 124 were synthesized, which contain portions represented by the following formulae, respectively, as the "Dye" portion contained in the formula (121). In the following formulae, n is the linker length (the number of carbon atoms). With respect to the compounds 113, 120, 122, 123, and 124, compounds whose linker lengths n were 3, 4, 5, and 6 were synthesized, respectively. The synthesis was carried out by the same method as that employed in Examples 1 to 4, 6, 8, 9, 12, 13, and 16 except for using dyes with corresponding structures, respectively, instead of the dye 107. The synthesis of the dyes that replace the dye 107 also was carried out in the same manner as in the synthesis of the dye 107 (Scheme 5 in Example 6) except that the structures of the raw materials were changed suitably. Furthermore, Compounds 113 and 120 have the same structures as those of Compounds 113 and 120 of the respective examples described above, respectively.

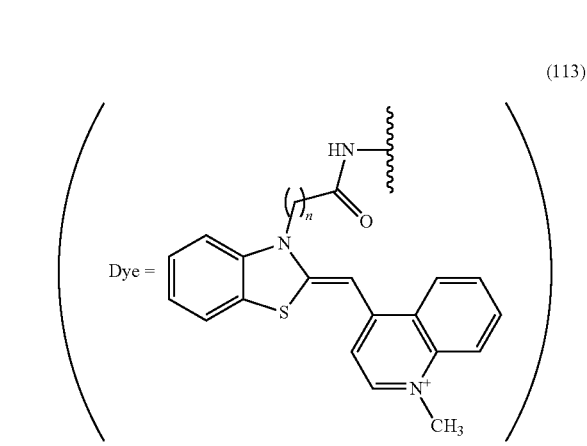

-continued

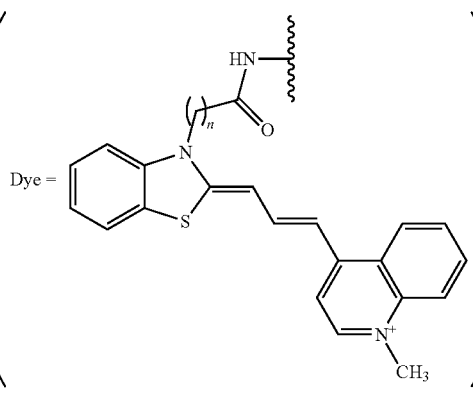

(120)

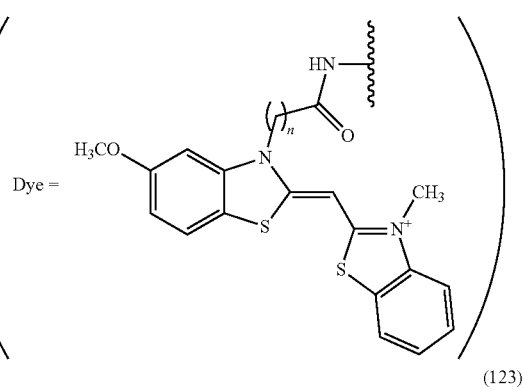

(122)

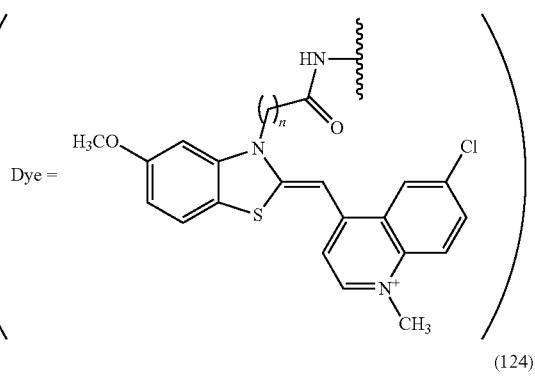

(123)

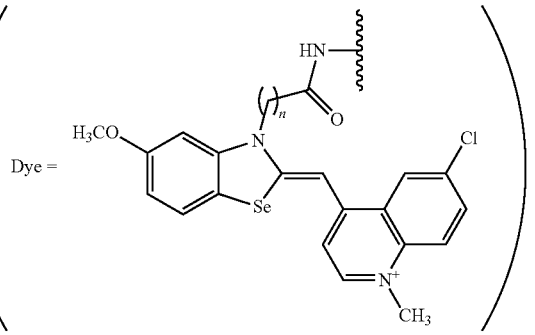

(124)

With respect to Compounds 113, 120, 122, 123, and 124, ODNs were synthesized, each of which was represented by a sequence of 5'-d(CGCAATX$_{(n)}$TAACGC)-3', where X is 113, 120, 122, 123, or 124, and n is the linker length. An ODN represented by a sequence of 5'-d(CGCAAT[113]$_{(n)}$TAACGC)-3' is identical to the aforementioned ODN1. An ODN represented by a sequence of 5'-d(CGCAAT[120]$_{(n)}$TAACGC)-3' is identical to the aforementioned ODN6. An ODN represented by a sequence of 5'-d(CGCAAT[122]$_{(n)}$TAACGC)-3' is referred to as an "ODN8". An ODN represented by a sequence of 5'-d(CGCAAT[123]$_{(n)}$TAACGC)-3' is referred to as an "ODN9". An ODN represented by a sequence of 5'-d(CGCAAT[124]$_{(n)}$TAACGC)-3' is referred to as an "ODN10". With respect to each of the ODN1, ODN6, ODN8, ODN9, and ODN10, ODNs with linker lengths n of 3, 4, 5, and 6 were synthesized, respectively.

With respect to each of the ODN1 (n=4), ODN6 (n=4), ODN8 (n=4), ODN9 (n=4), and ODN10 (n=4), after each of them was allowed to form a double strand together with a complementary strand, ODN1', the fluorescence emission spectrum was measured. The measurement conditions were the same as those employed in each example described above except for the excitation wavelength. The result is indicated in Table 9 below. In Table 9, $E_x$ denotes excitation wavelength, and $E_m$ indicates the maximum wavelength of fluorescence emission. The excitation wavelength $E_x$ was set so as to be almost equal to the maximum wavelength $\lambda_{max}$ of absorption.

TABLE 9

| Structure of double strand | $E_x$ | $E_m$ |
| --- | --- | --- |
| 5'-d(CGCAAT[113]$_{(4)}$TAACGC-3' (ODN1 (n = 4)/ODN1' | 514 nm | 528 nm |
| 5'-d(CGCAAT[120]$_{(4)}$TAACGC-3' (ODN6 (n = 4)/ODN1' | 650 nm | 654 nm |
| 5'-d(CGCAAT[122]$_{(4)}$TAACGC-3' (ODN8 (n = 4)/ODN1' | 436 nm | 456 nm |
| 5'-d(CGCAAT[123]$_{(4)}$TAACGC-3' (ODN9 (n = 4)/ODN1' | 534 nm | 550 nm |
| 5'-d(CGCAAT[124]$_{(4)}$TAACGC-3' (ODN10 (n = 4)/ODN1' | 541 nm | 563 nm |

As can be seen from Table 9, when the respective ODNs each formed a double strand, they exhibited different maximum wavelengths $E_m$ of fluorescence emission from one another in a wide wavelength range from 456 nm to 654 nm. That is, it was possible to carry out multicolor detection of complementary strand DNAs using the ODNs synthesized in this example (Example 24). Furthermore, with respect to Compounds (DNA strands) 113, 120, 122, 123, and 124 as well as ODN1, ODN6, ODN8, ODN9, and ODN10 of this reference example, their use in the same manner as in the respective examples described above, for example, detection of complementary strand RNA, dot blotting analysis, and detection of intracellular mRNA were carried out by multicolor, was confirmed.

Example 19

Using a SMAP primer set containing a labeled primer of the present invention, a mutation L858R (2573T>G) of EGFR exon 21 was detected.

(1) Template DNA, Cell Line

The template DNA was extracted from lung cancer cell line NCl—H1975 containing exon 21 point mutation L858R (American Type Culture Collection). The cell line is a heterozygote having one normal allele with respect to each mutation. A genomic DNA was extracted from the cell line by a conventional method and then was diluted to 40 ng/μL. This is referred to as a template DNA for full-match detection. In addition, the template DNA for mismatch detection used herein was a human genomic DNA, which was a wildtype homozygote with respect to exon 21 allele (manufactured by Promega Corporation). These template DNAs were used for the assay described later after being heat-treated at 98° C. for three minutes and then being cooled rapidly.

(2) Primer

Figure 34:
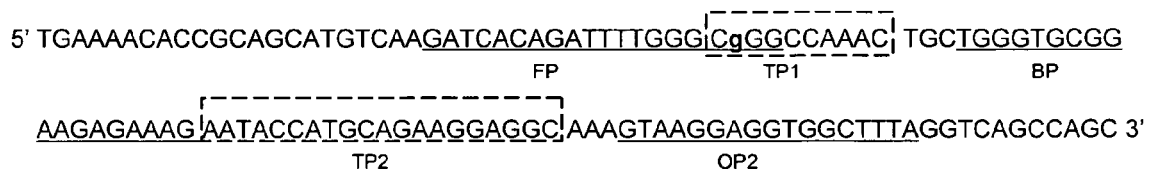
FIG. 34 shows a region containing a target nucleic acid sequence as well as sequences of various primers in an example.

Four types of primers were prepared for the SMAP primer set. These primers are shown in FIG. 34 together with the region (target region) containing a target nucleic acid sequence in exon 21. In FIG. 34, A shows the target region (SEQ ID NO. 14), B shows a folding primer (FP; the second primer; SEQ ID NO. 15), a turn-back primer (TP; the first primer; SEQ ID NO. 16), a boost primer (BP; the third primer; SEQ ID NO. 17), and an outer primer 2 (OP2; SEQ ID NO. 18). In FIG. 34A, the lower case "g" in the underlined portion FP is the mutation to be detected. In the case of a wildtype, this site is a lower case "t". In FIG. 34A, the underlined portion FP is the sequence contained in the 3' end of the folding primer. In FIG. 34A, the dotted frame TP1 shows the sequence contained in the 5' end of the turn-back primer, and the complementary strand to the dotted frame TP2 is the sequence contained in the 3' end of the turn-back primer. In FIG. 34A, the underlined portion BP is the sequence of the boost primer, and In FIG. 34B, the nucleotide residue (T) indicated with a bold letter in the underlined portion BP is the base labeled with a fluorescent atomic group (labeled structure) described later. Furthermore, in FIG. 34A, the complementary strand to the underlined portion OP2 is the sequence of the outer primer 2.

The FP was designed as a probe for mutation detection having homology with the target mutation site at the third nucleotide residue from the 3' end thereof. When a target mutation is present in the template DNA, the region containing the mutation and the FP for mutation detection are completely homologous at the mutated-base site, and extension from this primer FP can occur without being hindered.

In this example, as described above, the boost primer was used as the labeled primer. In this labeled primer, in the boost primer shown in FIG. 34B, the structure of the labeled nucleotide residue is represented by Formula (121), and the portions indicated with "Dye" in Formula (121) each are represented by Formula (113) indicated in Reference Example 6 (thiazole orange). In Formula (113), the linker length was n=4. With respect to the detection wavelength of the fluorescent atomic group represented by Formula (113), the excitation wavelength was 510 nm and the fluorescence wavelength was 530 nm. This labeled primer was synthesized by the same method as in the Example 8 or the Reference Example 6 described above except that it was an oligomer of SEQ ID NO. 17.

(3) SMAP Reaction

First, 25 µl of reaction solution having the composition indicated below was prepared, which was allowed to react at 60° C. During the reaction, while a 60° C. isothermal condition was maintained, fluorescence intensity of the reaction solution was monitored in real time using an Mx3005P system (trade name; manufactured by Stratagene). In a comparative example, an unlabeled boost primer with the same sequence was used instead of the labeled boost primer (labeled primer), and the fluorescence intensity thereof was monitored in real time in the same manner except that SYBR (registered trademark) Green I (Molecular Probes, Inc) was added to the following reaction solution as an intercalater for detection. The above-mentioned intercalater was added in such a manner as to be diluted 100,000 times in the reaction solution.

TABLE 10

| Composition of reaction solution | | |
|---|---|---|
| Tris-HCl (pH 8.0) | | 20 mM |
| KCl | | 10 mM |
| (NH$_4$)$_2$SO$_4$ | | 10 mM |
| Magnesium sulfate | | 8 mM |
| Tween20 | | 0.1% |
| Betaine | | 0.6 M |
| dNTPs | | 1.4 mM |
| 4 types of primers | FP | 2.0 µM |
| | TP | 2.0 µM |
| | BP | 1.0 µM |
| | OP | 0.25 µM |
| AacDNA polymerase* | | 6 units |
| Genomic DNA | | 40 ng |
| Total | | 25 µl |

*Manufactured by Kabushiki Kaisha Dnaform

Figure 35:
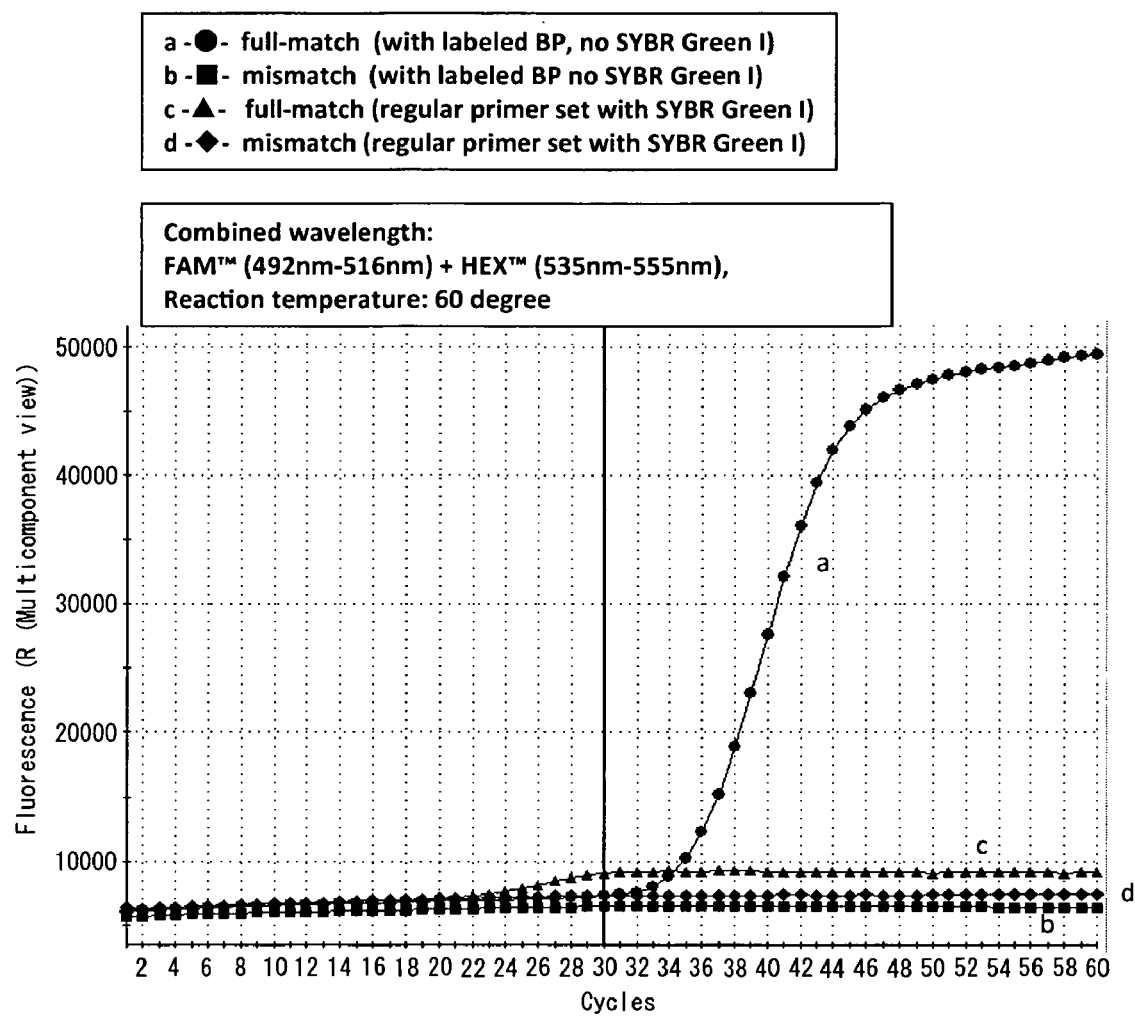
FIG. 35 is a graph showing an amplification profile obtained when an isothermal amplification reaction was carried out by the SMAP method in an example.
Figure 36:
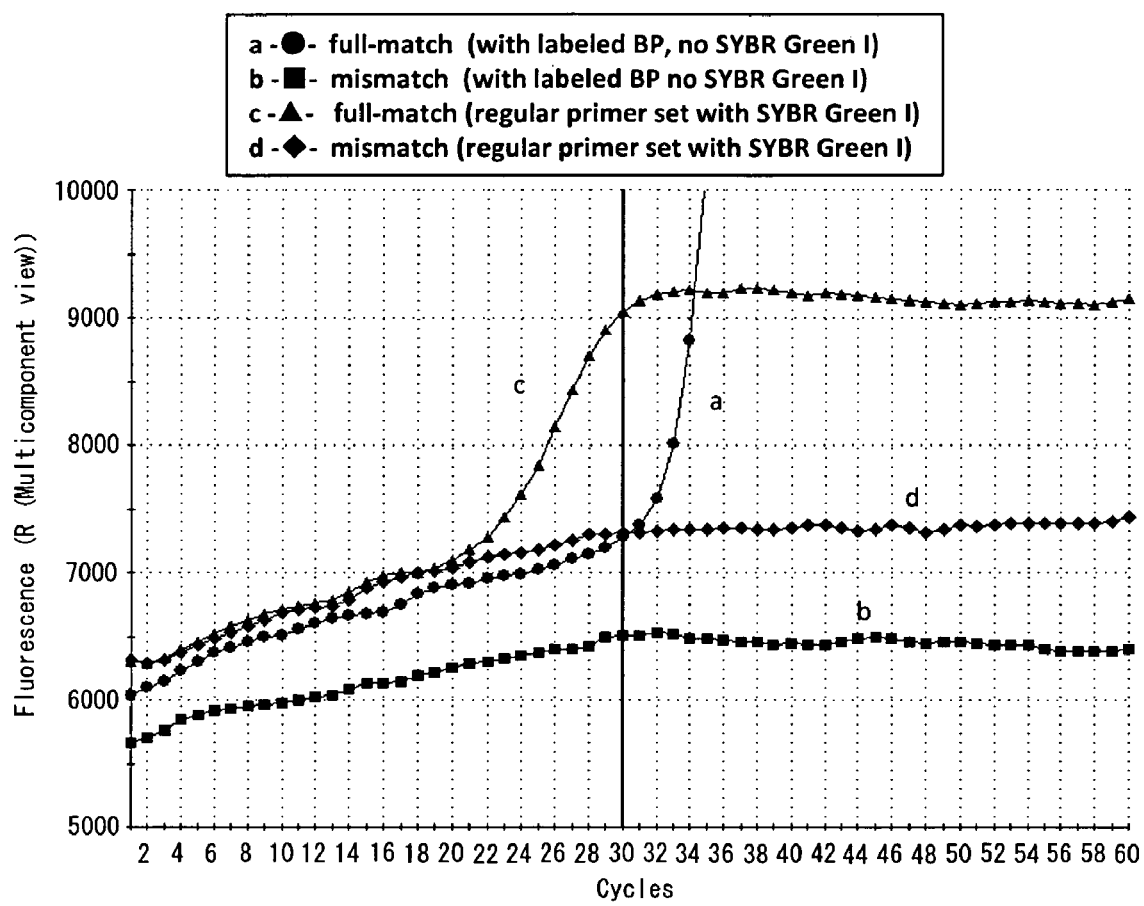
FIG. 36 is a partial enlarged view of FIG. 35.

The fluorescence intensity was detected in the wavelength range between the wavelength of FAM (excitation wavelength: 492 nm, fluorescence wavelength: 516 nm) and the wavelength of Hex (excitation wavelength: 535 nm, fluorescence wavelength: 555 nm). Thus, both the fluorescence intensity (Example) of the labeled primer and the fluorescence intensity of SYBR (registered trademark) Green I were measured. FIGS. 35 and 36 show the results. In FIGS. 35 and 36, "cycles" indicates "reaction time" (1 cycle=1 minute). FIG. 35 is a graph showing an amplification profile obtained when the isothermal amplification reaction was carried out by the SMAP method, and FIG. 36 is a partial enlarged graph thereof. In FIGS. 35 and 36, a-• indicates the result of the isothermal amplification reaction carried out using a template DNA for full-match detection and the labeled primer (labeled BP), b-■ indicates the result of the isothermal amplification reaction carried out using a template for mismatch detection and the labeled primer (labeled BP), c-▲ indicates the result of the isothermal amplification reaction carried out using a template DNA for full-match detection and the SYBR (registered trademark) Green I, and d-♦ indicates the result of the isothermal amplification reaction carried out using a template for mismatch detection and SYBR (registered trademark) Green I.

As shown in the FIGS. 35 and 36, in the comparative examples (▲, ♦) using the SYBR (registered trademark) Green I, a significant difference in fluorescence intensity between the full-match (▲) and the mismatch (♦) was observed from around 25 cycles. Specifically, when the fluorescence intensity that has reached a plateau was compared, the fluorescence intensity of the full-match (▲) was about 1.4 times that of the mismatch (♦). On the contrary, in the examples (•, ■) using the labeled primer, a rapid increase in fluorescence intensity of the full-match was observed from around 36 cycles and a very large difference was observed between the full-match (•) and the mismatch (■). Specifically, when a comparison was made with respect to the fluorescence intensity around, for example, 50 cycles, the full-match (•) had a fluorescence intensity that was approximately 7.3 times that of the mismatch (■). This difference was observed well, even visually. According to the present invention, as shown in FIGS. 35 and 36, since the fluorescence intensity of the full-match is very high, it also is possible to check the mutation visually. Furthermore, as shown in FIG. 36, which is a graph obtained by enlarging FIG. 35, since the fluorescence intensity of the mismatch (■) of the example is lower than that of mismatch (♦) of the comparative example, it is understood that according to the example, it was possible to reduce the background. Conceivably, this is because it is possible to eliminate fluorescence originating from DNA contained in the nucleic acid sample itself and fluorescence originating from nonspecific amplification of a region free from the target sequence, which is observed when using an intercalater such as the SYBR (registered trademark) Green I. In the case of the mismatch, amplification was not observed even after 60 minutes reaction. From the results described above, the present invention makes it possible to confirm the presence or absence of a mutation and amplification of target nucleic acid sequence with a very high sensitivity.

Example 20

A wildtype of human influenza H3N2 subtype and a Tamiflu resistant mutant type were detected using a SMAP primer set including a labeled primer of the present invention.

(1) Template DNA

A plasmid having a wildtype copy fragment of H3N2 subtype and a plasmid having a mutant type copy fragment with valine that had replaced 119$^{th}$ glutamic acid were obtained from Medical Center of The University of Tokyo. A plasmid DNA to serve as a template was amplified from RNA of H3N2 subtype by RT-PCR. A plasmid DNA thus obtained was heated at 95° C. for five minutes and this was used, as a template DNA, for the assay to be described later.

(2) Primer

The six types of primers indicated below were prepared for a SMAP primer set. These primers are shown in FIG. 37 together with the regions (target regions) containing a target nucleic acid sequence in $H_3N_2$ subtype. FIG. 37A is a schematic view showing a target region (SEQ ID NO. 19) of a wildtype and a target region (SEQ ID NO. 20) of a mutant type. FIG. 37B shows a turn-back primer (TP; the first primer; SEQ ID NO. 21), a folding primer (FP; the second primer; SEQ ID NO. 22), a wildtype boost primer (BPw; the third primer; SEQ ID NO. 23), a mutant-type boost primer (BPm; the third primer; SEQ ID NO. 24), an outer primer 1 (OP1; SEQ ID NO. 25), and an outer primer 2 (OP2; SEQ ID NO. 26). In FIG. 37A, in the case of the wildtype, the lower case "a" in the underlined portion BPw of 119E (wild) is the base to be detected, and in the case of the mutant-type, the lower case "t" in the underlined portion BPm of 119V (mutant) is the base to be detected. In FIG. 37B, the second base "T" from the 3' end in the BPw of 119E (wildtype) is the complementary base to the mutation (A) to be detected, and the second base "A" from the 3' end in the underlined portion BPm of 119V (mutant-type) is the complementary base to the mutation (T) to be detected. In FIG. 37A, the complementary strand of the dotted frame TP1 is the sequence contained in the 5' end of the turn-back primer, and the sequence in the dotted frame TP2 is a sequence contained in the 3' end of the turn-back primer. In FIG. 37A, the complementary strand of the underlined portion FP is a sequence contained in the 3' end of the folding primer. Furthermore, in FIG. 37A, the complementary strand of the underlined portion BPw is a sequence of the wildtype boost primer and that of the underlined portion BPm is a sequence of the mutant-type boost primer. In FIG. 37A, the underlined portion OP1 is the sequence of the outer primer 1, and the complementary strand of the underlined portion OP2 is a sequence of the outer primer 2.

In this example, the wildtype and mutant-type boost primers were used as labeled primers. In FIG. 37, the nucleotide residue (T) indicated with a bold letter in each of the underlined portions BPw and BPm is a base (labeled structure) labeled with a fluorescent atomic group. In the wildtype boost primer, the structure of the labeled nucleotide residue is represented by Formula (121), and the portions indicated with "Dye" in Formula (121) each are represented by Formula (113) indicated in Reference Example 6. In Formula (113), the linker length was n=4. With respect to the detection wavelength of the fluorescent atomic group represented by Formula (113), the excitation wavelength was 510 nm and the fluorescence wavelength was 530 nm. Furthermore, in the mutant type boost primer, the structure of the labeled nucleotide residue is represented by Formula (121), and the portions indicated with "Dye" in Formula (121) each are represented by Formula (120) indicated in Reference Example 6. In Formula (120), the linker length was n=4. With respect to the detection wavelength of the fluorescent atomic group represented by Formula (120), the excitation wavelength was 630 nm and the fluorescence wavelength was 650 nm. These labeled primers were synthesized in the same manner as in Example 8 or Reference Example 6 except that the base sequences were SEQ ID NO. 23 (BPw) and SEQ ID NO. 24 (BPm), respectively.

(3) SMAP Reaction

First, 25 μl of reaction solution with the composition indicated below was prepared on ice, which was allowed to react at 60° C. During the reaction, while a 60° C. isothermal condition was maintained, fluorescence intensity of the reaction solution was monitored in real time using the Mx3005P system (trade name, manufactured by Stratagene). The fluorescence intensity was detected, with the wavelength (492 nm-516 nm) of FAM and the wavelength (635 nm-665 nm) of Cy5 being employed as the detection wavelength range. In this manner, the fluorescence intensity of each labeled boost primer was measured. The fluorescent atomic group of the BPw for wildtype detection can be detected with the FAM wavelength, and the fluorescent atomic group of the BPm for mutant type detection can be detected with the Cy5 wavelength. The type and ratio of the template DNA and the type and ratio of the boost primer in the reaction solution are indicated in Table 12 below (Examples 20-1 to 20-2). Table 12 indicates the concentrations of the boost primers for wildtype detection and mutant type detection in the reaction solution as well as the copy numbers of the wildtype and mutant type in the template DNA. The results are shown in FIGS. 38 to 41. In each of FIGS. 38 to 41, "cycles" indicates "reaction time" (1 cycle=1 minute).

TABLE 11

| Composition of reaction solution | |
|---|---|
| Tris-HCl (pH 8.0) | 20 mM |
| KCl | 10 mM |
| $(NH_4)_2SO_4$ | 10 mM |
| Magnesium sulfate | 8 mM |
| Tween20 | 0.1% |
| Betaine | 0.6 M |
| dNTPs | 1.4 mM |
| Primers  FP | 2.0 μM |
| TP | 2.0 μM |
| BP | 1.0 μM |
| OP1 | 0.25 μM |
| OP2 | 0.25 μM |
| AacDNA polymerase* | 6 units |
| Template DNA (plasmid) | 6000 copies |
| Total | 25 μl |

*Manufactured by Kabushiki Kaisha Dnaform

TABLE 12

| | Reaction solution | Boost primer (μM) | | Template DNA (copy) | | |
|---|---|---|---|---|---|---|
| | | For wildtype detection | For mutant type detection | Wildtype | Mutant type | Total |
| Example 20-1 | a | 1.0 | 0.0 | 6000 | 0 | 6000 |
| | b | 1.0 | 0.0 | 0 | 6000 | 6000 |
| | c | 0.0 | 1.0 | 6000 | 0 | 6000 |
| | d | 0.0 | 1.0 | 0 | 6000 | 6000 |
| | e | 0.5 | 0.5 | 6000 | 0 | 6000 |
| | f | 0.5 | 0.5 | 0 | 6000 | 6000 |
| Example 20-2 | g | 0.5 | 0.5 | 5400 | 600 | 6000 |
| | h | 0.5 | 0.5 | 4500 | 1500 | 6000 |
| | i | 0.5 | 0.5 | 3000 | 3000 | 6000 |
| | j | 0.5 | 0.5 | 1500 | 4500 | 6000 |
| | k | 0.5 | 0.5 | 600 | 5400 | 6000 |

FIG. 38 shows graphs illustrating the amplification profile obtained when an isothermal amplification reaction was carried out with respect to the reaction solutions a to d of Example 20-1. FIGS. 38A and 38B show the results of detection of the fluorescence intensity at the FAM wavelength (492 nm/516 nm) and the Cy5 wavelength (635 nm/665 nm) with respect to the reaction solutions a and b of Example 20-1 in which the boost primer for wildtype detection was used and with respect to the reaction solutions c and d of Example 20-1 in which the boost primer for mutant type detection was used, respectively. In FIGS. 38A and 38B, ■ and □ each show the result of a wildtype DNA (wildtype plasmid), and • and ○ each show the result of a mutant type DNA (mutant type plasmid). As shown in FIG. 38A, when the boost primer for wildtype detection was used, a rapid increase in fluorescence intensity was observed at the FAM wavelength from around 27 cycles in the wildtype DNA (■) that fully matches with the boost primer for wildtype detection. On the other hand, in the mutant type DNA (•) that mismatches with the boost primer for wildtype detection, no increase in the fluorescence intensity was observed even after the 45 cycles. Furthermore, in these two reaction solutions, no increase in the fluorescence intensity was observed at the Cy5 wavelength (□ and ○). On the other hand, as shown in FIG. 38B, when the boost primer for mutant type detection was used, a rapid increase in the fluorescence intensity was observed at the Cy5 wavelength from around 27 cycles in the mutant type DNA (○) that fully matches with the boost primer for mutant type detection. On the other hand, in the wildtype DNA (□) that mismatches with the boost primer for mutant type detection, no increase in the fluorescence intensity was observed even after 45 cycles. Furthermore, in these two reaction solutions, no increase in the fluorescence intensity was observed at the FAM wavelength (■ and •). From these results, it was proved that it was possible to detect the wildtype DNA at the FAM wavelength using the boost primer for wildtype detection and it was possible to detect the mutant type DNA at the Cy5 wavelength using the boost primer for mutant type detection. It also was possible to observe the difference in fluorescence intensity satisfactorily even visually (hereinafter the same applies).

Figure 39:
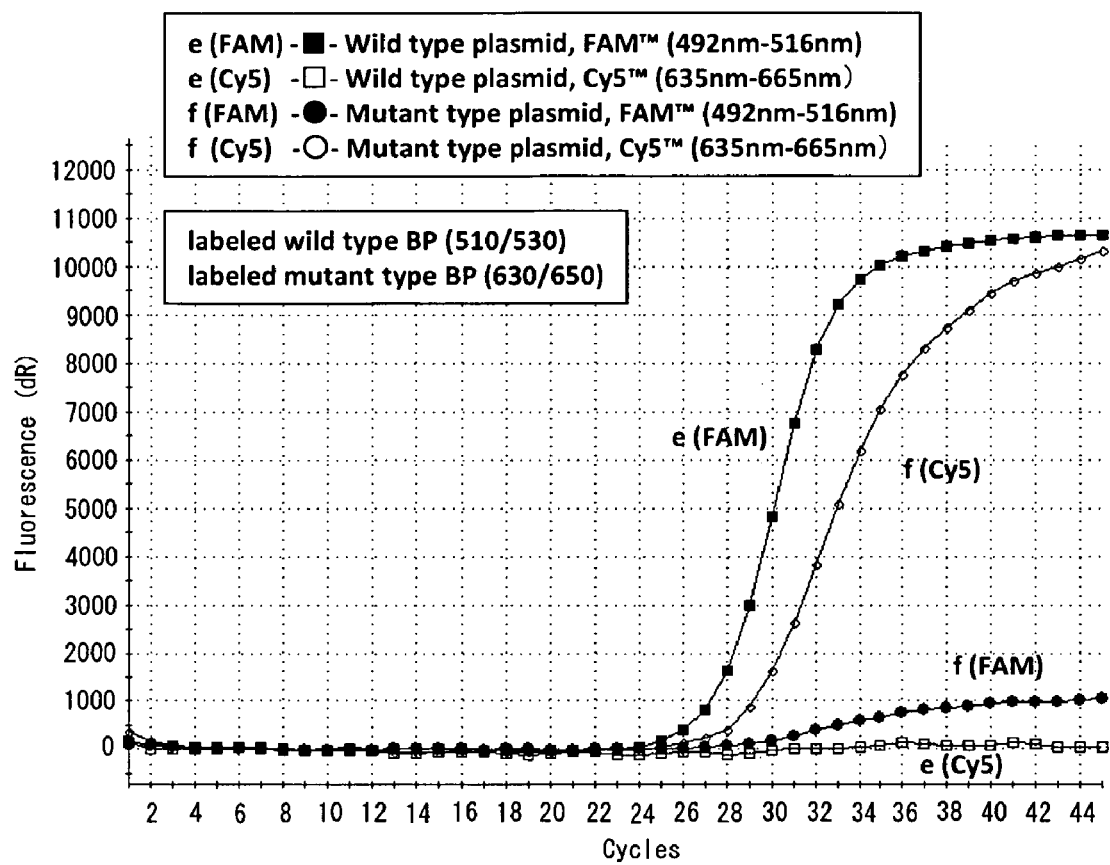
FIG. 39 shows graphs illustrating amplification profiles obtained when isothermal amplification reactions were carried out by the SMAP method in an example, and shows the results of fluorescence intensity detection carried out at the FAM wavelength (492 nm/516 nm) and the Cy5 wavelength (635 nm/665 nm), respectively, with respect to the reaction solutions e and f.

FIG. 39 shows graphs illustrating the amplification profiles obtained when an isothermal amplification reaction was carried out with respect to the reaction solutions e and f of Example 20-1. The reaction solutions each contain boost primers both for wildtype detection and for mutant type detection. In FIG. 39, ■, □, •, and ○ indicate the same results as in FIG. 38. As shown in FIG. 39, in the reaction solution e containing wildtype DNA, a rapid increase in the fluorescence intensity was observed at the FAM wavelength from around 27 cycles (■). On the other hand, no increase in the fluorescence intensity was observed at the Cy5 wavelength even after the 45 cycles (□). On the other hand, in the reaction solution f containing mutant type DNA, a rapid increase in the fluorescence intensity was observed at the Cy5 wavelength from around 29 cycles (○). On the other hand, no rapid increase in the fluorescence intensity occurred at the FAM wavelength even after the 45 cycles, and amplification hardly was observed (•). From these results, it was proved that when using the boost primers both for wildtype detection and for mutant type detection, it was possible to carry out detection of the wildtype at the FAM wavelength and detection of the mutant type at the Cy5 wavelength, in one reaction solution.

Figure 40:
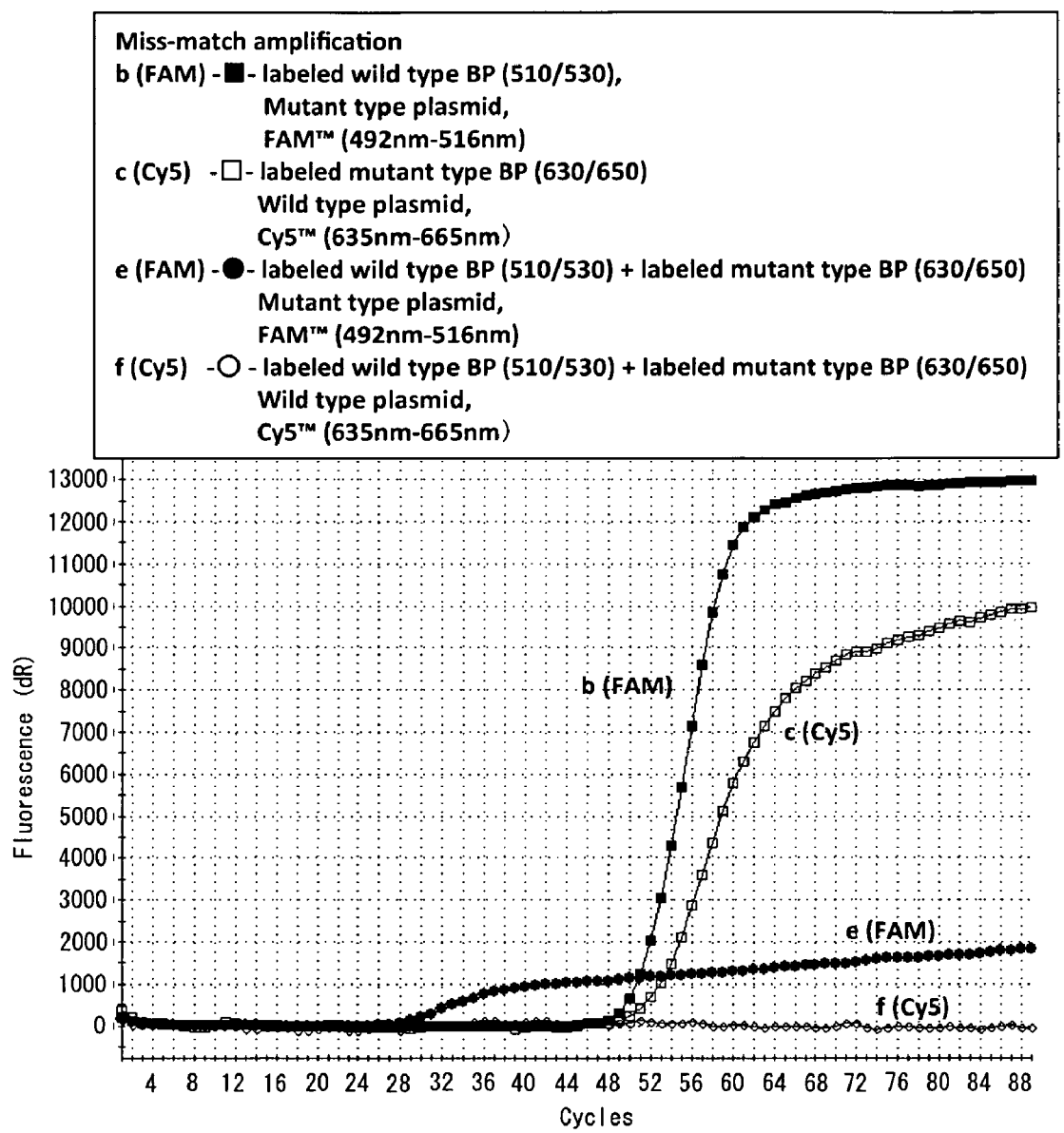
FIG. 40 is a graph showing amplification profiles obtained when isothermal amplification reactions were carried out by the SMAP method in an example, and shows the results of fluorescence intensity detection carried out at the FAM wavelength (492 nm/516 nm) and the Cy5 wavelength (635 nm/665 nm), respectively, with respect to the reaction solutions b, c, e, and f.

FIG. 40 is a graph showing the amplification profiles obtained when an isothermal amplification reaction was carried out with respect to the reaction solutions b, c, e, and f of Example 20-1. In the reaction solution b containing the boost primer for wildtype detection used therein, amplification of mismatch mutant type DNA caused by the boost primer for wildtype detection was observed from around 50 cycles (■). Furthermore, in the reaction solution c containing the boost primer for mutant type detection used therein, amplification of mismatch wildtype DNA caused by the boost primer for mutant type detection was observed from around 52 cycles (□). On the other hand, in the reaction solutions e and f containing both the boost primers for wildtype detection and for mutant type detection, no rapid increase in the fluorescence intensity occurred and the amplification of mismatch DNA hardly was observed even after 90 cycles. The reason thereof is described as follows. That is, since the boost primer for wildtype detection and the boost primer for mutant type detection were allowed to coexist in the reaction solutions, the full-match boost primer and the mismatch boost primer compete against each other, and thereby the bonding of the mismatch boost primer to DNA was suppressed. From these results, it was proved that it was possible to suppress the amplification of the mismatch DNA by using both the boost primer for wildtype detection and the boost primer for mutant type detection.

Figure 41A:
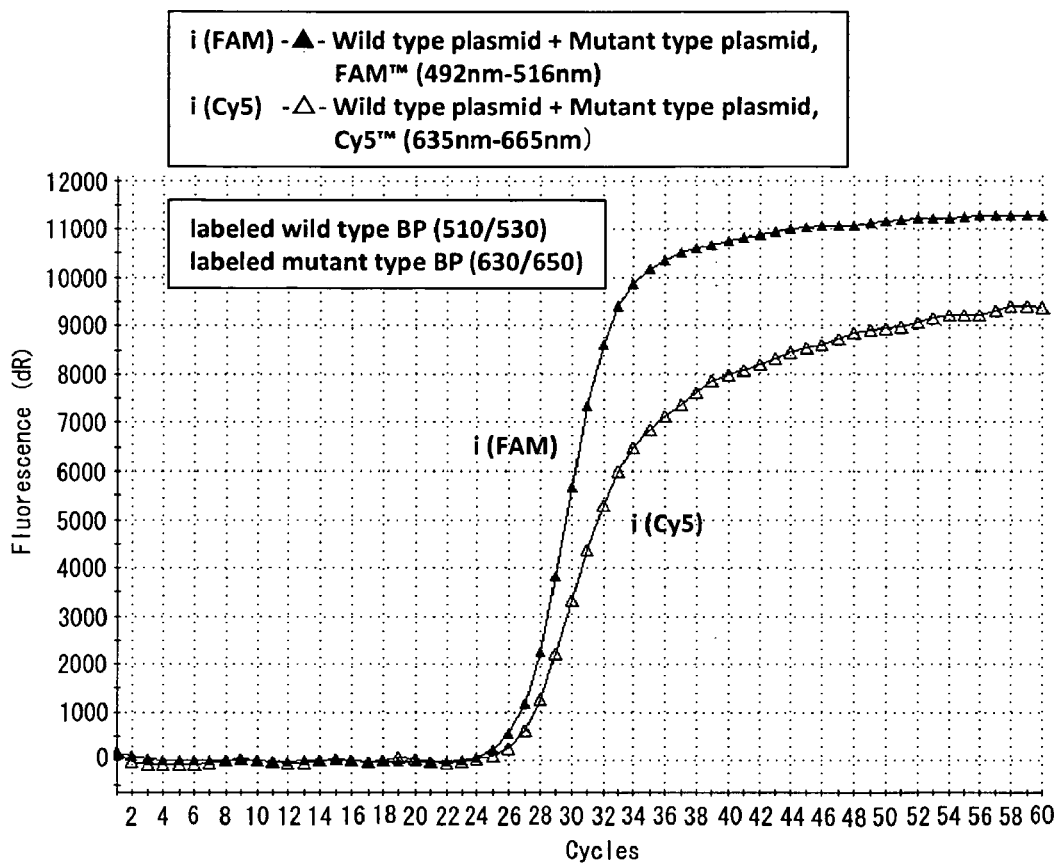
FIG. 41A is a graph showing amplification profiles obtained when isothermal amplification reactions were carried out by the SMAP method in an example, and shows the results of fluorescence intensity detection carried out at the FAM wavelength (492 nm/516 nm) and the Cy5 wavelength (635 nm/665 nm), respectively, with respect to the reaction solution i.

FIG. 41 shows graphs illustrating the amplification profiles obtained when an isothermal amplification reaction was carried out with respect to the reaction solutions g to k of Example 20-2. The reaction solutions each contain the boost primers both for wildtype detection and for mutant type detection as well as both wildtype DNA and mutant type DNA as template DNAs. In FIG. 41A, ▲ indicates the result of detection carried out at the FAM wavelength with respect to the reaction solution i of Example 20-2 and Δ indicates the result of detection carried out at the Cy5 wavelength with respect to the reaction solution i. As shown in FIG. 41A, rapid increases in the fluorescence intensity were observed at both the FAM and Cy5 wavelengths. From this result, it was proved that even when both the boost primers were allowed to coexist, it was possible to amplify DNA that fully matched with each boost primer and further it was possible to detect the amplification at each wavelength. FIG. 41B shows the result of detection carried out at the FAM wavelength with respect to the reaction solutions g to k of Example 20-2 and FIG. 41C shows the result of detection of the fluorescence intensity carried out at the Cy5 wavelength with respect to the reaction solutions g to k. As indicated in Table 12 above, the respective reaction solutions contained, as the template DNAs, wildtype DNA and mutant type DNA whose contents were changed. As shown in FIG. 41B, even when the ratio of the wildtype DNA that fully matched with the boost primer for wildtype detection decreased, an increase in fluorescence intensity was observed at the FAM wavelength. Furthermore, as shown in FIG. 41C, even when the ratio of the mutant type DNA that fully matched with the boost primer for mutant type detection decreased, an increase in fluorescence intensity was observed at the Cy5 wavelength. From these results, the following was proved. That is, in the case where both the boost primer for wildtype detection and the boost primer for mutant type detection were used, even when the content of wildtype DNA in the reaction solution was low, the wildtype DNA was detected at the FAM wavelength, and even when the content of mutant type DNA in the reaction solution was low, the mutant type DNA was detected at the Cy5 wavelength.

Example 21

Exon 21 of an EGFR gene was amplified by PCR using a primer set including a labeled primer of the present invention.
(1) Template DNA
A human genomic DNA (manufactured by Promega Corporation) was used.
(2) Primer
A primer set composed of an unlabeled forward primer (F1) and a labeled reverse primer (Labeled-R1) was used. Labeled-R1 was prepared by labeling the underlined nucleotide residue (T) with a fluorescent atomic group. The structure of the nucleotide residue thus labeled is represented by Formula (121), and each "Dye" portion in Formula (121) is represented by Formula (113) indicated in Reference Example 6. In Formula (113), the linker length was n=4. With respect to the detection wavelength of the fluorescent atomic group represented by Formula (113), the excitation wavelength was 510 nm and the fluorescence wavelength was 530 nm. This Labeled-R1 was synthesized by the same method as in Example 8 or Reference Example 6 except that the base sequence was SEQ ID NO. 28.

```
F1:
5'-AAACACCGCAGCATGTC-3'       (SEQ ID NO. 27)

Labeled-R1:
5'-TAAAGCCACCTCCTTAC-3'       (SEQ ID NO. 28)
```

Figure 42:
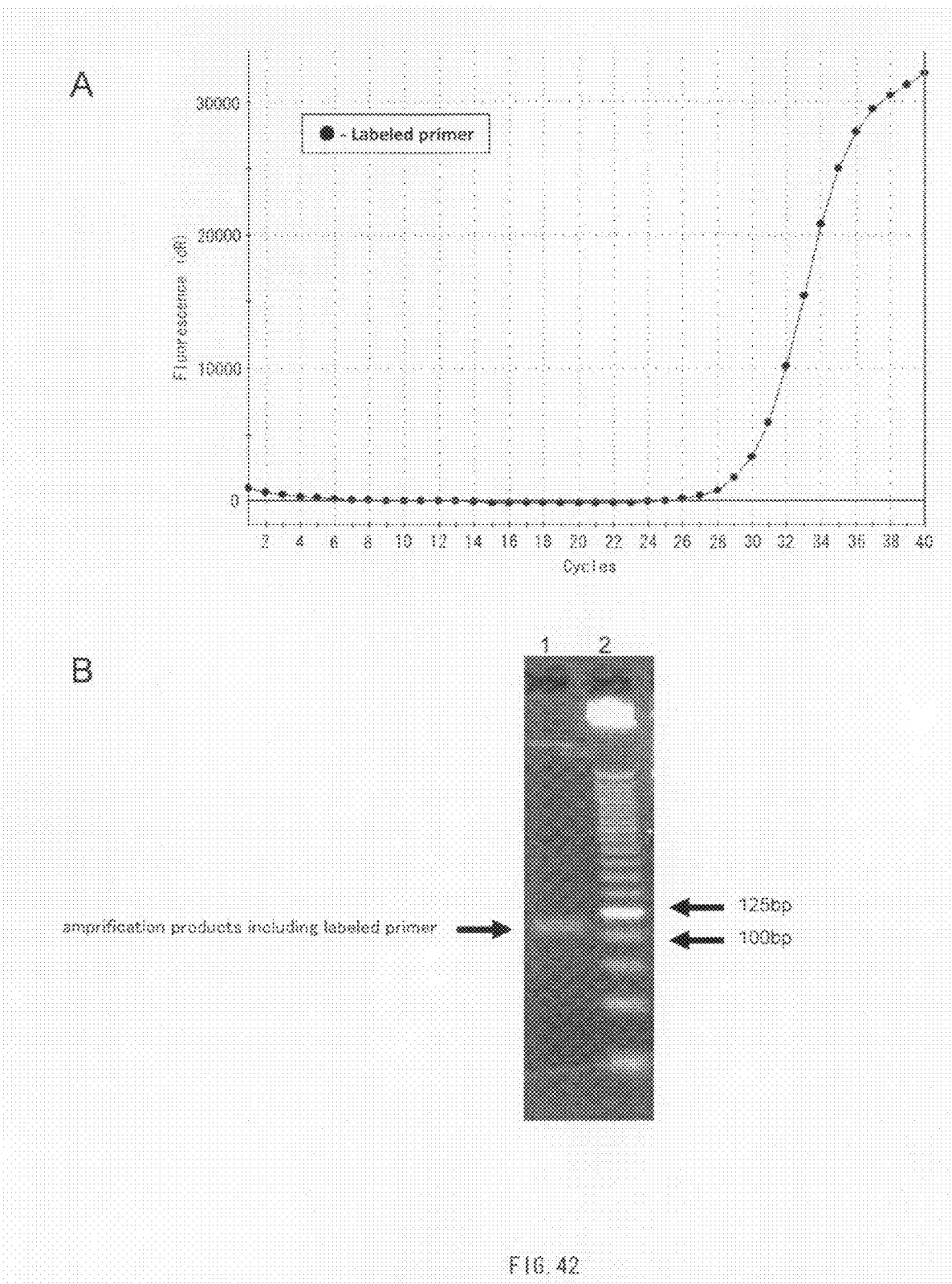
FIG. 42A is a graph showing an amplification profile obtained when an amplification reaction was carried out by the PCR method in an example.
FIG. 42B is an electrophoretogram of an amplification product obtained when a PCR reaction was carried out in an example.

The positional relationship between F1 and Labeled-R1 in a region (SEQ ID NO. 30) of exon 21 is as shown in the following underlined portions.
5'-AAACACCGCAGCATGTCAAGATCACAGATTTTG-
GGCGGGCCAAACTG
F1
CTGGGTGCGGAAGAGAAAGAATACCATG-
CAGAAGGAGGCAAA
GTAAGGAGGTGGCTTTA-3'
Labeled-R1
A primer set composed of F1 and Labeled-R1 described above was used. Using PrimeSTAR (registered trademark) HS DNA Polymerase (Takara), PCR was carried out according to the method described in the product instructions. The fluorescence intensity of the PCR reaction solution was monitored in real time using an Mx3000P system (manufactured by Stratagene). Specifically, after preheating was carried out at 98° C. for 10 seconds, PCR was carried out for 40 cycles, each of which was composed of 98° C. for 10 seconds, 69° C. for 10 seconds, and 72° C. for 10 seconds. This result is shown in FIG. 42A. FIG. 42A is a graph showing the PCR amplification curve obtained using the primer set including the Labeled-R1.
After completion of PCR, 9 μl of reaction solution was electrophoresed at 100 V using 4% NuSieve GTG Agarose (TAKARA BIO INC.). Thereafter, the gel obtained after the electrophoresis was dyed with ethidium bromide (EtBr), and thus nucleic acid was detected. FIG. 42B shows the electrophoretogram illustrating the result. In FIG. 42B, Lane 1 shows nucleic acid amplified by PCR carried out using a primer set including a labeled primer (Labeled-R1), and Lane 2 shows the result of electrophoresis carried out using 25 bp ladder marker.

As shown in FIG. 42A, it was proved that the labeled primer also was amplified by PCR. This was observed well even visually. Furthermore, as shown in FIG. 42B, the nucleic acid amplified using the labeled primer was checked by electrophoresis and thereby the target band was observed. Thus, it was proved that a primer labeled with the fluorescent atomic group (510/530) also functioned effectively by PCR.

Example 22

Exon 21 of an EGFR gene was amplified by PCR using a primer set including a labeled primer of the present invention, and a melting curve analysis was performed.
(1) Template DNA
A human genomic DNA (manufactured by Promega Corporation) was used.
(2) Primer
A primer set (Example) composed of an unlabeled forward primer (F1) and a labeled reverse primer (Labeled-R1) and a primer set (control) composed of an unlabeled forward primer (F1) and an unlabeled reverse primer (R1) were used. The above-mentioned label R1 (Labeled-R1) is identical to that used in Example 21. Furthermore, the positional relationship of R1 in a region (SEQ ID NO. 30) of exon 21 is identical to that of the label R1.

```
F1:
5'-AAACACCGCAGCATGTC-3'       (SEQ ID NO. 27)

R1:
5'-TAAAGCCACCTCCTTAC-3'       (SEQ ID NO. 29)

Labeled-R1:
5'-TAAAGCCACCTCCTTAC-3'       (SEQ ID NO. 28)
```

Figure 43:
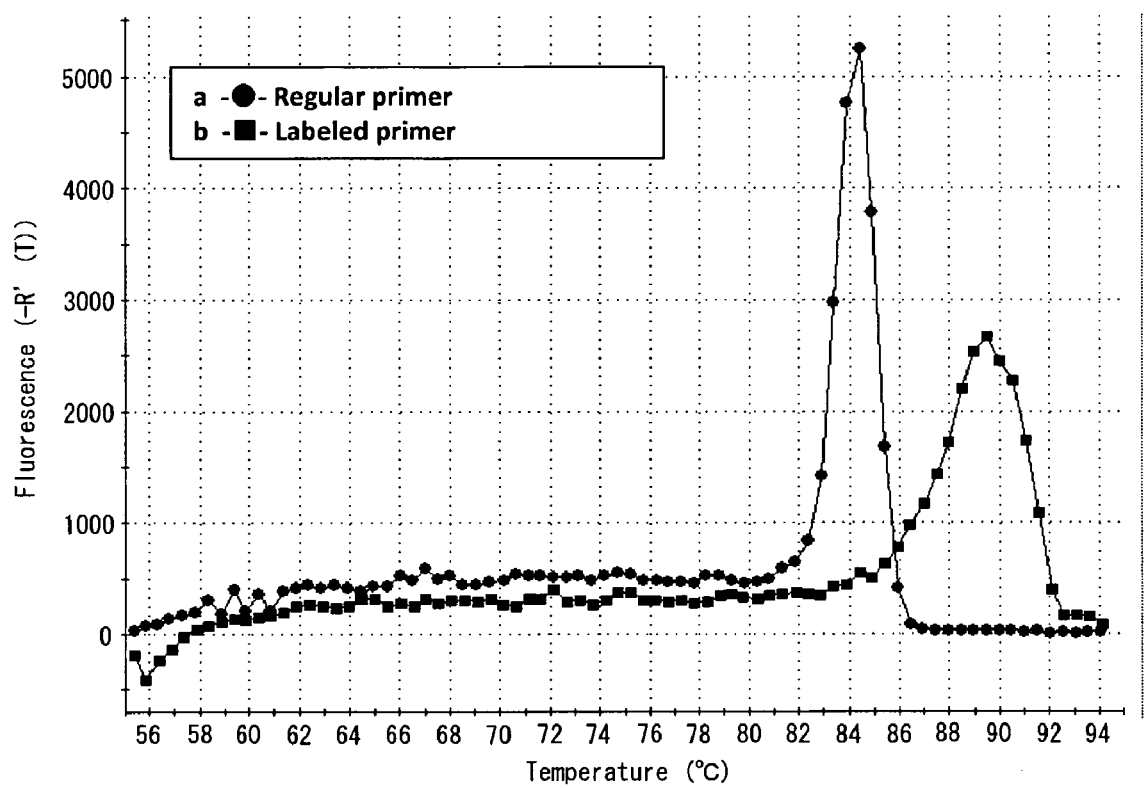
FIG. 43 is a graph showing melting curves in an example.

Using SYBR (registered trademark) Premix EX Taq (registered trademark) (manufactured by Takara) which is used a common primer set composed of F1 and R1 as well as a labeled primer set composed of F1 and Labeled-R1, PCR was carried out according to the method described in the product instructions. The fluorescence intensity of the PCR reaction solution was monitored in real time using the Mx3000P system (manufactured by Stratagene). Specifically, after preheating was carried out at 95° C. for 10 seconds, PCR was carried out for 40 cycles, each of which was composed of 95° C. for 30 seconds, 60° C. for one minute, and 72° C. for 30 seconds. After completion of PCR, subsequently, the product thus obtained was treated at 95° C. for one minute and at 55° C. for 30 seconds, thereafter, the temperature was raised to 95° C. at a rate of temperature increase of 2° C./1 min, and the product was treated at 95° C. for 30 seconds, which was carried out as a melting curve measurement step. Between 55° C. and 95° C., the fluorescence intensity was monitored in real time. These results are shown in FIG. 43. FIG. 43 is a graph showing a melting curve. In FIG. 43, ■ (labeled-primer) indicates the result with respect to Example in which a labeled primer set composed of F1 and Labeled-R1 was used (FAM wavelength: 492 nm/516 nm), and • (regular primer) indicates the result with respect to the control in which a primer set composed of F1 and R1 was used (FAM wavelength: 492 nm/516 nm).

As shown in FIG. 43, the melting curve (Example) obtained by PCR carried out using the labeled primer indicated a peak at a higher temperature as compared to the melting curve (control) obtained by PCR carried out using the unlabeled primer. From this result, it was proved that the labeled nucleic acid (primer) according to present invention allowed the Tm value to be increased as compared to the unlabeled primer. The increase in Tm value as described above indicated that the labeled nucleic acid of the present invention bound further strongly to a complementary DNA thereto as compared to a common unlabeled primer. That is, it was proved that the labeled nucleic acid of the present invention had the same function as that of oligonucleotide that increased the Tm value, such as generally used LNA or PNA, for example. From this result, it is considered that the labeled nucleic acid of the present invention also can be developed for the applied technology that increases the specificity of amplification, for example. It is easy to surmise that the labeled nucleic acid of the present invention is used not only for an experimental system in which LNA or PNA is used for increasing the Tm Value but also for a wider range of applications as compared to LNA or PNA in a molecular biological approach since it has ability to emit fluorescence that LNA or PNA does not have.

Example 23

Using a LAMP primer set including a labeled primer of the present invention, a region containing a mutation L858R of EGFR exon 21 was amplified.
(1) Template DNA
As in Example 19, the template DNA was extracted from lung cancer cell line NCI-H1975 containing an exon 21 point mutation L858R (American Type Culture Collection).
(2) Primer set
A LAMP primer set that fully matched with the aforementioned region containing the mutation was prepared. The primer set includes LF (SEQ ID NO. 31), LR (SEQ ID NO. 32), labeled or unlabeled BP (SEQ ID NO. 33), and OP (SEQ ID NO. 34). The ratio of the respective primers in the primer mix was as follows: LF:LR:BP:OP=8:8:4:1.
LF (EGFRex21(M)LF Primer)
5'-CCAAAATCTGGGAACGTACTGGTGAAACA-3'
LR (EGFRex21(M)LR Primer)
5'-CGAGCCAAACGCCTCCTTCTGCATGGTATT-3'
BP (boost primer; EGFR exon 21 BP3) 5'-TGGGTGCG-GAAGAGAAAG-3'
OP (Outer Primer2; EGFR exon 21 OP3) 5'-TAAAGCCAC-CTCCTTAC-3'
With respect to the labeled BP, a predetermined nucleotide was labeled with the fluorescent atomic group described below. The nucleotide indicated with a bold letter and an underline in the sequence indicated in the table below is the labeled site. In BP-1 indicated below, the structure of the labeled nucleotide residue is represented by Formula (121). In Formula (121), each portion indicated with "Dye" is represented by Formula (113) indicated in Reference Example 6. In Formula (113), the linker length was n=4. With respect to the detection wavelength of the fluorescent atomic group represented by Formula (113), the excitation wavelength is 510 nm and the fluorescence wavelength is 530 nm. Furthermore, in BP-2 indicated below, the structure of the labeled nucleotide residue is represented by Formula (121). In Formula (121), each portion indicated with "Dye" is represented by Formula (123) indicated in Reference Example 6. In Formula (123), the linker length was n=4. With respect to the detection wavelength of the fluorescent atomic group represented by Formula (123), the excitation wavelength is 530 nm and the fluorescence wavelength is 550 nm. These labeled primers each were synthesized by the same method as Example 8 or Reference Example 6 except that the base sequence was SEQ ID NO. 33 (BP).

TABLE 13

| | Labeled-primer | | Fluorescence atomic group | Detection wavelength |
|---|---|---|---|---|
| Example 23-1 | Labeled-BP (BP-1) | 5'-TGGGTGCGGAAGAGAAAG-3' | Formula 113 (510/530) | TET filter 517 nm/538 nm |
| Example 23-2 | Labeled-BP (BP-2) | 5'-TGGGTGCGGAAGAGAAAG-3' | Formula 123 (530/550) | HEX filter 535 nm/555 nm |
| Control | | — | — (SYBR Green I) | FAM filter 492 nm/516 nm |

25 μL of reaction solution having the composition indicated below was prepared and was allowed to react at 60° C. for one hour. During the reaction, while a 60° C. isothermal condition was maintained, fluorescence intensity of the reaction solution was monitored in real time using the Mx3000P system (trade name; manufactured by Stratagene). For control, using an unlabeled primer set, further SYBR (registered trademark) Green I (Moleculor Probes, Inc) was added to the reaction solution in such a manner that the concentration thereof was diluted 100,000 times, and thereby measurement was carried out in the same manner.

TABLE 14

| Composition of reaction solution | |
|---|---|
| Tris-HCl (pH 8.0) | 20 mM |
| KCl | 10 mM |
| (NH$_4$)$_2$SO$_4$ | 10 mM |
| Magnesium sulfate | 8 mM |
| Tween20 | 0.1% |
| Betaine | 0.6 M |
| dNTPs | 1.4 mM |
| Primers  LF | 2.0 μM |
| LR | 2.0 μM |
| BP or labeled-BP | 1.0 μM |
| OP | 0.25 μM |
| AacDNA polymerase* | 6 units |
| Genomic DNA | 40 ng |
| Total | 25 μl |

*Manufactured by Kabushiki Kaisha Dnaform

Figure 44:
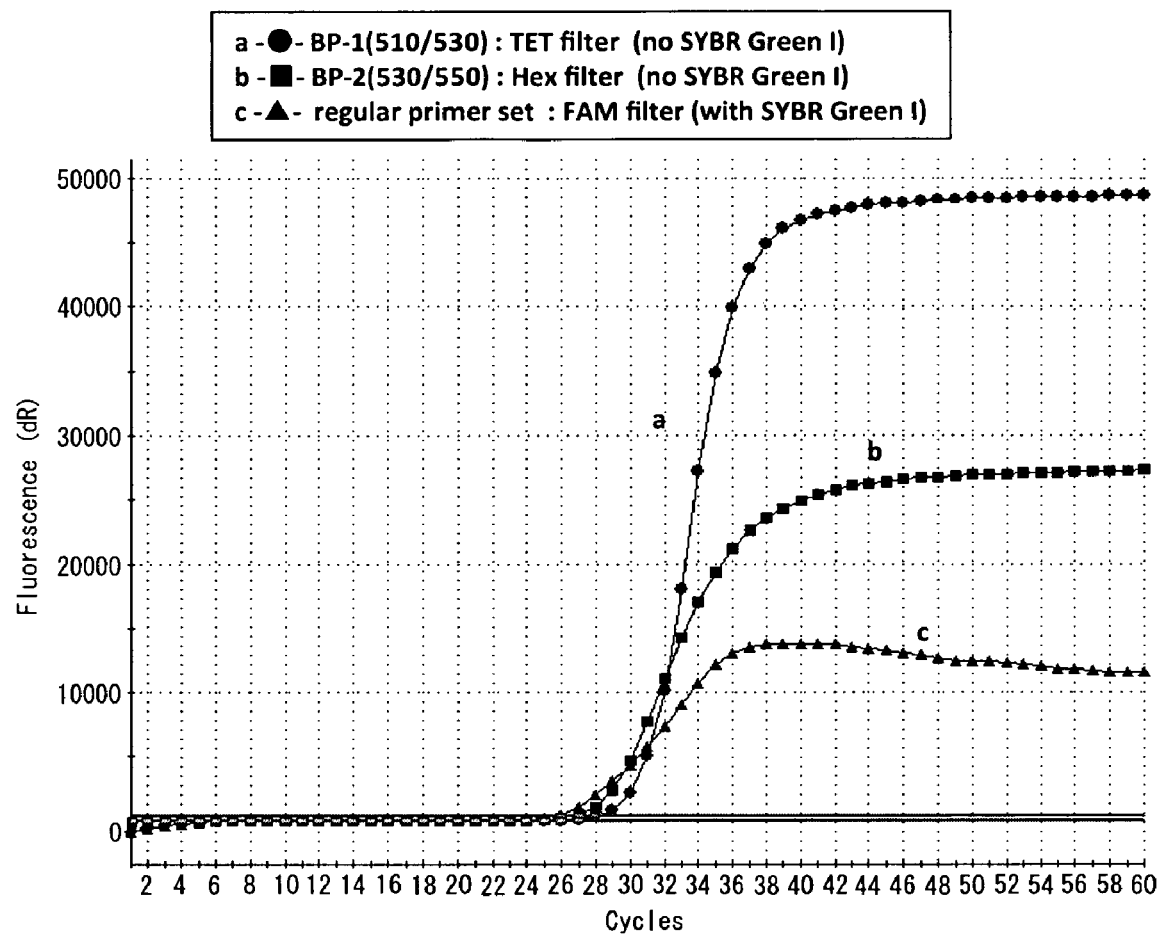
FIG. 44 is a graph showing an amplification profile obtained when an isothermal amplification reaction was carried out by the LAMP method in an example.

These results are shown in FIG. 44. FIG. 44 is a graph showing amplification profiles obtained when an isothermal amplification reaction was carried out by the LAMP method. In FIG. 44, • indicates the result obtained in Example 23-1 in which BP-1 was used, □ indicates the result obtained in Example 23-2 in which BP-2 was used, and ▲ indicates the result with respect to the control. In FIG. 44, "cycles" indicates "reaction time" (1 cycle=1 minute).

As shown in FIG. 44, it was proved that Examples 23-1 to 23-2, in each of which the labeled primer of the present invention was used, allowed amplification to be confirmed also by the LAMP method as in the case of the control. In Example 23-1 in which BP-1 labeled with a fluorescent atomic group (510/530) represented by Formula (113) was used, the fluorescence value in the plateau was considerably higher as compared to that of Example 23-2 in which BP-2 labeled with a fluorescent atomic group (530/550) represented by Formula (123) was used. The difference was observed well even visually. Thus, it was proved that the aforementioned fluorescent atomic group was excellent in detection sensitivity as a label to be used in the primer of the present invention.

As described above, in the case where the primer of the present invention is prepared as labeled nucleic acid containing a structure expressed by the formula described above, when, for example, it is used for a method of amplifying a target nucleic acid sequence, amplification of the target nucleic acid sequence can be detected effectively. Furthermore, since amplification can be detected effectively as described above, for example, the presence or absence of a target mutation in a target nucleic acid sequence can be detected with excellent sensitivity. Since the present invention is excellent in, for example, detection sensitivity of nucleic acid, it can be used for a wide range of applications, for example, study, clinical use, diagnosis, in vitro gene detection, and in vivo gene detection.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A primer for amplifying a target nucleic acid sequence, wherein the primer is a labeled nucleic acid including at least one of structures represented by the following formulae (16), (16b), (17) and (17b) and exhibits an exciton effect:

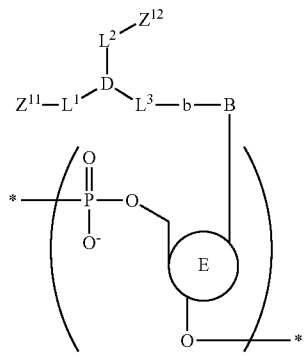

(16)

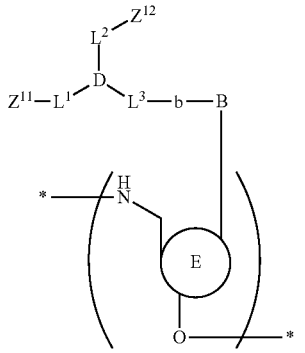

(16b)

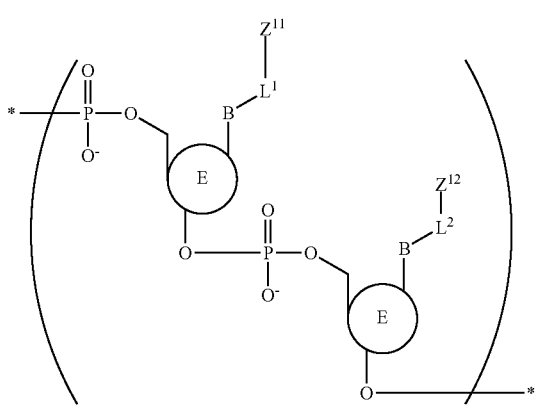

(17)

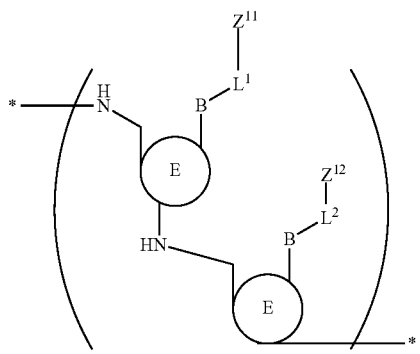

(17b)

where in the formulae (16), (16b), (17) and (17b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a fluorescent atomic group that exhibits an exciton effect, and may be identical to or different from each other, $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formulae (16) and (16b), $L^1$ and $L^2$ are each the linker, $L^3$, D, and b may not be present, and $L^1$ and $L^2$ may be bonded directly to B, where in the formulae (16) and (17), E is the atomic group described in item (i), and at least one O atom in a phosphoric acid linkage may be substituted with an S atom, in the formulae (16b) and (17b), E is the atomic group described in item (ii), and in the formulae (17) and (17b), the respective Bs may be identical to or different from each other, and the respective Es may be identical to or different from each other.

2. The primer according to claim 1, wherein in the formulae (16), (17), (16b) and (17b), the main chain length (the number of main chain atoms) of each of $L^1$, $L^2$, and $L^3$ is an integer of 2 or more.

3. The primer according to claim 1, wherein in the formulae (16), (17), (16b) and (17b), $Z^{11}$ and $Z^{12}$ are each independently a group derived from thiazole orange, oxazole yellow, cyanine, hemicyanine, another cyanine dye, methyl red, an azo dye, or a derivative thereof.

4. The primer according to claim 1, wherein $Z^{11}$ and $Z^{12}$ are each independently an atomic group represented by any one of the following formulae (7) to (9):

(7)

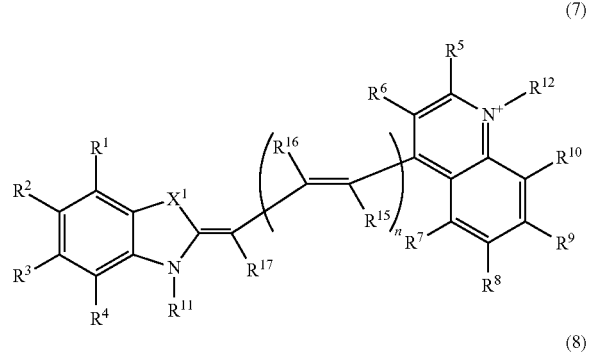

(8)

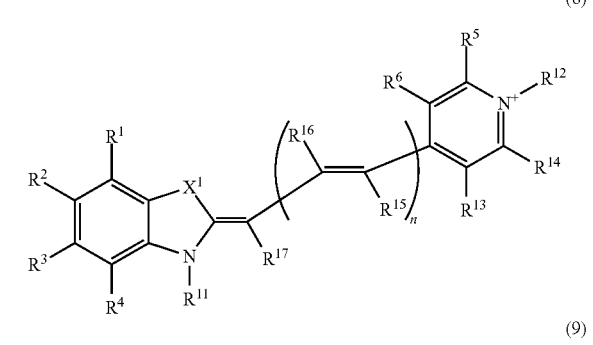

(9)

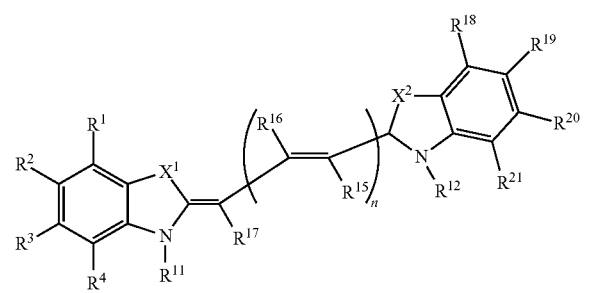

where in the formulae (7) to (9),
$X^1$ and $X^2$ are S or O,
n is 0 or a positive integer,
$R^1$ to $R^{10}$ and $R^{13}$ to $R^{21}$ are each independently a hydrogen atom, a halogen atom, a lower alkyl group, a lower alkoxy group, a nitro group, or an amino group,
one of $R^{11}$ and $R^{12}$ is a linking group that is bonded to $L^1$ or $L^2$ in the formulae (16), (17), (16b) and (17b), and the other is a hydrogen atom or a lower alkyl group,
when a plurality of $R^{15}$s are present in the formula (7), (8), or (9), they may be identical to or different from each other,
when a plurality of $R^{16}$s are present in the formula (7), (8), or (9), they may be identical to or different from each other, and
$X^1$, $X^2$ and $R^1$ to $R^{21}$ in $Z^{11}$ and $X^1$, $X^2$ and $R^1$ to $R^{21}$ in $Z^{12}$ may be identical to or different from each other, respectively.

5. The primer according to claim 4, wherein in the formulae (7) to (9),
in $R^1$ to $R^{21}$, the lower alkyl group is a linear or branched alkyl group with a carbon number of 1 to 6, and the lower alkoxy group is a linear or branched alkoxy group with a carbon number of 1 to 6.

6. The primer according to claim 4, wherein in the formulae (7) to (9),
in $R^{11}$ and $R^{12}$, the linking group is a polymethylene carbonyl group with a carbon number of at least 2 and is bonded to $L^1$ or $L^2$ in the formulae (16), (16b), (17) and (17b) in a carbonyl group moiety.

7. The primer according to claim 1, further comprising unlabeled nucleic acid having the same nucleic sequence with the labeled nucleic acid.

8. A primer set for amplifying a target nucleic acid sequence,
wherein the primer set comprises a pair of primers, and at least one of the pair of primers is a primer according to claim 1.

9. The primer set according to claim 8, wherein the primer set is used for an isothermal amplification method.

10. The primer set according to claim 9, wherein the isothermal amplification method is at least one selected from the group consisting of SDA method, improved SDA method, NASBA method, LAMP method, ICAN method, 3SR method, TMA method, Q-beta replicase method, SMAP method, Invader method, and RCA method.

11. The primer set according to claim 9, further comprising polymerase having strand displacement ability.

12. The primer set according to claim 9, further comprising a mismatch binding protein.

13. The primer set according to claim 12, wherein the mismatch binding protein is at least one protein selected from the group consisting of MutS, MSH2, and MSH6.

14. The primer set according to claim 9, wherein the pair of primers is of an asymmetric type in which one primer is different in morphology from the other primer.

15. The primer set according to claim 14, wherein the pair of primers includes a first primer and a second primer,
the first primer contains, in a 3' end portion, a sequence (Ac') that hybridizes to a sequence (A) of a 3' end portion of a target nucleic acid sequence, and contains, on a 540 side of the sequence (Ac'), a sequence (B') that hybridizes to a complementary sequence (Bc) to a sequence (B) present on a 5' side with respect to the sequence (A) in the target nucleic acid sequence, and
the second primer contains, in a 3' end portion, a sequence (Cc') that hybridizes to a sequence (C) of a 3' end portion of a complementary sequence to the target nucleic acid sequence, and contains, on a 5' side of the sequence (Cc'), a folded sequence (D-Dc') that contains, on the same strand, two nucleic acid sequences that hybridize with each other.

16. The primer set according to claim 14, wherein either one of the first primer or the second primer is the labeled nucleic acid.

17. The primer set according to claim 14, further comprising a third primer,
wherein the third primer hybridizes to the target nucleic acid sequence or the complementary sequence thereto and does not compete with other primers for hybridizing the target nucleic acid sequence or the complementary sequence thereto, and
when an amplification product of the first primer or second primer is brought into a single-stranded state partially, the third primer can anneal to a target nucleic acid sequence present in a moiety that is in the single-stranded state, so that a new origin of complementary strand synthesis is provided for a target nucleic acid sequence in the amplification product.

18. The primer set according to claim 17, wherein the third primer is the labeled nucleic acid in addition to or instead of either one of the first primer or the second primer.

19. The primer set according to claim 9, wherein the pair of primers is of a symmetrical type in which one primer is identical in morphology to the other primer.

20. The primer set according to claim 19, wherein the primer set is used for a LAMP method.

21. The primer set according to claim 8, wherein the primer set is used for a polymerase chain reaction (PCR) method.

22. The primer set according to claim 8, further comprising at least two types of primers according to claim 1, with the at least two types of primers having fluorescent atomic groups that are different in detection wavelength from each other.

23. A kit for nucleic acid amplification that is used for a nucleic acid amplification method for amplifying a target nucleic acid sequence,
wherein the kit comprises a primer according to claim 1, or a primer set according to claim 8.

24. The kit for nucleic acid amplification according to claim 20, wherein the kit is a kit for nucleic acid amplification to be used for an isothermal amplification method and comprises a primer set according to claim 9.

25. The kit for nucleic acid amplification according to claim 23, wherein the kit is a kit for nucleic acid amplification to be used for a PCR method, and comprises a primer set according to claim 21.

26. The kit for nucleic acid amplification according to claim 23, further comprising at least two types of primers according to claim 1, with the at least two types of primers having fluorescent atomic groups that are different in detection wavelength from each other.

27. A mutation detection kit that is used for a mutation detection method for detecting the presence or absence of a mutation in a target nucleic acid sequence,
wherein the mutation detection kit comprises a kit for nucleic acid amplification according to claim 23.

28. A method of amplifying a target nucleic acid sequence contained in a nucleic acid sample, comprising:
(A) preparing the nucleic acid sample,
(B) adding a primer according to claim 1 or a primer set according to claim 8 to the nucleic acid sample prepared in (A), and
(C) amplifying the target nucleic acid sequence contained in the nucleic acid sample using the primer according to claim 1 or the primer set according to claim 8.

29. The nucleic acid amplification method according to claim 28, wherein nucleic acid amplification in (C) is a nucleic acid amplification reaction carried out by an isothermal amplification method.

30. The nucleic acid amplification method according to claim 29, wherein the isothermal amplification method is at least one selected from the group consisting of SDA method, improved SDA method, NASBA method, LAMP method, ICAN method, 3SR method, TMA method, Q-beta replicase method, SMAP method, Invader method, and RCA method.

31. The nucleic acid amplification method according to claim 29, wherein the isothermal amplification method is an amplification method using a polymerase having strand displacement ability.

32. The nucleic acid amplification method according to claim 29, wherein in (C), nucleic acid amplification is carried out in the presence of a mismatch binding protein.

33. The nucleic acid amplification method according to claim 32, wherein the mismatch binding protein is at least one protein selected from the group consisting of MutS, MSH2, and MSH6.

34. The nucleic acid amplification method according to claim 29, wherein the primer set is an asymmetric type in which one primer is different in morphology from the other primer.

35. The nucleic acid amplification method according to claim 29, wherein the primer set is a symmetrical type in which one primer is identical in morphology to the other primer.

36. The nucleic acid amplification method according to claim 28, wherein the nucleic acid amplification carried out in (C) is a nucleic acid amplification reaction by a PCR method.

37. The nucleic acid amplification method according to claim 36, wherein the amplification in (C) comprises a polymerase chain reaction (PCR) method.

38. The nucleic acid amplification method according to claim 28, wherein in (C), at least two types of primers according to a primer as defined as follows are used:
a primer for amplifying a target nucleic acid sequence,
wherein the primer is a labeled nucleic acid including at least one of structures represented by the following formulae (16), (16b), (17) and (17b) and exhibits an exciton effect:

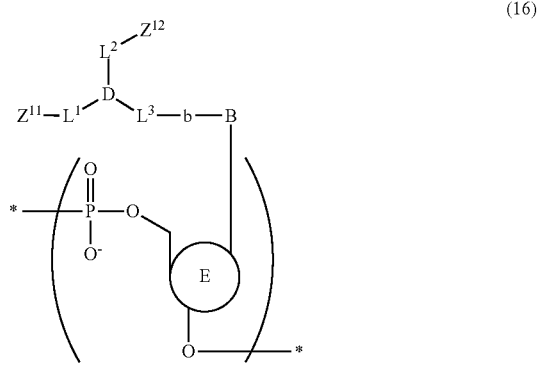

(16)

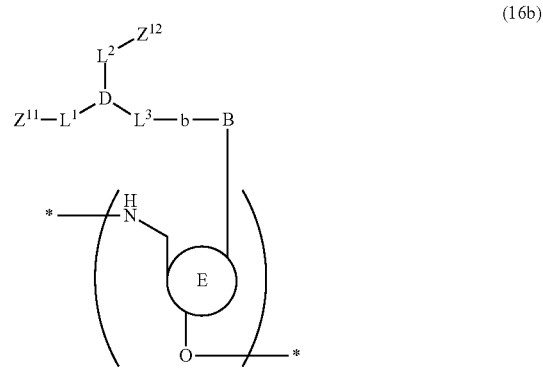

(16b)

-continued

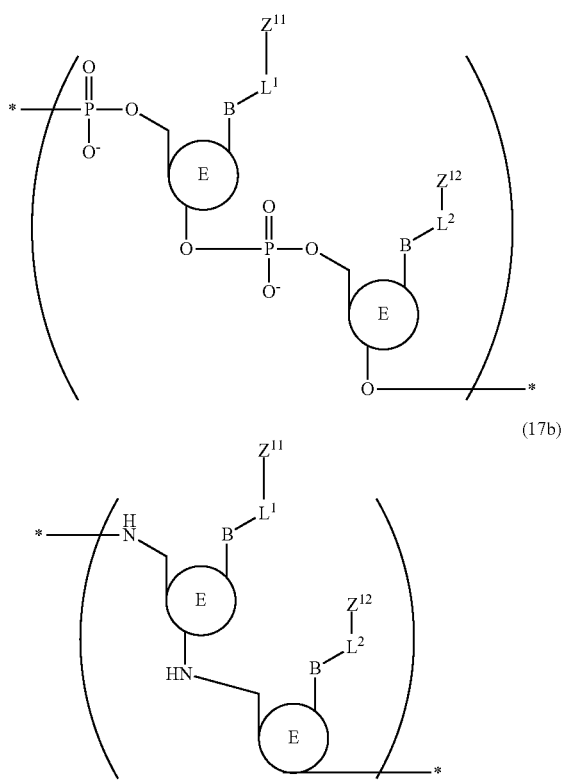

(17)

(17b)

where in the formulae (16), (16b), (17) and (17b),

B is an atomic group having a natural nucleobase (adenine, guanine, cytosine, thymine, or uracil) skeleton or an artificial nucleobase skeleton, E is:

(i) an atomic group having a deoxyribose skeleton, a ribose skeleton, or a structure derived from either one of them, or (ii) an atomic group having a peptide structure or a peptoid structure, $Z^{11}$ and $Z^{12}$ are each a fluorescent atomic group that exhibits an exciton effect, and may be identical to or different from each other, $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formulae (16) and (16b), $L^1$ and $L^2$ are each the linker, $L^3$, D, and b may not be present, and $L^1$ and $L^2$ may be bonded directly to B, where in the formulae (16) and (17), E is the atomic group described in item (i), and at least one O atom in a phosphoric acid linkage may be substituted with an S atom, in the formulae (16b) and (17b), E is the atomic group described in item (ii), and in the formulae (17) and (17b), the respective Bs may be identical to or different from each other, and the respective Es may be identical to or different from each other;

wherein the at least two types of primers have fluorescent atomic groups that are different in detection wavelength from each other.

39. The nucleic acid amplification method according to claim 28, wherein the target nucleic acid sequence is a nucleic acid sequence with a mutation, and in (C), the following primers are used: the primer in (C) having a sequence completely complementary to a region containing a mutation site in the target nucleic acid sequence and another primer having a sequence completely complementary to the region containing the mutation site except for the mutation site.

40. A method of detecting the presence or absence of a mutation in a target nucleic acid sequence contained in a nucleic acid sample, comprising:

(a) amplifying the target nucleic acid sequence contained in the nucleic acid sample by a nucleic acid amplification method according to claim 28, (b) measuring a fluorescence intensity before and after amplifying the target nucleic acid sequence in (a), and (c) detecting the presence or absence of a mutation by comparing the fluorescence intensities measured in (b).

41. The mutation detection method according to claim 40, wherein the mutation is substitution, deletion, or insertion of a base.

42. The mutation detection method according to claim 40, wherein in (a), the target nucleic acid sequence is amplified using at least two types of primers according to a primer as defined as follows:

a primer for amplifying a target nucleic acid sequence, wherein the primer is a labeled nucleic acid including at least one of structures represented by the following formulae (16), (16b), (17) and (17b) and exhibits an exciton effect:

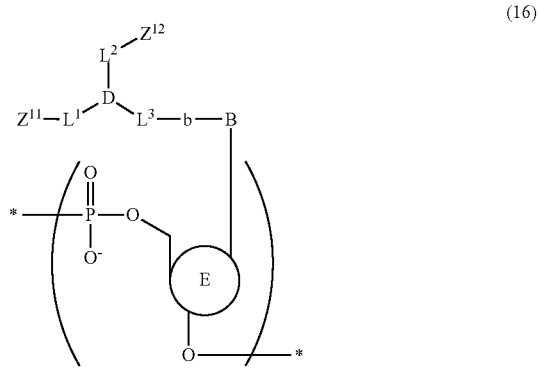

(16)

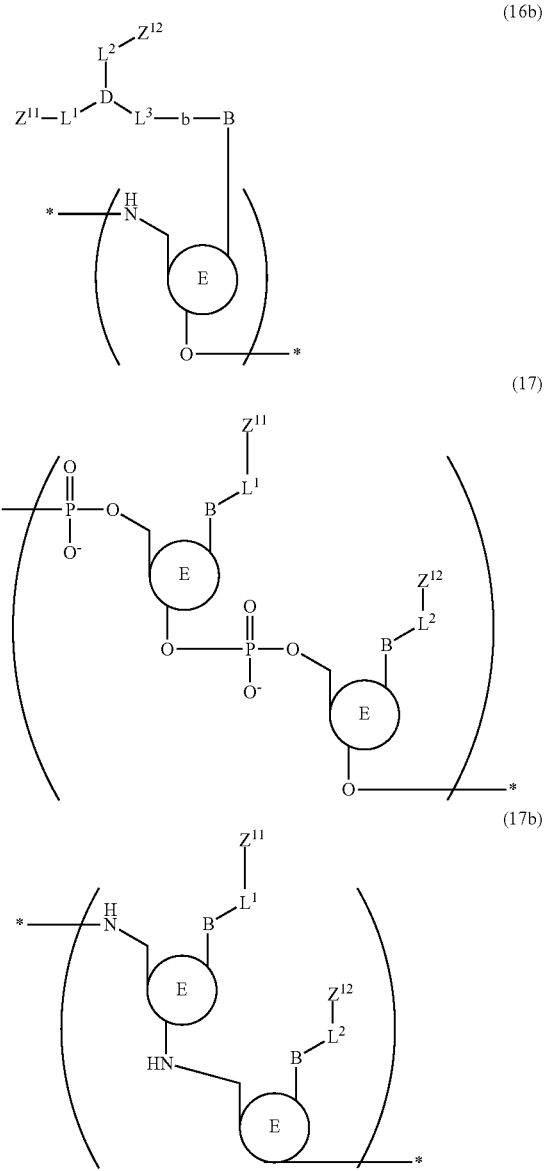

where in the formulae (16), (16b), (17) and (17b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a fluorescent atomic group that exhibits an exciton effect, and may be identical to or different from each other, $L^1$, $L^2$, and $L^3$ are each a linker (a linking atom or an atomic group), the main chain length (the number of main chain atoms) is arbitrary, they each may or may not contain each of C, N, O, S, P, and Si in the main chain, they each may or may not contain each of a single bond, a double bond, a triple bond, an amide bond, an ester bond, a disulfide bond, an imino group, an ether bond, a thioether bond, and a thioester bond in the main chain, and $L^1$, $L^2$, and $L^3$ may be identical to or different from one another, D is CR, N, P, P=O, B, or SiR, and R is a hydrogen atom, an alkyl group, or an arbitrary substituent, b is a single bond, a double bond, or a triple bond, or in the formulae (16) and (16b), $L^1$ and $L^2$ are each the linker, $L^3$, D, and b may not be present, and $L^1$ and $L^2$ may be bonded directly to B, where in the formulae (16) and (17), E is the atomic group described in item (i), and at least one O atom in a phosphoric acid linkage may be substituted with an S atom, in the formulae (16b) and (17b), E is the atomic group described in item (ii), and in the formulae (17) and (17b), the respective Bs may be identical to or different from each other, and the respective Es may be identical to or different from each other;

wherein the at least two types of primers have fluorescent atomic groups that are different in detection wavelength from each other, and in (c), fluorescence intensity of each of the fluorescent atomic groups is measured with each detection wavelength corresponding to each of the fluorescent atomic groups.

43. The mutation detection method according to claim 40, wherein in (a), the following primers are used: the primer in (a) having a sequence completely complementary to a region containing a mutation site in the target nucleic acid sequence and another primer having a sequence completely complementary to the region containing the mutation site except for the mutation site.

44. A method of improving the specificity of a primer to a target nucleic acid sequence in an amplification reaction that comprises amplifying the target nucleic acid sequence using at least two types of primers, wherein the specificity is improved by using one of the primers having a fluorescent atomic group according to claim 1 and having a sequence completely complementary to a region containing a mutation site in a target nucleic acid sequence and the other primer having a sequence completely complementary to the region containing the mutation site except for the mutation site.

45. The primer according to claim 4, wherein $Z^{11}$ and $Z^{12}$ are each independently an atomic group represented by the formula (7) or (8), and $Z^{11}$ and $Z^{12}$ represented by the formula (7) or (8) are groups represented by the following formula (19) or (20):

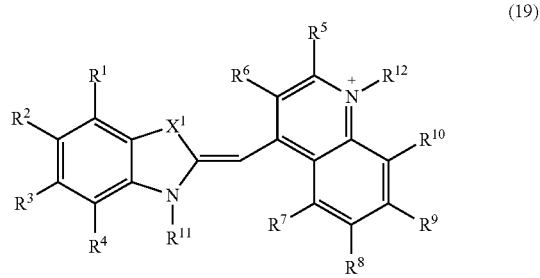

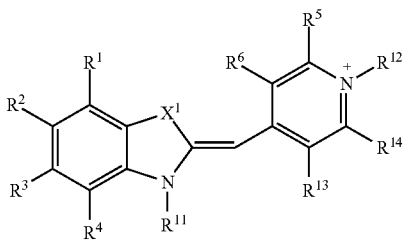

(20)

where in the formulae (19) and (20),
$X^1$, $R^1$ to $R^{10}$, $R^{13}$ and $R^{14}$, $R^{11}$, and $R^{12}$ are the same as those in the formulae (7) to (9).

46. The primer according to claim 45, wherein $Z^{11}$ and $Z^{12}$ are each independently an atomic group represented by the formula (19),
where in the formula (19),
$X^1$ is S,
$R^1$ to $R^{10}$ are hydrogen atoms,
one of $R^{11}$ and $R^{12}$ is a linking group that is bonded to $L^1$ or $L^2$ in the formulae (16), (17), (16b), and (17b), and the other is a methyl group.

47. The primer according to claim 45, wherein $Z^{11}$ and $Z^{12}$ are each independently an atomic group represented by the formula (19),
where in the formula (19),
$X^1$ is S,
$R^1$, $R^4$, $R^5$, $R^6$, $R^7$, $R^9$, and $R^{10}$ are hydrogen atoms,
$R^2$, $R^3$, and $R^{12}$ are methyl groups,
$R^8$ is a halogen atom, and
$R^{11}$ is a linking group that is bonded to $L^1$ or $L^2$ in the formulae (16), (17), (16b), and (17b).

48. The primer according to claim 4, wherein $Z^{11}$ and $Z^{12}$ are each independently an atomic group represented by the formula (7),
where in the formula (7),
$X^1$ is S,
n is 1
$R^1$ to $R^{10}$, $R^{15}$, $R^{16}$, and $R^{17}$ are hydrogen atoms,
$R^{11}$ is a linking group that is bonded to $L^1$ or $L^2$ in the formulae (16), (17), (16b), and (17b), and
$R^{12}$ is a methyl group.

49. The primer according to claim 4, wherein $Z^{11}$ and $Z^{12}$ are each independently an atomic group represented by any one of the following chemical formulae:

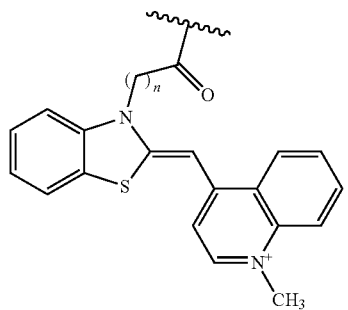

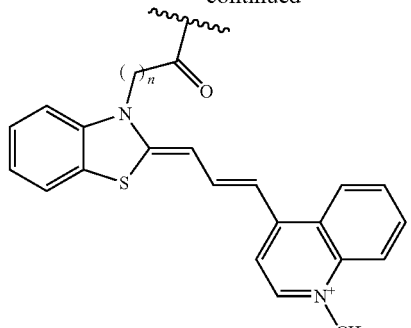

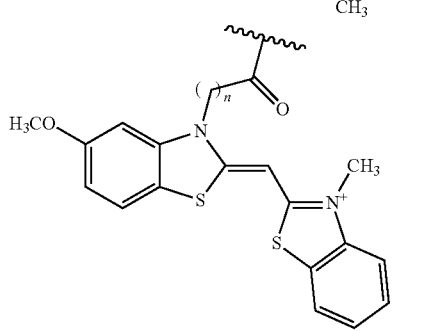

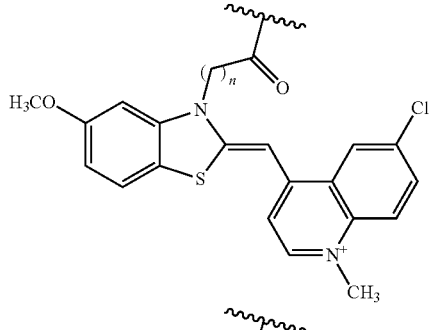

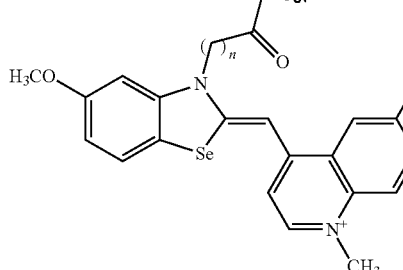

where in each of the chemical formulae,
n is a positive integer.

50. The primer according to claim 1, wherein in the formulae (16), (17), (16b), and (17b),
B is an atomic group having a natural nucleobase (adenine, guanine, cytosine, thymine, or uracil) skeleton.

51. The primer according to claim 1, wherein in the formulae (16), (17), (16b), and (17b),
B is an atomic group having an artificial nucleobase skeleton, and the artificial nucleobase is 2-amino-6-(N,N-dimethylamino)purine pyridine-2-one, 5-methylpyridine-2-one, 2-amino-6-(2-thienyl)purine, pyrrole-2-carboaldehyde, 9-methylimidazo[(4,5)-b]pyridine, 5-iodo-2-oxo(1H)pyridine, 2-oxo-(1H)pyridine, 2-amino-6-(2-thiazolyl)purine, 7-(2-thienyl)-imidazo[4,5-b]pyridine, bromothymine, azaadenine, or azaguanine.

52. The primer according to claim 1, wherein a structure represented by the formula (16) is a structure represented by the following formula (16-1) or (16-2),
a structure represented by the formula (16b) is a structure represented by the following formula (16b-1) or (16b-2),
a structure represented by the formula (17) is a structure represented by the following formula (17-1), and
a structure represented by the formula (17b) is a structure represented by the following formula (17b -1),

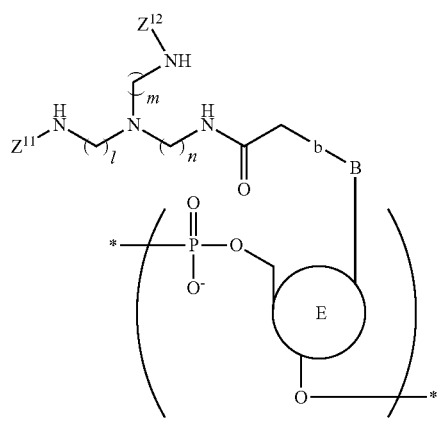

(16-1)

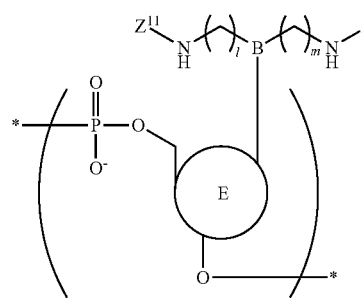

(16-2)

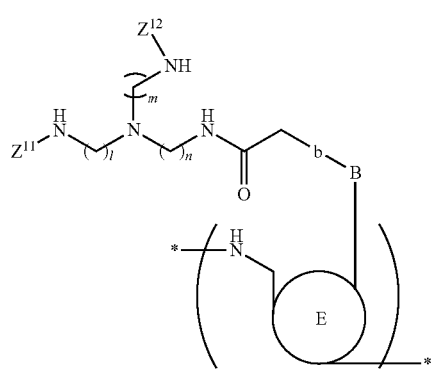

(16b-1)

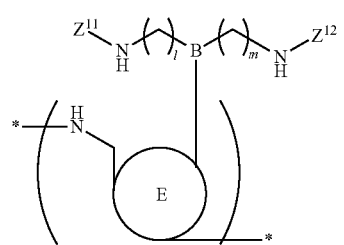

(16b-2)

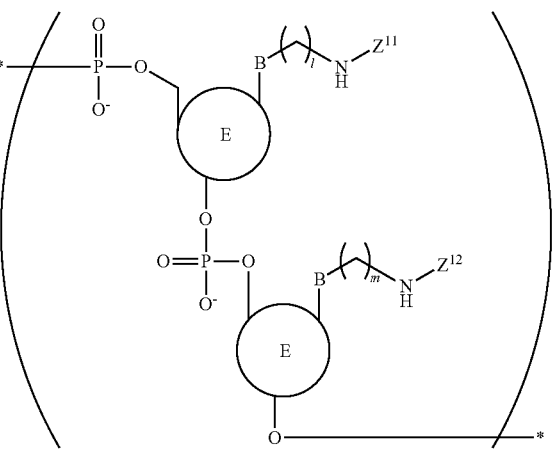

(17-1)

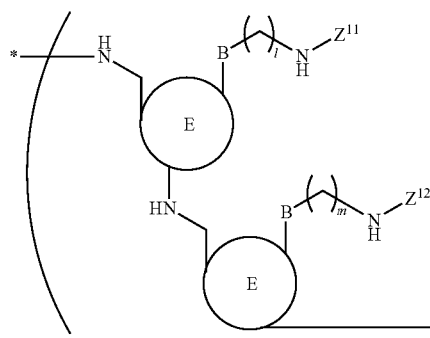

(17b-1)

where in the formulae (16-1), (16-2), (16b-1), (16b-2), (17-1), and (17b-1), l, m, and n are arbitrary, they may be identical to or different from each other, they each may or may not contain each of C, N, O, S, P, and Si in the main chain, and they each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are the same as those in the formulae (16), (16b), (17), and (17b), and in the formulae (16-1), (16-2), and (17-1), at least one O atom in a phosphoric acid linkage may be substitute with an S atom.

53. The primer according to claim 52, wherein in the formulae (16-1), (16-2), (16b-1), (16b-2), (17-1), and (17b-1), each of l, m, and n is an integer of 2 or more.

54. The primer according to claim 1, comprising at least one of a nucleotide structure represented by the following formula 106, 110, 113, or 117 or a structure of a geometric isomer thereof, a stereoisomer thereof, or a salt thereof,

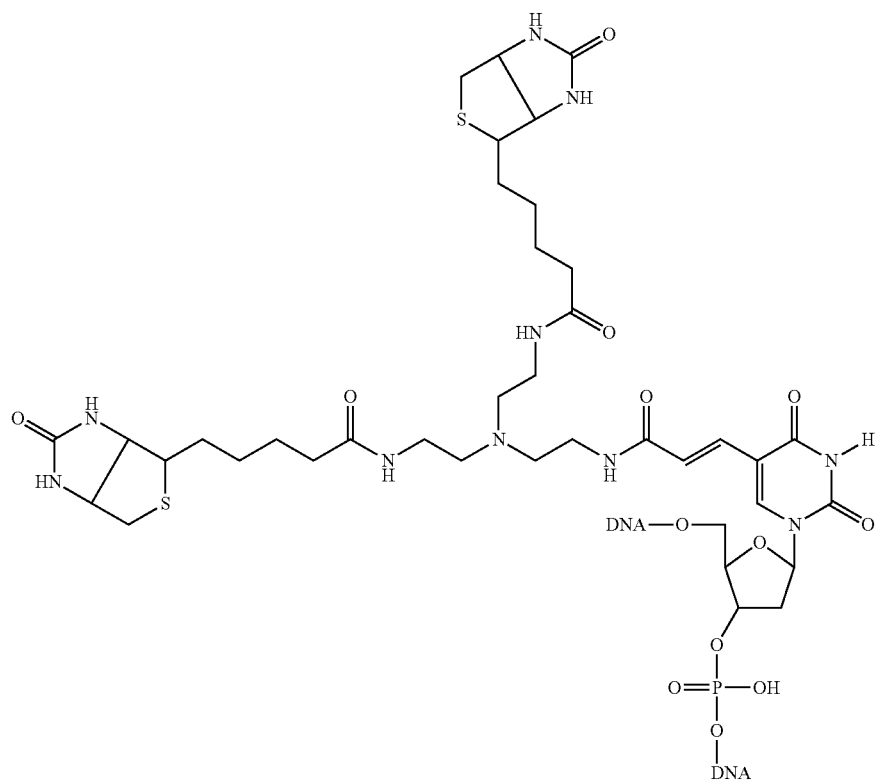
106
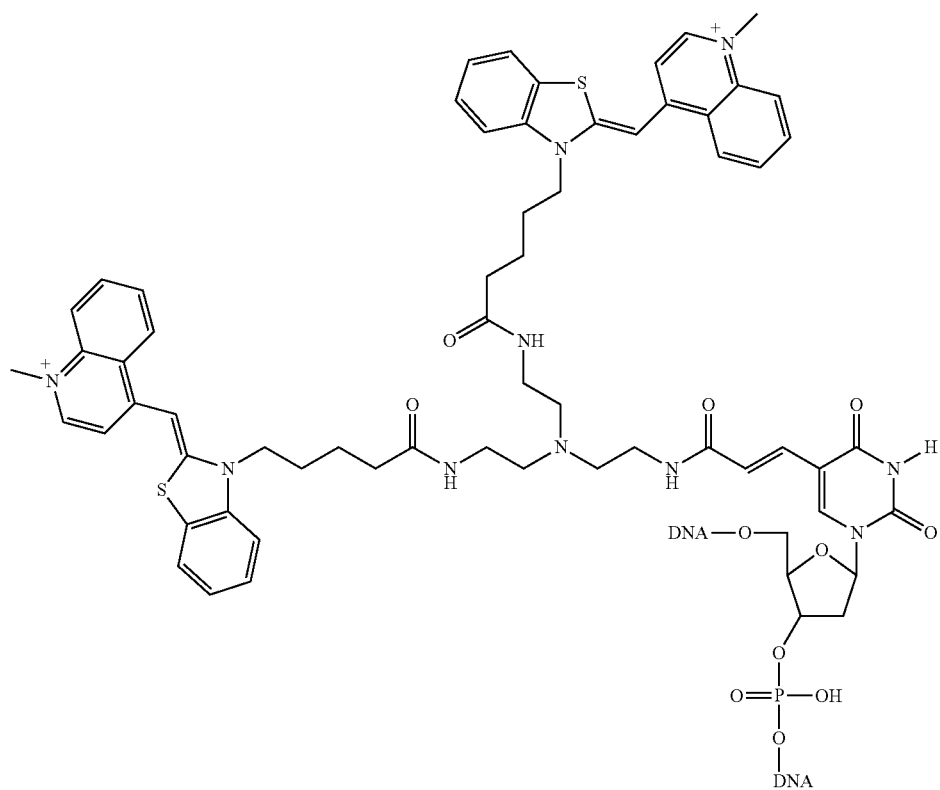
110

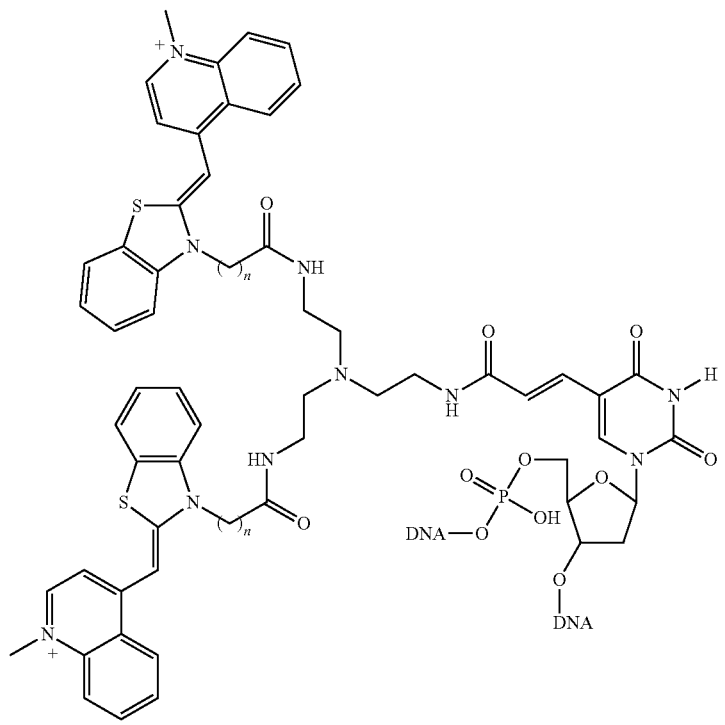
113
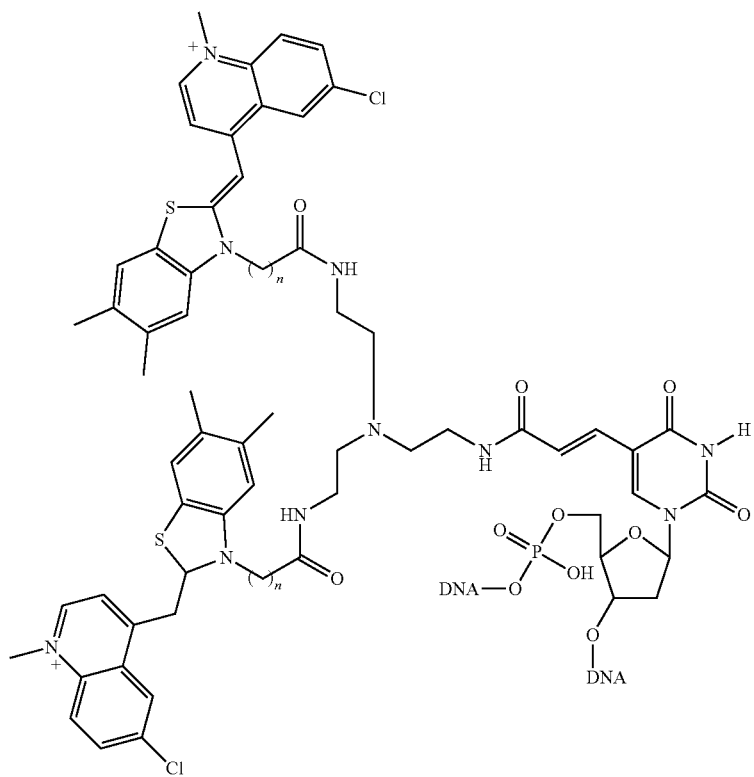
117
where in the formulae 106, 110, 113, and 117,
n is a positive integer.

55. The primer according to claim 1, comprising at least one of nucleotide structures represented by the following formulae 120, 122, 123, and 124, geometric isomers thereof, stereoisomers thereof, and salts thereof:
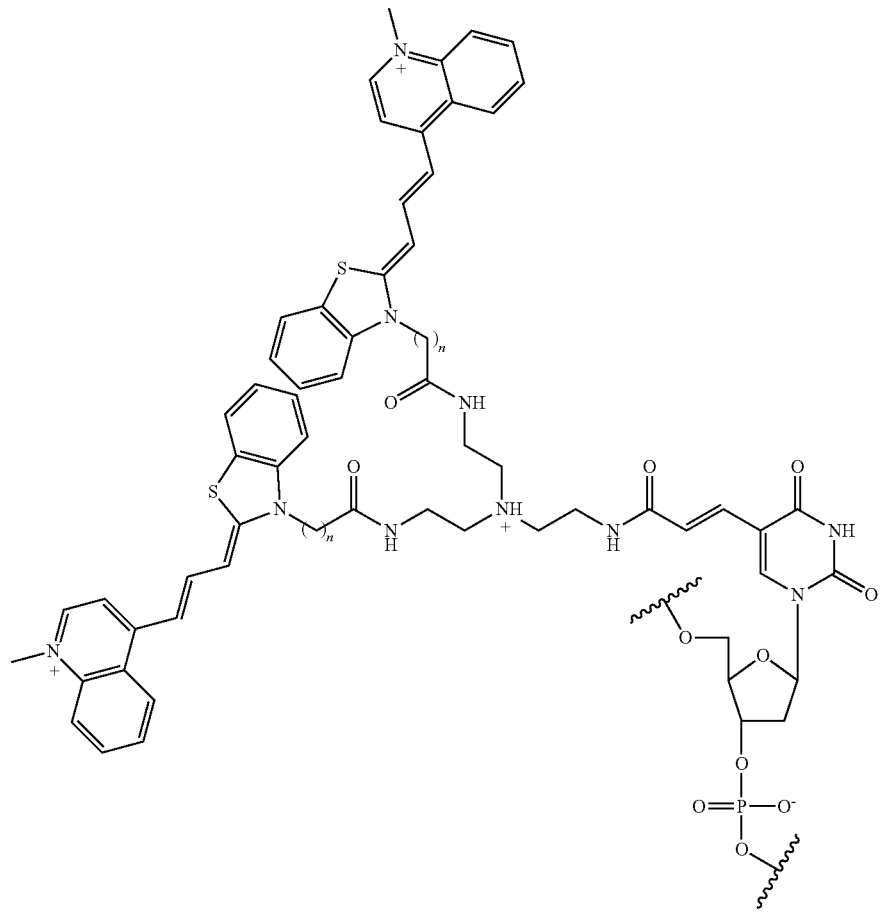
(120)
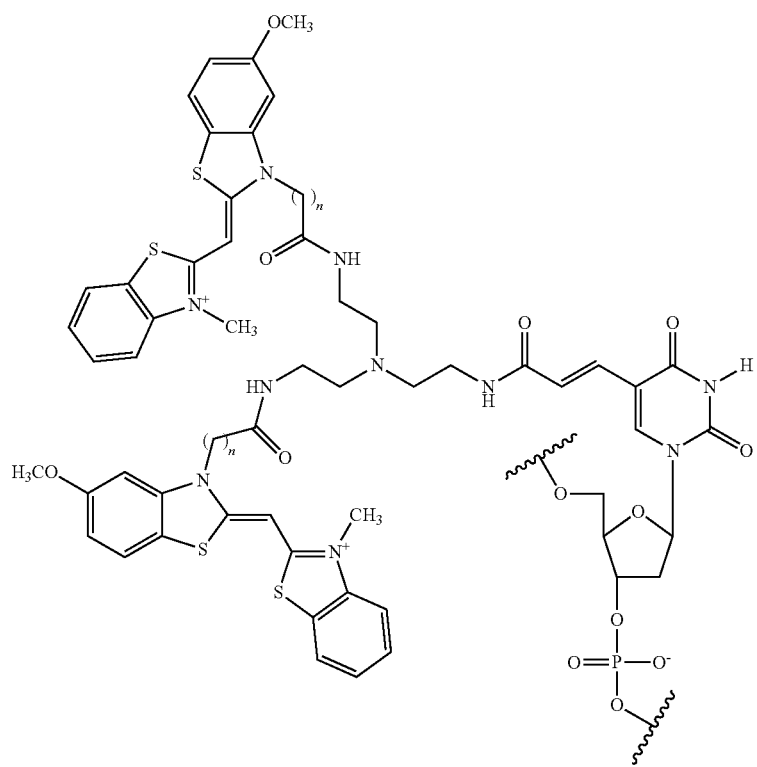
(122)

-continued
(123)
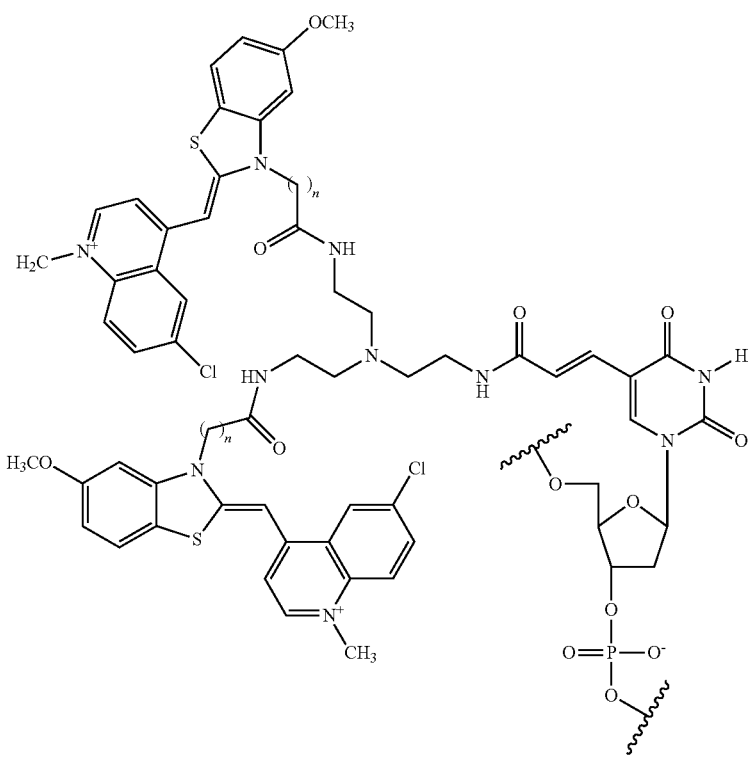
(124)
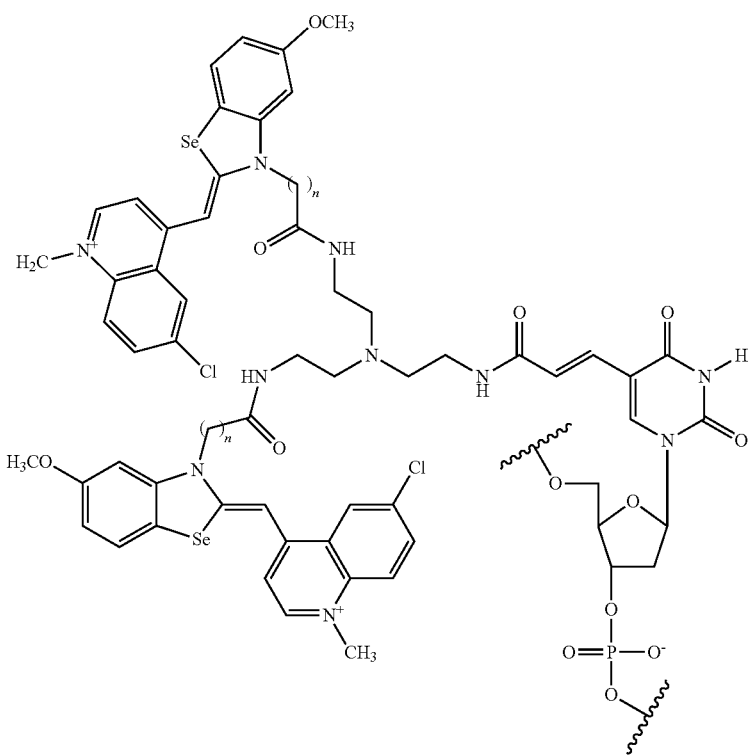

where in the formulae 120, 122, 123, and 124, n is a positive integer.

56. The primer according to claim 1, comprising a structure in which at least two structures selected from a nucleotide structure represented by the following formula 114, geometric isomers thereof, stereoisomers thereof, and salts thereof are linked to each other,

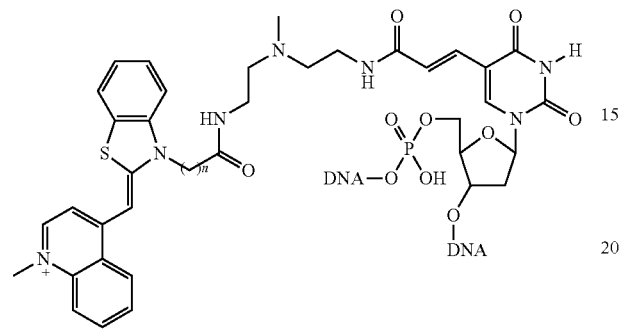

where in the formula 114, n is a positive integer, at least one nucleotide structure 114 is further included at a neighboring position to the nucleotide structure 114, and an oxygen atom at a 3-position of deoxyribose is shared with a neighboring phosphoester bond.

57. The primer, according to claim 54, wherein a length n of the linker is in a range of 2 to 6.

58. The primer according to claim 1, wherein the primer comprises about 2 to 100 base pairs.

* * * * *

UNITED STATES PATENT AND TRADEMARK OFFICE
CERTIFICATE OF CORRECTION

PATENT NO. : 8,067,162 B2
APPLICATION NO. : 12/075198
DATED : November 29, 2011
INVENTOR(S) : Hayashizaki et al.

It is certified that error appears in the above-identified patent and that said Letters Patent is hereby corrected as shown below:

In the Claims

Column 125, claim 1, lines 35-50, delete:

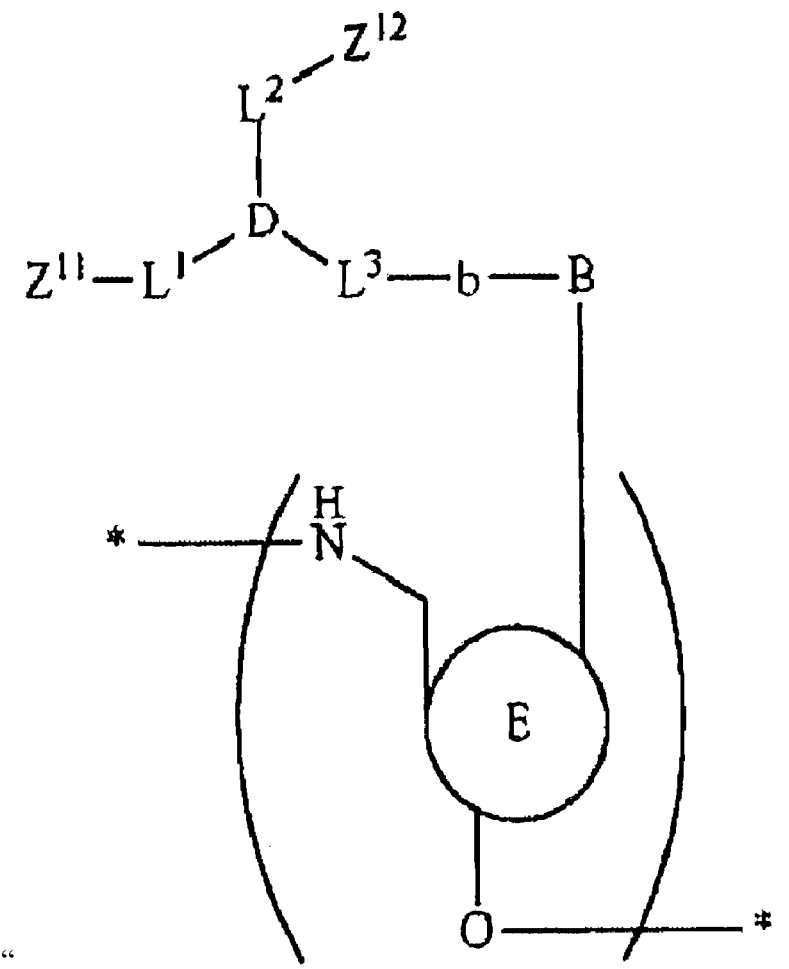

"       "

Signed and Sealed this
Twenty-ninth Day of December, 2015

Michelle K. Lee
*Director of the United States Patent and Trademark Office* and insert
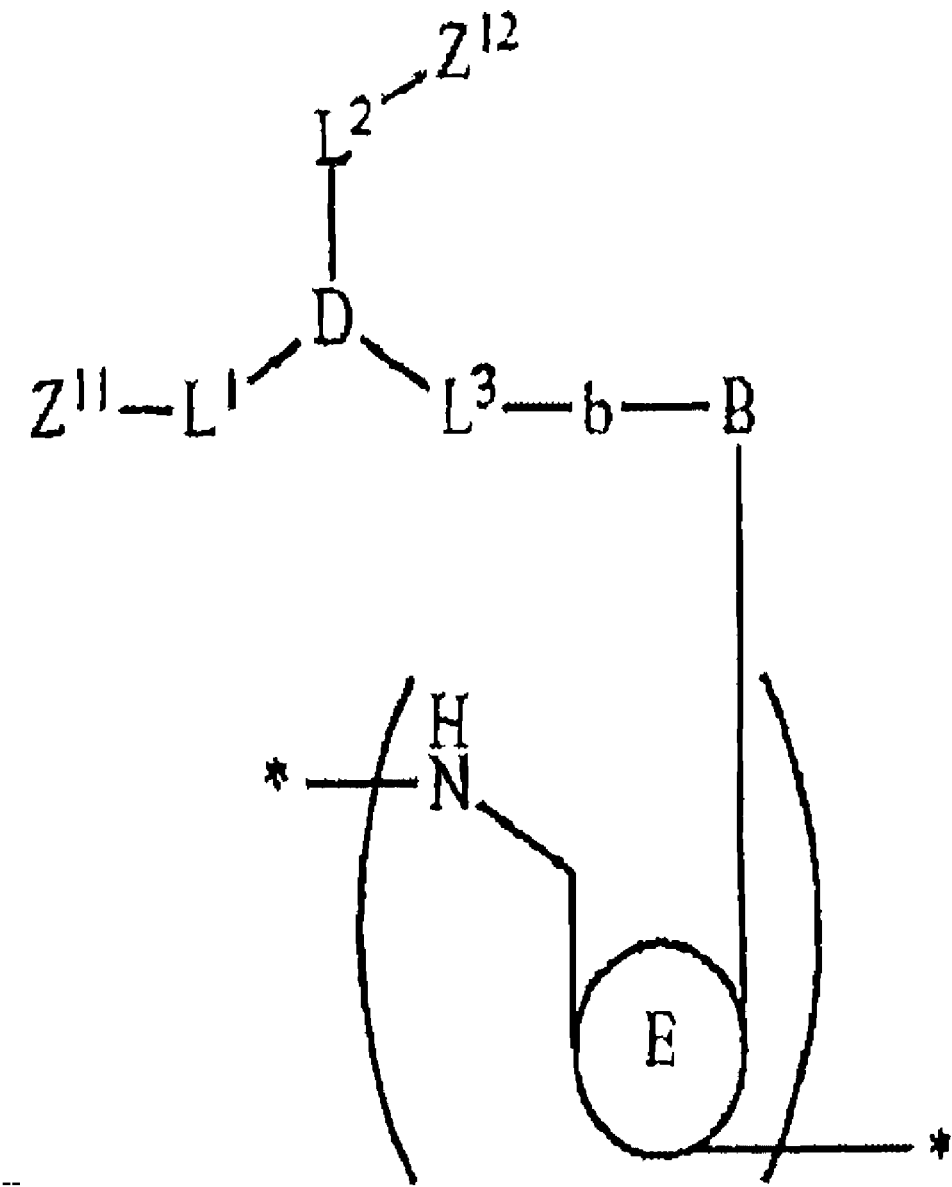
Column 128, claim 15, lines 43-44, delete "on a 540 side" and insert --on a 5' side--.

Column 130, claim 38, lines 52-67, delete:
"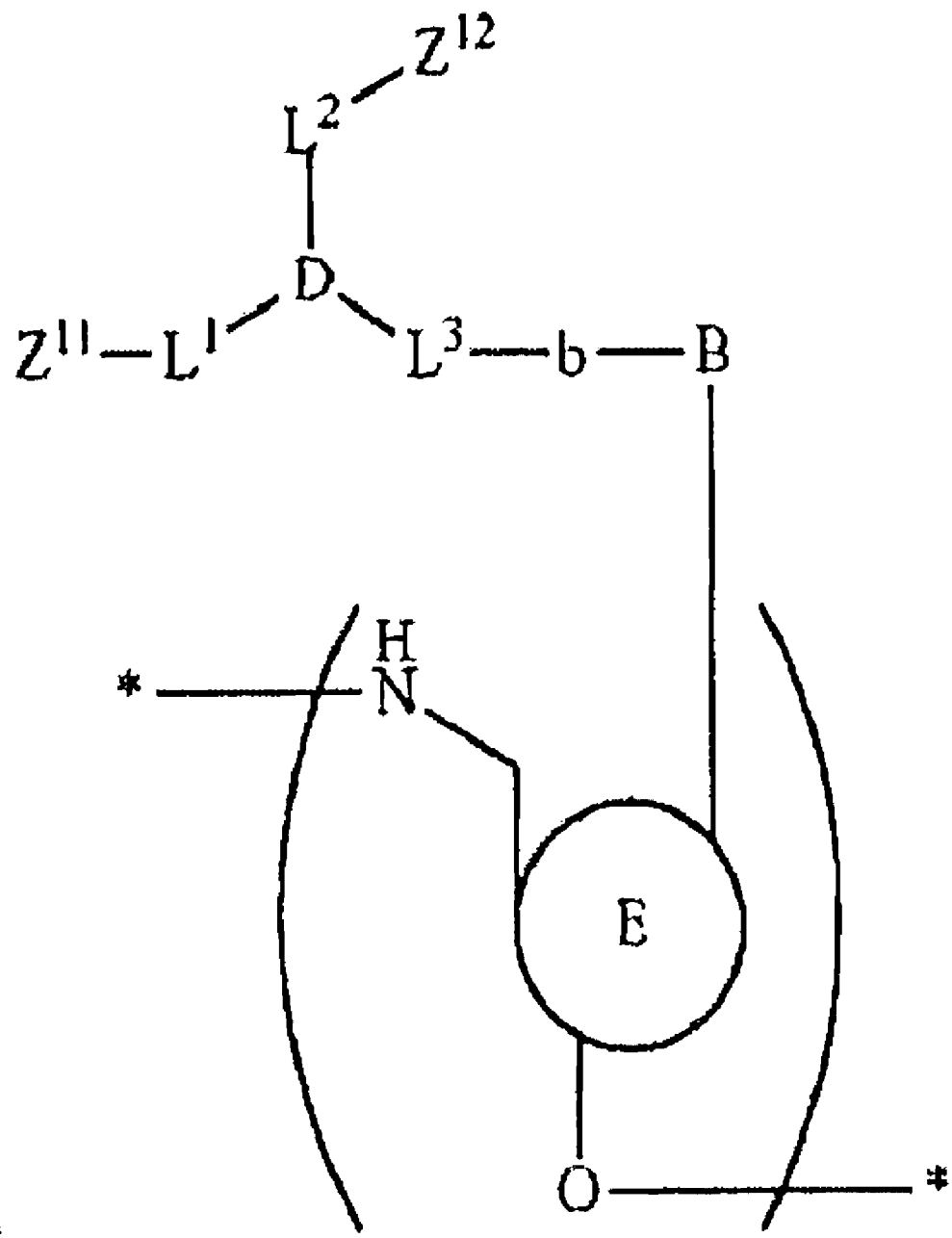"

and insert
(16b)
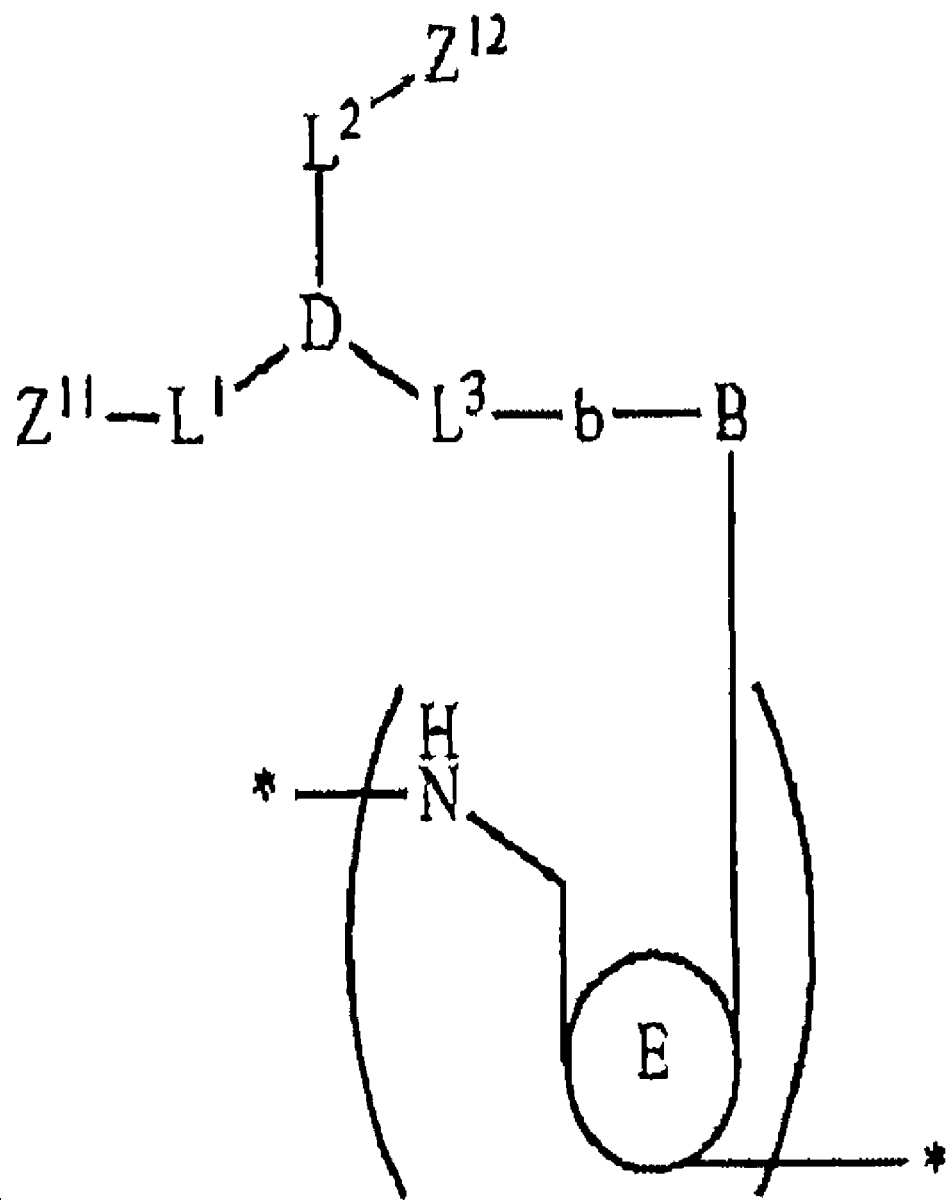

CERTIFICATE OF CORRECTION (continued)
U.S. Pat. No. 8,067,162 B2

Column 133, claim 42, lines 1-15, delete:

"
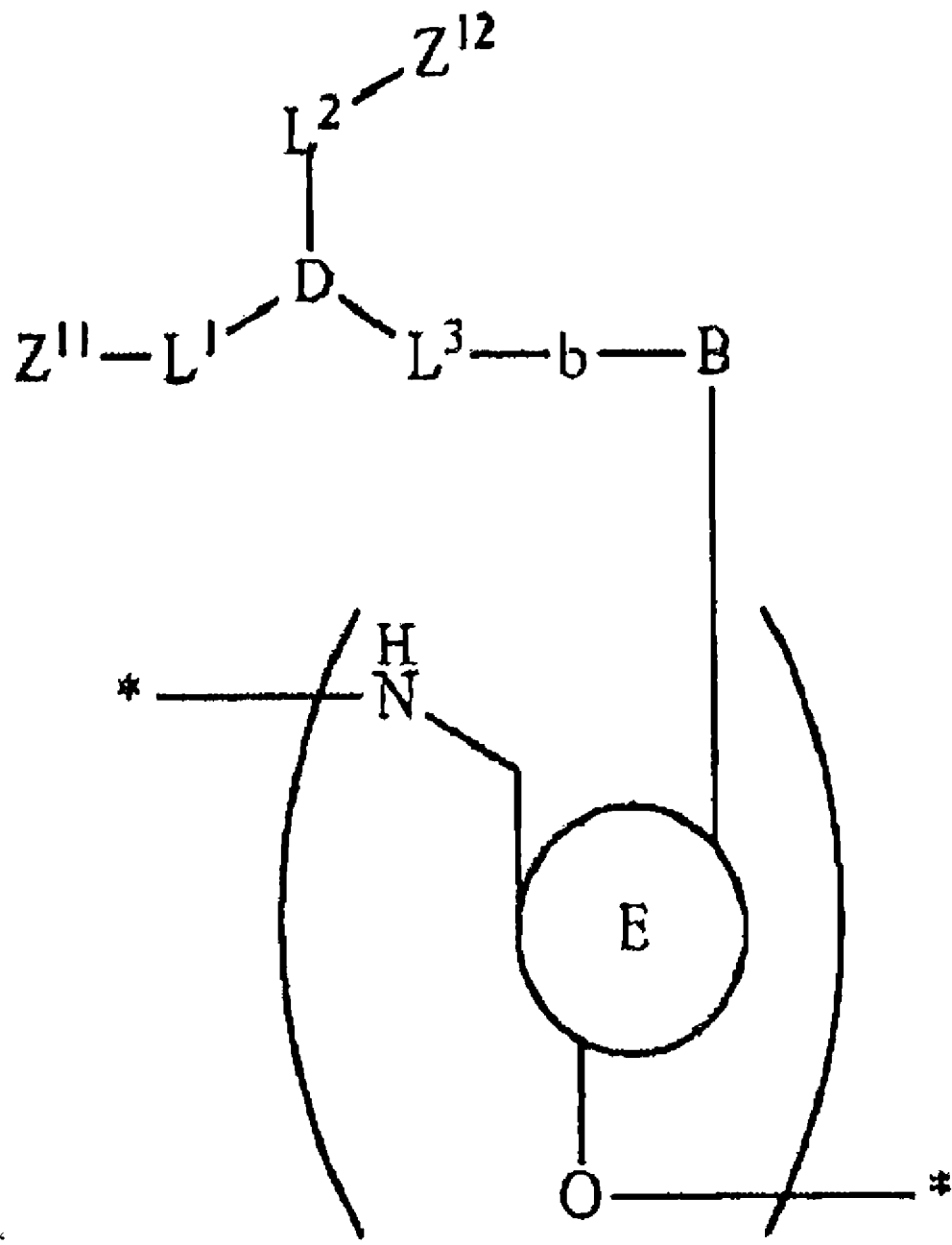
"

and insert
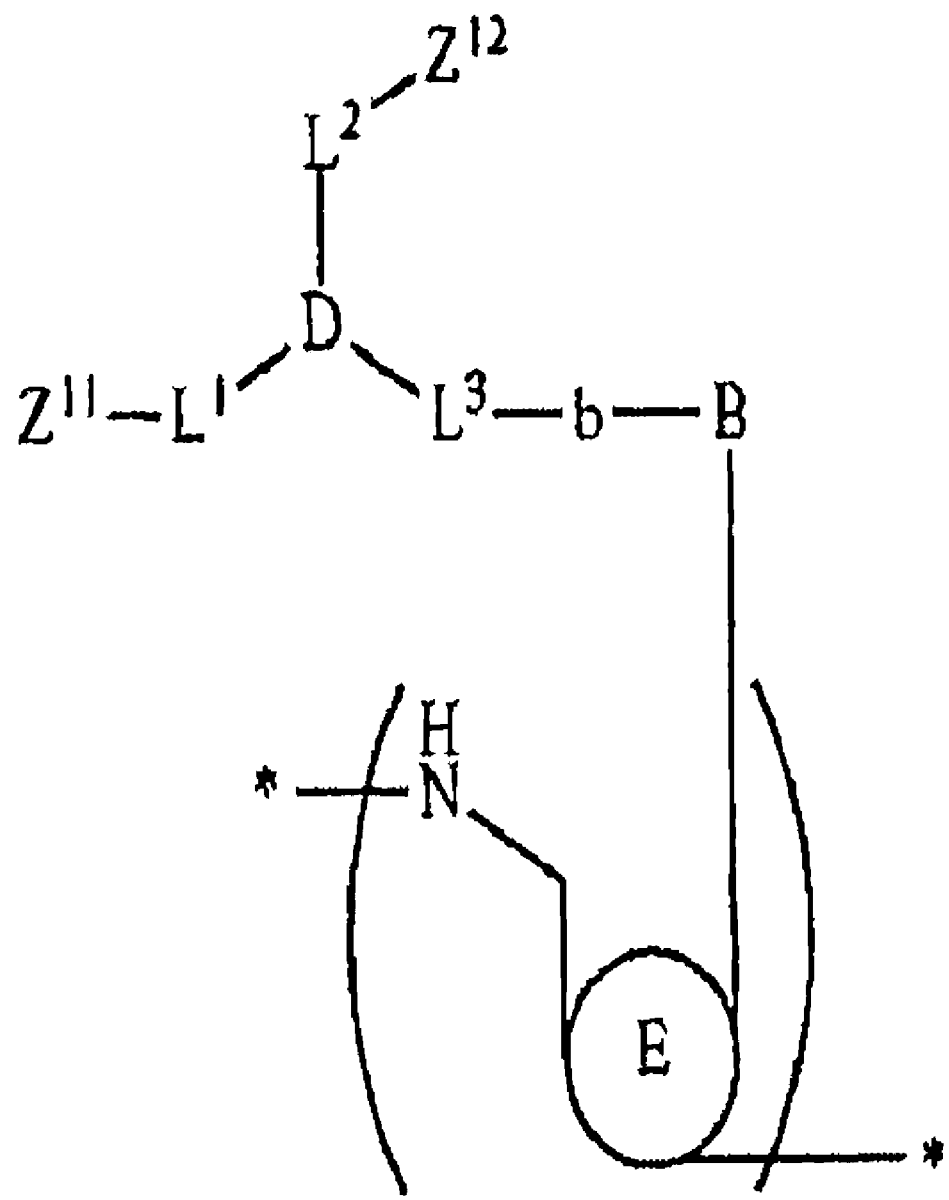
(16b)